US008367056B2

(12) United States Patent
Sehgal et al.

(10) Patent No.: US 8,367,056 B2
(45) **Date of Patent: *Feb. 5, 2013**

(54) IN VIVO AND EX VIVO GENE TRANSFER INTO RENAL TISSUE USING GUTLESS ADENOVIRUS VECTORS

(75) Inventors: Lakshman R. Sehgal, Monarch Beach, CA (US); Jonathan Wong, Palot Alto, CA (US)

(73) Assignee: Biovec, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/023,314

(22) Filed: Feb. 8, 2011

(65) Prior Publication Data

US 2011/0196022 A1 Aug. 11, 2011

Related U.S. Application Data

(63) Continuation of application No. 12/778,360, filed on May 12, 2010, now Pat. No. 8,048,410, which is a continuation of application No. 12/320,434, filed on Jan. 26, 2009, which is a continuation-in-part of application No. 11/650,478, filed on Jan. 8, 2007, now Pat. No. 7,501,114, which is a continuation-in-part of application No. 10/725,013, filed on Dec. 2, 2003, now Pat. No. 7,179,459.

(60) Provisional application No. 60/430,099, filed on Dec. 2, 2002.

(51) Int. Cl.

| | |
|---|---|
| ***A01N 63/00*** | (2006.01) |
| ***C07H 21/04*** | (2006.01) |
| ***C12N 15/00*** | (2006.01) |

(52) U.S. Cl. ..................... 424/93.2; 536/24.5; 536/24.1; 435/320.1; 424/93.6

(58) Field of Classification Search ........................ None
See application file for complete search history.

(56) References Cited

U.S. PATENT DOCUMENTS

| | | | | |
|---|---|---|---|---|
| 4,826,811 | A | 5/1989 | Sehgal et al. | |
| 4,868,116 | A | 9/1989 | Morgan et al. | |
| 5,061,688 | A | 10/1991 | Beissinger et al. | |
| 5,339,346 | A | 8/1994 | White | |
| 5,438,041 | A | 8/1995 | Zheng et al. | |
| 5,449,614 | A | 9/1995 | Danos et al. | |
| 5,466,668 | A | 11/1995 | Glaser et al. | |
| 5,639,625 | A | 6/1997 | Carson et al. | |
| 5,661,033 | A | 8/1997 | Ho et al. | |
| 5,827,824 | A | 10/1998 | Light et al. | |
| 5,863,760 | A | 1/1999 | Light et al. | |
| 5,869,230 | A | 2/1999 | Sukhatme | |
| 5,916,874 | A | 6/1999 | Fujiwara et al. | |
| 5,919,619 | A | 7/1999 | Tullis | |
| 5,981,225 | A | 11/1999 | Kochanek et al. | |
| 5,985,846 | A | 11/1999 | Kochanek et al. | |
| 5,994,132 | A | 11/1999 | Chamberlain et al. | |
| 6,083,750 | A | 7/2000 | Chamberlain et al. | |
| 6,207,455 | B1 | 3/2001 | Chang | |
| 6,290,949 | B1 | 9/2001 | French et al. | |
| 6,328,958 | B1 | 12/2001 | Amalfitano et al. | |
| 6,334,194 | B1 | 12/2001 | Hihara | |
| 6,335,011 | B1 | 1/2002 | Podsakoff et al. | |
| 6,342,214 | B1 | 1/2002 | Tryggvason et al. | |
| 6,888,047 | B1 | 5/2005 | Wu et al. | |
| 7,132,277 | B1 | 11/2006 | Bett et al. | |
| 7,160,539 | B2 | 1/2007 | Munn et al. | |
| 7,179,459 | B2 | 2/2007 | Sehgal et al. | |
| 7,481,998 | B2 | 1/2009 | Sehgal et al. | |
| 7,501,114 | B2 | 3/2009 | Sehgal et al. | |
| 7,687,058 | B2 | 3/2010 | Sehgal et al. | |
| 2002/0068713 | A1 | 6/2002 | Rade et al. | |
| 2002/0081695 | A1 | 6/2002 | Bednarik et al. | |
| 2002/0193336 | A1 | 12/2002 | Elkins et al. | |
| 2003/0003077 | A1 | 1/2003 | Borunda et al. | |
| 2003/0185801 | A1 | 10/2003 | Vogels et al. | |
| 2004/0198683 | A1 | 10/2004 | Sehgal et al. | |
| 2005/0106124 | A1 | 5/2005 | Sehgal et al. | |
| 2006/0240437 | A1* | 10/2006 | Krolewski et al. | 435/6 |
| 2007/0044164 | A1* | 2/2007 | Dickins et al. | 800/14 |
| 2007/0184027 | A1 | 8/2007 | Seghal et al. | |
| 2007/0212334 | A1* | 9/2007 | Sehgal et al. | 424/93.2 |
| 2008/0318882 | A1 | 12/2008 | Wang et al. | |
| 2009/0214627 | A1* | 8/2009 | Maines | 424/450 |
| 2010/0154068 | A1* | 6/2010 | Yu et al. | 800/3 |

FOREIGN PATENT DOCUMENTS

| | | | |
|---|---|---|---|
| WO | 96/06933 | A1 | 3/1996 |
| WO | 99/14346 | A1 | 3/1999 |
| WO | 00/46360 | A1 | 8/2000 |
| WO | 01/29058 | A1 | 4/2001 |
| WO | 2004/050844 | A2 | 6/2004 |

OTHER PUBLICATIONS

Supplementary European Search Report mailed Aug. 25, 2011 (Application No. EP 07772782.4, based on PCT Application No. PCT/US2007/006371, filed Mar. 14, 2007).

Parks, et al., "Effects of stuffer DNA on transgene expression from helper-dependent adenovirus vectors", J. Viral. 70 (10): 8027-8034, Oct. 1999.

GenBank Acc. No. M26434, "Human hypoxanthine phosphoribosyltransferease (HPRT) gene, complete cds". US Natl. Library of Med., Bethesda, MD, USA, Nov. 26, 2001.

Orkin, et al., "Report and Recommendations of the Panel to Assess the NIH Investment in Research on Gene Therapy", US National Institutes of Health, Bethesda, MD, USA, Dec. 7, 1995.

(Continued)

*Primary Examiner* — Richard Schnizer
(74) *Attorney, Agent, or Firm* — Ping Wang; Andrews Kurth LLP

(57) ABSTRACT

A method for treating a renal disease in a subject is disclosed. The method includes administering into a kidney of the subject with an effective amount of a gutless adenoviral vector containing a polynucleotide encoding a therapeutic agent. The gutless adenoviral vector contains the nucleotide sequence of SEQ ID NO:13 or SEQ ID NO:15 and expresses the therapeutic agent in a kidney tissue of the subject.

8 Claims, 18 Drawing Sheets

OTHER PUBLICATIONS

Verma, et al., "Gene therapy—promises, problems and prospects", Nature 389: 239-242,1997.
Rosenberg, et al., Gene therapist, heal thyself, Science 287: 1751,2000.
Zuckerbraun, B.S., "Vascular gene therapy: a reality of the 21st century", Arch. Surg. 137- 854-861, Jul. 2002.
Esmon, C.T., "Protein C in sepsis", Ann. Med. 34: 598-605, 2002.
Waugh, et al., "Local Overexpression of Thrombomodulin for In Vivo Prevention of Arterial Thrombosis in a Rabbit Model", Circulation Research, vol. 84, No. 1, pp. 84-92, 1999.
Waugh, et al., "Thrombomodulin Overexpression to Limit Neointima Formation", Circulation, vol. 102, No. 3, pp. 332-337, 2000.
Vassalli, et al., "Gene therapy for arterial thrombosis", Cardiovascular Research, vol. 19, No. 6, pp. 459-459,1997.
Umana, et al., "Efficient FLPe recombinase enables scalable production of helper-dependent adenoviral vectors with negligible helper-virus contamination", Nature Biotechnology, vol. 19, No. 6, pp. 582-585, 2001.
Wen, et al., "Human Thrombomodulin: Complete eDNA Sequence and Chromosome Localization of the Gene", Biochemistry, vol. 26, pp. 4350-4357,1987.
Borroni, et al., "Peripheral Blood Abnormalities in Alzheimer Disease: Evidence for Early Endothelial Dysfunction", Alzheimer Disease and Associated Disorders, vol. 16, No. 3, pp. 150-155,2002.
McKay, et al., "Gene Transfer Therapy in Vascular Disease", Cardiovascular Drug Reviews, vol. 19, No. 3, pp. 245-262, 2001.
Ausbel, et al., (eds) Greene Publishing Associates, "Current Protocols in Molecular Biology", Sections 9.10-9.14,1989.
Ng, et al., "Development of a FLP/fre System for Generating Helper-Dependent Adenoviral Vectors", Molecular Therapy, vol. 3, No. 5, pp. 809-815, 2001.
Bledsoe, et al., "Cytokine production in motor neurons by poliovirus replicon vector gene delivery", Nature Biotechnol., vol. 18. pp. 964-969, 2000.
Chen, et al., "Low-Dose Vaccinia Virus-Mediated Cytokine Gene Therapy of Glioma", Journal of Immunotherapy, vol. D 24, pp. 46-57, 2001.
Chen, et al., "Gene therapy for brain tumors: Regression of experimental gliomas by adenovirus-mediated gene transfer in vivo", Proc. Natl. Acad. Sci. USA, vol. 91, pp. 3054-3057, 1994.
Cui, et al., "Plasmid DNA-Entrapped Nanoparticles Engineered from Microemulsion Precursers: In Vitro and In Vivo Evaluation", Bioconjugate Chern., vol. 13, pp. 1319-1327, 2002.
Curiel, "Strategies to Adapt Adenoviral Vectors for Targeted Delivery", Annals New York Academy of Sciences, vol. 886, pp. 158-171, 1991.
Gossen, et al., "Transcriptional Activation by Tetracyclines in Mammalian Cells", Science, vol. 268, pp. 1766-1769, 1995.
Gossen, et al., "Tight control of gene expression in mammalian cells by tetracycline-responsive promoters", Proc. Natl. Acad. Sci. USA, vol. 89, pp. 5547-5551, 1992.
Fink, et al., "Gene Transfer to Neurons Using Herpes Simplex Virus-Based Vectors", Annual Rev. Neurosci., vol. 19, pp. 265-287,1996.
Flotte, et al., "Gene Expression from Adeno-associated Virus Vectors in Airway Epithelial Cells", Am. J. Respir. Cell. Mol. Biol., vol. 7, pp. 349-356,1992.
Green, et al., "A New Scalable Method for the Purification of Recombinant Adenovirus Vectors", Human Gene Therapy, vol. 13, pp. 1921-1934,2002.
Haj-Ahmand, et al., "Development of a Helper-Independent Human Adenovirus Vector and Its Use in the Transfer of the Herpes Simplex Virus Thymidine Kinase Gene", J. Virol., vol. 57., pp. 267-273, 1986.
Howell, et al., "High-Level Dystrophin Expression After Adenovirus-Mediated Dystrophin Minigene Transfer to Skeletal Muscle of Dystrophic Dogs: Prolongation of Expression with Immunosuppression", Human Gene Therapy, vol. 9, pp. 629-634, 1998.
Kay, et al., "Evidence for gene transfer and expression of factor IX in haemophilia B patients treated with an AAV vector", Nature Genetics, vol. 24, pp. 257-261, 2000.
Kessler, et al., "Gene delivery to skeletal muscle results in sustained expression and systemic delivery of a therapeutic protein", Proc. Natl. Acad. Sci. USA, vol. 96, pp. 14082-14087, 1996.
Kistner, et al., "Doxycycline-mediated quantitative and tissue-specific control of gene expression in transgenic mice", Proc. Natl. Acad. Sci. USA, vol. 93, pp. 10933-10938, 1996.
Magari, et al., "Pharmacologic Control of a Humanized Gene Therapy System Implanted into Nude Mice", J. Clin. Invest., vol. 100, pp. 173-206, 1997.
Miller, "Progress Toward Human Gene Therapy", Blood, vol. 76, pp. 271-278,1990.
Muzyczka, et al., "Use of Adeno-Associated Virus as a General Transduction Vector for Mammalian Cells", Curro Topics in Micro. and Immunology, vol. 158, pp. 97-129,1990.
Naldni, et al., "In Vivo Gene Delivery and Stable Transduction of Nondividing Cells by a Lentiviral Vector", Science, vol. 272, pp. 263-267, 1996.
No, et al., "Ecdysone-inducible gene expression in mammalian cells and transgenic mice", Proc. Natl. Acad. Sci., USA, vol. 93, pp. 3346-3351, 1996.
Pruchnic, et al., "The Use of Adeno-Associated Virus to Circumvent the Maturation-Dependent Viral Transduction of Muscle Fibers", Human Gene Therapy, vol. 11, pp. 521-536, 2000.
Ragot, et al., "Efficient adenovirus-mediated transfer of a human minidystrophin gene to skeletal muscle of mdx mice", Nature, vol. 361, pp. 647-650,1993.
Romano, et al., "Latest Developments in Gene Transfer: Achievements, Perspectives, and Controversies Over Therapeutic Applications", Stem Cells, vol. 18, pp. 19-39, 2000.
Ropert, "Liposomes as a gene delivery system", Brazilian Journal of Medical and Biological Research, vol. 32, pp. 163-169,1999.
Sakhuja, et al., "Optimization of the Generation and Propagation of Gutless Adenoviral Vectors", Human Gene Therapy, vol. 14, pp. 243-254, 2003.
Samulski, et al., "Helper-Free Stocks of Recombinant Adeno-Associated Viruses: Normal Integration Does Not Require Viral Gene Expression", Journal of Virology, vol. 63, No. 9, pp. 3822-3828,1989.
Schwarze, et al., "In Vivo Protein Transduction: Delivery of a Biologically Active Protein into the Mouse", Science, vol. 285,pp. 1569-1572, 1999.
Song, et al., "Sustained secretion of human alpha-1 antitrypsin from murine muscle transduced with adeno-associated virus vectors", Proc. Natl. Acad. Sci. USA, vol. 95, pp. 14348-14384, 1998.
Suzuki, et al., "Structure and expression of human thrombomodulin, a thrombin receptor on endothelium acting as a cofactor for protein C activation", EMBO Journal, vol. 6, pp. 1891-1897, 1987.
Wahlfors, et al., "Evaluation of recombinant alphaviruses as vectors in gene therapy", Gene Therapy, vol. 7, pp. 472-480, 2000.
Wang, et al., "A regulatory system for use in gene transfer", Proc. Natl. Acad. Sci. USA, vol. 91, pp. 8180-8184,1994.
Wang, et al., "Ligand-inducible and liver-specific target gene expression in transgenic mice", Nature Biotechnology, vol. 15, pp. 239-243, 1997.
Yamashita, et al., "Electroporation-mediated Interleukin-12 Gene Therapy Hepatocellular Carcinoma in the Mice Model", Cancer Research, vol. 61, pp. 1005-1012,2001.
Ye, et al., "Regulated Delivery of Therapeutic Proteins After In Vivo Somatic Cell Gene Transfer", Science, vol. 283, pp. 88-91, 1999.
Yi, et al., "A Cationic Lipid Emulsion/DNA Complex as a Physically Stable and Serum-Resistant Gene Delivery System", Pharmaceutical Research, vol. 17, No. 3, pp. 314-320, 2000.
Xiao, et al., "Efficient Long-Term Gene Transfer into Muscle Tissue of Immunocompetent Mice by Adeno-Associated Virus Vector", Journal of Virology, vol. 70, No. 11, pp. 8098-8108, 1996.
Xiao, et al., "Adeno-Associated Virus as a Vector for Liver-Directed Gene Therapy", Journal of Virology, vol. 72, No. 12, pp. 10222-10226, 1998.
Zhang, et al., "Long-term expression of human alpha-1 antitrypsin gene in mouse liver achieved by intravenous administration of plasmid DNA using a hydrodynamics-based procedure", Gene Therapy, vol. 7, pp. 1344-1349,2000.

Cui, et al., "Genetic Immunization Using Nanoparticles Engineered from Microemulsion Precursors" Pharmaceutical Research, vol. 19, No. 7, pp. 939-946, 2002.
Kibbe, et al., "Handbook of Pharmaceutical Excipients", 3rd Edition, Pharmaceutical Press London UK, 2000.
Lee, et al., "Crit. Rev. Ther.", Drug Carrier Systems, vol. 14, pp. 173-206, 1997.
Harui, et al., "Vaccination with helper-dependent adenovirus enhances the generation of transgene-specific CTL", Gene Therapy, vol. 11, pp. 1617-1626,2004.
Johansson, et al., "Adenoviral-Mediated Expression of Porphobilinogen Deaminase in Liver Restores the Metabolic Defect in a Mouse Model of Acute Intermittent Porphyria", Molecular Therapy, vol. 10, pp. 337-343, 2004.
Fu, et al., "Overexpression of SR-BI by Adenoviral Vector Reserves the Fibrate-Induced Hypercholesterolemia of Apolipoprotein E-Deficient Mice", Journal of Biological Chemistry, vol. 278, pp. 52559-52563, 2003.
Brevetti, et al., "Overexpression of endothelial nitric oxide synthase increases skeletal muscle blood flow and oxygenation in severe rat hund limb ischemia", The Society for Vascular Sugery, pp. 820-826, 2003.
Li, et al., J. Vase. Surg. 32: 804-813, 2000.
Tohda, et al., Arteriosclerosis, Thrombosis, and Vascular Biology, 18: 1861-1869, 1998.
Kurosawa, et al., J. Biol. Chern., 263(13): 5993-5996,1988.
Tabuchi, et al., Eur. J. Card. Thor. Surg., 26: 995-1000, 2004.
Miller, et al., FASEB J., 9: 190-199, 1995.
Crystal, Science, 270: 404-410,1995.
Read, et al., Adv. Gen., 53: 19-46, 2005.
Search Result for SEQ 10 No. 13 in U.S. Appl. No. 11/685,474.
Marth, et al., Nature Genetics, 23(4): 452-456, 1999.
Wheelan, et al., Genome Research, 11(11), 1952-1957,2001.
Kibbe, et al., "Gene Therapy for Restenosis", Circ. Res., vol. 86, pp. 829-833, 2000.
Shears, et al., "Efficient Inhibition of Intimal Hyperplasia by Adenovirus-Mediated Inducible Nitric Oxide Synthase Gene Transfer to Rats and Pigs In Vivo", J. Am. Coli. Surg., vol. 187, No. 3, pp. 295-306, 1998.
Ross, "The pathogenesis of.atherosclerosis: a perspective for the 1990s", Nature, vol. 362, pp. 801-809, 1993.
Sadler, "Thrombomodulin Structure and Function", Tehomb Haemost, vol. 78, pp. 392-395,1997.
Esmon, "Thrombomodulin as a model of molecular mechanisms that modulate protease specificity and function at the vessel surface", Faseb J., vol. 9, pp. 946-955,1995.
Salomaa, et al., "Soluble thrombomodulin as a predictor of incident coronary heart disease and symptomless carotid artery atherosclerosis in the Atherosclerosis Risk in Communities (ARIC) Study: a case-cohort study", Lancet, vol. 353,pp. 1729-1734, 1999.
Palmer, et al., "Nitric oxide release accounts for the biological activity of enothelium-derived relaxing factor", Nature, vol. 88, pp. 4651-4655,1991.
Kubes, et al., "Nitric oxide: An endogenous modulator of leukocyte adhesion", Proc. Natl. Acad. Sci. USA, vol. 88, pp. 4651-4655,1991.
Steg, et al., "Reduction of Restenosis After Angioplasty in an Atheromatous Rabbit Model by Suicide Gene Therapy", Circulation vol. 96, pp. 401-411,1997.
Van Belle, et al., "Accelerated Endothelialization by Local Deliery of Recombinant Human Vascular Endothelial Growth Factor Reduces In-Stent Intimal Formation", Biochem. and Biophs. Res. Communications, vol. 235, pp. 311-316, 1997.
Salyapongse, et al., "Gene Therapy and Tissue Engineering", Tissue Engineering, vol. 26, No. 4, pp. 663-676,1999.
Kon, et al., "Bone Morphogenetic Protein-2 Stimulates Differentiation of Cultured Spinal Ligament Cells from Patients with Ossification of the Posterior Longitudinal Ligament", Calcif. Tissue Int., vol. 60, pp. 291-296,1997.
Kibbe, et al., J. Vase. Surg., 34: 156-65,2001.
He, et al., PNAS, 95: 2509-2514,1998.
Marmur, et al., "Strand Separation and Specific Recombination in Deoxyribonucleic Acids: Biological Studies", PNAS USA, vol. 46, pp. 453-461,1960.
Doty, et al., "Strand Separation and Specific Recombination in Deoxyribonucleic Acids: Physical Chemical Studies", PNAS USA, vol. 46, pp. 461-476, 1960.
Sambrook, et al., "Analysis of Genomic DNA by Southern Hybridization", Molecular Cloning: A Laboratory Manual, vol. II, pp. 9.31-9.62,1989.
Zushi, et al., "Aspartic acid 349 in the forth epidermal growth factor-like structure of human thrombomodulin plays a role in its Ca(2+)-mediated binding to protein C", The Journal of Biological Chemistry, vol. 266, No. 30, pp. 19886-19889, 1991.
Parks, et al., "A helper-dependent adenovirus vector system: Removal of helper virus by Cre-mediated excision of the viral packaging signal", PNAS, vol. 93, pp. 13565-13570, 1996.
Lieber, et al., "Recombinant Adenoviruses with Large Deletions Generated by Cre-Mediated Excision Exhibit Different Biological Properties Compared with First-Generation Vectors In Vitro and In Vivo", J. Virol., vol. 70, pp. 8944-8960, 1996.
Dittman, et al., "Human Thrombomodulin: Complete eDNA Sequence and Chromosome Localization of the Gene", Biochemistry, vol. 26, pp. 4350-4357,1987.
Beauchamp, et al., "Development of a FLP/frt System for Generating Helper-Dependent Adenoviral Vectors", Molecular Therapy, vol. 3, No. 5, pp. 809-815, 2001.
Nabel, et al., Science, vol. 249, pp. 1285-1288, 1990.
Tsiang, et al., "Functional domains of membrane-bound human thrombomodulin. EGF-like domains four to six and the serine/threonine-rich domain are required for cofactor activity", The Journal of Biological Chemistry, vol. 267, No. 9, pp. 6164-6170, 1992.
Nagashima, et al., "Alanine-scanning mutagenesis of the epidermal growth factor-like domains of human thrombomodulin identifies critical residues for its cofactor activity", The Journal of Biological Chemistry, vol. 268., No. 4,pp. 2888-2892,1993.
Gerlitz, et al., "Identification of the predominant glycosaminoglycan-attachment site in soluble recombinant human thrombomodulin: potential regulation of functionality by glycosyltransferase competition for serine474", The Biochemical Journal, vol. 295, pp. 131-140,1993.
Lin, et al., "Modulation of glycosaminoglycan additional in naturally expressed and recombinant human thrombomodulin", The Journal of Biological Chemistry, vol. 269, No. 40, pp. 25021-25030,1994.
Adler, et al., "The structure of a 19-residue fragment from the C-loop of the fourth epidermal growth factor-like domain of thrombomodulin", The Journal of Biological Chemistry, vol. 270, No. 40, pp. 23366-23372, 1995.
Weiler-Guettler, et al., "A targeted point mutation in thrombomodulin generated viable mice with a prethrombotic state", The Journal of Clinical Investigation, vol. 101, No. 9, pp. 1983-1991, 1998.

* cited by examiner

Left Inverted Terminal Repeat: 1-103

Encapsidation Signal (Ψ): 183-331

HPRT Introns: 365-10557

Right Inverted Terminal Repeat: 10571-10673 pBR322 ori: 10877-11544

Kanamycin Resistance Gene: 12353-13144

Click # LEO20060420163824
Thu, Apr 20, 2006 16:38:44
Bin:HR (4), FOV15, f1, 0.2s
Filter: Open
Camera: IVIS 176, SI620EEV Click # LEO20060420165341
Thu, Apr 20, 2006 16:53:58
Bin:HR (4), FOV15, f1, 0.2s
Filter: Open
Camera: IVIS 176, SI620EEV Click # LEO20060420164755
Thu, Apr 20, 2006 16:48:15
Bin:HR (4), FOV15, f1, 0.2s
Filter: Open Click # LEO20060420164220
Thu, Apr 20, 2006 16:42:39
Bin:HR (4), FOV15, f1, 0.2s
Filter: Open
Camera: IVIS 176, SI620EEV

IN VIVO AND EX VIVO GENE TRANSFER INTO RENAL TISSUE USING GUTLESS ADENOVIRUS VECTORS

This application is a continuation of U.S. patent application Ser. No. 12/778,360, filed on May 12, 2010, which is a continuation of U.S. patent application Ser. No. 12/320,434, filed on Jan. 26, 2009, which is a continuation-in-part of U.S. patent application Ser. No. 11/650,478, now U.S. Pat. No. 7,501,114, filed on Jan. 8, 2007, which is a continuation-in-part application of U.S. patent application Ser. No. 10/725,013, now U.S. Pat. No. 7,179,459, filed on Dec. 2, 2003, which claims priority from U.S. Provisional Application Ser. No. 60/430,099 filed on Dec. 2, 2002. The entirety of all of the aforementioned applications is incorporated herein by reference.

FIELD

The present invention is directed to methods and compositions for the gene transfer into renal tissues and, in particular, is directed to methods and compositions for in vivo or ex vivo gene transfer to renal tissue using gutless adenovirus vector.

BACKGROUND

Kidney-targeted gene transfer has the potential to revolutionize the treatment of renal diseases. Transplanted kidneys also provide an ideal setting for ex vivo gene transfer. Several in vivo gene transfer methods have been attempted to target certain renal structures, for example, the HVJ-liposome method and renal perfusion of adenovirus for glomerular cells, intravenous injection of oligonucleotides (ODNs) for proximal tubule, intra-arterial injection of adenovirus followed by cold incubation with a vasodilator for interstitial vasculature of the outer medulla and adenoviral injection into the renal pelvis for the inner medullary collecting duct. As an ex vivo gene transfer method targeting the glomerulus, the transfusion of genetically-modified mesangial cells has been attempted. Implantation of genetically-modified tubular epithelial cells into the subcapsular region has been employed for ex vivo transfection to the interstitium.

However, although gene therapy theoretically has the distinct potential to treat renal disease at the most fundamental level, its application has been limited by the availability of an adequate system for long term gene delivery to the kidney. There still exists a need for improved gene transfer techniques, especially gene transfer vectors that are capable of mediating effective gene transfer into renal tissues with low toxicity.

SUMMARY

One aspect of the present invention relates to methods for treating a renal disease in a mammal. In one embodiment, the method comprises the step of infusing the kidney with a gutless adenoviral vector comprising a polynucleotide encoding a therapeutic agent and a regulatory element operably linked to the polynucleotide, wherein the gutless adenoviral vector comprises the nucleotide sequence of SEQ ID NO:13 or SEQ ID NO:15. In a related embodiment, the gutless adenovirus vector is infused through the vena renalis. In another related embodiment, the gutless adenovirus vector is infused through the superior mesenteric artery.

In another embodiment, the method comprises the steps of: administering a therapeutically effective amount of a gutless adenovirus vector into a segment of a renal blood vessel in vivo, wherein the gutless adenovirus vector comprises the nucleotide sequence of SEQ ID NO:13 or SEQ ID NO:15, and is capable of expressing a therapeutic agent. In a related embodiment, the gutless adenovirus vector is administered using a stent.

Another aspect of the present invention pertains to a method for improving allograft survival. The method comprises the steps of: perfusing a kidney harvested from an organ donor with a gutless adenovirus vector carrying a nucleotide sequence encoding a immune modulator and a regulatory element operably linked to the nucleotide sequence; and transplanting the perfused kidney into a subject. In a related embodiment, the immune modulator is indoleamine dioxygenase.

Another aspect of the present invention pertains to a gutless adenovirus vector comprising a polynucleotide encoding a therapeutic protein, a renal tissue specific regulatory element operably linked to the polynucleotide sequence; and a stuffer comprising the nucleotide sequence of SEQ ID NO:13 or SEQ ID NO:15.

Another aspect of the present invention pertains to a gutless adenovirus vector comprising a polynucleotide encoding an indoleamine dioxygenase, a regulatory element operably linked to the polynucleotide sequence; and a stuffer comprising the nucleotide sequence of SEQ ID NO:13 or SEQ ID NO:15.

Yet another aspect of the present invention pertains to a pharmaceutical composition for treating a renal vascular disease, comprising the gutless adenovirus vector described above and a pharmaceutically acceptable carrier.

DETAILED DESCRIPTION

Figure 1:
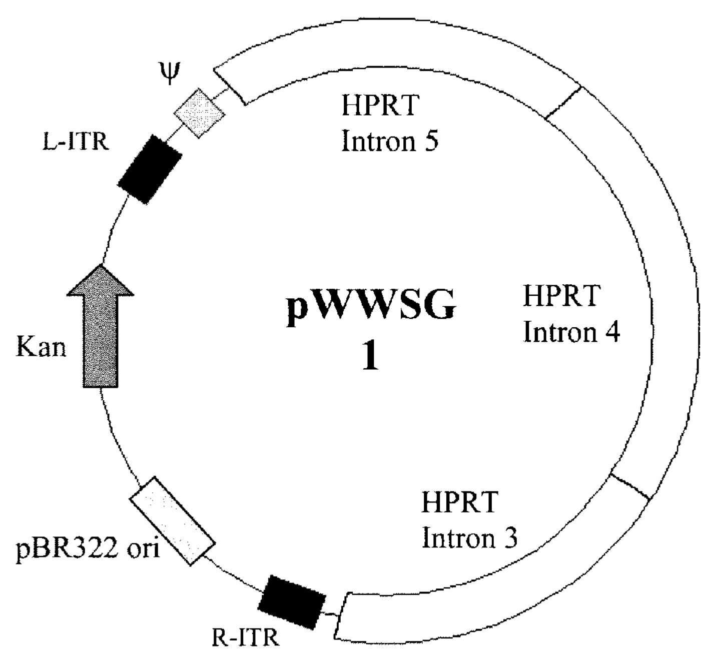
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating renal diseases and improving kidney allograft survival using gene transfer technologies. One aspect of the present invention relates to a method for treating a renal disease by infusing the kidney in vivo with an effective amount of gutless adenovirus vector carrying a DNA sequence encoding a therapeutic agent. The virus-mediated expression of the therapeutic agent in renal tissue ameliorates symptoms of the renal diseases. This local approach eliminates the need to inject a large quantity of virus into a patient and hence significantly reduces the viral-related toxicity.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The Gutless Adenovirus Vector

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The genome of an adenovirus can be manipulated such that it encodes and expresses a gene product of interest but is inactivated in terms of its ability to replicate in a normal lyric viral life cycle (Curie D T, *Ann N Y Acad Sci* 886, 158-171 [1991]). Suitable adenoidal vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells, muscle cells and renal cells Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA).

The so-called "gutless" adenovirus vectors contain a minimal amount of adenovirus DNA (i.e., the inverted terminal repeats and encapsidation signal) and are incapable of expressing any adenovirus antigens (hence the term "gutless"). The gutless adenovirus vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., *J. Virol.* 70:8944-8960 (1996).

The "inverted terminal repeats (ITRs)" of adenovirus are short elements located at the 5' and 3' termini of the linear adenoviral genome, respectively and are required for replication of the viral DNA. The left ITR is located between 1-130 bp in the Ad genome (also referred to as 0-0.5 mu). The right ITR is located from about 3,7500 bp to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward. The "encapsidation signal" or "packaging sequence" of adenovirus refers to the ψ sequence which comprises five (AI-AV) packaging signals and is required for encapsidation of the mature linear genome; the packaging signals are located from about 194 to 358 bp in the Ad genome (about 0.5-1.0 mμ).

In one embodiment, a viral backbone shuttle vector is used for the construction of gutless adenovirus vectors. The viral backbone shuttle vector contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb (SEQ ID NO: 1). In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1. In another embodiment, the viral backbone shuttle vector of the present invention comprises the nucleotide sequence of SEQ ID NO:13 or SEQ ID NO:15.

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may contain coding sequence for a protein, an iRNA agent, or an antisense RNA. The foreign DNA may further contain regulatory elements operably linked to the coding sequence. The term "operably linked," as used herein, refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence. Similarly, intervening untranscribed sequences can be present between an enhancer sequence and the coding sequence and the enhancer sequence can still be considered "operably linked" to the coding sequence.

Examples of regulatory elements include, but are not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human origin.

Renal Specific Expression

In one embodiment, the therapeutic agent is expressed in a tissue-specific manner either using a renal-specific regulatory element or using an inducible regulatory element combined with kidney-specific induction. Examples of renal-specific regulatory element include, but are not limited to, high-capacity (type 2) $Na^+$/glucose cotransporter gene (Sglt2)promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

Examples of inducible regulatory elements include, but are not limited to, regulatory elements that responded to exogenous signals or stresses, such as heat, hormones, hypoxia, cytokines or metal ions, as well as artificial inducible systems such as the tetracycline inducible system, the FK506/rapamycin inducible system, the RU486/mifepristone inducible system, and the ecdysone inducible system. These systems are briefly described below.

Tet-on/off system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

In one embodiment, a kidney tissue is infected with a gutless virus containing an inducible regulatory element. The infected tissue is then exposed to an inducing agent, such as tetracycline or rapamycin, or an inducing condition such as local heating or hypoxia, to induce expression of the therapeutic agent. The inducible system thus allows kidney specific expression of the therapeutic agent and minimizes the side effect of the therapeutic agent. In addition, the level and duration of the therapeutic agent expression may also be controlled by the dose of the inducing agent and the frequency of inducing agent administration. In one embodiment, the coding sequence of the therapeutic agent is controlled by the tet-on system and the expression of the therapeutic agent can be induced by an oral dose of tetracycline.

The Renal Diseases

The renal disease can be any disease or disorder that affects the function of the kidneys and for which a therapeutic gene or genes have been identified. Examples of the renal diseases include, but are not limited to, glomerulonephritis, renal vein thrombosis, diabetic nephropathy, ischemia/reperfusion injury (shock kidneys), hypertension, proteinuric kidney diseases (post glomerulonephritis), ischemic nephropathy, obstruction nephropathy, atheroembolic renal disease, chronic nephritis, congenital nephrotic syndrome, interstitial nephritis, lupus nephritis, membranoproliferative glomerulonephritis, membranous nephropathy, minimal change disease, necrotizing glomerulonephritis, nephropathy—IgA, nephrosis (nephrotic syndrome), post-streptococcal GN, reflux nephropathy, renal artery embolism, renal artery stenosis, and renal underperfusion.

The Therapeutic Agents

The therapeutic agent can be any molecule that is, when expressed in a renal tissue or in the proximity of a renal tissue, capable of ameliorating symptoms of a renal disease. The therapeutic agents include, but are not limited to, proteins, iRNA agents and antisense RNA. The term "expression," as used herein, refers to the process of transcription of mRNA from a coding sequence and/or translation of mRNA into a polypeptide.

The term "iRNA agent," as used herein, refers to small nucleic acid molecules used for RNA interference (RNAi), such as short interfering RNA (siRNA), double-stranded RNA (dsRNA), microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like.

The term "antisense RNA," as used herein, refers to a nucleotide sequence that comprises a sequence substantially complementary to the whole or a part of an mRNA molecule and is capable of binding to the mRNA.

Protein as a Therapeutic Agent

In one embodiment, the therapeutic agent is a protein or peptide capable of ameliorates symptoms of the renal disease. For example, the therapeutic agent can be thrombomodulin for treating renal vein thrombosis (RVT) or an antibody that binds specifically to a target molecule which is involved in a renal disease (e.g., an inflammatory cytokine which has been found to be associated with the chronic kidney disease (CKD)).

The term "antibody", as used herein, is defined as an immunoglobulin that has specific binding sites to combine with an antigen. The term "antibody" is used in the broadest possible sense and may include but is not limited to an antibody, a recombinant antibody, a genetically engineered antibody, a chimeric antibody, a monospecific antibody, a bispecific antibody, a multispecific antibody, a chimeric antibody, a heteroantibody, a monoclonal antibody, a polyclonal antibody, a camelized antibody, a deimmunized antibody, a humanized antibody and an anti-idiotypic antibody. The term "antibody" may also include but is not limited to an antibody fragment such as at least a portion of an intact antibody, for instance, the antigen binding variable region. Examples of antibody fragments include Fv, Fab, Fab', F(ab'), $F(ab')_2$, Fv fragment, diabody, linear antibody, single-chain antibody molecule, multispecific antibody, and/or other antigen binding sequences of an antibody.

Examples of the therapeutic protein include, but are not limited to, thrombomodulin (TM), cytokines such as IL-1, IL-2, IL-3, IL-4, IL-5, IL-6, IL-7, IL-8, IL-9, IL-10, IL-11, IL-12, IL-13, IL-14, IL-15 and other interleukins; hematopoetic growth factors such as erythropoietin; colony stimulating factors such as G-CSF, GM-CSF, M-CSF, SCF and thrombopoietin; growth factors such as BNDF, BMP, GGRP, EGF, FGF, GDNF, GGF, HGF, IGF-1, IGF-2; KGF, myotrophin, NGF, OSM, PDGF, somatotrophin, TGF-$\alpha$, TGF-$\beta$, and VEGF; antiviral cytokines such as interferons, antiviral proteins induced by interferons, TNF-$\alpha$, and TNF-$\beta$; proteins involved in immune responses such as antibodies, CTLA4, hemagglutinin, MHC proteins, VLA-4, and kallikrein-kininogen-kinin system; ligands such as CD4; growth factor receptors including EGFR, PDGFR, FGFR, and NGFR, GTP-binding regulatory proteins, interleukin receptors, ion channel receptors, leukotriene receptor antagonists, lipoprotein receptors, steroid receptors, T-cell receptors, thyroid hormone receptors, TNF receptors; tissue plasminogen activator; transmembrane receptors; transmembrane transporting systems, such as calcium pump, proton pump, Na/Ca exchanger, MRP1, MRP2, P170, LRP, and cMOAT; transferrin; and tumor suppressor gene products such as APC, brca1, brca2, DCC, MCC, MTS1, NF1, NF2, nm23, p53 and Rb, and variants thereof.

A "variants" of a polypeptide is a polypeptide that differs from a native polypeptide in one or more substitutions, deletions, additions and/or insertions, such that the bioactivity of the native polypeptide is not substantially diminished or enhanced. In other words, the bioactivity of a variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the—and/or C-terminal of the mature protein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

A variant preferably exhibits at least about 70%, more preferably at least about 90% and most preferably at least about 95% sequence homology to the original polypeptide.

The term "variant" also includes a polypeptides that is modified from the original polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

In one embodiment, the therapeutic protein is a native TM or a TM variant for the treatment of renal vein thrombosis (RVT). RVT has numerous etiologies, it occurs most commonly in patients with nephrotic syndrome (i.e., >3 g/d protein loss in the urine, hypoalbuminemia, hypercholesterolemia, edema). The syndrome is responsible for a hypercoagulable state. The excessive urinary protein loss is associated with decreased antithrombin III, a relative excess of fibrinogen, and changes in other clotting factors; all lead to a propensity to clot. Numerous studies have demonstrated a direct relationship between nephrotic syndrome and both arterial and venous thromboses. Why the renal vein is susceptible to thrombosis is unclear. The renal vein also may contain thrombus after invasion by renal cell cancer. Other less common causes include renal transplantation, Behçet syndrome, hypercoagulable states, and antiphospholipid antibody syndrome.

Thrombomodulin (TM) is an integral membrane glycoprotein expressed on the surface of endothelial cells (Sadler et al., *Trhomb Haemost.,* 78:392-95 [1997]). It is a high affinity thrombin receptor that converts thrombin into a protein C activator. Activated protein C then functions as an anticoagulant by inactivating two regulatory proteins of the clotting system, namely factors Va and VI [I]a (Esmon et al., *Faseb J.,* 9:946-55 [1995]). The latter two proteins are essential for the function of two of the coagulation proteases, namely factors IXa and Xa. TM thus plays an active role in blood clot formation in vivo and can function as a direct or indirect anticoagulant.

TM and several other proteins or enzymes have been shown to reduce the process of intimal hyperplasia, whose evolution is the causes of late graft failure. For instance, Nitric oxide synthase, an enzyme expressed by endothelial cells has been shown in animal models to inhibit intimal hyperplasia, especially the inducible enzyme (iNOS) (Salmaa et al., *Lancet,* 353:1729-34 [1999]; Palmer et al., *Nature,* 327:524-26 [1987]; Kubes et al., *PNAS USA.,* 88:4651-5 [1991]).

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

siRNA as the Therapeutic Agent

In another embodiment, short interfering RNAs (siRNA) are used as a therapeutic agent to inhibit a disease-related gene expression. For example, elevated levels of transforming growth factor-$\beta_1$ (TGF-$\beta_1$) and platelet-derived growth factor (PDGF) have been associated with the development of glomerular injury. Therefore, inhibition of the expression of TGF-$\beta_1$ and/or PDGF in kidney tissues may be used to prevent or reduce glomerular injury.

siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

siRNAs can be expressed in vivo from adenovirus vectors. This approach can be used to stably express siRNAs in kidney tissues. In one embodiment, siRNA expression vectors are engineered to drive siRNA transcription from polymerase III (pol III) transcription units. Pol III transcription units are suitable for hairpin siRNA expression, since they deploy a short AT rich transcription termination site that leads to the addition of 2 bp overhangs (UU) to hairpin siRNAs—a feature that is helpful for siRNA function. Any 3' dinucleotide overhang, such as UU, can be used for siRNAs. In some cases, G residues in the overhang may be avoided because of the potential for the siRNA to be cleaved by RNase at single-stranded G residues.

With regard to the siRNA sequence itself, it has been found that siRNAs with 30-50% GC content can be more active than those with a higher G/C content in certain cases. Moreover, since a 4-6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database. Any target sequences with more than 16-17 contiguous base pairs of homology to other coding sequences may be eliminated from consideration in certain cases.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., *Proc. Natl. Acad. Sci*. USA 99: 5515-5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., *Nature Biotechnology* 20:500-505, 2002).

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

In another embodiment, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

Route of Administration

The gutless adenovirus may be introduced into the kidney by intravenous, intraarterial, or retrograde infusion. In one embodiment, the virus is infused through the vene renalis. In another embodiment, the virus is infused through the superior mesenteric artery. In yet another embodiment, the virus is infused through a retrograde catheter into the pyelic cavity. Since only a relatively small amount of virus is needed for the kidney infusion, the virus-related toxicity is reduced. In yet another embodiment, the kidney is perfused with the virus, i.e., the virus enters the kidney through the vene renalis or the superior mesenteric artery, and is collected through the superior mesenteric artery or vene renalis. Since the leftover virus does not enter the blood circulation, a large amount of virus may be used for the perfusion. In addition, a close-circuit perfusion allows constant exposure to virus over an extended period of time (e.g., 10-60 minutes) and hence significantly increases the number of infected cells.

In another embodiment, the virus is administered into a segment of a renal blood vessel in vivo. In a related embodiment, the gutless adenovirus vector is administered using a stent. The viral vector is embedded in the stent and is released only at a treatment site. Since the viral infection is restricted at the treatment site and the surrounding area, only a small amount of the virus is needed and the virus-related toxicity is reduced.

Another aspect of the present invention relates to a method for improving allograft survival. The method comprises the steps of perfusing a kidney harvested from an organ donor with a gutless adenovirus vector carrying a nucleotide sequence encoding an immune modulator and a regulatory element operably linked to the nucleotide sequence; and transplanting the perfused kidney into a subject. The term “immune modulator,” as used herein, refers to a polypeptide or a polynucleotide capable of modulating an immune response and improving allograft survival.

In one embodiment, the immune modulator is indoleamine dioxygenase (IDO). IDO is an enzyme that is expressed in the placenta and plays an important role in foeto-maternal tolerance. IDO metabolizes the amino acid tryptophan. The function of T cells, the most important cell-type involved in organ transplant rejection, is dependent on tryptophan. In addition, the metabolites of tryptophan (kynurenines) are toxic to T-cells. It has been shown that over-expression of IDO in renal tissues protects against renal transplant damage.

Typically, kidneys must be preserved prior to transplantation to obtain proper pathology assessment of the suitability of the organ for transplantation. Lack of proper preservation leads to degradation of organ function due to thrombosis (blood clotting), ischemia (lack of oxygen), or ischemia followed by reperfusion (the restoration of blood flow upon transplantation). These events bring about inflammation, cell death, and eventually failure of the organ. Kidney preservation is a process in which the renal artery is connected to a kidney perfusion machine in order to simulate the normal process by which nutrients are supplied to the kidney. A solution is continuously perfused through a closed circuit which includes the kidney, which is typically maintained at a low temperature (e.g., 5° C.) to reduce the cell metabolic rate and oxygen consumption. During the perfusion process, the perfusion pressure, flow, and vascular resistance, as well as the organ’s chemistries, including base excess, oxygen saturation, calcium, potassium, hematocrit, $pO_2$, pH, and bicarbonate, are monitored closely to prevent tissue damage. The adenovirus vectors can be added to the perfusion solution and infect the kidney tissue during the perfusion period. Kidney perfusion solutions are commercially available. In one embodiment, the kidney perfusion solution is Lactated Ringer’s solution.

In one embodiment, the regulatory element is a constitutive promoter, such as CMV or RSV promoter. In another embodiment, the gutless adenovirus contains the nucleotide sequence of SEQ ID NO:25 or SEQ ID NO:26.

In another embodiment, the gutless adenovirus is suspended in the perfusion solution to a final concentration of $10^9$-$10^{12}$ particles/ml and perfused for a period of 10-120 minutes.

Another aspect of the present invention pertains to a gutless adenovirus vector comprising a polynucleotide encoding a therapeutic agent, a renal-specific regulatory element or inducible regulatory element operably linked to the polynucleotide sequence; and a stuffer comprising the nucleotide sequence of SEQ ID NO:13 or SEQ ID NO:15.

In one embodiment, the renal-specific regulatory element is selected from the group consisting of high-capacity (type 2) $Na^+$/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

In another embodiment, the inducible regulatory element is selected from the group consisting of heat inducible regulatory elements, hormone inducible regulatory elements, hypoxia inducible regulatory elements, cytokine inducible regulatory elements, metal ion inducible regulatory elements, and artificial inducible regulatory elements.

Yet another aspect of the present invention pertains to a pharmaceutical composition for treating a renal vascular disease, comprising the gutless adenovirus vector described above and a pharmaceutically acceptable carrier. As used herein, a "pharmaceutically acceptable carrier" is intended to include any and all solvents, solubilizers, stabilizers, absorbents, bases, buffering agents, controlled release vehicles, diluents, emulsifying agents, humectants, dispersion media, antibacterial or antifungal agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The pharmaceutical composition is formulated to be compatible with its intended route of administration. Solutions or suspensions used for parenteral application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In all cases, the injectable composition should be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

It is especially advantageous to formulate parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The present invention is further illustrated by the following examples which should not be construed as limiting. The contents of all references, patents and published patent applications cited throughout this application, as well as the Figures and Tables are incorporated herein by reference.

EXAMPLE 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At by 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at bp 3667 and there was also an EcoRI site inside the MCS at bp 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 bp fragment that was cloned into the EcoRI/XbaI digested viral backbone. Then the HPRT source was digested with only XbaI yielding a 2715 bp fragment. One of the XbaI sites in this cut is the same XbaI site that was cut from the EcoRI/XbaI double digest in step 1. The viral backbone was cut with only XbaI and the 2715 bp fragment was inserted.

Overall, from the HPRT source, the HPRT stuffer sequence is inserted into the viral backbone in reverse orientation, hence intron 5, then 4, then 3. The 2715 bp fragment was inserted and checked to follow the original source sequence. The new plasmid is designated as pShuttle-ITR-HPRT (SEQ ID NO:1).

EXAMPLE 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)-1 Creation of pCMV-hTM The insertion of hTM into the gutless adenovirus backbone first required the creation of a CMV-hTM expression cassette. The intermediate vector used was pcDNA3.1/Zeo(+) (Invitrogen). A CMV promoter is available commercially and a CMV promoter was cloned into the multiple cloning sites (MCS) at the XbaI/EcoRV restriction enzyme site locations. The CMV from ps5 was removed using XbaI/EcoRV. pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo (+) plasmid. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]). The human TM cDNA (SEQ ID NO:5) was obtained from Dr. Sadler (Dittman et al., *Biochemistry,* 26(14):4350-4357 [1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)-2 Creation of pShuttle-ITR-HPRT-CMV-TM

The expression cassette in pCMV-hTM was removed by digesting with PmeI. The gutless adenovirus backbone pshuttle-ITR-HPRT was linearized using SmaI which cuts the plasmid at bp 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)-3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                        (SEQ ID NO: 8)
5'-gtaacactgg cccaggaggc ctttctggtg acccc-3'

                                        (SEQ ID NO: 9)
3'-tgacc gggtcctccg gaaagaccac tggggatt-5'
```

Creation of pTMadap-Stuffer1

Based on the published sequence HSU71148 of the human X chromosome region q28 the following PCR primers were synthesized:

```
Forward:
                                   (SEQ ID NO: 10)
5' TAGTTCCTTCTGCCTGGAATAC 3'

Reverse:
                                   (SEQ ID NO: 11)
5' CAAGTCACAAGGATGGACTACA 3'
```

Amplification of a human DNA sample resulted in the amplification of a 18524 bp DNA fragment (stuffer 1, SEQ ID NO: 12). Stuffer 1 was cut with the restriction enzymes BstEII and SfiI and the resulting fragment of approximately 18371 bp was inserted into the BsteII and SfiI sites of pTMadap, resulting in pTMadap-stuffer1.

2(a)-4 Creation of pTMadap-Stuffer1-Short

To reduce the size of the stuffer1 fragment in pTMadap-stuffer1, pTMadap-stuffer1 was digested with SanDI and BstEII and the resulting DNA ends were modified by a fill-in reaction with Klenow. Re-ligation resulted in the 25207 bp vector pTMadap-stuffer1-short. The sequence of stuffer1-short fragment is shown in SEQ ID NO:13.

2(a)-5 Creation of pTMadap-Stuffer1-Short-Stuffer2

The plasmid p2-2 (SEQ ID NO: 14, obtained from GenBank) was cut with NotI and the resulting fragment of approximately 5954 bp (stuffer 2, SEQ ID NO: 15) was inserted into the NotI site of pTMadap-stuffer1short, resulting in pTMadap-stuffer1-short-stuffer2.

2(a)-6 Removal of PacI Site from pTMadap-Stuffer1Short-Stuffer2

Figure 2:
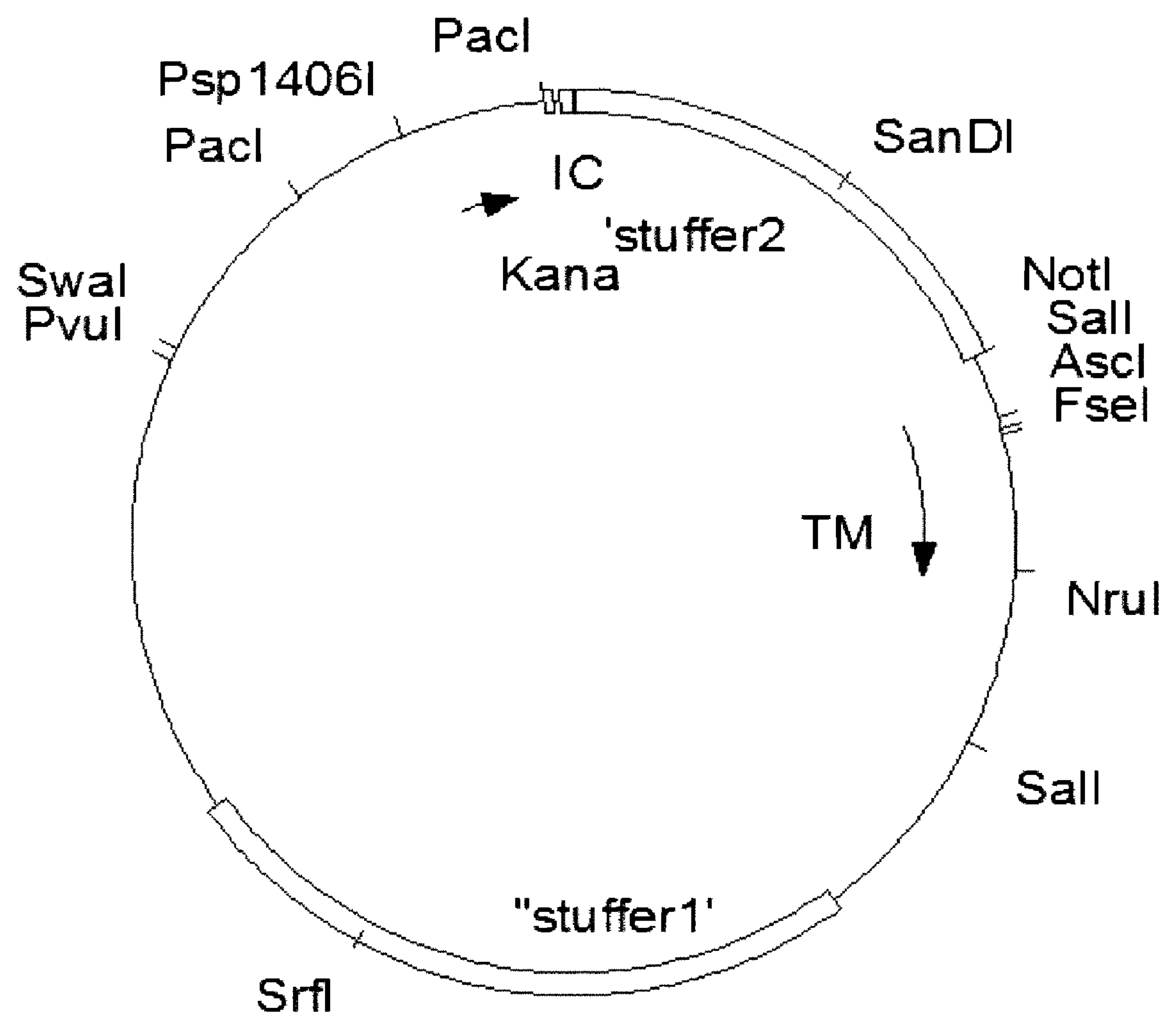
FIG. 2 is a schematic drawing of an embodiment of the full length backbone vector pTM-final.

Plasmid pTMadap-stuffer1-short-stuffer2 was cut with AclI and BsiW1. The resulting 28790 bp fragment was isolated from gel. pShuttle-ITR-HPRT (SEQ ID NO:1) was cut with AclI and Acc65I. The resulting 1966 bp fragment was ligated into the isolated 28790 bp fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette. pcDNA3.1/Zeo (+) was again used. First, a portion of the vector from the end of the MCS, restriction enzyme site Apal, to the beginning of the SV40 poly A, restriction site Nael, was removed and the vector relegated to itself. Then the LacZ gene was inserted into the vector MCS using NotI/XbaI. The expression cassette, containing CMV promoter, LacZ gene, and SV40 poly A, was removed using Nrul/Sall retraction enzymes and blunt-end cloned into the gutless adenovirus at the Smal restriction enzyme site.

EXAMPLE 3

Preparation of Gutless Adenovirus Carrying Human Thrombomodulin Gene (Gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 μg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy,* 3(5):809-815 [2001]; Umana et al., *Nature Biotechnology,* 19:582-585 [2001]

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernatant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500 ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETOH. Cotton swabs (one swab for each tube) were used to completely dry out the tube, and two tubes were used per sample.

14. Preparation of the first gradient: 2.5 mL CsCl-Density 1.25, and 2.5 mL CsCl-Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/ml. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris-pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5 10, and 15 μg/ml. (BSA is fine). Sample cuvettes were prepared using 1-10 μl of sample, depending on estimate of titer. (Sample OD must be within the linear range of the standard line.) OD was taken at 595λ and formula of the line was calculated from standards. The protein concentration of the samples was calculated using this formula. The following formula was used to convert protein concentration to titer: $[12.956+224.15\ (\mu g/ml)]\times 10^8$.

EXAMPLE 4

Figure 3:
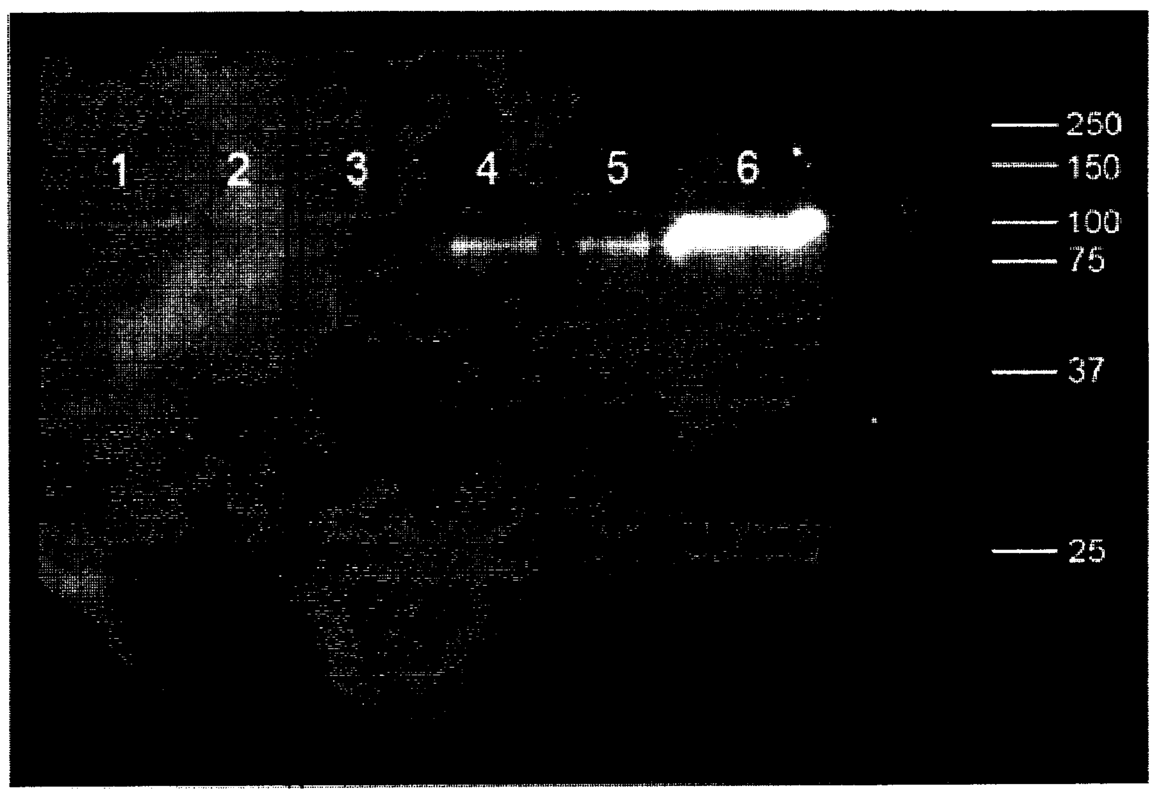
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

Expression of Human Thrombomodulin (hTM) In Vitro (A) Expression of hTM in HEK 293 Cells Transfected with pTM-Final HEK 293 cells were cultured in a 6 well cluster and transfected with 1 μg of pTM-final. After 24 hours, the cells were washed with PBS and lysed in 125 μl RIPA buffer with protease inhibitors Protein samples (16 μl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 μl Igepal ca-630, 50 mg sodium deoxycholate, 500 μl 20% SDS, 10 mM β-mercapto ethanol, and 1 ml 10×PBS, and add water to a final volume of 10 ml at room temperature. A cocktail of protease inhibitors containing 11.5 μl PMSF (from 34.8 mg/ml in isopropanol, 64 μl Benzamidine (from 15.6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(B) Expression of hTM in P2 Lysate of 293FLP Cells

Figure 4:
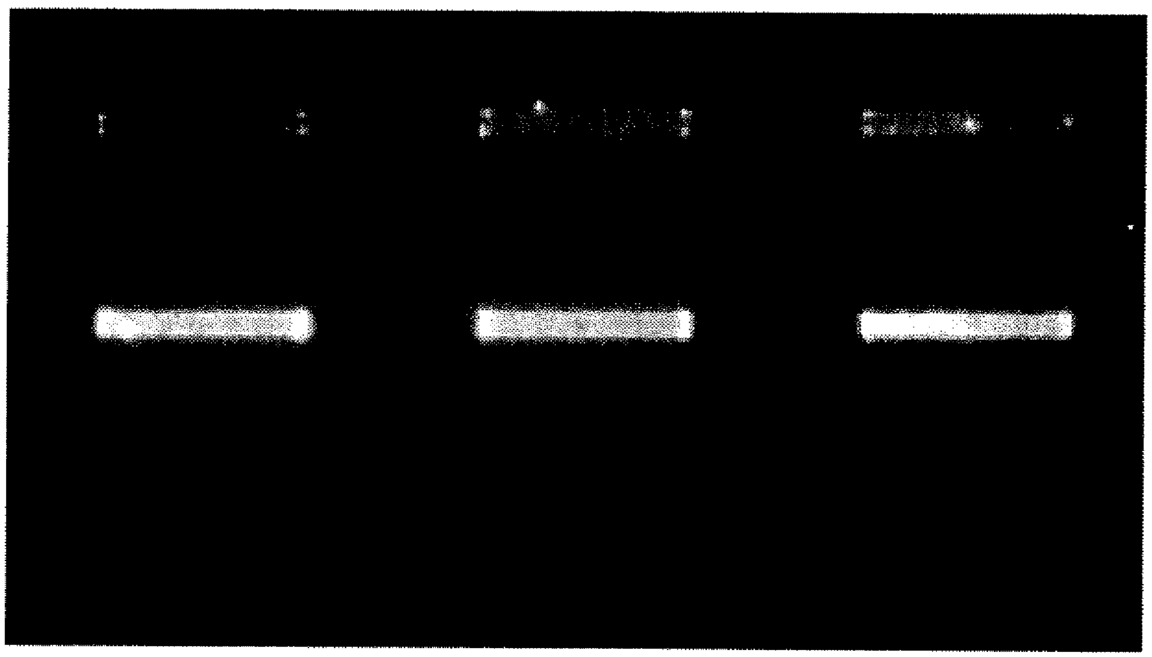
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 250 μl RIPA buffer. 7 ul of 5× loading buffer was added to 35 μl of the lysed cells and the resulting solution was immersed in boiling water for 3 minutes. 5 and 30 ul of boiled cell lysate were diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenolblue. The RIPA buffer was prepared as described in Example 4(A). A cocktail of protease inhibitors containing 11, 5 μl PMSF (from 34, 8 mg/ml in isopropanol, 64 μl Benzamidine (from 15, 6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
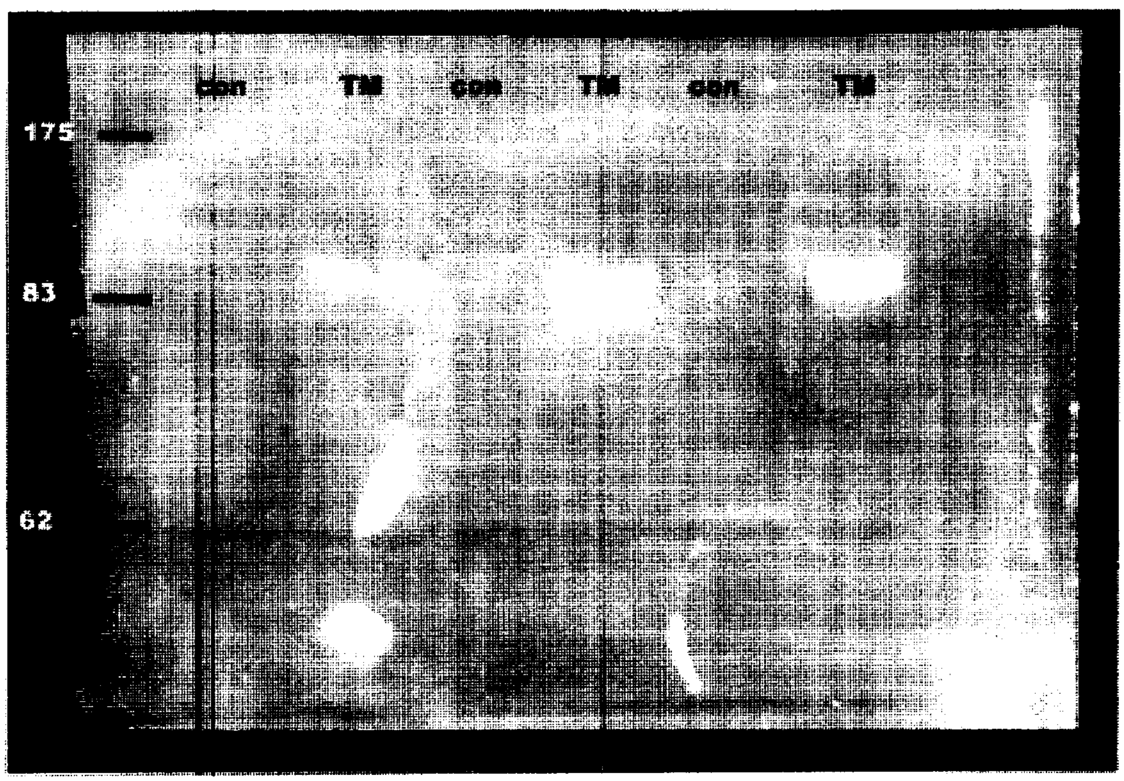
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM Expression in HEK 293 Cells Infected with TM Gutless Virus Passage 1-6

The TM-vector backbone was released by digestion with PacI. 293CRE cells were cultured in a 60 mm dish at 80% confluency. Cells were transfected with 5 μg of PacI digested TM-vector backbone. After 24 hours, 2% DMEM-F12 containing helper virus with a MOI of 10 was added. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=1. This procedure was repeated until P=6.

Figure 6:
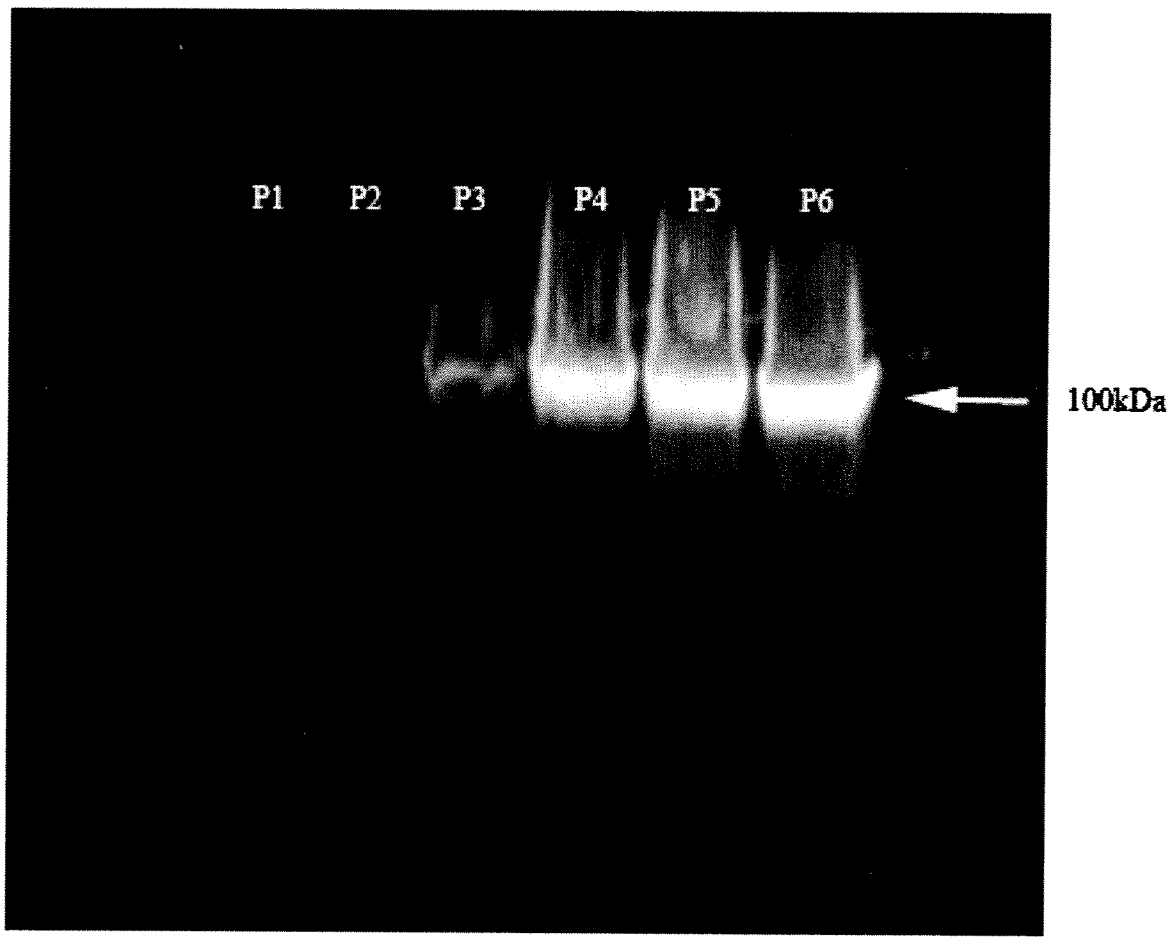
FIG. 6 is a picture of a Western bolt showing TM expression in CRE cells at passage number 1-6 (P1-P6).
Figure 7A:
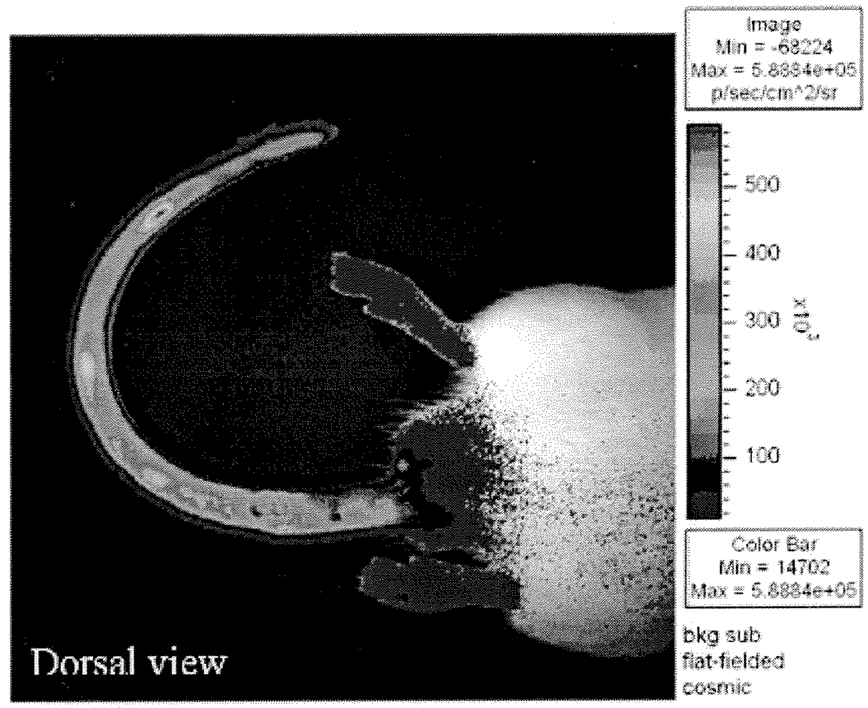
FIGS. 7A-7C is a composite of images showing gutless adenovirus-mediated luciferase expression in rat tail vein.
Figure 7A:
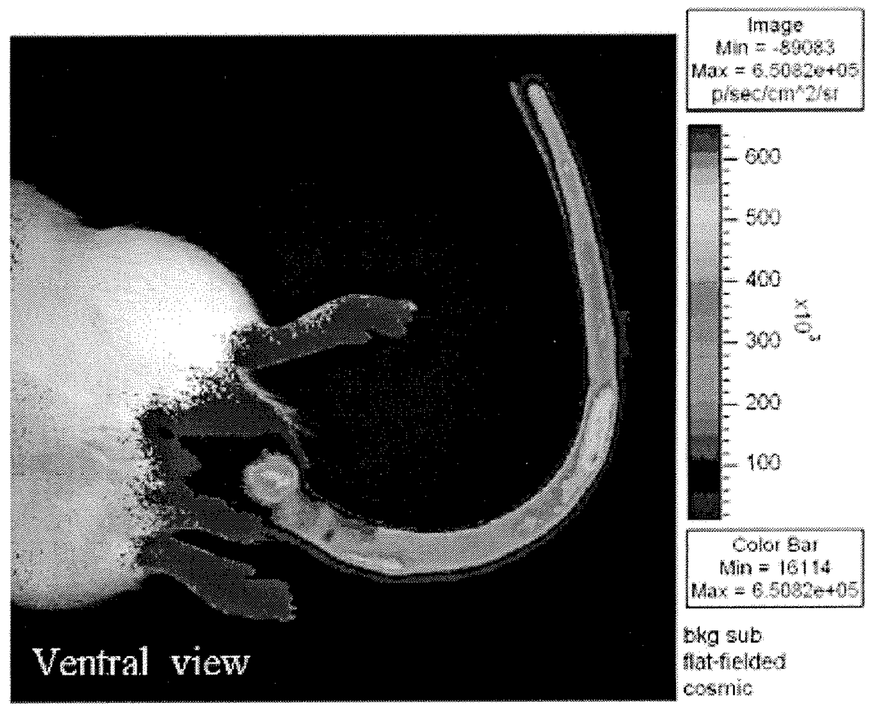
Figure 7B:
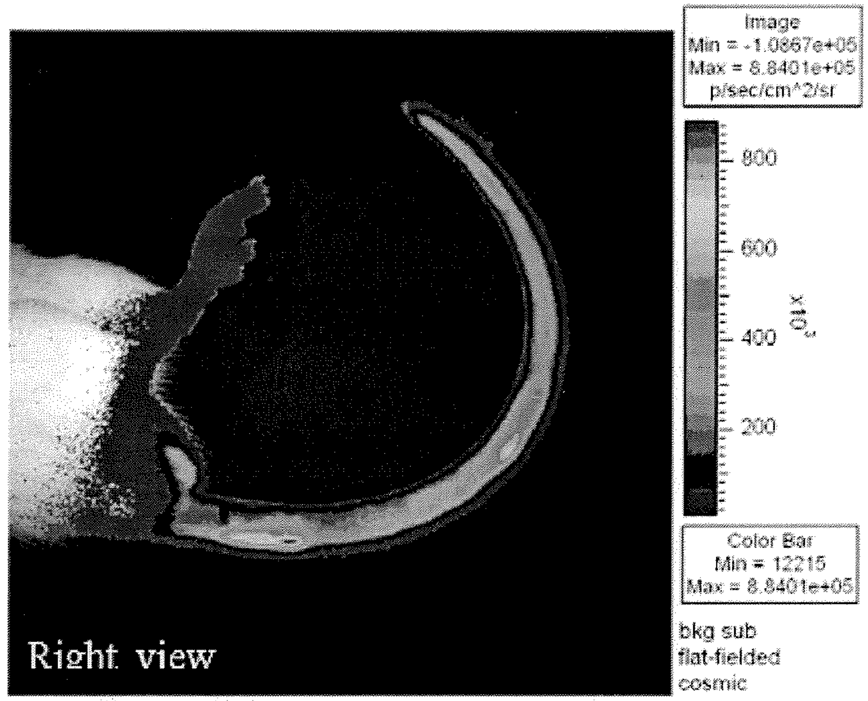
Figure 7B:
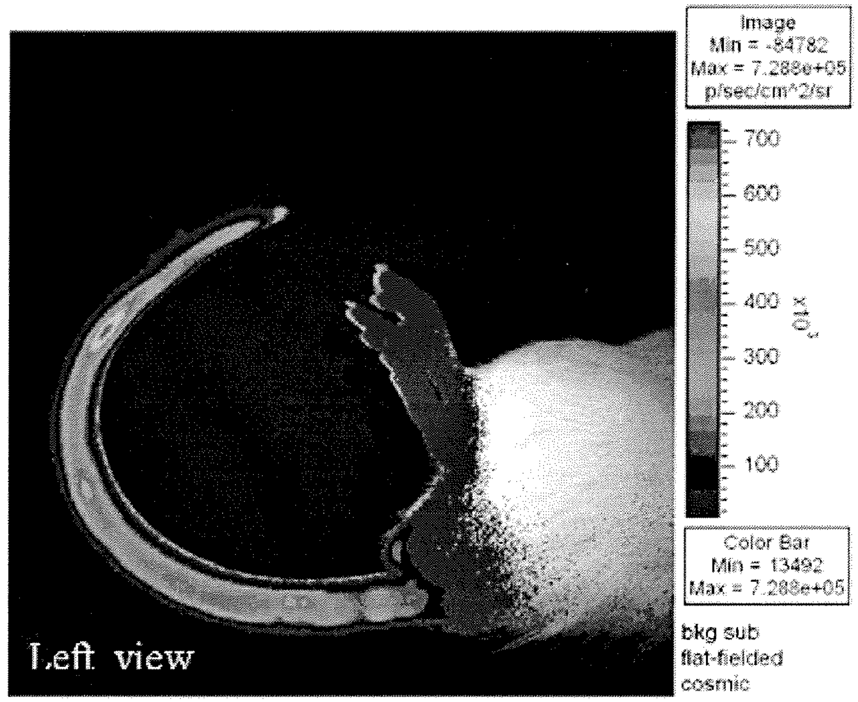
Figure 7C:
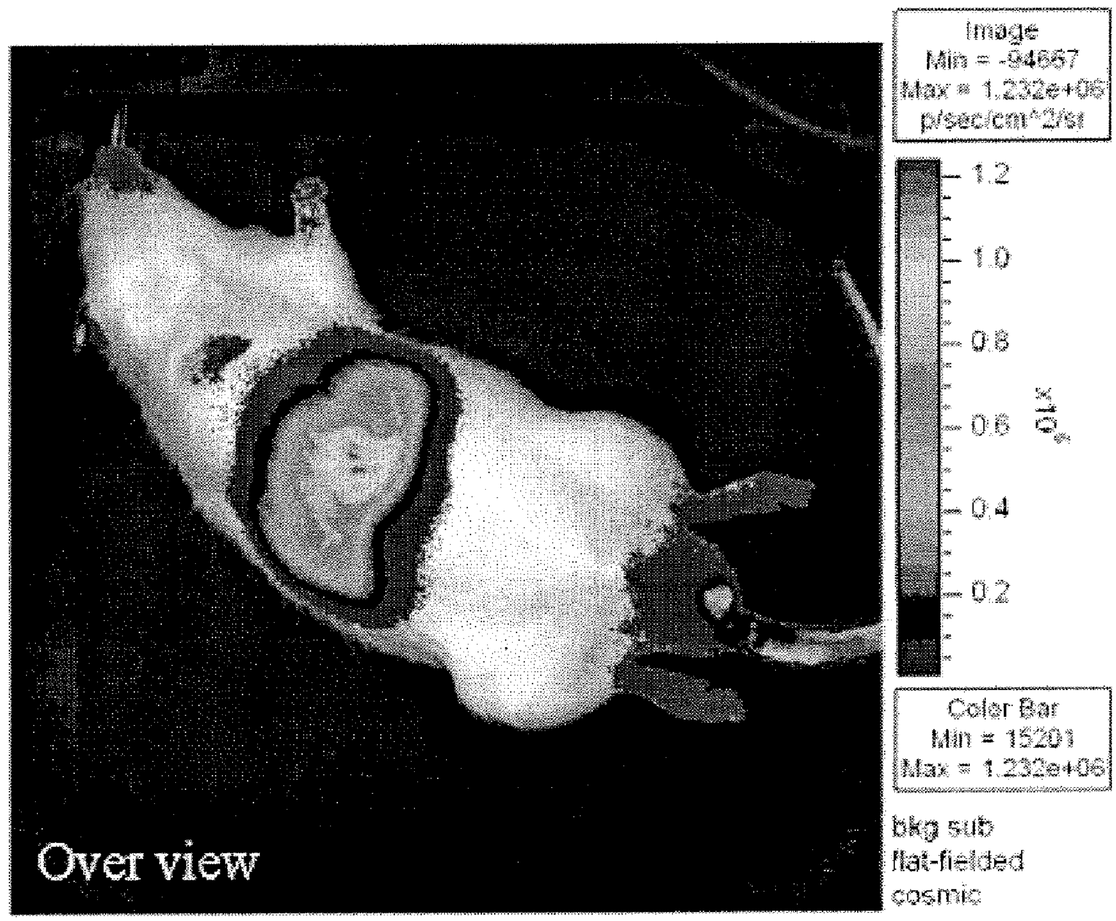

HEK 293 cells were cultured in a 6 well cluster and transfected with 200 μl of TM gutless virus of passage 1-6. After 24 hours, the cells were washed with PBS and lysed in 125 μl RIPA buffer. Protein samples (16 μl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins. As shown in FIG. 6, TM expression is higher in cells infected with virus of higher passage numbers, indicating successful amplification of TM gutless virus in 293CRE cells.

The RIPA buffer (10 ml) was prepared as follows: 100 μl Igepal ca-630, 50 mg sodium deoxycholate, 500 μl 20% SDS, 10 mM β-mercapto ethanol, 1 ml 10×PBS, add water to make up 10 ml. Immediately before use, the following protease inhibitors were added to the RIPA buffer: 115 μl PMSF (from 34.8 mg/ml in isopropanol), 64 μl Benzamidine (from 15.6 mg/ml stock), 100 μl sodium orthovanadate (100 mM), 5 μl pepstatin (from 1 mg/ml stock), 1 μl leupeptin (from 5 mg/ml stock), 1 μl aprotin (from 5 mg/ml stock).

EXAMPLE 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Expression of TM by Intravenous Infusion of Viral Vectors

Material and Methods

Infection with gutless TM virus: 3 male Wistar rats weighing approximately 300 grams were intravenously injected in the tail vein with a low dose of gutless TM virus (approximately $2\times10^{10}$ viral particles) in a total volume of 500 ul of sucrose buffer. After three weeks, the animals were sacrificed and liver tissue and blood plasma was collected and immediately frozen in liquid nitrogen.

TM expression in the liver was determined by western blotting. Approximately 500 mg of liver tissue was homogenized in 2 ml of RIPA buffer. Liver protein samples (20 μg) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins.

Detection of rat Anti-TM antibodies in the plasma of TM infected rats: HEK 293 cells were cultured in a 6 well cluster. 3 wells were infected with 100 μl of TM gutless virus (approximately $4\times10^{9}$ virus particles) and 3 wells received no virus. After 24 hours, non-infected and TM infected cells were washed with PBS and lysed in 125 μl RIPA buffer. Protein samples (16 μl) were separated on a 7.5% polyacrylamide/SDS gel and transferred to nitrocellulose membrane. Blots containing protein from both TM expressing cells and non-infected cells were incubated with primary antibody TM (c-17) (1:2000, Santa Cruz) or plasma from TM infected rats (1:20, 1:100 and 1:1000 dilution). Detection of primary antibodies was performed using Polyclonal Rabbit Anti-Goat Immunoglobulins/HRP (1:4000, DakoCytomation) and Polyclonal Rabbit Anti-Rat Immunoglobulins/HRP (1:4000, DakoCytomation), respectively. RIPA buffer was prepared as described in Example 4.

Figure 8:
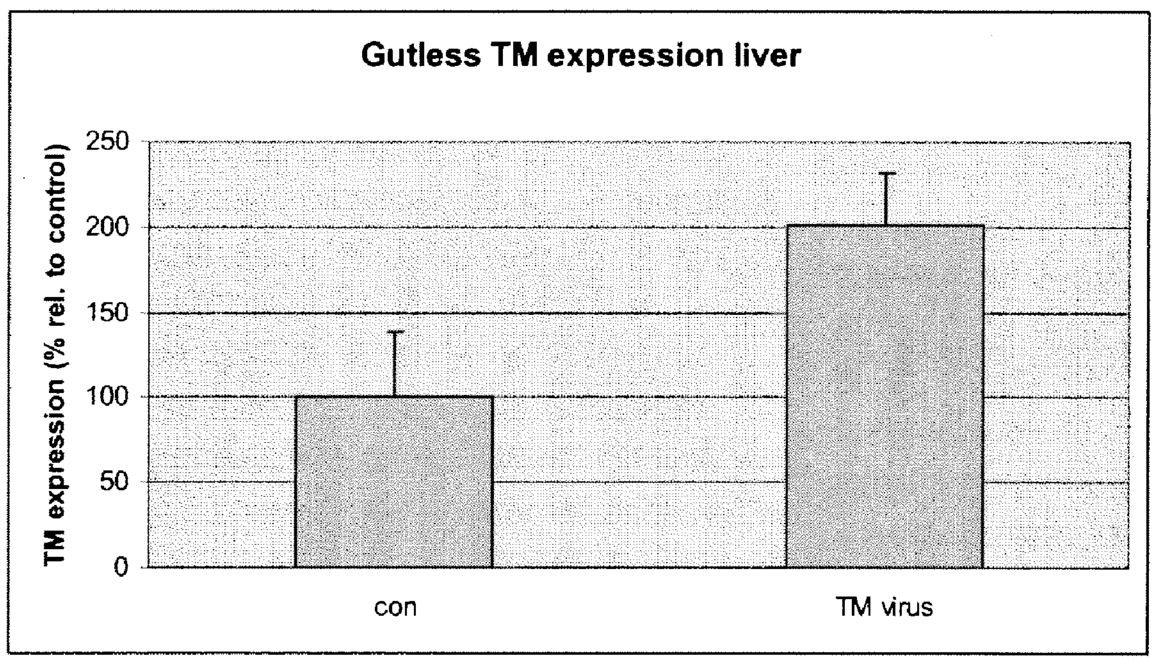
FIG. 8 is a diagram showing TM expression in livers of non-infected rats (con) and TM gutless virus infected rats (TM virus).

TM expression in the liver: No adverse effects of the injection of gutless TM virus could be detected. Animals displayed normal growth characteristics and did not suffer from excessive bleeding. Three weeks after injection, animals were sacrificed and no internal bleeding could be detected. Liver TM expression was evaluated using western-blot. TM expression was elevated two-fold above background levels, indicating modest over-expression of TM gutless virus in the liver three weeks after infection (FIG. 8).

Figure 9:
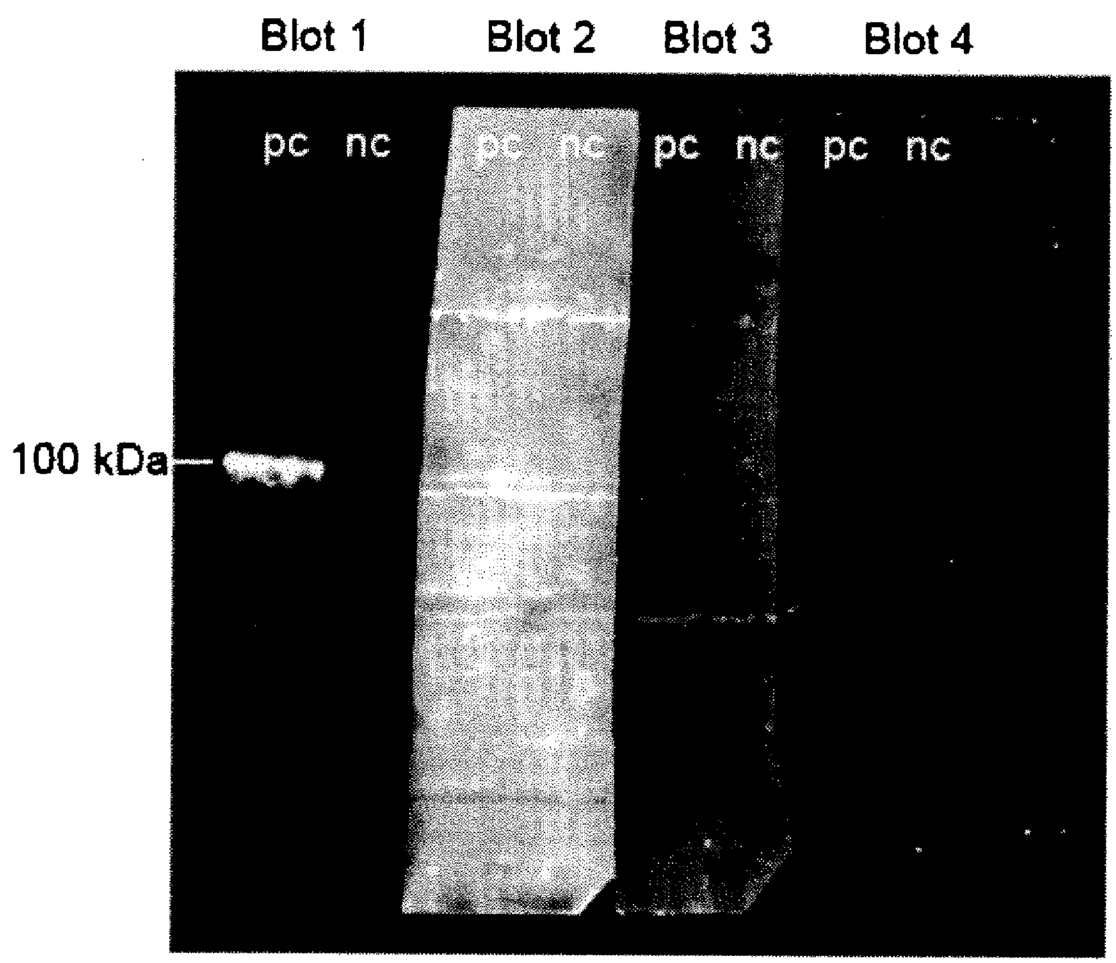
FIG. 9 is a picture of Western blots using a anti-TM antibody (blot 1) and plasma from animals infected with TM virus (blots 2-4).

To detect TM antibodies in the plasma of rats infected with the gutless TM virus, four western blots were made. Each blot contains a protein sample from human cells expressing TM (positive control) and a sample from the same cells that do not produce TM (negative control). Blot 1 was probed with a commercial antibody against TM (FIG. 9, blot 1), indicating the presence of human TM only in the positive control lane. Blots 2, 3 and 4 were probed with plasma from animals infected with TM virus in the dilution 1:20, 1:100 and 1:1000, respectively. Although some immunoreactivity is observed, the plasma of rats did not lead to the specific detection of TM in the positive control lane. Therefore, the plasma of these rats do not contain detectable levels of rat IgG antibodies against human TM.

Conclusion: Intravenous administration of low dose gutless TM virus into rat tail vein resulted in modest expression of TM in the liver of the recipient rats three weeks after injection. The viral injection did not result in the production of IgG antibodies against TM.

EXAMPLE 9

Adenovirus-Mediated In Vivo Gene Transfer To Vena Cava

Inbred male Brown Norway rats (BN/rijHsd, Harlan, Netherlands) with an age of 11 weeks were used. Animals were housed in a light and temperature controlled environment and fed standard rodent chow and water ad libitum. Rats were anaesthetized with isoflurane (3% in $O_2$). The vene cava with the branches was exposed by a mid-line incision. The vene cava was clamped just below the vene renalis of the left kidney. All accessible sidebranches of the vena cava in the region between the vena renalis and the bifurcation were also clamped. The virus particles were administered through an insulin syringe (29-gauge needle) with a volume of 290 ul containing $2\times10^{11}$ virus particles. After injection of the viral solution, the syringe with needle was not removed from the vena cava but remained in place during the following incubation period of 20 minutes. Subsequently, the clamps on the sidebranches of the vene cava were removed. The transfected segment of vena cava was washed by making a puncture with a needle 25-gauge needle just below the clamp near the vena renalis. The expelled blood containing excess virus was absorbed with a cotton bud. After bleeding a volume of approximately 0.5 ml, the bleeding was stopped by applying a pressure on the puncture site with a cottonswab. Subsequently, the clamp near the vene renalis was released and the abdomen was sutured. For post-operative pain relief, the rats received buprenorphin (Temgesic®) 10 μg/kg subcutaneously. The rats were allowed to recover with access to water and food ad libitum.

Two days after the transfection procedure, rats were anaesthetized with isoflurane (3% in $O_2$). The vene cava was exposed by a mid-line incision and clamped just below the vena renalis of the left kidney. The abdomen was temporarily closed during the incubation time of 2 hours. Subsequently, the abdomen was reopened and blood was collected from the aorta. The vena cava was harvested from the bifurcation till above the clamp. The vene cava was opened longitudinally and the thrombus was removed and placed in saline for size evaluation. The results of the experiment were summarized in Table I.

TABLE I

Vena cava thrombus in the experimental animals

| Group | Thrombus size in individual animals |
|---|---|
| sucrose | 1623.98 |
| | 1507.23 |
| | 239.84 |
| | 398.25 |
| | 107.97 |
| | 32.24 |
| | 85.40 |
| gfp virus | 97.00 |
| | 107.13 |
| | 158.93 |
| | 0.00 |
| | 89.04 |
| | 87.63 |
| | 1281.56 |
| | 137.13 |
| TM virus | 0.00 |
| | 280.04 |
| | 0.00 |
| | 0.00 |
| | 140.21 |
| | 60.65 |
| | 0.00 |
| | 108.69 |

EXAMPLE 10

Adenovirus-Mediated Gene Transfer to Kidney Via Intravenous Infusion

This example describes the procedure for slowly infusing a recombinant adenovirus into the renal circulation. Male Sprague-Dawley rats (100-150 g) were injected intramuscularly with 20,000 units of penicillin, anesthetized with ketamine (70 mg/kg, ip) and xylazine (7 mg/kg, ip) and underwent surgical exposure of the right kidney, the aorta and the right renal blood vessels. The right renal blood flow was interrupted by clamping the aorta above and below the right renal artery and the superior mesenteric artery (SMA). This setting selectively excluded the right kidney without interrupting the blood circulation through the left kidney and allowed infusion of vines into the right kidney through the SMA. A 27-gauge winged infusion needle was inserted into the SMA and fixed in place with a microaneurism clamp. 1.5 ml of recombinant adenovirus in phosphate buffered saline (PBS) containing 5 units of heparin/ml were slowly infused into the right kidney with a Razel A-99 syringe pump at a flow rate of 0.1 ml/min. The right kidney was packed with ice during the infusion to minimize ischemic damage. Renal circulation was reestablished at the end of infusion. The abdominal cavity was closed with sutures. The animal was placed on a warm pad to recover from the anesthesia and was returned to its cage after recovery.

EXAMPLE 11

Adenovirus-Mediated Gene Transfer to Kidney Via Balloon Catheter

In this application, a catheter is inserted in a vein near or in the kidney. Both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 12

In Vivo Treatment with Virus Containing Stent

In this application, a virus-coated stent is placed at a treatment site in or near the kidney. Alternatively, the virus may be embedded in the stent and is releases gradually through a time-releasing mechanism well-known to one skilled in the art.

EXAMPLE 13

Construction of Gutless Adenovirus Vectors Carrying the IDO Gene

Rat and human IDO cDNA were amplified by RT-PCR using the following set of primers:

```
Forward primer (containing a FseI
restriction site):
                                    (SEQ ID NO: 17)
5'-TATTTATTGGCCGGCCGCGTTAAGATACATTGATGAG-3'

Reverse primer (containing a SbfI
restriction site):
                                    (SEQ ID NO: 18)
5'-TATTTATTCCTGCAGGTCGTAGGTCAAGGTAGTAGA-3'.
```

The amplified rat IDO cDNA (SEQ ID NO:19) and human IDO cDNA (SEQ ID NO:20) were cloned into expression plasmids pAdTrackCMV-rIDO and pAdTrackCMV-hIDO, respectively.

Expression cassettes comprising a CMV promoter, IDO cDNA and poly-adenylation signal were constructed using PCR. PCR primers were equipped with additional restriction enzyme sites to facilitate cloning into the gutless backbone vector.

```
Forward primer (containing a FseI
restriction site):
                                    (SEQ ID NO: 17)
tatttattggccggccCGCGTTAAGATACATTGATGAG

Reverse primer (containing a SbfI
restriction site):
                                    (SEQ ID NO: 18)
tatttattcctgcaggTCGTAGGTCAAGGTAGTAGA
```

Figure 10:
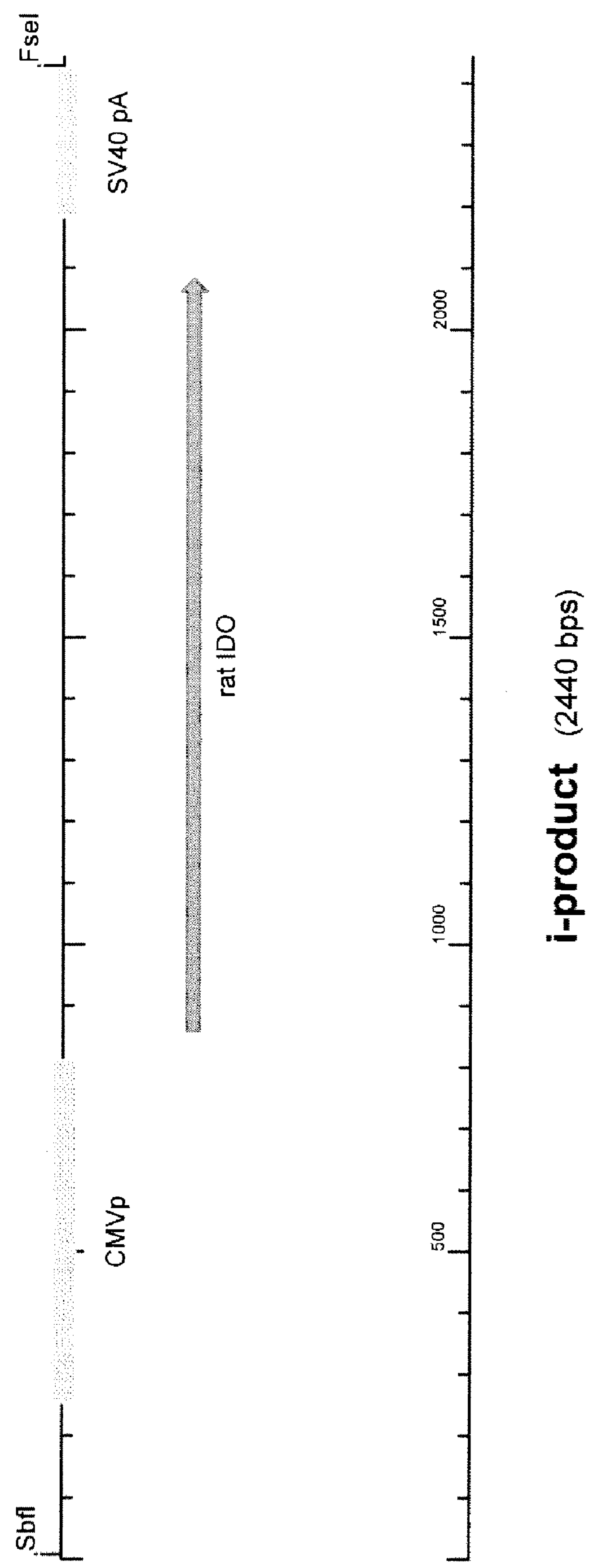
FIG. 10 is a schematic drawing of an embodiment of the rat IDO expression cassette.
Figure 11:
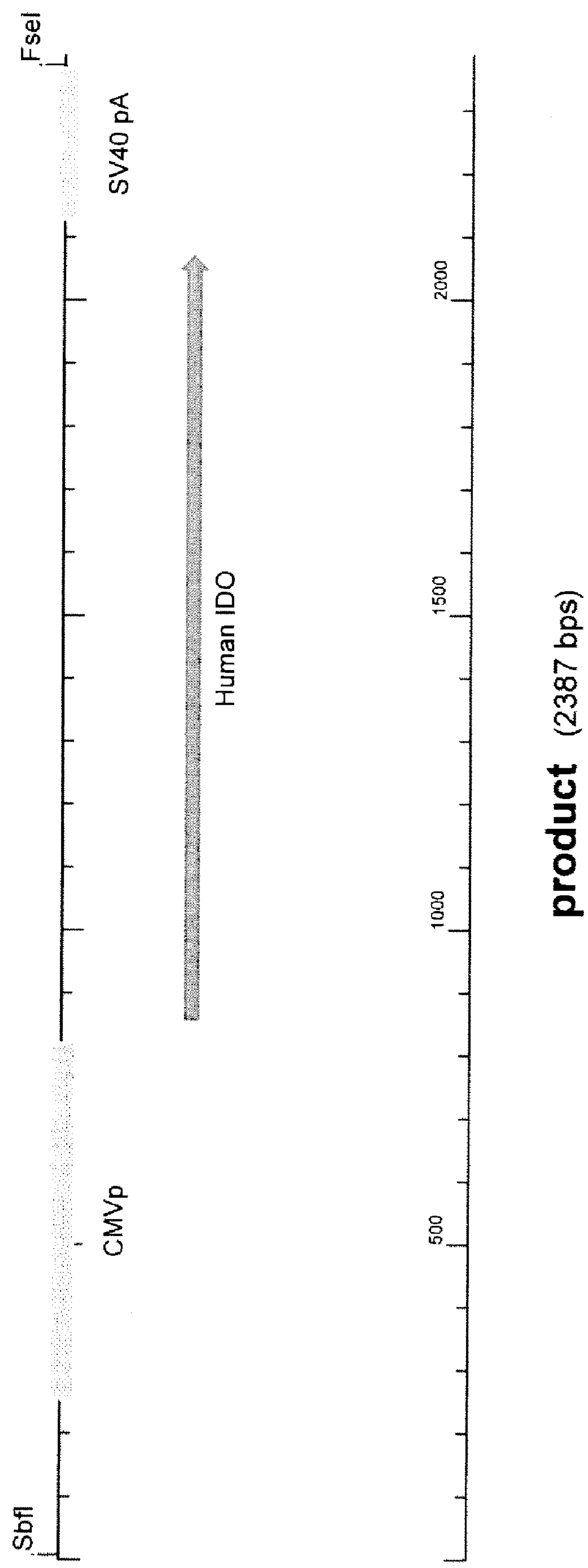
FIG. 11 is a schematic drawing of an embodiment of the human IDO expression cassette.

The resulting PCR fragments were cloned into pGEM-T-EASY for sequencing and cloning. Sequencing confirmed the presence of rat IDO expression cassette (FIG. 10, SEQ ID NO:21) and human IDO expression cassette (FIG. 11, SEQ ID NO:22).

Figure 12:
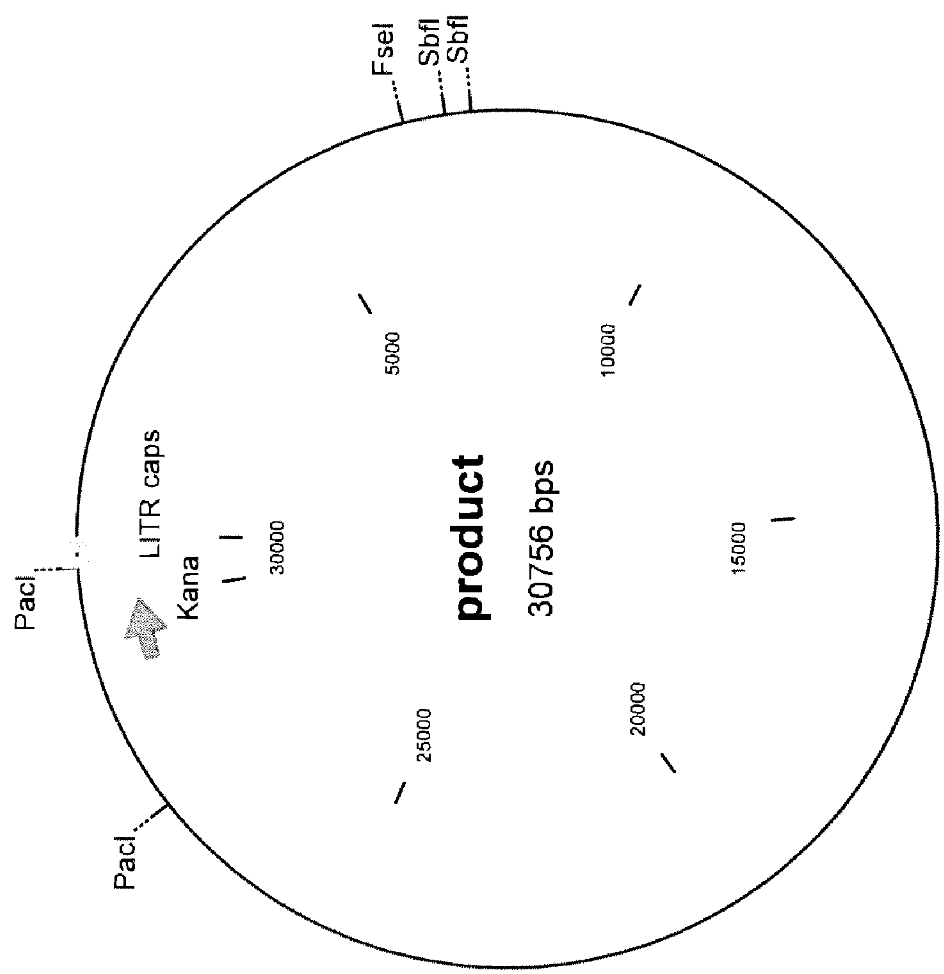
FIG. 12 is a schematic drawing of a gutless backbone vector.
Figure 13:
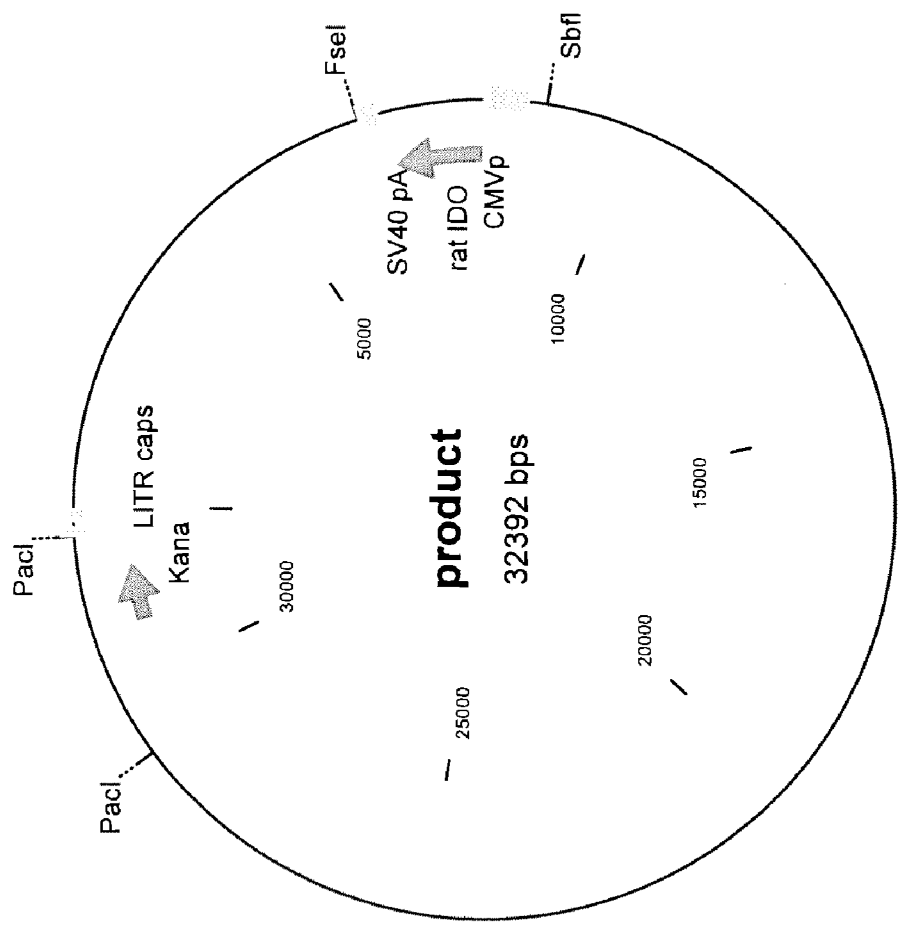
FIG. 13 is a schematic drawing of an embodiment of the rat gutless IDO backbone vector.
Figure 14:
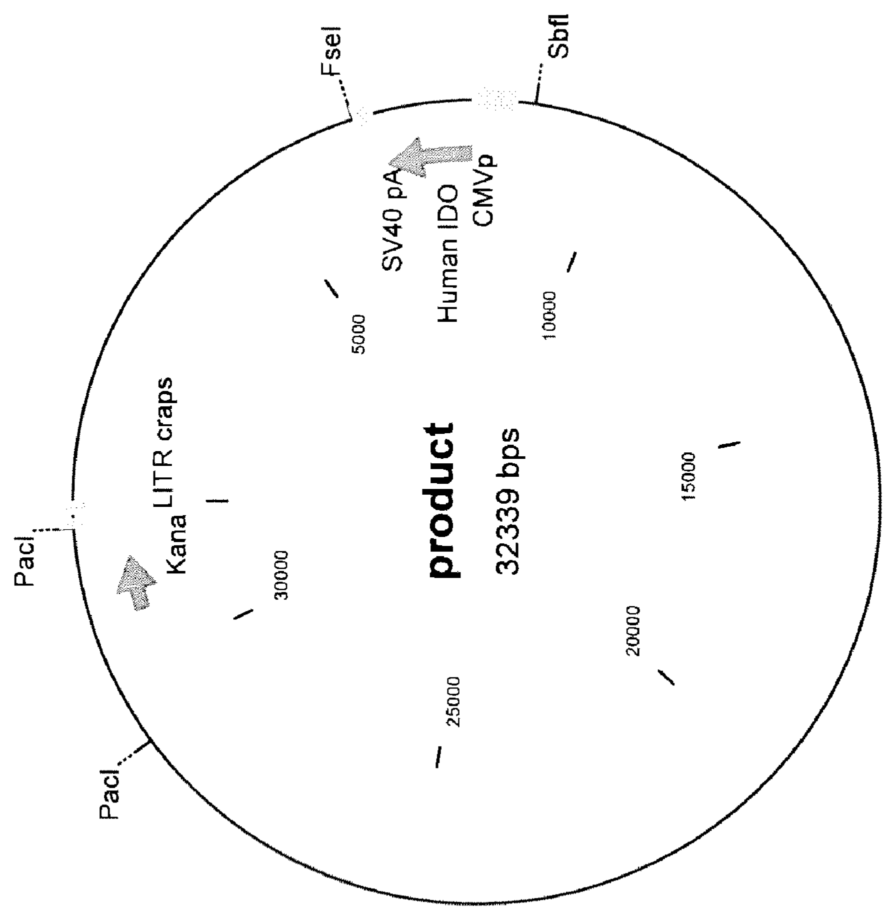
FIG. 14 is a schematic drawing of an embodiment of the human gutless IDO backbone vector.

The gutless backbone (SEQ ID NO:23, FIG. 12) was cut with SbfI and FseI to release the TM expression cassette. The backbone was subsequently dephosphorylated to prevent vector self-ligation. Rat and human IDO expression cassettes were released from pGEM-T-Easy by digestion with FseI and SbfI and ligated into the FseI and SbfI sites of the gutless backbone. The resulting constructs prIDO-final (FIG. 13, SEQ ID NO:24) and phIDO-final (FIG. 14, SEQ ID NO:25) were cloned in *E-coli* DH5α. DNA midipreps were generated for the production of high quality plasmid DNA. Gutless adenovirus containing rat IDO or human IDO was produced using the procedure described in Example 3.

EXAMPLE 14

Perfusion of Kidney Transplant with Gutless Adenovirus Vectors Carrying the IDO Gene The experiment was carried out in Fisher-Lewis kidney transplantation model. Gutless adenoviruses carrying the IDO gene (Ad.TIDO) or luciferase gene (Ad.TL) were surface-modified with cyclic arginine-glycine-aspartic acid (RGD) peptides through a bifunctional poly(ethyleneglycol) linker for integrin alpha(v)beta(3) specific delivery. The resulting RGD modified viruses were designated RGD-Ad.TIDO and Ad.TL. The transplanted kidneys were incubated with either ROD-AdTIDO (n=6) or RGD-AdTL (n=5) at 4° C. for 20 min with saline. The transplanted animals were sacrificed at day 7. The transplanted kidneys were isolated and subjected to Western blot and immunohistological examination.

Figure 15:
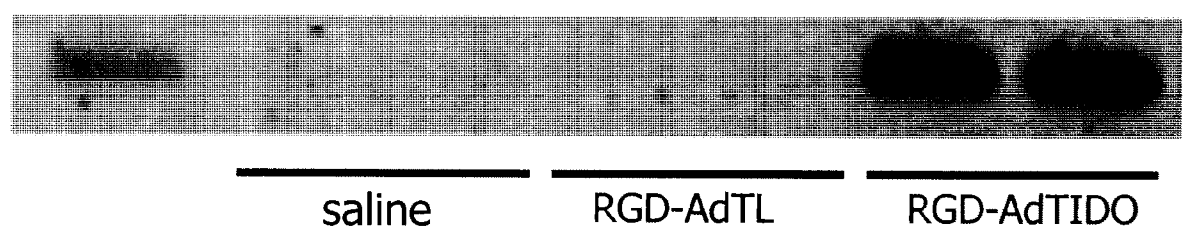
FIG. 15 is a picture of a Western blot showing gutless adenovirus mediated IDO expression in transplanted kidney (lane 1=hIDO control, other lanes as indicated)
Figure 16A:
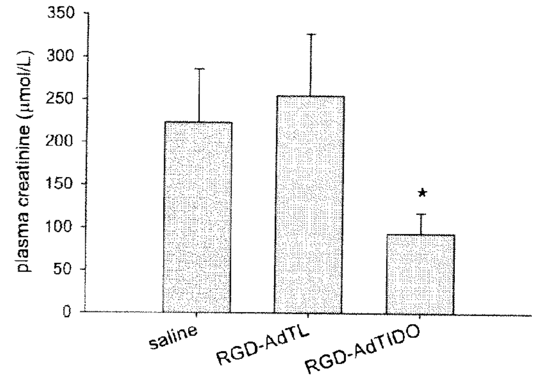
FIG. 16 is a composite of graphs showing reduction of plasma creatinin levels (panel A), ED-1 staining (panel B), CD8 staining (panel C) and smooth muscle actin score (panel D) in kidney tissue infected by gutless adenovirus carrying the IDO gene.
Figure 16B:
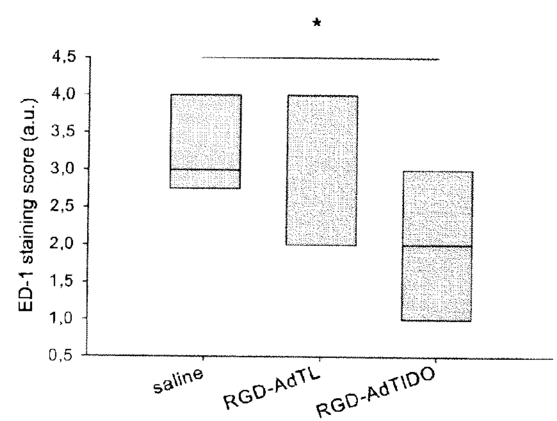
Figure 16C:
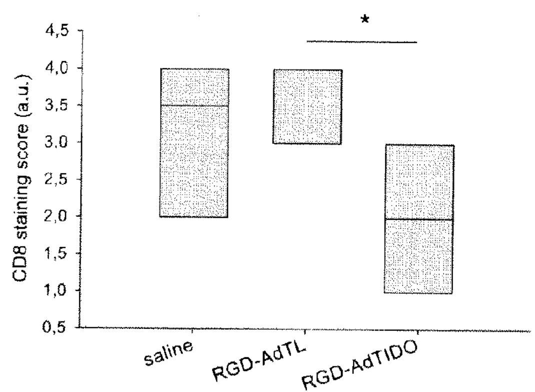
Figure 16D:
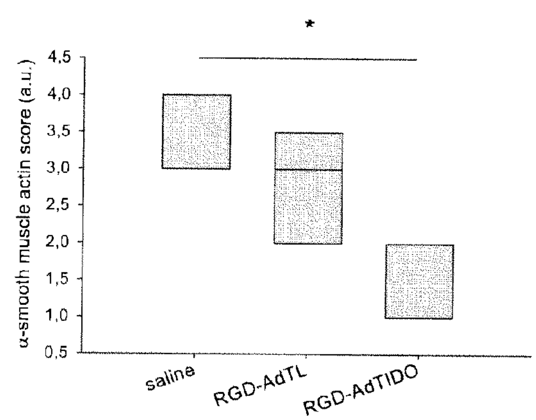

As shown in FIG. 15, IDO expression was detected in the kidneys infected with RGD-AdTIDO but not in kidneys infected with RGD-AdTL. FIGS. 16A-16D shows that, comparing to kidneys perfused with saline or control virus (RGD-AdTL), kidneys infected with RGD-AdTIDO showed reduced plasma creatinin levels (FIG. 16A). Kidneys infected with RGD-AdTIDO also showed reduced tissue damage, as evidenced by the reduced ED-1 staining (FIG. 16B), reduced macrophage influx (FIG. 16C, CD-8 staining for T-lymphocytes), and reduced fibrotic response (FIG. 16D, staining for smooth muscle actin).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

LIST OF THE SEQUENCES

SEQ ID NO:1 (pShuttle-ITR/HPRT)
SEQ ID NO:2 (human TM amino acid sequence)
SEQ ID NO:3 (human TM nucleotide sequence)
SEQ ID NO:4 (CMV promoter)
SEQ ID NO:5 (hTM cDNA)
SEQ ID NO:6 (CMV-hTM expression cassette)
SEQ ID NO:7 (pTMadap)
SEQ ID NO:8 (BstII linker)
SEQ ID NO:9 (SfiI linker)
SEQ ID NO:10 (Forward PCR primer)
SEQ ID NO:11 (Reverse PCR primer)
SEQ ID NO:12 (Stuffer1)
SEQ ID NO: 13 (Stuffer 1-Short)
SEQ ID NO:14 (p2-2)
SEQ ID NO:15 (Stuffer 2)
SEQ ID NO:16 (pTM-final)
SEQ ID NO: 17: IDO RT-PCR forward primer (containing a FseI restriction site)
SEQ ID NO: 18: IDO RT-PCR reverse primer (containing a SbfI restriction site)
SEQ ID NO:19: rat IDO cDNA
SEQ ID NO:20: human IDO cDNA
SEQ ID NO:21: rat IDO expression cassette
SEQ ID NO:22: human IDO expression cassette
SEQ ID NO:23: gutless backbone vector
SEQ ID NO:24: prIDO-final
SEQ ID NO:25: phIDO-final

What is claimed is:

1. A gutless adenovirus vector, comprising a polynucleotide encoding a therapeutic agent;

a renal-specific regulatory element operably linked to said polynucleotide sequence; and a vector backbone comprising the nucleotide sequence of SEQ ID NO:23, except that a thrombomodulin expression cassette containing a Fse-SbfI fragment has been removed from SEQ ID NO:23, and wherein said therapeutic agent is an iRNA agent or an antisense RNA.

2. The gutless adenovirus vector of claim 1, wherein said renal-specific regulatory element is selected from the group consisting of high-capacity (type 2) $Na^+$/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

3. A pharmaceutical composition, comprising:

a gutless adenovirus vector comprising:

a polynucleotide encoding an iRNA agent or an antisense;

a renal-specific regulatory element operably linked to said polynucleotide sequence;

a vector backbone comprising the nucleotide sequence of SEQ ID NO:23, except that a thrombomodulin expression cassette containing a Fse-SbfI fragment has been removed from SEQ ID NO:23; and a pharmaceutically acceptable carrier.

4. The pharmaceutical composition of claim 3, wherein said renal-specific regulatory element is selected from the group consisting of high-capacity (type 2) $Na^+$/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

5. The pharmaceutical composition of claim 3, wherein said iRNA agent or an antisense RNA inhibits TGF-β1 expression.

6. The pharmaceutical composition of claim 3, wherein said shRNA inhibits platelet-derived growth factor expression.

7. A gutless adenovirus vector, comprising:

a polynucleotide encoding a therapeutic agent;

a renal-specific regulatory element operably linked to said polynucleotide sequence, wherein said renal-specific regulatory element is selected from the group consisting of high-capacity (type 2) $Na^+$/glucose cotransporter gene (Sglt2) promoter, and Nkcc2/Slc12a1 gene promoter; and a vector backbone comprising the nucleotide sequence of SEQ ID NO:23, except that a thrombomodulin expression cassette containing a Fse-SbfI fragment has been removed from SEQ ID NO:23, wherein said therapeutic agent is an iRNA agent or an antisense RNA.

8. A pharmaceutical composition comprising:

the gutless adenovirus vector of claim 7, and a pharmaceutically acceptable carrier.

* * * * *

SEQUENCE LISTING

<160> NUMBER OF SEQ ID NOS: 25

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 1

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tactggtacc gcggccgcct    360

cgagtctaga actagtggat cccccgggct gcaggaattc tgatggctct caaaattcct    420

gcctccttta gggataaaag actttaagac tttttaacaa aaaagaaaaa gaaaaaaaaa    480

attcctgcct cctggtgtac acacacagaa gggttccctc cccttgaatg tgaccaggat    540

ctgtgaaaat aacgggatag ccgctcctgt gattaggtta tgtggtagac tagagcaaga    600

ttctcctgct ggttttgaag aagtcagctg ccatgttgtg agactgtcat gggctagggc    660

atgagccttt aaatatctgg gagcaacccc tggccagcag ccagtgagaa aacgggccct    720

cagtcctaca atcacaagga actaaattct gccaacaacc tgaaggaact ttgaagagga    780

tcatgagtcc cttgattcag cttgatgagc ccctgagcag aggatacagc taacttgtac    840

tagggaagta taaaaaacat gcatgggaat gatatatatc aactttaagg ataattgtca    900

tacttctggg aatgaaggga aagaaatggg gctttagttg tattatgatc tttaatttct    960

caaaaaaaat aagatcagaa gcaaatatgg caaaatgtta atacttttgt gggtacgtag   1020

gtattcagca taccctttt tctgagttca aaatatttta taattaaaat gaaatgcagg   1080

ccaggcacag tggctcatgc ctataatacc agcactttgc gaggccgagg tgggaggatg   1140

gcttgaggcc agaccagcct ggccaacatg gcaaaacccc atctctactt aaaaaaaaaa   1200

aaactatata tatatatatg tgtgtgtgtg tgtatatata tatatgtata tatatttata   1260

tatgtgtgta tatatatata tgtatatata tttatatatg tgtgtgtata tatatatata   1320

cacacacaca catatataca tacatacata cacacacaca cacacacaat tagccaggca   1380

tggtggcgca cacctgtagt cccagctact tgggaggctg agacatgaga attgcttgaa   1440

cctgggaggc agagtagtta gtgagctgag atcataccac tgcactccag cctggtgaca   1500

gagtgagact ctgtcttaaa aaaaataaaa attaaaatta aatgcaaaag gtccaagtga   1560

attgaagagg aaaggggtat caaggaaggt tttgtggagg tgacgtttga gctgggtctt   1620

aaatgactta aacatgggat aagaagggag ggaataagga catttcaggt acgagaaata   1680

aggagcaaac agtggaaaca acctaacgtc tgtcaaccag tgaatggata acaaaaatgt   1740

aattcagatg gtatccaact tacgatggtt caacatgaga tttttctgac tttaggatag   1800

atttatcaaa gtagtaaatc cattttcaac ttatgatatt ttcaacttca gatgggttta   1860

tcaggacaca gttgaggaac acctgtctat ccatacaatt tggcaataaa aaggaaatga   1920

gtgcagatat actccacaac atgaatgaac cttgaaaaca ttaagtgaga gaagccagat   1980
```

```
acaaaaggcc acatattgta tgattctatt tatacaaaat gtccagaata ggcaaatctt   2040
atagacagca agtaggtaga tgatcagttt gctaggtgct gggggaaggg gaaatgggga   2100
gtgatggcta aggggattgg gtttctttgt ggggcaatga aaatgtttta aaattgagcg   2160
tgataatgat tgcacaatgc tgcatatata tataatctat agattatata tatataaaga   2220
gaggctgtta gacagtgata agtgatatat atatatatat acatagagag agagagagag   2280
agagagagag gctgttagtg ataagtgatc aggaaaataa aagtattgag gaggaatacg   2340
aagttgacgg tgtgaaaaca tgagatttta tataggatgg ccagggaagg ccttaatgag   2400
aaagtgactt atgagtaaaa acaagggatc ctaaacctta gcatgcatca gaatcactcg   2460
gaaacttgtt aaagcatagc ttgctgggcc tcatcacaga tattttgatt cggtaggttc   2520
ttgtctgata ttaatacttt tggtctaggg aaccacattt tgagaaccac tgagctaaag   2580
gaagtaaagg tttcccttag tttactagct ggtaacccta ggaaactgct tagcctctcg   2640
gtgctaagat acaaaatact ttagcacata ataacacatg gaaaatagtc tataaattat   2700
aaatattatt ttttatgtac caaatattac ataagacaaa atctaagcaa gatatatata   2760
tatatacata aaatataaga tatatatgta tatattatat atagataaat agagagagag   2820
agttatgttt agaaagaaaa tacttcaaac taaaaaaaga gaggtaggaa gtataccatt   2880
ccattattgg taaaaacaaa ttactaagta gtctttacaa aaaaccaatc tcactccttt   2940
agaacacaag cccaccatta aaactgatgc agaggaattt ctctccctgg cttaccttta   3000
ggatggtgca tactaagtta gaaaagtcat aaatgttata ttaaaagtaa atgtgaactt   3060
acttccacaa tcaagacatt ctagaagaaa aagagaaatg aaaatcagta caatgaataa   3120
aacggtattt ccaattataa gtcaaatcac atcataacaa ccctaaggaa ttatccaaac   3180
tcttgttttt agatgcttta ttatatcaaa ctctccttta aacaagtggc ccatctgctg   3240
ggatttggaa gcctgtaata ctgaaatttt catcataatg gaaattttaa aaacagaatt   3300
tgacccacct gtttttaaaa cactttcatt acttaacaag aggtctaatc ttgggcaagt   3360
cttgaaattt ctctggcctt agtttcccat gtgttaaatg aaacttgaag cagttggtct   3420
cttatagtct cctgactcta acattctaag aattatattt gtacaataac tcaaaaatca   3480
cataatttaa tttaccatat ggactccaaa atatattttc tcattaggct aaacttgatc   3540
tgcattttct ggatgtgtcc atattcttgg actacactaa aacatgatac caatgcttcc   3600
tctcaccata aaccctcact tcgctttcta catttaagaa ttttatagct ggaagagtcc   3660
ttaacagaaa ataccatcta ataattaccc ctcaaaatcg agaaagtcct atctgttctt   3720
atgctagtta taagaatgag gcagcatttc acataatggt tataaacact gccacaagaa   3780
gattcatgat gtgttgttta tctgtagctc tcatcatact ctgtcatata actatagcat   3840
taagatttta atgttctata tattcttcta agacagtgtt taccagagta aggcacaaaa   3900
gatccactgg tttgcaagaa agattagaac ttttaaattt tttacctcac cttgtttaat   3960
ctatattttt gtatgtattt tgtaacatat atattattat taccataaat catatataat   4020
ttaaaatgca tatattaggg gtaaatgctc aggaaacttt ttataaattg ggcatgcaaa   4080
tacaagtttg aagactcact gttctaggta ttaaaagtaa agttataacc aagtaaagct   4140
tccacctttt catgtctcaa agcagtttat tgttggaggt aagatctctt agaagcctaa   4200
acaggtccaa gtacagaatg aagtaaggct agcccataac ttgtggcaag caattcatac   4260
tatttctctc atgctgagct ctcctcagtg aagcagctac tatagacaac tgcagcctat   4320
tggtagccta ttttacaggc aggaaaaaaa ttacttttta ttcaaagtgg aactcaggac   4380
```

```
atggggagaa aatgaataca aaaaataggg tcaatccaaa ggcacacagc aaatgagtaa   4440
cacagttatg tttttttccc atttgtatga ggtcccagta aattctaagt aaactgcaaa   4500
tttaataata cactaaaaaa gccatgcaat tgttcaaatg aatcccagca tggtacaagg   4560
agtacagaca ctagagtcta aaaaacaaaa gaatgccatt attgagtttt tgaattatat   4620
caagtagtta catctctact taataaatga gaaaaacgag gataagaggc catttgataa   4680
aatgaaaata gccaagaagt ggtattagag acttgaatac aggtattcgg gtccaaagtt   4740
catctgctca aatactaact ggggaaaaga gggaaaaata tttatataca tatatatctg   4800
cacacaaaaa tacccccaaa agacaaaatg aggccaggca gggtggctca cacccgtaat   4860
cccggtactt tgggaggctg aggcaggtgg atacctgaga tcaggagttg gagatcagcc   4920
tggtcaacat ggtgaaaccc tgtctctact aaagataaaa aaattagcca ggcatggtgg   4980
cgtgcgcctg taatcccagc tacttgggag tctgaggcag gagaatcact tgaactggga   5040
aggggaggtt gcagtgagcc aagatcgtac tactgcactc cagcctgggc agcagagtga   5100
gactccatca caaaaataaa taaataaata aaatacaatg aaacagaaag ttcaaataat   5160
cccataatct taccaccaag aaataacttt cactcgttat acttattgat ttttccataa   5220
taaatgtact ttactgtgac tatcatgaaa agaaagttat tttagaaaca gagaactgtt   5280
tcagatcaaa tctatgtagt agaacagagc cattaggtgg gaaagacgag atcaaactaa   5340
atctcagaag gcctaaaagg ctaggtccat tccagcacta aaaactgacc agacaagtaa   5400
tggcttcaac agcttctaaa tatggacaaa gcatgctgaa agggaaggac aggtctaaca   5460
gtggtatatg aaatgaacag gaggggcaaa gctcatttct cctctgaagt tttccaaaga   5520
tgctgaggag gacattagtt tgacatgacc ctgatatggg acaagataat ttcacagaag   5580
ttttacatgt taaagttttc ttatagatac tcattcaagt aagcaatgaa cactaaaatc   5640
taaagaaaga aaagagcttt agagtcaggt ctgtattcaa attcaagctc taccacttac   5700
tggttctgtg actttgggca agtcttttaa ccttattaag tcttaatttc ctgatttgta   5760
aaatggggat atcgtctccc tcacaggatt gttgtgaaac ttttatgaga ttaatgcctt   5820
tatatttggc atagtgtaag taaacaataa ctggcagctt caaaaaaaaa aagcagtagc   5880
attccatcat ttattattgg ttactctcaa aaagtttttc aatgtactag aagataaata   5940
ttcaaatacc ttaatatctc cattattttc aggtaaacag catgctcctg aacaaccaat   6000
gggtcaacaa ataaattaaa agggaaatct aaaaacatct tgatattaaa ctacatggaa   6060
gcacaatata ccaaaaccaa tggttcacac taggagaatt ttaaggtaca agaaaactct   6120
ttgagatttc ttaaaataat agtatgtctg aatttattga gtgatttacc agaaactgtt   6180
gtaagagctc tacttgcatt atagcactta atcctcttaa ctctatggct gctattatca   6240
acctcaccct aatcacatat gggacacaga gaggttaagt aacttgccca aggtcagagt   6300
taggaagtac taagccatgc tttgaatcag ttgtcaggct ccggaactca cactttcagc   6360
cactacataa tactgctttg ctatctttta ggaaactatg tgagtctacc tcacatagac   6420
tcacataggt ttgttttttt ttttttttta aaggctatct tttcccccat caatgttttt   6480
tgaaggatcc caaattagag tcccacagag gcagacagca gtacttgaca atatggacat   6540
ttaaggttaa tgttggattc tactgtcttt ttactacatg acctagggaa cgataattaa   6600
cctagactgc ttccaagggt taaataaccc atttagttat actatgtaaa ttatctctta   6660
gtgattgatt gaaagcacac tgttactaat tgactcggta tgaagtgctt tttttcttc    6720
cctttcaaga tacatacctt tccagttaaa gttgagagat catctccacc aattactttt   6780
```

```
atgtcccctg ttgactggtc attctagtta aaaaaaaaaa aaactatata tatatatatc   6840
tacacacaca tatgtatatg tatatcctta tgtacacaca caaacttcaa attaaatgag   6900
aactagaaga tttgagaagt tagctagcta atatccatag cattatgata ttctaaatga   6960
tatgaattat aagaattagg tttcctgaaa tgaatgacta gaaaactttc aagtagagat   7020
tagtaaaaat taaaaagtcc taatcggcca ttactgattt gatgttttta agagtcctaa   7080
aaaatgggtt acatccattt ttaagtgggt agtattataa cagccaccca tcttcaatca   7140
cagtgatttc tgaattgtga gggaagttat tagcatgaca ggtgtctggt tctggccctg   7200
tacgattccc atgagtcaag caaattgtaa gggctggtct atatcacacc caaccccaag   7260
gatatgtccc tcaaaagtct agcccaggcc ccgtcatctt cagcatcatc tgggaaacca   7320
ggtctgatta gtagtccttt aaggaatacc tcttaggctc ccattttact gctatcacag   7380
aatccaataa aacccttaca ggagattcaa tgggaaatgc tcaacaccca ctgtagttgg   7440
tggtgacaat gaccataatt tggctgtgct ggattcagga cagaaaattt gggtgaaaga   7500
gcaggtgaac aaaagagctt cgacttgccc tagcagagag caagccatac cataccacaa   7560
agccacagca attacaacgg tgcagtacca gcacagtaaa tgaacaaagt agagcccaga   7620
aacagaccca gaactatatg aggatttagt atacaataaa gatggtattt cgagtcagta   7680
gggaaaagat gaattattca ataaatgatg tttggccaac tagtaaccca tttgggaaaa   7740
aataaaagta tggtccctac ctcacagcat acacaaaaat aaattccaga cggattaaaa   7800
tctaaatgta aaaaataaag ccataagtgg actggaagaa aatagagaat ttttttaac   7860
atccgtagaa agggtaaaaa cccaggcatg acatgaacca aaactgaaga ggttctgtaa   7920
caaatacccc cttttatata ttgggctcca acaataagaa cccataggaa aatggagaat   7980
gaacacaaat agacaattta tagaagagaa ggttataagg tgtaaaatta tatctatctg   8040
agaaacaaac actaaaacaa tgtgattcta ctgttctccc acccatactg gcaaaactta   8100
agcctgataa tatgctgagg ggaaataagc actcttgttg gtgagagtat taattggcat   8160
agcttctttt gaaaatgaca tagcaatacc tgttaaaatt gcaaacatgc atgtcactta   8220
atccagtaat cccacttctg ggaatcaatg ctacaaaaac actgacaagt atacaaagat   8280
acattcaaga gtgttcactg ggccgggtgc ggtggcttca tgcctgtaat cccagggagg   8340
cagaggcaag acgatcgctt gaccccagga gttcaaggcc agcccgagaa acacagcaag   8400
accctgtctc tcttttttt atttaaaaaa taaatgttca ctgtatcagt tgttcacaaa   8460
aacaaaccaa catgtccatt aacagggaac catttaaatt aatcaagttc atctacacaa   8520
tgtaatacca tgcaactatt aaaaagcacc tgataatcca aagcacactg agacagaata   8580
atgctattaa aaacaccaag tagtggaaca ctgtgttgcc tatgacacca tttttattca   8640
acatttaaac aaatttgtaa cagcaattac atgagtagtg acaatggcgt ttatgagact   8700
tttcactttt atgtgcttct atttttgtta tgcttctata tatacatcca tttattatgg   8760
agtgttactt tcaaaaatca caaatgggcc agtattattt ggtgttgcaa ggtgagcata   8820
tgacttctga tatcaacctt tgcatattac ttctcaattt agggaaatta cagacatccc   8880
ttattctaac taacttaaaa cccagcattt caaacataca gaattgatgg ggaaaaaaaa   8940
gaaagaagaa agaaagaaaa ggcaacaagc ttcagatgac agtgactcac atcaaattat   9000
ttataaaatc tgttaaatag tgccatcttc tggagatacc tggtattaca gtccaactcc   9060
agttgatgtc tttacagaga caagaggaat aaaggaaaaa atattcaaga actgaaaagt   9120
atggagtcat ggaaaaattg ctgtgatcca aaggctacgg tgataggaca agaaacaaga   9180
```

```
gaactccaag cagtaagaca ctgctgttct attagcatcc aaacctccat actcctgttt   9240
gccccaaggc ttttttaaaa aatagagaca ggatctcact attttgctca ggctggtctt   9300
gaactcctgg actcaagcta tcctcctgcc tcggcctcct aaagtgccga gattacaggc   9360
ttgagtcacc atacctggct atttattttt tcttaactct cttgcctggc ctatagccac   9420
catggaagct aataaagaat attaatttaa gagtaatggt atagttcact acattggaat   9480
acaggtataa gtgcctacat tgtacatgaa tggcatacat ggatcaatta ccccacctgg   9540
gtggccaaag gaactgcgcg aacctccctc cttggctgtc tggaacaagc ttcccactag   9600
atccctttac tgagtgcctc cctcatcttt aattatggtt aagtctagga taacaggact   9660
ggcaaaggtg aggggaaagc ttcctccaga gttgctctac cctctcctct accgtcctat   9720
ctcctcactc ctctcagcca aggagtccaa tctgtcctga actcagagcg tcactgtcaa   9780
ctacataaaa ttgccagaga agctctttgg gactacaaac acataccctt aatgtcttta   9840
tttctatttt gtctacctct tcagtctagg tgaaaaaata ggaaggataa tagggaagaa   9900
ctttgtttat gcctacttat ccgcccctag gaattttgaa aacctctagg tagcaataag   9960
aactgcagca tggtatagaa aaagaggagg aaagctgtat agaaatgcat aataaatggg  10020
caggaaaaga actgcttgga acaaacaggg aggttgaact ataaggagag aaagcagaga  10080
ggctaatcaa caaggctggg ttcccaagag ggcatgatga gactattact aaggtaggaa  10140
ttactaaggg ctccatgtcc ccttagtggc ttagtactat gtagcttgct ttctgcagtg  10200
aacttcagac ccttctttta ggatcctaga atggactttt tttttttatc ggaaaacagt  10260
cattctctca acattcaagc aggccccaag tctaccacac tcaatcacat tttctcttca  10320
tatcataatc tctcaaccat tctctgtcct tttaactgtt tttctatacc ctgatcaaat  10380
gccaacaaaa gtgagaatgt tagaatcatg tatttttaga ggtagactgt atctcagata  10440
aaaaaaaagg gcagatattc cattttccaa aatatgtatg cagaaaaaat aagtatgaaa  10500
ggacatatgc tcaggtaaca agttaatttg tttacttgta ttttatgaat tccctaaaac  10560
ctacgtcacc cgccccgttc ccacgccccg cgccacgtca caaactccac cccctcatta  10620
tcatattggc ttcaatccaa aataaggtat attattgatg atgttaatta acatgcatgg  10680
atccatatgc ggtgtgaaat accgcacaga tgcgtaagga gaaaataccg catcaggcgc  10740
tcttccgctt cctcgctcac tgactcgctg cgctcggtcg ttcggctgcg gcgagcggta  10800
tcagctcact caaaggcggt aatacggtta tccacagaat caggggataa cgcaggaaag  10860
aacatgtgag caaaaggcca gcaaaaggcc aggaaccgta aaaaggccgc gttgctggcg  10920
tttttccata ggctccgccc ccctgacgag catcacaaaa atcgacgctc aagtcagagg  10980
tggcgaaacc cgacaggact ataaagatac caggcgtttc cccctggaag ctccctcgtg  11040
cgctctcctg ttccgaccct gccgcttacc ggatacctgt ccgcctttct cccttcggga  11100
agcgtggcgc tttctcatag ctcacgctgt aggtatctca gttcggtgta ggtcgttcgc  11160
tccaagctgg gctgtgtgca cgaacccccc gttcagcccg accgctgcgc cttatccggt  11220
aactatcgtc ttgagtccaa cccggtaaga cacgacttat cgccactggc agcagccact  11280
ggtaacagga ttagcagagc gaggtatgta ggcggtgcta cagagttctt gaagtggtgg  11340
cctaactacg gctacactag aaggacagta tttggtatct gcgctctgct gaagccagtt  11400
accttcggaa aaagagttgg tagctcttga tccggcaaac aaaccaccgc tggtagcggt  11460
ggtttttttg tttgcaagca gcagattacg cgcagaaaaa aaggatctca agaagatcct  11520
ttgatctttt ctacggggtc tgacgctcag tggaacgaaa actcacgtta agggattttg  11580
```

```
gtcatgagat tatcaaaaag gatcttcacc tagatccttt taaattaaaa atgaagtttt  11640

aaatcaatct aaagtatata tgagtaaact tggtctgaca gttaccaatg cttaatcagt  11700

gaggcaccta tctcagcgat ctgtctattt cgttcatcca tagttgcctg actccccgtc  11760

gtgtagataa ctacgatacg ggagggctta ccatctggcc ccagtgctgc aatgataccg  11820

cgagacccac gctcaccggc tccagattta tcagcaataa accagccagc cggaagggcc  11880

gagcgcagaa gtggtcctgc aactttatcc gcctccatcc agtctattaa ttgttgccgg  11940

gaagctagag taagtagttc gccagttaat agtttgcgca acgttgttgc cattgctgca  12000

gccatgagat tatcaaaaag gatcttcacc tagatccttt tcacgtagaa agccagtccg  12060

cagaaacggt gctgaccccg gatgaatgtc agctactggg ctatctggac aagggaaaac  12120

gcaagcgcaa agagaaagca ggtagcttgc agtgggctta catggcgata gctagactgg  12180

gcggttttat ggacagcaag cgaaccggaa ttgccagctg gggcgccctc tggtaaggtt  12240

gggaagccct gcaaagtaaa ctggatggct ttcttgccgc caaggatctg atggcgcagg  12300

ggatcaagct ctgatcaaga gacaggatga ggatcgtttc gcatgattga acaagatgga  12360

ttgcacgcag gttctccggc cgcttgggtg gagaggctat tcggctatga ctgggcacaa  12420

cagacaatcg gctgctctga tgccgccgtg ttccggctgt cagcgcaggg gcgcccggtt  12480

ctttttgtca agaccgacct gtccggtgcc ctgaatgaac tgcaagacga ggcagcgcgg  12540

ctatcgtggc tggccacgac gggcgttcct tgcgcagctg tgctcgacgt tgtcactgaa  12600

gcgggaaggg actggctgct attgggcgaa gtgccggggc aggatctcct gtcatctcac  12660

cttgctcctg ccgagaaagt atccatcatg gctgatgcaa tgcggcggct gcatacgctt  12720

gatccggcta cctgcccatt cgaccaccaa gcgaaacatc gcatcgagcg agcacgtact  12780

cggatggaag ccggtcttgt cgatcaggat gatctggacg aagagcatca ggggctcgcg  12840

ccagccgaac tgttcgccag gctcaaggcg agcatgcccg acggcgagga tctcgtcgtg  12900

acccatggcg atgcctgctt gccgaatatc atggtggaaa atggccgctt ttctggattc  12960

atcgactgtg gccggctggg tgtggcggac cgctatcagg acatagcgtt ggctacccgt  13020

gatattgctg aagagcttgg cggcgaatgg gctgaccgct tcctcgtgct ttacggtatc  13080

gccgctcccg attcgcagcg catcgccttc tatcgccttc ttgacgagtt cttctgaatt  13140

ttgttaaaat tttgttaaa tcagctcatt ttttaaccaa taggccgaaa tcggcaaaat  13200

cccttataaa tcaaaagaat agaccgagat agggttgagt gttgttccag tttggaacaa  13260

gagtccacta ttaaagaacg tggactccaa cgtcaaaggg cgaaaaaccg tctatcaggg  13320

cgatggccca ctacgtgaac catcacccta atcaagtttt ttggggtcga ggtgccgtaa  13380

agcactaaat cggaacccta aagggagccc ccgatttaga gcttgacggg gaaagccggc  13440

gaacgtggcg agaaaggaag ggaagaaagc gaaaggagcg ggcgctaggg cgctggcaag  13500

tgtagcggtc acgctgcgcg taaccaccac acccgccgcg cttaatgcgc cgctacaggg  13560

cgcgtccatt cgccattcag gatcgaatta attcttaatt aa                      13602
```

```
<210> SEQ ID NO 2
<211> LENGTH: 575
<212> TYPE: PRT
<213> ORGANISM: Homo sapiens

<400> SEQUENCE: 2

Met Leu Gly Val Leu Val Leu Gly Ala Leu Ala Leu Ala Gly Leu Gly
1               5                   10                  15
```

```
Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445
```

```
Gly Phe Cys Ser Gly Val Cys His Asn Leu Pro Gly Thr Phe Glu Cys
    450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Pro Ala Val Gly Leu
            500                 505                 510

Val His Ser Gly Leu Leu Ile Gly Ile Ser Ile Ala Ser Leu Cys Leu
        515                 520                 525

Val Val Ala Leu Leu Ala Leu Leu Cys His Leu Arg Lys Lys Gln Gly
    530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575


<210> SEQ ID NO 3
<211> LENGTH: 1725
<212> TYPE: DNA
<213> ORGANISM: Homo sapiens

<400> SEQUENCE: 3

atgcttgggg tcctggtcct tggcgcgctg gccctggccg gcctggggtt ccccgcaccc      60

gcagagccgc agccgggtgg cagccagtgc gtcgagcacg actgcttcgc gctctacccg     120

ggccccgcga ccttcctcaa tgccagtcag atctgcgacg gactgcgggg ccacctaatg     180

acagtgcgct cctcggtggc tgccgatgtc atttccttgc tactgaacgg cgacggcggc     240

gttggccgcc ggcgcctctg gatcggcctg cagctgccac ccggctgcgg cgaccccaag     300

cgcctcgggc ccctgcgcgg cttccagtgg gttacgggag acaacaacac cagctatagc     360

aggtgggcac ggctcgacct caatggggct cccctctgcg gcccgttgtg cgtcgctgtc     420

tccgctgctg aggccactgt gcccagcgag ccgatctggg aggagcagca gtgcgaagtg     480

aaggccgatg gcttcctctg cgagttccac ttcccagcca cctgcaggcc actggctgtg     540

gagcccggcg ccgcggctgc cgccgtctcg atcacctacg gcaccccgtt cgcggcccgc     600

ggagcggact tccaggcgct gccggtgggc agctccgccg cggtggctcc cctcggctta     660

cagctaatgt gcaccgcgcc gcccggagcg gtccaggggc actgggccag ggaggcgccg     720

ggcgcttggg actgcagcgt ggagaacggc ggctgcgagc acgcgtgcaa tgcgatccct     780

ggggctcccc gctgccagtg cccagccggc gccgccctgc aggcagacgg gcgctcctgc     840

accgcatccg cgacgcagtc ctgcaacgac ctctgcgagc acttctgcgt tcccaacccc     900

gaccagccgg gctcctactc gtgcatgtgc gagaccggct accggctggc ggccgaccaa     960

caccggtgcg aggacgtgga tgactgcata ctggagccca gtccgtgtcc gcagcgctgt    1020

gtcaacacac agggtggctt cgagtgccac tgctacccta actacgacct ggtggacggc    1080

gagtgtgtgg agcccgtgga cccgtgcttc agagccaact gcgagtacca gtgccagccc    1140

ctgaaccaaa ctagctacct ctgcgtctgc gccgagggct tcgcgcccat tccccacgag    1200

ccgcacaggt gccagatgtt ttgcaaccag actgcctgtc cagccgactg cgaccccaac    1260

acccaggcta gctgtgagtg ccctgaaggc tacatcctgg acgacggttt catctgcacg    1320

gacatcgacg agtgcgaaaa cggcggcttc tgctccgggg tgtgccacaa cctccccggt    1380

accttcgagt gcatctgcgg gcccgactcg gcccttgccc gccacattgg caccgactgt    1440
```

```
gactccggca aggtggacgg tggcgacagc ggctctggcg agccccgcc cagcccgacg   1500
cccggctcca ccttgactcc tccggccgtg gggctcgtgc attcgggctt gctcataggc   1560
atctccatcg cgagcctgtg cctggtggtg gcgcttttgg cgctcctctg ccacctgcgc   1620
aagaagcagg gcgccgccag ggccaagatg gagtacaagt gcgcggcccc ttccaaggag   1680
gtagtgctgc agcacgtgcg gaccgagcgg acgccgcaga gactc                   1725
```

<210> SEQ ID NO 4
<211> LENGTH: 649
<212> TYPE: DNA
<213> ORGANISM: Homo sapiens
<220> FEATURE:
<221> NAME/KEY: misc_feature
<222> LOCATION: (1)..(649)
<223> OTHER INFORMATION: n= a, c, g, t, unknown or other

<400> SEQUENCE: 4

```
tctagacgcg ttgacattga ttattgacta gttattaata gtaatcaatt acggggtcat     60
tagttcatag cccatgatat catatggagt tccgcgttac ataacttacg gtaaatggcc    120
cgcctggctg accgcccaac gaccccgcc cattgacgtc aataatgacg tatgttccca     180
tagtaacgcc aatagggact ttccattgac gtcaatgggt ggagtattta cggtaaactg    240
cccacttggc agtacatcaa gtgtatcata tgccaagtac gcccccctat tgacgtcaat    300
gacggtaaat ggcccgcctg gcattatgcc cagtncatga ccttatggga ctttcctact    360
tggcagacat ctacgtatta gtcatcgcta ttaccatggt gatgcggttt tggcagtaca    420
tcaatgggcg tggatagcgg tttgactcac ggggatttcc caagtctcca ccccattgac    480
gtcaatggga gtttgttttg gcaccaaaat caacgggact ttccaaaatg tcgtaacaac    540
tccgccccat tgacgcaaat gggcggtagg cgtgtacggt gggaggtcta tataagcaga    600
gctctctggc taactagaga acccctgctt actggcttat cgagatatc                649
```

<210> SEQ ID NO 5
<211> LENGTH: 3693
<212> TYPE: DNA
<213> ORGANISM: Homo sapiens

<400> SEQUENCE: 5

```
ggcagcgcgc agcggcaaga agtgtctggg ctgggacgga caggagaggc tgtcgccatc     60
ggcgtcctgt gcccctctgc tccggcacgg ccctgtcgca gtgcccgcgc tttccccggc    120
gcctgcacgc ggcgcgcctg ggtaacatgc ttggggtcct ggtccttggc gcgctggccc    180
tggccggcct ggggttcccc gcacccgcag agccgcagcc gggtggcagc cagtgcgtcg    240
agcacgactg cttcgcgctc tacccgggcc ccgcgacctt cctcaatgcc agtcagatct    300
gcgacggact gcggggccac ctaatgacag tgcgctcctc ggtggctgcc gatgtcattt    360
ccttgctact gaacggcgac ggcggcgttg gccgccggcg cctctggatc ggcctgcagc    420
tgccacccgg ctgcggcgac cccaagcgcc tcgggcccct gcgcggcttc cagtgggtta    480
cgggagacaa caacaccagc tatagcaggt gggcacggct cgacctcaat ggggctcccc    540
tctgcggccc gttgtgcgtc gctgtctccg ctgctgaggc cactgtgccc agcgagccga    600
tctgggagga gcagcagtgc gaagtgaagg ccgatggctt cctctgcgag ttccacttcc    660
cagccacctg caggccactg gctgtggagc ccggcgccgc ggctgccgcc gtctcgatca    720
cctacggcac cccgttcgcg gcccgcggag cggacttcca ggcgctgccg gtgggcagct    780
ccgccgcggt ggctcccctc ggcttacagc taatgtgcac cgcgccgccc ggagcggtcc    840
```

-continued

```
aggggcactg ggccagggag gcgccgggcg cttgggactg cagcgtggag aacggcggct    900
gcgagcacgc gtgcaatgcg atccctgggg ctccccgctg ccagtgccca gccggcgccg    960
ccctgcaggc agacgggcgc tcctgcaccg catccgcgac gcagtcctgc aacgacctct   1020
gcgagcactt ctgcgttccc aaccccgacc agccgggctc ctactcgtgc atgtgcgaga   1080
ccggctaccg gctggcggcc gaccaacacc ggtgcgagga cgtggatgac tgcatactgg   1140
agcccagtcc gtgtccgcag cgctgtgtca acacacaggg tggcttcgag tgccactgct   1200
accctaacta cgacctggtg gacggcgagt gtgtggagcc cgtggacccg tgcttcagag   1260
ccaactgcga gtaccagtgc cagcccctga accaaactag ctacctctgc gtctgcgccg   1320
agggcttcgc gcccattccc cacgagccgc acaggtgcca gatgttttgc aaccagactg   1380
cctgtccagc cgactgcgac cccaacaccc aggctagctg tgagtgccct gaaggctaca   1440
tcctggacga cggtttcatc tgcacggaca tcgacgagtg cgaaaacggc ggcttctgct   1500
ccggggtgtg ccacaacctc cccggtacct tcgagtgcat ctgcgggccc gactcggccc   1560
ttgcccgcca cattggcacc gactgtgact ccggcaaggt ggacggtggc gacagcggct   1620
ctggcgagcc cccgcccagc ccgacgcccg gctccacctt gactcctccg gccgtggggc   1680
tcgtgcattc gggcttgctc ataggcatct ccatcgcgag cctgtgcctg gtggtggcgc   1740
ttttggcgct cctctgccac ctgcgcaaga agcagggcgc cgccagggcc aagatggagt   1800
acaagtgcgc ggccccttcc aaggaggtag tgctgcagca cgtgcggacc gagcggacgc   1860
cgcagagact ctgagcggcc tccgtccagg agcctggctc cgtccaggag cctgtgcctc   1920
ctcaccccca gctttgctac caaagcacct tagctggcat tacagctgga gaagaccctc   1980
cccgcacccc ccaagctgtt ttcttctatt ccatggctaa ctggcgaggg ggtgattaga   2040
gggaggagaa tgagcctcgg cctcttccgt gacgtcactg gaccactggg caatgatggc   2100
aattttgtaa cgaagacaca gactgcgatt tgtcccaggt cctcactacc gggcgcagga   2160
gggtgagcgt tattggtcgg cagccttctg ggcagacctt gacctcgtgg gctagggatg   2220
actaaaatat ttattttttt taagtattta ggtttttgtt tgtttccttt gttcttacct   2280
gtatgtctcc agtatccact ttgcacagct ctccggtctc tctctctcta caaactccca   2340
cttgtcatgt gacaggtaaa ctatcttggt gaattttttt ttcctagccc tctcacattt   2400
atgaagcaag ccccacttat tccccattct tcctagtttt ctcctcccag gaactgggcc   2460
aactcacctg agtcacccta cctgtgcctg accctacttc ttttgctctt agctgtctgc   2520
tcagacagaa cccctacatg aaacagaaac aaaaacacta aaaataaaaa tggccatttg   2580
ctttttcacc agatttgcta atttatcctg aaatttcaga ttcccagagc aaaataattt   2640
taaacaaagg ttgagatgta aaaggtatta aattgatgtt gctggactgt catagaaatt   2700
acacccaaag aggtatttat ctttactttt aaacagtgag cctgaatttt gttgctgttt   2760
tgatttgtac tgaaaaatgg taattgttgc taatcttctt atgcaatttc cttttttgtt   2820
attattactt atttttgaca gtgttgaaaa tgttcagaag gttgctctag attgagagaa   2880
gagacaaaca cctcccagga gacagttcaa gaaagcttca aactgcatga ttcatgccaa   2940
ttagcaattg actgtcactg ttccttgtca ctggtagacc aaaataaaac cagctctact   3000
ggtcttgtgg aattgggagc ttgggaatgg atcctggagg atgcccaatt agggcctagc   3060
cttaatcagg tcctcagaga atttctacca tttcagagag gccttttgga atgtggcccc   3120
tgaacaagaa ttggaagctg ccctgcccat gggagctggt tagaaatgca gaatcctagg   3180
ctccacccca tccagttcat gagaatctat atttaacaag atctgcaggg ggtgtgtctg   3240
```

```
ctcagtaatt tgaggacaac cattccagac tgcttccaat tttctggaat acatgaaata   3300

tagatcagtt ataagtagca ggccaagtca ggcccttatt ttcaagaaac tgaggaattt   3360

tctttgtgta gctttgctct ttggtagaaa aggctaggta cacagctcta gacactgcca   3420

cacagggtct gcaaggtctt tggttcagct aagctaggaa tgaaatcctg cttcagtgta   3480

tggaaataaa tgtatcatag aaatgtaact tttgtaagac aaaggttttc ctcttctatt   3540

ttgtaaactc aaaatatttg tacatagtta tttatttatt ggagataatc tagaacacag   3600

gcaaaatcct tgcttatgac atcacttgta caaaataaac aaataacaat gtgaaaaaaa   3660

aaaaaaaaaa aaaaaaaaaa aaaaaaaaaa aaa                                3693
```

```
<210> SEQ ID NO 6
<211> LENGTH: 4457
<212> TYPE: DNA
<213> ORGANISM: Homo sapiens
<220> FEATURE:
<221> NAME/KEY: misc_feature
<222> LOCATION: (1)..(4457)
<223> OTHER INFORMATION: n= a, c, g, t, unknown or other

<400> SEQUENCE: 6

gtttaaacgg gccctctaga cgcgttgaca ttgattattg actagttatt aatagtaatc     60

aattacgggg tcattagttc atagcccatg atatcatatg gagttccgcg ttacataact    120

tacggtaaat ggcccgcctg gctgaccgcc caacgacccc cgcccattga cgtcaataat    180

gacgtatgtt cccatagtaa cgccaatagg gactttccat tgacgtcaat gggtggagta    240

tttacggtaa actgcccact tggcagtaca tcaagtgtat catatgccaa gtacgccccc    300

ctattgacgt caatgacggt aaatggcccg cctggcatta tgcccagtnc atgaccttat    360

gggactttcc tacttggcag acatctacgt attagtcatc gctattacca tggtgatgcg    420

gttttggcag tacatcaatg ggcgtggata gcggtttgac tcacggggat ttccaagtc     480

tccaccccat tgacgtcaat gggagtttgt tttggcacca aaatcaacgg gactttccaa    540

aatgtcgtaa caactccgcc ccattgacgc aaatgggcgg taggcgtgta cggtgggagg    600

tctatataag cagagctctc tggctaacta gagaacccct gcttactggc ttatcgagat    660

atctgcagaa ttcatctgtc gactgctacc ggcagcgcgc agcggcaaga agtgtctggg    720

ctgggacgga caggagaggc tgtcgccatc ggcgtcctgt gcccctctgc tccggcacgg    780

ccctgtcgca gtgcccgcgc tttccccggc gcctgcacgc ggcgcgcctg ggtaacatgc    840

ttggggtcct ggtccttggc gcgctggccc tggccggcct ggggttcccc gcacccgcag    900

agccgcagcc gggtggcagc cagtgcgtcg agcacgactg cttcgcgctc tacccgggcc    960

ccgcgacctt cctcaatgcc agtcagatct gcgacggact gcggggccac ctaatgacag   1020

tgcgctcctc ggtggctgcc gatgtcattt ccttgctact gaacggcgac ggcggcgttg   1080

gccgccggcg cctctggatc ggcctgcagc tgccacccgg ctgcggcgac cccaagcgcc   1140

tcgggcccct gcgcggcttc cagtgggtta cgggagacaa caacaccagc tatagcaggt   1200

gggcacggct cgacctcaat ggggctcccc tctgcggccc gttgtgcgtc gctgtctccg   1260

ctgctgaggc cactgtgccc agcgagccga tctgggagga gcagcagtgc gaagtgaagg   1320

ccgatggctt cctctgcgag ttccacttcc cagccacctg caggccactg gctgtggagc   1380

ccggcgccgc ggctgccgcc gtctcgatca cctacggcac cccgttcgcg gcccgcggag   1440

cggacttcca ggcgctgccg gtgggcagct ccgccgcggt ggctcccctc ggcttacagc   1500

taatgtgcac cgcgccgccc ggagcggtcc aggggcactg ggccagggag gcgccgggcg   1560
```

```
cttgggactg cagcgtggag aacggcggct gcgagcacgc gtgcaatgcg atccctgggg   1620
ctccccgctg ccagtgccca gccggcgccg ccctgcaggc agacgggcgc tcctgcaccg   1680
catccgcgac gcagtcctgc aacgacctct gcgagcactt ctgcgttccc aaccccgacc   1740
agccgggctc ctactcgtgc atgtgcgaga ccggctaccg gctggcggcc gaccaacacc   1800
ggtgcgagga cgtggatgac tgcatactgg agcccagtcc gtgtccgcag cgctgtgtca   1860
acacacaggg tggcttcgag tgccactgct accctaacta cgacctggtg gacggcgagt   1920
gtgtggagcc cgtggacccg tgcttcagag ccaactgcga gtaccagtgc cagcccctga   1980
accaaactag ctacctctgc gtctgcgccg agggcttcgc gcccattccc cacgagccgc   2040
acaggtgcca gatgttttgc aaccagactg cctgtccagc cgactgcgac cccaacaccc   2100
aggctagctg tgagtgccct gaaggctaca tcctggacga cggtttcatc tgcacggaca   2160
tcgacgagtg cgaaaacggc ggcttctgct ccggggtgtg ccacaacctc cccggtacct   2220
tcgagtgcat ctgcgggccc gactcggccc ttgcccgcca cattggcacc gactgtgact   2280
ccggcaaggt ggacggtggc gacagcggct ctggcgagcc cccgcccagc ccgacgcccg   2340
gctccacctt gactcctccg gccgtggggc tcgtgcattc gggcttgctc ataggcatct   2400
ccatcgcgag cctgtgcctg gtggtggcgc ttttggcgct cctctgccac ctgcgcaaga   2460
agcagggcgc cgccagggcc aagatggagt acaagtgcgc ggccccttcc aaggaggtag   2520
tgctgcagca cgtgcggacc gagcggacgc cgcagagact ctgagcggcc tccgtccagg   2580
agcctggctc cgtccaggag cctgtgcctc ctcacccccca gctttgctac caaagcacct   2640
tagctggcat tacagctgga gaagaccctc cccgcacccc ccaagctgtt ttcttctatt   2700
ccatggctaa ctggcgaggg ggtgattaga gggaggagaa tgagcctcgg cctcttccgt   2760
gacgtcactg gaccactggg caatgatggc aattttgtaa cgaagacaca gactgcgatt   2820
tgtcccaggt cctcactacc gggcgcagga gggtgagcgt tattggtcgg cagccttctg   2880
ggcagacctt gacctcgtgg gctagggatg actaaaatat ttattttttt taagtattta   2940
ggtttttgtt tgtttccttt gttcttacct gtatgtctcc agtatccact ttgcacagct   3000
ctccggtctc tctctctcta caaactccca cttgtcatgt gacaggtaaa ctatcttggt   3060
gaattttttt ttcctagccc tctcacattt atgaagcaag ccccacttat tccccattct   3120
tcctagtttt ctcctcccag gaactgggcc aactcacctg agtcacccta cctgtgcctg   3180
accctacttc ttttgctctt agctgtctgc tcagacagaa cccctacatg aaacagaaac   3240
aaaaacacta aaaataaaaa tggccatttg ctttttcacc agatttgcta atttatcctg   3300
aaatttcaga ttcccagagc aaaataattt taaacaaagg ttgagatgta aaaggtatta   3360
aattgatgtt gctggactgt catagaaatt acacccaaag aggtatttat ctttactttt   3420
aaacagtgag cctgaatttt gttgctgttt tgatttgtac tgaaaaatgg taattgttgc   3480
taatcttctt atgcaatttc cttttttgtt attattactt atttttgaca gtgttgaaaa   3540
tgttcagaag gttgctctag attgagagaa gagacaaaca cctcccagga gacagttcaa   3600
gaaagcttca aactgcatga ttcatgccaa ttagcaattg actgtcactg ttccttgtca   3660
ctggtagacc aaaataaaac cagctctact ggtcttgtgg aattgggagc ttgggaatgg   3720
atcctggagg atgcccaatt agggcctagc cttaatcagg tcctcagaga atttctacca   3780
tttcagagag gccttttgga atgtggcccc tgaacaagaa ttggaagctg ccctgcccat   3840
gggagctggt tagaaatgca gaatcctagg ctccacccca tccagttcat gagaatctat   3900
atttaacaag atctgcaggg ggtgtgtctg ctcagtaatt tgaggacaac cattccagac   3960
```

```
tgcttccaat tttctggaat acatgaaata tagatcagtt ataagtagca ggccaagtca   4020
ggcccttatt ttcaagaaac tgaggaattt tctttgtgta gctttgctct ttggtagaaa   4080
aggctaggta cacagctcta gacactgcca cacagggtct gcaaggtctt tggttcagct   4140
aagctaggaa tgaaatcctg cttcagtgta tggaaataaa tgtatcatag aaatgtaact   4200
tttgtaagac aaaggttttc ctcttctatt ttgtaaactc aaaatatttg tacatagtta   4260
tttatttatt ggagataatc tagaacacag gcaaaatcct tgcttatgac atcacttgta   4320
caaaataaac aaataacaat gtgaaaaaaa aaaaaaaaaa aaaaaaaaaa aaaaaaaaaa   4380
aaaggtagca gtcgacagat gaattccacc acactggact agtggatccg agctcggtac   4440
caagcttaag tttaaac                                                  4457
```

```
<210> SEQ ID NO 7
<211> LENGTH: 17534
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: misc_feature
<222> LOCATION: (1)..(17534)
<223> OTHER INFORMATION: n= a, c, g, t, unknown or other

<400> SEQUENCE: 7

catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tactggtacc gcggccgcct    360
cgagtctaga actagtggat cccccaaacg ggccctctag acgcgttgac attgattatt    420
gactagttat taatagtaat caattacggg gtcattagtt catagcccat gatatcatat    480
ggagttccgc gttacataac ttacggtaaa tggcccgcct ggctgaccgc ccaacgaccc    540
ccgcccattg acgtcaataa tgacgtatgt tcccatagta acgccaatag ggactttcca    600
ttgacgtcaa tgggtggagt atttacggta aactgcccac ttggcagtac atcaagtgta    660
tcatatgcca agtacgcccc ctattgacg tcaatgacgg taaatggccc gcctggcatt    720
atgcccagtn catgacctta tgggactttc ctacttggca gacatctacg tattagtcat    780
cgctattacc atggtgatgc ggttttggca gtacatcaat gggcgtggat agcggtttga    840
ctcacgggga tttccaagt ctccacccca ttgacgtcaa tgggagtttg ttttggcacc    900
aaaatcaacg ggactttcca aaatgtcgta acaactccgc cccattgacg caaatgggcg    960
gtaggcgtgt acggtgggag gtctatataa gcagagctct ctggctaact agagaacccc   1020
tgcttactgg cttatcgaga tatctgcaga attcatctgt cgactgctac cggcagcgcg   1080
cagcggcaag aagtgtctgg gctgggacgg acaggagagg ctgtcgccat cggcgtcctg   1140
tgcccctctg ctccggcacg gccctgtcgc agtgcccgcg ctttccccgg cgcctgcacg   1200
cggcgcgcct gggtaacatg cttggggtcc tggtccttgg cgcgctggcc ctggccggcc   1260
tggggttccc cgcacccgca gagccgcagc cgggtggcag ccagtgcgtc gagcacgact   1320
gcttcgcgct ctacccgggc cccgcgacct tcctcaatgc cagtcagatc tgcgacggac   1380
```

```
tgcggggcca cctaatgaca gtgcgctcct cggtggctgc cgatgtcatt tccttgctac   1440
tgaacggcga cggcggcgtt ggccgccggc gcctctggat cggcctgcag ctgccacccg   1500
gctgcggcga ccccaagcgc ctcgggcccc tgcgcggctt ccagtgggtt acgggagaca   1560
acaacaccag ctatagcagg tgggcacggc tcgacctcaa tggggctccc ctctgcggcc   1620
cgttgtgcgt cgctgtctcc gctgctgagg ccactgtgcc cagcgagccg atctgggagg   1680
agcagcagtg cgaagtgaag gccgatggct tcctctgcga gttccacttc ccagccacct   1740
gcaggccact ggctgtggag cccggcgccg cggctgccgc cgtctcgatc acctacggca   1800
ccccgttcgc ggcccgcgga gcggacttcc aggcgctgcc ggtgggcagc tccgccgcgg   1860
tggctcccct cggcttacag ctaatgtgca ccgcgccgcc cggagcggtc caggggcact   1920
gggccaggga ggcgccgggc gcttgggact gcagcgtgga gaacggcggc tgcgagcacg   1980
cgtgcaatgc gatccctggg gctccccgct gccagtgccc agccggcgcc gccctgcagg   2040
cagacgggcg ctcctgcacc gcatccgcga cgcagtcctg caacgacctc tgcgagcact   2100
tctgcgttcc caaccccgac cagccgggct cctactcgtg catgtgcgag accggctacc   2160
ggctggcggc cgaccaacac cggtgcgagg acgtggatga ctgcatactg gagcccagtc   2220
cgtgtccgca gcgctgtgtc aacacacagg gtggcttcga gtgccactgc taccctaact   2280
acgacctggt ggacggcgag tgtgtggagc ccgtggaccc gtgcttcaga gccaactgcg   2340
agtaccagtg ccagcccctg aaccaaacta gctacctctg cgtctgcgcc gagggcttcg   2400
cgcccattcc ccacgagccg cacaggtgcc agatgttttg caaccagact gcctgtccag   2460
ccgactgcga ccccaacacc caggctagct gtgagtgccc tgaaggctac atcctggacg   2520
acggtttcat ctgcacggac atcgacgagt gcgaaaacgg cggcttctgc tccggggtgt   2580
gccacaacct ccccggtacc ttcgagtgca tctgcgggcc cgactcggcc cttgcccgcc   2640
acattggcac cgactgtgac tccggcaagg tggacggtgg cgacagcggc tctggcgagc   2700
ccccgcccag cccgacgccc ggctccacct tgactcctcc ggccgtgggg ctcgtgcatt   2760
cgggcttgct cataggcatc tccatcgcga gcctgtgcct ggtggtggcg cttttggcgc   2820
tcctctgcca cctgcgcaag aagcagggcg ccgccagggc caagatggag tacaagtgcg   2880
cggccccttc caaggaggta gtgctgcagc acgtgcggac cgagcggacg ccgcagagac   2940
tctgagcggc ctccgtccag gagcctggct ccgtccagga gcctgtgcct cctcaccccc   3000
agctttgcta ccaaagcacc ttagctggca ttacagctgg agaagaccct ccccgcaccc   3060
cccaagctgt tttcttctat tccatggcta actggcgagg gggtgattag agggaggaga   3120
atgagcctcg gcctcttccg tgacgtcact ggaccactgg gcaatgatgg caattttgta   3180
acgaagacac agactgcgat ttgtcccagg tcctcactac cgggcgcagg agggtgagcg   3240
ttattggtcg gcagccttct gggcagacct tgacctcgtg ggctagggat gactaaaata   3300
tttatttttt ttaagtattt aggtttttgt ttgtttcctt tgttcttacc tgtatgtctc   3360
cagtatccac tttgcacagc tctccggtct ctctctctct acaaactccc acttgtcatg   3420
tgacaggtaa actatcttgg tgaatttttt tttcctagcc ctctcacatt tatgaagcaa   3480
gccccactta ttccccattc ttcctagttt tctcctccca ggaactgggc caactcacct   3540
gagtcaccct acctgtgcct gaccctactt cttttgctct tagctgtctg ctcagacaga   3600
acccctacat gaaacagaaa caaaaacact aaaaataaaa atggccattt gctttttcac   3660
cagatttgct aatttatcct gaaatttcag attcccagag caaaataatt ttaaacaaag   3720
gttgagatgt aaaaggtatt aaattgatgt tgctggactg tcatagaaat tacacccaaa   3780
```

-continued

```
gaggtattta tctttacttt taaacagtga gcctgaattt tgttgctgtt ttgatttgta   3840
ctgaaaaatg gtaattgttg ctaatcttct tatgcaattt cctttttttgt tattattact   3900
tatttttgac agtgttgaaa atgttcagaa ggttgctcta gattgagaga agagacaaac   3960
acctcccagg agacagttca agaaagcttc aaactgcatg attcatgcca attagcaatt   4020
gactgtcact gttccttgtc actggtagac caaaataaaa ccagctctac tggtcttgtg   4080
gaattgggag cttgggaatg gatcctggag gatgcccaat tagggcctag ccttaatcag   4140
gtcctcagag aatttctacc atttcagaga ggccttttgg aatgtggccc ctgaacaaga   4200
attggaagct gccctgccca tgggagctgg ttagaaatgc agaatcctag gctccacccc   4260
atccagttca tgagaatcta tatttaacaa gatctgcagg gggtgtgtct gctcagtaat   4320
ttgaggacaa ccattccaga ctgcttccaa ttttctggaa tacatgaaat atagatcagt   4380
tataagtagc aggccaagtc aggcccttat tttcaagaaa ctgaggaatt ttctttgtgt   4440
agctttgctc tttggtagaa aaggctaggt acacagctct agacactgcc acacagggtc   4500
tgcaaggtct ttggttcagc taagctagga atgaaatcct gcttcagtgt atggaaataa   4560
atgtatcata gaaatgtaac ttttgtaaga caaaggtttt cctcttctat tttgtaaact   4620
caaaatattt gtacatagtt atttatttat tggagataat ctagaacaca ggcaaaatcc   4680
ttgcttatga catcacttgt acaaaataaa caaataacaa tgtgaaaaaa aaaaaaaaaa   4740
aaaaaaaaaa aaaaaaaaaa aaaaggtagc agtcgacaga tgaattccac cacactggac   4800
tagtggatcc gagctcggta ccaagcttaa gtttgggctg caggaattct gatggctctc   4860
aaaattcctg cctcctttag ggataaaaga ctttaagact ttttaacaaa aaagaaaaag   4920
aaaaaaaaaa ttcctgcctc ctggtgtaca cacacagaag ggttccctcc ccttgaatgt   4980
gaccaggatc tgtgaaaata acgggatagc cgctcctgtg attaggttat gtggtagact   5040
agagcaagat tctcctgctg gttttgaaga agtcagctgc catgttgtga gactgtcatg   5100
ggctagggca tgagccttta aatatctggg agcaacccct ggccagcagc cagtgagaaa   5160
acgggccctc agtcctacaa tcacaaggaa ctaaattctg ccaacaacct gaaggaactt   5220
tgaagaggat catgagtccc ttgattcagc ttgatgagcc cctgagcaga ggatacagct   5280
aacttgtact agggaagtat aaaaaacatg catgggaatg atatatatca actttaagga   5340
taattgtcat acttctggga atgaagggaa agaaatgggg ctttagttgt attatgatct   5400
ttaatttctc aaaaaaaata agatcagaag caaatatggc aaaatgttaa tacttttgtg   5460
ggtacgtagg tattcagcat acccttttttt ctgagttcaa aatattttat aattaaaatg   5520
aaatgcaggc caggcacagt ggctcatgcc tataatacca gcactttgcg aggccgaggt   5580
gggaggatgg cttgaggcca gaccagcctg gccaacatgg caaaacccca tctctactta   5640
aaaaaaaaaa aactatatat atatatatgt gtgtgtgtgt gtatatatat atatgtatat   5700
atatttatat atgtgtgtat atatatatat gtatatatat ttatatatgt gtgtgtatat   5760
atatatatac acacacacac atatatacat acatacatac acacacacac acacacaatt   5820
agccaggcat ggtggcgcac acctgtagtc ccagctactt gggaggctga gacatgagaa   5880
ttgcttgaac ctgggaggca gagtagttag tgagctgaga tcataccact gcactccagc   5940
ctggtgacag agtgagactc tgtcttaaaa aaaataaaaa ttaaaattaa atgcaaaagg   6000
tccaagtgaa ttgaagagga aaggggtatc aaggaaggtt ttgtggaggt gacgtttgag   6060
ctgggtctta aatgacttaa acatgggata agaagggagg gaataaggac atttcaggta   6120
cgagaaataa ggagcaaaca gtggaaacaa cctaacgtct gtcaaccagt gaatggataa   6180
```

```
caaaaatgta attcagatgg tatccaactt acgatggttc aacatgagat ttttctgact   6240
ttaggataga tttatcaaag tagtaaatcc attttcaact tatgatattt tcaacttcag   6300
atgggtttat caggacacag ttgaggaaca cctgtctatc catacaattt ggcaataaaa   6360
aggaaatgag tgcagatata ctccacaaca tgaatgaacc ttgaaaacat taagtgagag   6420
aagccagata caaaaggcca catattgtat gattctattt atacaaaatg tccagaatag   6480
gcaaatctta tagacagcaa gtaggtagat gatcagtttg ctaggtgctg ggggaagggg   6540
aaatggggag tgatggctaa ggggattggg tttctttgtg gggcaatgaa aatgttttaa   6600
aattgagcgt gataatgatt gcacaatgct gcatatatat ataatctata gattatatat   6660
atataaagag aggctgttag acagtgataa gtgatatata tatatatata catagagaga   6720
gagagagaga gagagagagg ctgttagtga taagtgatca ggaaaaataa agtattgagg   6780
aggaatacga agttgacggt gtgaaaacat gagattttat ataggatggc cagggaaggc   6840
cttaatgaga aagtgactta tgagtaaaaa caagggatcc taaaccttag catgcatcag   6900
aatcactcgg aaacttgtta aagcatagct tgctgggcct catcacagat attttgattc   6960
ggtaggttct tgtctgatat taatactttt ggtctaggga accacatttt gagaaccact   7020
gagctaaagg aagtaaaggt ttcccttagt ttactagctg gtaacactgg cccaggaggc   7080
ctttctggtg acccctaagg aattatccaa actcttgttt ttagatgctt tattatatca   7140
aactctcctt taaacaagtg gcccatctgc tgggatttgg aagcctgtaa tactgaaatt   7200
ttcatcataa tggaaatttt aaaaacagaa tttgacccac ctgtttttaa aacactttca   7260
ttacttaaca agaggtctaa tcttgggcaa gtcttgaaat ttctctggcc ttagtttccc   7320
atgtgttaaa tgaaacttga agcagttggt ctcttatagt ctcctgactc taacattcta   7380
agaattatat ttgtacaata actcaaaaat cacataattt aatttaccat atggactcca   7440
aaatatattt tctcattagg ctaaacttga tctgcatttt ctggatgtgt ccatattctt   7500
ggactacact aaaacatgat accaatgctt cctctcacca taaaccctca cttcgctttc   7560
tacatttaag aattttatag ctggaagagt ccttaacaga aaataccatc taataattac   7620
ccctcaaaat cgagaaagtc ctatctgttc ttatgctagt tataagaatg aggcagcatt   7680
tcacataatg gttataaaca ctgccacaag aagattcatg atgtgttgtt tatctgtagc   7740
tctcatcata ctctgtcata taactatagc attaagattt taatgttcta tatattcttc   7800
taagacagtg tttaccagag taaggcacaa aagatccact ggtttgcaag aaagattaga   7860
acttttaaat tttttacctc accttgttta atctatattt ttgtatgtat tttgtaacat   7920
atatattatt attaccataa atcatatata atttaaaatg catatattag gggtaaatgc   7980
tcaggaaact ttttataaat tgggcatgca aatacaagtt tgaagactca ctgttctagg   8040
tattaaaagt aaagttataa ccaagtaaag cttccacctt ttcatgtctc aaagcagttt   8100
attgttggag gtaagatctc ttagaagcct aaacaggtcc aagtacagaa tgaagtaagg   8160
ctagcccata acttgtggca agcaattcat actatttctc tcatgctgag ctctcctcag   8220
tgaagcagct actatagaca actgcagcct attggtagcc tattttacag gcaggaaaaa   8280
aattactttt tattcaaagt ggaactcagg acatggggag aaaatgaata caaaaaatag   8340
ggtcaatcca aaggcacaca gcaaatgagt aacacagtta tgttttttc ccatttgtat   8400
gaggtcccag taaattctaa gtaaactgca aatttaataa tacactaaaa aagccatgca   8460
attgttcaaa tgaatcccag catggtacaa ggagtacaga cactagagtc taaaaaacaa   8520
aagaatgcca ttattgagtt tttgaattat atcaagtagt tacatctcta cttaataaat   8580
```

```
gagaaaaacg aggataagag gccatttgat aaaatgaaaa tagccaagaa gtggtattag   8640
agacttgaat acaggtattc gggtccaaag ttcatctgct caaatactaa ctggggaaaa   8700
gagggaaaaa tatttatata catatatatc tgcacacaaa aataccccca aaagacaaaa   8760
tgaggccagg cagggtggct cacacccgta atcccggtac tttgggaggc tgaggcaggt   8820
ggatacctga gatcaggagt tggagatcag cctggtcaac atggtgaaac cctgtctcta   8880
ctaaagataa aaaaattagc caggcatggt ggcgtgcgcc tgtaatccca gctacttggg   8940
agtctgaggc aggagaatca cttgaactgg gaaggggagg ttgcagtgag ccaagatcgt   9000
actactgcac tccagcctgg gcagcagagt gagactccat cacaaaaata aataaataaa   9060
taaaatacaa tgaaacagaa agttcaaata atcccataat cttaccacca agaaataact   9120
ttcactcgtt atacttattg atttttccat aataaatgta ctttactgtg actatcatga   9180
aaagaaagtt attttagaaa cagagaactg tttcagatca aatctatgta gtagaacaga   9240
gccattaggt gggaaagacg agatcaaact aaatctcaga aggcctaaaa ggctaggtcc   9300
attccagcac taaaaactga ccagacaagt aatggcttca acagcttcta aatatggaca   9360
aagcatgctg aaagggaagg acaggtctaa cagtggtata tgaaatgaac aggaggggca   9420
aagctcattt ctcctctgaa gttttccaaa gatgctgagg aggacattag tttgacatga   9480
ccctgatatg ggacaagata atttcacaga agttttacat gttaaagttt tcttatagat   9540
actcattcaa gtaagcaatg aacactaaaa tctaaagaaa gaaaagagct ttagagtcag   9600
gtctgtattc aaattcaagc tctaccactt actggttctg tgactttggg caagtctttt   9660
aaccttatta agtcttaatt tcctgatttg taaaatgggg atatcgtctc cctcacagga   9720
ttgttgtgaa acttttatga gattaatgcc tttatatttg gcatagtgta agtaaacaat   9780
aactggcagc ttcaaaaaaa aaaagcagta gcattccatc atttattatt ggttactctc   9840
aaaaagtttt tcaatgtact agaagataaa tattcaaata ccttaatatc tccattattt   9900
tcaggtaaac agcatgctcc tgaacaacca atgggtcaac aaataaatta aaagggaaat   9960
ctaaaaacat cttgatatta aactacatgg aagcacaata taccaaaacc aatggttcac  10020
actaggagaa ttttaaggta caagaaaact ctttgagatt tcttaaaata atagtatgtc  10080
tgaatttatt gagtgattta ccagaaactg ttgtaagagc tctacttgca ttatagcact  10140
taatcctctt aactctatgg ctgctattat caacctcacc ctaatcacat atgggacaca  10200
gagaggttaa gtaacttgcc caaggtcaga gttaggaagt actaagccat gctttgaatc  10260
agttgtcagg ctccggaact cacactttca gccactacat aatactgctt tgctatcttt  10320
taggaaacta tgtgagtcta cctcacatag actcacatag gtttgttttt tttttttttt  10380
taaaggctat cttttccccc atcaatgttt tttgaaggat cccaaattag agtcccacag  10440
aggcagacag cagtacttga caatatggac atttaaggtt aatgttggat tctactgtct  10500
ttttactaca tgacctaggg aacgataatt aacctagact gcttccaagg gttaaataac  10560
ccatttagtt atactatgta aattatctct tagtgattga ttgaaagcac actgttacta  10620
attgactcgg tatgaagtgc tttttttttct tccctttcaa gatacatacc tttccagtta  10680
aagttgagag atcatctcca ccaattactt ttatgtcccc tgttgactgg tcattctagt  10740
taaaaaaaaa aaaaactata tatatatata tctacacaca catatgtata tgtatatcct  10800
tatgtacaca cacaaacttc aaattaaatg agaactagaa gatttgagaa gttagctagc  10860
taatatccat agcattatga tattctaaat gatatgaatt ataagaatta ggtttcctga  10920
aatgaatgac tagaaaactt tcaagtagag attagtaaaa attaaaaagt cctaatcggc  10980
```

```
cattactgat ttgatgtttt taagagtcct aaaaaatggg ttacatccat ttttaagtgg  11040
gtagtattat aacagccacc catcttcaat cacagtgatt tctgaattgt gagggaagtt  11100
attagcatga caggtgtctg gttctggccc tgtacgattc ccatgagtca agcaaattgt  11160
aagggctggt ctatatcaca cccaacccca aggatatgtc cctcaaaagt ctagcccagg  11220
ccccgtcatc ttcagcatca tctgggaaac caggtctgat tagtagtcct ttaaggaata  11280
cctcttaggc tcccatttta ctgctatcac agaatccaat aaaaccctta caggagattc  11340
aatgggaaat gctcaacacc cactgtagtt ggtggtgaca atgaccataa tttggctgtg  11400
ctggattcag gacagaaaat ttgggtgaaa gagcaggtga acaaaagagc ttcgacttgc  11460
cctagcagag agcaagccat accataccac aaagccacag caattacaac ggtgcagtac  11520
cagcacagta aatgaacaaa gtagagccca gaaacagacc cagaactata tgaggattta  11580
gtatacaata aagatggtat ttcgagtcag tagggaaaag atgaattatt caataaatga  11640
tgtttggcca actagtaacc catttgggaa aaaataaaag tatggtccct acctcacagc  11700
atacacaaaa ataaattcca gacggattaa aatctaaatg taaaaaataa agccataagt  11760
ggactggaag aaaatagaga atttttttta acatccgtag aaagggtaaa aacccaggca  11820
tgacatgaac caaaactgaa gaggttctgt aacaaatacc ccttttata tattgggctc  11880
caacaataag aacccatagg aaaatggaga atgaacacaa atagacaatt tatagaagag  11940
aaggttataa ggtgtaaaat tatatctatc tgagaaacaa acactaaaac aatgtgattc  12000
tactgttctc ccacccatac tggcaaaact taagcctgat aatatgctga ggggaaataa  12060
gcactcttgt tggtgagagt attaattggc atagcttctt ttgaaaatga catagcaata  12120
cctgttaaaa ttgcaaacat gcatgtcact taatccagta atcccacttc tgggaatcaa  12180
tgctacaaaa acactgacaa gtatacaaag atacattcaa gagtgttcac tgggccgggt  12240
gcggtggctt catgcctgta atcccaggga ggcagaggca agacgatcgc ttgaccccag  12300
gagttcaagg ccagcccgag aaacacagca agaccctgtc tctctttttt ttatttaaaa  12360
aataaatgtt cactgtatca gttgttcaca aaaacaaacc aacatgtcca ttaacaggga  12420
accatttaaa ttaatcaagt tcatctacac aatgtaatac catgcaacta ttaaaaagca  12480
cctgataatc caaagcacac tgagacagaa taatgctatt aaaaacacca agtagtggaa  12540
cactgtgttg cctatgacac catttttatt caacatttaa acaaatttgt aacagcaatt  12600
acatgagtag tgacaatggc gtttatgaga cttttcactt ttatgtgctt ctatttttgt  12660
tatgcttcta tatatacatc catttattat ggagtgttac tttcaaaaat cacaaatggg  12720
ccagtattat ttggtgttgc aaggtgagca tatgacttct gatatcaacc tttgcatatt  12780
acttctcaat ttagggaaat tacagacatc ccttattcta actaacttaa aacccagcat  12840
ttcaaacata cagaattgat ggggaaaaaa aagaaagaag aaagaaagaa aaggcaacaa  12900
gcttcagatg acagtgactc acatcaaatt atttataaaa tctgttaaat agtgccatct  12960
tctggagata cctggtatta cagtccaact ccagttgatg tctttacaga gacaagagga  13020
ataaaggaaa aaatattcaa gaactgaaaa gtatggagtc atggaaaaat tgctgtgatc  13080
caaaggctac ggtgatagga caagaaacaa gagaactcca agcagtaaga cactgctgtt  13140
ctattagcat ccaaacctcc atactcctgt ttgccccaag gctttttttaa aaaatagaga  13200
caggatctca ctattttgct caggctggtc ttgaactcct ggactcaagc tatcctcctg  13260
cctcggcctc ctaaagtgcc gagattacag gcttgagtca ccatacctgg ctatttattt  13320
tttcttaact ctcttgcctg gcctatagcc accatggaag ctaataaaga atattaattt  13380
```

```
aagagtaatg gtatagttca ctacattgga atacaggtat aagtgcctac attgtacatg  13440
aatggcatac atggatcaat taccccacct gggtggccaa aggaactgcg cgaacctccc  13500
tccttggctg tctggaacaa gcttcccact agatcccttt actgagtgcc tccctcatct  13560
ttaattatgg ttaagtctag gataacagga ctggcaaagg tgaggggaaa gcttcctcca  13620
gagttgctct accctctcct ctaccgtcct atctcctcac tcctctcagc caaggagtcc  13680
aatctgtcct gaactcagag cgtcactgtc aactacataa aattgccaga gaagctcttt  13740
gggactacaa acacataccc ttaatgtctt tatttctatt ttgtctacct cttcagtcta  13800
ggtgaaaaaa taggaaggat aatagggaag aactttgttt atgcctactt atccgcccct  13860
aggaattttg aaaacctcta ggtagcaata agaactgcag catggtatag aaaaagagga  13920
ggaaagctgt atagaaatgc ataataaatg ggcaggaaaa gaactgcttg gaacaaacag  13980
ggaggttgaa ctataaggag agaaagcaga gaggctaatc aacaaggctg ggttcccaag  14040
agggcatgat gagactatta ctaaggtagg aattactaag ggctccatgt ccccttagtg  14100
gcttagtact atgtagcttg ctttctgcag tgaacttcag acccttcttt taggatccta  14160
gaatggactt ttttttttta tcggaaaaca gtcattctct caacattcaa gcaggcccca  14220
agtctaccac actcaatcac attttctctt catatcataa tctctcaacc attctctgtc  14280
cttttaactg tttttctata ccctgatcaa atgccaacaa aagtgagaat gttagaatca  14340
tgtatttta gaggtagact gtatctcaga taaaaaaaaa gggcagatat tccattttcc  14400
aaaatatgta tgcagaaaaa ataagtatga aaggacatat gctcaggtaa caagttaatt  14460
tgtttacttg tattttatga attccctaaa acctacgtca cccgccccgt tcccacgccc  14520
cgcgccacgt cacaaactcc accccctcat tatcatattg gcttcaatcc aaaataaggt  14580
atattattga tgatgttaat taacatgcat ggatccatat gcggtgtgaa ataccgcaca  14640
gatgcgtaag gagaaaatac cgcatcaggc gctcttccgc ttcctcgctc actgactcgc  14700
tgcgctcggt cgttcggctg cggcgagcgg tatcagctca ctcaaaggcg gtaatacggt  14760
tatccacaga atcaggggat aacgcaggaa agaacatgtg agcaaaaggc cagcaaaagg  14820
ccaggaaccg taaaaaggcc gcgttgctgg cgtttttcca taggctccgc ccccctgacg  14880
agcatcacaa aaatcgacgc tcaagtcaga ggtggcgaaa cccgacagga ctataaagat  14940
accaggcgtt tccccctgga agctccctcg tgcgctctcc tgttccgacc ctgccgctta  15000
ccggatacct gtccgccttt ctcccttcgg gaagcgtggc gctttctcat agctcacgct  15060
gtaggtatct cagttcggtg taggtcgttc gctccaagct gggctgtgtg cacgaacccc  15120
ccgttcagcc cgaccgctgc gccttatccg gtaactatcg tcttgagtcc aacccggtaa  15180
gacacgactt atcgccactg gcagcagcca ctggtaacag gattagcaga gcgaggtatg  15240
taggcggtgc tacagagttc ttgaagtggt ggcctaacta cggctacact agaaggacag  15300
tatttggtat ctgcgctctg ctgaagccag ttaccttcgg aaaaagagtt ggtagctctt  15360
gatccggcaa acaaaccacc gctggtagcg gtggtttttt tgtttgcaag cagcagatta  15420
cgcgcagaaa aaaaggatct caagaagatc ctttgatctt ttctacgggg tctgacgctc  15480
agtggaacga aaactcacgt taagggattt tggtcatgag attatcaaaa aggatcttca  15540
cctagatcct tttaaattaa aaatgaagtt ttaaatcaat ctaaagtata tatgagtaaa  15600
cttggtctga cagttaccaa tgcttaatca gtgaggcacc tatctcagcg atctgtctat  15660
ttcgttcatc catagttgcc tgactccccg tcgtgtagat aactacgata cgggagggct  15720
taccatctgg ccccagtgct gcaatgatac cgcgagaccc acgctcaccg gctccagatt  15780
```

```
tatcagcaat aaaccagcca gccggaaggg ccgagcgcag aagtggtcct gcaactttat  15840

ccgcctccat ccagtctatt aattgttgcc gggaagctag agtaagtagt tcgccagtta  15900

atagtttgcg caacgttgtt gccattgctg cagccatgag attatcaaaa aggatcttca  15960

cctagatcct tttcacgtag aaagccagtc cgcagaaacg gtgctgaccc cggatgaatg  16020

tcagctactg ggctatctgg acaagggaaa acgcaagcgc aaagagaaag caggtagctt  16080

gcagtgggct tacatggcga tagctagact gggcggtttt atggacagca agcgaaccgg  16140

aattgccagc tggggcgccc tctggtaagg ttgggaagcc ctgcaaagta aactggatgg  16200

ctttcttgcc gccaaggatc tgatggcgca ggggatcaag ctctgatcaa gagacaggat  16260

gaggatcgtt tcgcatgatt gaacaagatg gattgcacgc aggttctccg gccgcttggg  16320

tggagaggct attcggctat gactgggcac aacagacaat cggctgctct gatgccgccg  16380

tgttccggct gtcagcgcag gggcgcccgg ttctttttgt caagaccgac ctgtccggtg  16440

ccctgaatga actgcaagac gaggcagcgc ggctatcgtg gctggccacg acgggcgttc  16500

cttgcgcagc tgtgctcgac gttgtcactg aagcgggaag ggactggctg ctattgggcg  16560

aagtgccggg gcaggatctc ctgtcatctc accttgctcc tgccgagaaa gtatccatca  16620

tggctgatgc aatgcggcgg ctgcatacgc ttgatccggc tacctgccca ttcgaccacc  16680

aagcgaaaca tcgcatcgag cgagcacgta ctcggatgga agccggtctt gtcgatcagg  16740

atgatctgga cgaagagcat caggggctcg cgccagccga actgttcgcc aggctcaagg  16800

cgagcatgcc cgacggcgag gatctcgtcg tgacccatgg cgatgcctgc ttgccgaata  16860

tcatggtgga aaatggccgc ttttctggat tcatcgactg tggccggctg ggtgtggcgg  16920

accgctatca ggacatagcg ttggctaccc gtgatattgc tgaagagctt ggcggcgaat  16980

gggctgaccg cttcctcgtg ctttacggta tcgccgctcc cgattcgcag cgcatcgcct  17040

tctatcgcct tcttgacgag ttcttctgaa ttttgttaaa atttttgtta aatcagctca  17100

tttttaacc aataggccga aatcggcaaa atcccttata aatcaaaaga atagaccgag  17160

atagggttga gtgttgttcc agtttggaac aagagtccac tattaaagaa cgtggactcc  17220

aacgtcaaag ggcgaaaaac cgtctatcag ggcgatggcc cactacgtga accatcaccc  17280

taatcaagtt ttttggggtc gaggtgccgt aaagcactaa atcggaaccc taaagggagc  17340

ccccgattta gagcttgacg gggaaagccg gcgaacgtgg cgagaaagga agggaagaaa  17400

gcgaaaggag cgggcgctag ggcgctggca agtgtagcgg tcacgctgcg cgtaaccacc  17460

acacccgccg cgcttaatgc gccgctacag ggcgcgtcca ttcgccattc aggatcgaat  17520

taattcttaa ttaa                                                   17534
```

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8

```
gtaacactgg cccaggaggc ctttctggtg acccc                            35
```

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
tgaccgggtc ctccggaaag accactgggg att 33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tagttccttc tgcctggaat ac 22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
caagtcacaa ggatggacta ca 22

<210> SEQ ID NO 12
<211> LENGTH: 18524
<212> TYPE: DNA
<213> ORGANISM: Homo sapiens

<400> SEQUENCE: 12
tagttccttc tgcctggaat acttcctcat ctcacttgct ttcctgcctg gcagcttcct 60
acttgccctc tggaaccagc tctagggtca ccacatctct gcttctgagt gcctcctcag 120
acacagtctg tatttcctct tccaagctct catcacaaac attgtgctgt attatatgtt 180
tctgtgtggt cttccttcta tgaggaagcc ttggaaagca ggagacttat tttagtcttc 240
tttatgtttc ttttattccc aacacattat gtctgcccca tagacctttt caataaatga 300
ttattgagtt agtgactcct tttacatgct gacaaatgtg gctcttatta ctccccattt 360
cagtatcaca tatttgtaaa agtgaatcct tcttaatcgt tttacttttc tcctagtaaa 420
ttcctcatct atgcctgtct gctgctgttc tctgtgctgc tggcccttcg tttggatggc 480
atcatacagt ggagttactg ggctgtcttt gctccaatat ggctgtggaa gttaatggtc 540
attgttggag cctcagttgg aactggagtc tgggcacgaa atcctcaata tcggtaatac 600
tgctttatac aacccattgg tctctagcat gagggagcaa tatcttgact tttctcactt 660
ttgatgaagt aaggaccatt ttattttcta cctatctggg gtcttagaac tatagtataa 720
gctaacagat ctcttctgtg tttttgaaaa tttagtcttt ggtatgtatt ttcttacaaa 780
agcagtgcca tttgggggta agttgccagc cagctcacag atgcctatat aatccaaaat 840
gcacccaaaa tacagaactg gtatgccata ctagactaag cagcatgaaa ccaccctgtt 900
tttaggaaaa gacactcata ttatgtttgg tcatgaaaga tctttctcca atacagtttt 960
ggaactgggg ctccccttgt cccaccctcc tagtcccaga gctttaggac tattagcagt 1020
gtaggggagg tggcttgacc aggagaccat gagtccctga gacagcagct ggggaatgag 1080
gaaagtcaaa gattggatgc cgagaaggaa agcagagcct ttgggggcag gggagagggg 1140
taccctttac cgtttccaac tcttgccctc cctgctcttg gatgcctccg ctggcccaaa 1200

-continued

```
ttcctgggag ttgctcacgc cagcatgcaa cctgcttgtt gctgggacct gcgagagtct   1260
ttcccttctc tgccacagag actgtaacta cataaaggga aaaaggggga cttaagactg   1320
ggaggctatt atgaacctcc actgggaaaa tgaggagtac aggaattccc agaaggcagc   1380
tgctcatgtg ggaaaagtgt aaagttgaaa ctaccgcacc tttttttttt tttttttttt   1440
tttttttttt ttgagacaga gtttcgctct tgttgcccag gctggagtgc aatggtgtga   1500
tctcggccca ctgcagcctc cacatcccgg gttcaagtga ttctcctgcc tcggcctcct   1560
gagtagctgg gattacaggc acctgccacc atgcccagct aattttttgt atttttagta   1620
gagatagggt ttcaccatgc caggctagtt ttgaactcct gacatcaggt gatccacccg   1680
ccttggcctc ctgaagtgct gggattacag gtgtgagcca ccacgtccgg ccactacatc   1740
aactttttaa atttttgttt actaaatatg aaaatgattc agattgtgta aattacatat   1800
cacatacatg tctaagaact gtaaaacagt tacacagaga gccttggcag gtgagggaca   1860
ttcatgtata gctgtttcag agttcttaga ttttttttga aagattgatg acctgtgtgg   1920
ctgtatgtgt tttatttttt tatgagatat tttcagatat ctaatattaa ttgcttctca   1980
aagaatgcaa agttaaataa acatttaggt tctactaatt gatatttaga atatattcaa   2040
acttctcttt gttggtctta tttaagatgt tttgagcaag gaaaggaatt gtgtatgtgg   2100
ggttgaatgt aaggaatgta caggcgtggt cattctcatg ttaacattaa ccagtggaac   2160
atggttgggt cctacaggaa taacctctga tagcattttc tctatgatct aacttccggt   2220
gtatttgtca cccacaatac atgtatatca taaatgttca tctgtatttt gaataaacat   2280
tgtaggcctt tcagatgcat tatagagcct tttcctgatt agcggcctta ccattgctca   2340
attgtagatc tgttaaggtt attgtgcatg atacttagct aattaaactg attttgtttg   2400
agaacagttt taactcttgt tcttctttct ctttcatgtg caggtgttaa tttatcttaa   2460
tggaatagaa aggaaaatga aaatcattta tacgttttat ttgcatttaa aaatagcacc   2520
taacaatagt tactactatc ttgaaatata actggcactt gttcatagaa ctagagttat   2580
ttttataata ttgtgtgaag ggtggtttac atggtttctt gaaaaatgag gatcatgaga   2640
cttaaggggt atttgcctgg ttttagcagc agaagcaaat cagcttgaat aatcttggaa   2700
gtaactcttg ttgttgaatt taaagatgtg aacagaagtg tttatgtaca ttgtcaggga   2760
aataagaact ggctattact tttgagaata tccttatacg gttaaaacat taaattctgg   2820
tttggttgta atgttcattt tgtattatgt agtagttctt cgatgtttca gagattgcct   2880
accaaagctt aggtttaagt tagctttcta cctgatttcc ctttgctttt gtcaaatttt   2940
caagtaaaat tcaaagtata aatataagtt ggtatttgcc ctgaactgct tgcttatagt   3000
ggagattctg aactgagggt gtttttcttct tctctccctt ttttagagca gaaggagaaa   3060
cgtgtgtgga gtttaaagcc atgttgattg cagtgggcat ccacttgctc ttgttgatgt   3120
ttgaagttct ggtctgtgac agaatcgaga gaggaagcca tttctggctc ctggtcttca   3180
tgccgctgtt ctttgtttcc ccggtgtctg ttgcagcttg cgtttggggc tttcgacatg   3240
acaggtcact agaggtgaga tttcatatat ttaagaatgt tttccacttt gggaggtcaa   3300
ggcaggtgga tcacttgagg tcaggagttt gagaccagcc tggccaacat ggtgaaaccc   3360
catctctact aataatacaa aaattagccg ggtgtggtgg catgcgccag taatcccagc   3420
ttctccggag gctgaggcgg gagaatctct tgaacccagg aggcggaggt tgcagtgagc   3480
caagattgaa ccattgcact ccagcctggg tgacagaatg aaactccgtc ttaaaaaaaa   3540
aaaaaaagaa tgttttcaaa agtaaaatat tttgctcagt tattcagatg tcaatttctt   3600
```

-continued

```
acccttttgtt aggaagagct tgatcattac caactctaca tcatgagaca acaaggcaac   3660
aaaagatgat ggaaataaca atttttcttt cttcacttag aacactagct tttcacccag   3720
gacatcagcc ttctcccagc ttcacatcct gtatcaatca gacagaaaca gaactgatag   3780
gttagataca gatatatgta taaagagagt taaggaactg gctcacatta ctgtggggct   3840
ggcaagtctg aaatctccag ggcaggtgaa caggctggag acctaggagg agttgacact   3900
gcagtcctgg cacagaattt tttcctctcc aggaaaccac agtttttgct tttaaggcct   3960
tcacctgatt gcatgaggcc cacccatgct atggagggta gtctccttta ttcaaagtca   4020
gtaccttcac tgcaacagca agcttagtgt ttgattaaat aactgggtac tatagcccag   4080
ccaagttgac actcaaaact gaccatctcc ccacctcaga ccccatgatt tagcacctcc   4140
cctgctgtct ggttagctta tcctgatgtg cccctgtgtt tgtttattca ttcaataaac   4200
atttatcaag tatttactag atgccaagcc ctttttccct aagcatagag gatatgcaga   4260
tgaataaaat accaggacta gtaataatag taatgaaagt aattgcagat aacgtttatt   4320
gagcacttac tgtgtgccag gcattgtgcg aggcacatta catgtggtag ttttcttact   4380
aactaactct gtgaggtagg tccagagaag ataagtcatt tgttcatggc cacatgtgaa   4440
ggggcaggac caggattccg tttgagtcag cccgactcta aagcccgggc acataactac   4500
ataactgcat agaagctgag ggcccaaagc tgaatactga tgggttgagg ggagaactag   4560
aggctgtaga tgcctggttt tgagccgtgt ggatgaagag tgaagggaga agactgcagt   4620
tggcttagga agtaaacata gcagctgtag ggtgggtcag gcatataagc ctagacccca   4680
ggtatgggcg tgaggggaag gtatgtagac agagggacgg tgatggagca aggccctgtg   4740
ggactcaggg agaatgggac ctagagcacc aggaagggtt tggccttgaa caaggggagc   4800
tattccctga ttttcatgct ggtggaaagg ccacagcatg ggtatagtgg taggtaggag   4860
tgagccgtgg agggagagta tctgatggtc cactttcacc ctccctacaa ttcccagttt   4920
atatcaggga cttgagcatc catggatttt ggtatccaca gggggtcctg gaaccaatcc   4980
cccacagata ctgagggaca actatacaag gactaggact gcattgggcc tgaattacag   5040
aaagtaagtc tttcatatat tcacactcta ggcattcctg cccttggaag aaacaacata   5100
ccaggagctg agctccctcc tcctgtgatg caagaacagt acctatgttg gtgagggggt   5160
ggtctggagt aggctcatac agagatggga aggaggagtt gagggtctgc caggaagccc   5220
tgtgttggga gggaagggat ggcatttttg ggacacattg aagcctagag gcaggaaaca   5280
ctccatcagc tgagtggact gtggcgattc agatccgacg ggagcacaag gtggaaagga   5340
aggaactgtg ggagttgaga agagagggag cctctacaga gggattgggg caaatagggg   5400
ccacgtcctc agcccacaga gcatgtgctg aagtgcccca ggcaccccag tgcactcaca   5460
gggcaccagg ggatagtgga cattttgagg aaaacagtaa tacctgacat ttgttgggac   5520
accatacaaa ctactagctt gaaatagttt acaggtttat ttttaggcca cactgcattc   5580
ctttcagtga cgtcgtatct ttaagaagct gggttttcag cagttgctgt gaaaacaaaa   5640
aaggctaatg ctgtgtgaaa atccgggtga agaacaggta acgagtggga gcaccttgtc   5700
tgattccaag gcgtgggaaa tggtgagcta cctgacaggc acacgcatcc cactgggaat   5760
tagttttggt tatttaagaa taatattaac atttttcttt agatttatat gaattatttt   5820
ttctagtggc tacttagaaa tacttactaa gttagatgta attacttaaa tcagtgcaac   5880
tgttggcatt cccagccaca ttagggattt cttttggcct agaggtctat ggaggaatta   5940
ctaaattccc catgtaccta tgtactgaga acttttggga agctctgggc ctggtcccag   6000
```

-continued

```
atttcaattt tgtgggcaag aatgtacttt accagagtga ggagcagcct gcagggcgtt    6060
tgggctggag gcgggaggtt agtaaggggt tgctgaagtg gtaggcggat ggtgccgaag    6120
aaggcctcac taggcagtca tcatcaggat aggaagtggg cacgggattc aggagaaatc    6180
tggactttac agtggacagg atgtggtgac tgaacgtgac agtgtgggaa aaagaatgca    6240
gggtgattcc cgggctcatg gcttgagaaa tgagaccact gttgtgcctc caagtgacat    6300
gggaggctat agaaagtgac atgggaggct atagaaagtg acatgggagg ccatagaaag    6360
tgacatggga ggccatagaa agtgacatgg gaggccatag aaagtgacaa gggaggccat    6420
agaaagtgac atgggaggcc atagtgacat gggaggccat agaaagtgac atgggaggct    6480
atagaaagtg acatgggagg ccatagaaag tgacatggga ggccatagaa agtgacatgg    6540
gaggccatag tgacatggga ggccatagaa agtgacatgg gaggctatag aaagaggaga    6600
tacaaggttc taagtgcagg cgataatgat ctctatttgg gactggcttc atttgaggtg    6660
cctttaggag agccgagtgg cctatgcaca gctgggtctg ctatgcagca ggaaggctaa    6720
gttggagaca gatgtgagaa ctaaccatga aggaggtaat aatgcagacc aagggtctgg    6780
ttgaaatttc ttctccccca gtccagggtg cagcgggtga gtgaaaatat gtgtgtttgt    6840
gtgtctgtct tcctagtcgg gagagaagac tgagtttgtg gctctgcgga gcatcaccat    6900
ttaaggaggg ggaaaaggag acagaaggaa ttaccagaac actccagagg gctccaagac    6960
tgtatggtgg gatctagatg gccaggagga ggggagcaaa aaggaaagag tcatccacag    7020
tatcagtagg atgccagttg aagtgttttt gctgcctccc ggttatcggt gactttgatg    7080
aaagctgtct tctggtggtc atgggggtgg aggccagatc acaaggaagc tgggaatggt    7140
agatgagata gtaggggctt gcatattcat tactgtctcg cagagagaaa cctgaggcta    7200
agaggggtct tggatcaaag gatggggtgg gtttatctgg tttcggggct tttgttttta    7260
atgagaagga gtcatttctg tgctgctagg agggatcaat ggaataggtg gggttaaaga    7320
tacagtacgg aatctacagt tgatggcttg atgtgacaag gtcctcaagg agcctgaaag    7380
gaaggggtgg ggtccaaggg caaaaccgag gtatgagaag aaggatgcac aaggatggtt    7440
tcgagtagac agtattgttg gtagggacat gaaggaagtt tagtggtcta ttgcagctag    7500
cctgtgttcc cagtgaacct ggaaacaagg ttctcatctg tgctcaggcc tcaggccaga    7560
aagggcaagg cagcagaggg gcaaggcagc aggctgagcc ccatttcccc ttgccataat    7620
actgctgtgc ccctctggta ccgaaaatca ggagtttcca gtgcaatata atattataca    7680
agttacactg tattataatg tgtattgtct tttagtgtgt taaccaaatt actgcagtat    7740
taaatgcaaa ttatactttg tttaactgat tcttctcttc atttttagtt agaaatcctg    7800
tgttctgtca acattctcca gtttatattc attgccttaa gactggacaa gatcatccac    7860
tggccctggc ttgtatgtaa cttttaaaat ccttaaataa acttcttttt tattataaaa    7920
gtaattcata ttcactgtac aaagcttgga aaagacggac aagcagaagt aatagcctaa    7980
tagtcaccca taatcccacc atggggagat aacatggtta gtgtttttat gtctgtgttt    8040
tatacaaaca gtttggatat aactgtgtgc accattttgt atcctgattt ttttgtttta    8100
atgttgtatc ataaacattt tatcatgtta ataaaaggtc tttataaaca tgacttctaa    8160
agtttaattg atacaaaata ttcttcaagt gcatgtatca gaccatcctc ttatttctaa    8220
aatatggtat ttccattgtt gccagtgttg aatgatttta aatcatactg cagtatatat    8280
gtttatgcat taaaattttt gccttttgtt ttttggttgt tttcttagga aatagtccag    8340
aaatagtgtt actgagctag aggttgggaa ctatttgaga ttcctatata cgtatactgc    8400
```

-continued

```
actgccaact tgcttttcca aaagccatac ctggccaggc gcagtggctt acacttacag   8460
tcccagcact ttgggaggcc gaggtgagct gatcacttga gctcaggagt tcgagaccaa   8520
cctgtgcaat gtagcaagac cctgtctcaa aagaaaaaaa aaaaaagcca tacccattta   8580
cactcttgct ggtggtggca tctatgtcat gcttctaaac tgtgacttca gttactgggc   8640
atttggttga aattaactgt gaataaatgg gtagatggat gcagagatag aaagataagt   8700
ggcaaggtag aaattagaga acacagtata gattccacta ttaaatgcat ggaaaaaaga   8760
tggagactaa aggcagaaga gttccattgc cactgggagg taaggtcatg ctagtgtttt   8820
tgttcggttt tattttctct gttgtttgat gtataatttt gcatacaata tattttatgt   8880
attaaatata gctaccctta aaaagtgaaa agtatagtaa agaattggga gcagagaaga   8940
aatgaaggga acctaagtat actccatatt taaagatggg aataatcact tctgcccaaa   9000
gtctttgata aaacattcat aataaaaaat attcagtcac tcatcctaca acttcacagt   9060
gctgtatctg gagaatggtc attgggttca aaactgtttc tgttgtgacg tgaaggaaac   9120
atatctaaac aagaccaaat tttttcgtat aagatactgt cagggaaaaa aaagattagt   9180
aattttgaga gctttccaca aatgagaaga aagatttttt ctgcccttca tcctctgtag   9240
atcccagttg atgaagcagt ctgagtacat gtttcccata gtgagcaaga gaaaacaagg   9300
aagcctattg agatctaaca ttccacccat gaagggaact tcagtaaaaa ggagaatctc   9360
atcacagaat ggggaacggg gaagaaaggc tgtgcataga ctctgcagag aaacctacaa   9420
tcaagaactg gtcaggagaa gtaaaattcg tatgccaact caaatcatag atctaaaaga   9480
aaatgtaaaa ctatagatct gttaggaaat aacataggac agaatctttg gggtttgcaa   9540
ttaggcagag agtacttaga aatggcactg ttaatatggt ccatacgaga gagaaatcat   9600
aaatttggac ttcctcaaaa ttaaaatgaa atgaagacag gccacagact gggagaaaat   9660
atttgcaaag cacacatcaa aacactgact tgcacccaga acatacagag aactcttaaa   9720
aactcaaaac tgcaaaaaga aacacctaaa aattggcaaa agagttgaca atttgcgaag   9780
gggatataca catggcgaaa aagcacagga aaagatgctc aacgccatta caggttaggg   9840
aagacaaact acaaccagga tgagggcccg aaacacatgg cttcagaatg gtgaaactca   9900
gcaacactga cgaggccacg tgcctgggag gatgcagagg aactgggaca ctccagtgtt   9960
actggcggga aggcaggtgg tacgggcact gtagaaaatg gtttggccat ctctgatgca  10020
gttaaaagcg cacttcccgt gggacttggc tgccccactc ctgggtataa gatttacccc  10080
cagagaagtg aaagcgcgca gccttgtaga aacccacaca ccagtgtttg tagcagtctt  10140
gtttgcattt tggatagcgg ccttgtttgg ttttcacaaa ccaccctcag cggacagtca  10200
gataaactgt aggcatccat acaatggaat accactcaga tctgagaggg aacgacctgt  10260
ggatacaggg agggaacaac ttggatgaat ctcattagag acattatgtg gatggcggga  10320
agccagtctc aacaggttac ttgtctcgcg atgccatcta cataaagttc cagcagagac  10380
aaaagtacag tgagagaaca gatcagtgtt tgccggggct aatggtgggg acggtgtgat  10440
agtgaaggga cagcacggag agttttgcag ggtgacagac ctcttctgca tcctgccaac  10500
ggctgtgtga atctacttgt gtgaagactc agggaactca caccaaagga agacggtcac  10560
ttttcctact gtatgataga taattaataa aaagggagaa cggaggagtg tcgtcccagg  10620
aggcagggca ggagggcgaa gacgtgtcac aggggagcct ggccaagtgg cgcccccgga  10680
actcgtcctc tgggcttgtg tgtggatgag acaaggtcta cctggtacga cagggacata  10740
ctgggaatgc gcccttgccg tggaggcggg gacccggcag cgctacgtat ccagcatcaa  10800
```

```
cctgtatcca gcatcaaccc gccaagttca ctaacttggt aggggtgagg ttagggatcc  10860
ttaggagccc aggcagccag actttctggg gagcccattc ccatttgtgt tgccaaagta  10920
cccccagcag gttgtgggaa tgttgcctgt gaagagagtc tgttggggtg agatcttgtg  10980
tgtgtgcaca gggtgacagt tgtgtcccat ttcccgggaa gctgtgatgg cagcagaacc  11040
tagaggagcc tgagagagtg tgggagagtg ggcctctgga agagtagagg ctgcggagcc  11100
aggtgcaggg ctgtctgtca cccaaaggaa gagggactga tgactcactg agcgtgtgtg  11160
tcccctggtg gcagcaggcc ccatagtgaa cataccatac cttttctgtc ctgagcgatg  11220
ctcccagcag tcctgggaga tggaacggtc cttattcggc tcacaggaag gaccgcctta  11280
actggacaga cacagcaagg tgctaaagat gccttccatc agaggccagg ttggaagctc  11340
taaagagact tctcttgctg ttctctcacc cacccccagg ttgtgtgtgt cccgctgtgg  11400
attctcatgt cctttctgtg cctggtggtc ctctactaca ttgtgtggtc cgtcttgttc  11460
ttgcgctcta tggatgtgat tgcggacagc gcaggacaca cataaccatg gccctgagct  11520
ggatgaccat cgtcgtgccc cttcttacat ttgaggtaag cgttccacgg gaagcctctt  11580
cagcccctga agcttgcgct tcccctgaca ggattctgca cccctagaaa ggcagcctct  11640
gtccctcgag ctcacagtga gcccactcca ggagaggggga gagaacacag ccatctccga  11700
gagggagctt cggtgaaagg agagcatcct tcctttctct tgggggcagc acgtggggct  11760
ggcagggaga agagtgcacc tttttagcca tggtgcctct gtatggctcc agtttccact  11820
ctggggaaag cagagtggga tgtcagattt gtgtattgga gtcacgtgga gaattctaga  11880
atgggagctg ttgactcctt agaacaaaca cccggaggag tttgccataa aactgctggc  11940
actgggaact tttcaagtgg ataggctatt gccgagctct gaagagggac ataaaagctc  12000
atttcgagct ttccccaggg ataggtggtt tcctgccttt ttctggcggt gctgatgttc  12060
cctcttgtgg gagctcacgc gggggtgggg tggtggggag gaactgccta atgaagtctg  12120
gcttccgcct ctgcccattt tcggtgctgg catcaaccgg gactatgtct ctttctttag  12180
attctgctgg ttcacaaact ggatggccac aacgccttct cctgcatccc gatctttgtc  12240
ccccttttggc tctcgttgat cacgctgatg gcaaccacat ttggacagaa gggaggaaac  12300
cactgtatgt actcagcatt tcagaagtcc ttggtgtgtg tctggggggg gaccaggggg  12360
tggggggtgg cggatagaag tctaggaagg gatgagtccc cgagggcccc aatttagaag  12420
cttgtgtggg aaagtgaggg ctgaggaaat tctgggacct tctaagggaa gggcatgccg  12480
taactctggt gttctgctgg cctgcaccgg gacttttctc gcagtgcacg ctgccatttg  12540
aggtagaacc agacacggca ggcaacctct cagagatccc gttccctcct ctgcaaaatg  12600
gggatcaaga cagattcttc ccaggcccgg gagggtttga tggaaaatcc acatctccca  12660
cccaaacctg ggattcatcc taggtccctg ttggccgctc tgcctccccc atatccttgc  12720
tgccatcacc cgagtcttgc ctgtcttgcc ttgctaacac tctattcccc tccacctgct  12780
tgctgaggca gacacttcca aaacgatctc tgcagagggt gccttcctgg caaggctgtg  12840
ggctccatgg cacggaagcc cagagcattg cccttcggaa agccagtggg tttgggggca  12900
gggcctcact gcagcccagc agcccgggct gtgcttgctg tttgtgcctc tgccccctac  12960
cccgcacccg ggagcaggga gggcttgcac cgagctgaca ctccagtagc ctacagagag  13020
gagtagtggg actgggaaag tggctttaag gtggctccat gagttcaggc cccctcctgg  13080
ccaacccgtg catgactacc gccctcacgg attccagagg gtgacagaaa tcttgttctt  13140
gggtggcact gtcatccatg agtttatcct ggctggagaa gattagcgga agacaccgta  13200
```

-continued

```
gtctgcgcac cacagatatt ttgagactca ctggagcagt agttctcaaa tttgggcatc  13260
cagcagaatc ccaaaagggc caggaaaagg ggaccgctgg agcccaccct agcccgactc  13320
agtttctgga ggtctgggct ggggcccgag aatggcatcc ctaactaggc cccgtggacg  13380
ctgtccctgc cggtccggga accccactcc aagcaccaca gagctagcat ttgcacttct  13440
tccccatttt gggtactcaa gccctgttca ggctttgtga ctcaggagtc tggataaagt  13500
atgttatgac attgtaggag tgaaacttct tgttacggaa agaaagttaa caggaaggtc  13560
agttgagcct cgtgtgtgaa ataaaaaatt cttatttttc agggtggttt ggtatccgca  13620
aagatttctg tcagtttctg cttgaaatct tcccatttct acgagaatat ggaaacattt  13680
cctatgatct ccatcacgaa gataatgaag aaaccgaaga gaccccagtt ccggagcccc  13740
ctaaaatcgc acccatgttt cgaaagaagg ccagggtggt cattacccag agccctggga  13800
agtatgtgct cccacctccc aaattaaata tcgaaatgcc agattagatg ccacttccgg  13860
ggacagagct taagtggact gggacgcact ctctccgcct tcctctgccc cctcgttcac  13920
cccgcagacc agaaccagta ctggagctgg gtctccaggt acgtccatct catgccttgt  13980
ttgcatccag cgcctatcag ccactcacca cgacgggacg cggaagtggc aggtgacggg  14040
ggtgtgtgcc agcagatgcg gatgccagga agagtgtgag aacaggggtg ggattaccgt  14100
ctgtctggga ggggctccag gtacccctct tccccgtcag acccactggg agatggctgc  14160
ttgccaggcc cccagaagga acatctgtct atacggtgct gaaatcccaa tcaaaagtat  14220
tgtttagaaa tgtatttctc cacagggctg acctcctgca gctcgctgag cactcccagg  14280
tcctcagcac tcccaggtcg tggctggggc agtcagtagg aactgtaact atgtctctga  14340
tgcaccacgt gtttagacac agcacagtcc tttttctgt tcctactgtg gaagtagttt  14400
ctctttgggc atgctgacag cagtttttca tagcctcacg gatgagccct ttctacggga  14460
gtgactccat gcttgtatac agagtattta tacaaatgtt ttagcatctt catatgcggt  14520
gttaacccct agttctgtac agcatattct gttcaagtat ttttttacaa gcttgtgctg  14580
taggcacatg ccttctgctg cagaagtgga cgcccgtggc acactccccc cccccccccg  14640
tggggtgcca cgccttcatg ggacattgcc acttctgccc tggaactcgt gcaggtacgt  14700
agtagctgct actgccacaa cggcaacacc aagcaagaga tggtccatgc ttttctgacg  14760
ttctcagaat agtggctagc ttcaaacctg acaagcgctg cttgaagccg gaacactaga  14820
gaatgttgct gagagcagaa acggccacgc gggtcacgac tatgcgtggg aaagtctcaa  14880
gcttccctcc tgccagcaac aagaaggctt tggagtaggc atgatgtttt cacgtgtgcg  14940
tgccgtttct ccaagcactg caggttccac cgtgtgtcag aggctgcaag tttaacatcc  15000
tcctgcctga aaacaaatag gtcctttgct gaaaagaggg taaaaaaaga gctttgatct  15060
tctcagccag gagaagaggg tggtgttttc acgcgggcaa ctgctcgccg gcctacatgg  15120
ggttaattca agtctgctgc gagcacgact ccgcccttgg cactggcctc cagcaagccc  15180
tgttctcttt ggggtacagg ggaacgggat ggtttagact ttcctgctca gtgtgtaaaa  15240
aatgtagcta aagccactat ttttgctctc cttaagctgt tcaataaacc ggttcctcat  15300
tttacacgtg catgatgtgt atcttctttg ctggatgggc caggaaactg gagtggtcct  15360
ctcagccagc ctcagaggaa agaaatctct agctggcaca ggcagccagt gagtgaggct  15420
ggcggctgca ggggcacagc ctttagaatg agtccttcag tgcacaggtc ccagggtata  15480
cggggtagtg ggaggaagga ggggacgcct cgcagatgcc actgttggct gggctacacc  15540
ttgccacact tgttactgct taggaggctt tctggagtgt tccttgggtg ctacgacaat  15600
```

```
ctgcagcaga cactgtcctt tcaccgctcc tggtcctcgt ttgctcccca gtgatgtcaa  15660
cagctgagga ctgctcacgc tgcaacaaaa ggctctgcag tcgctgtcta gcttgcccta  15720
gtcgtctcta gagttctgcc tgaactgaaa ctcaagtggg gttcagctca tgacttgtgg  15780
caattgacca ggaaattcac cagttgctgt ggctggaagg attttcagtc ctgtgggttg  15840
taaccagagg ccacaggtgg attctgcctt aggctcatga gatttccgac ttgctgttga  15900
agaaaatgcc ttgtgaagtg acaacagtag ctctgaccca actgccggtg cctcgctagt  15960
tcctatacgt cccactggat cctcacagcc ccgggaagca ggtgctacta ctcttatccc  16020
cgggaggaga cagaggccga gagaggttaa gtgacgtgcc caagtcacac agctcggcag  16080
cggccgggtt gagcatcagc agtctgtttg cagacccctc actgtcaccc cctgagccag  16140
tgcgccttgg gccctgcggt caggatgtct caagcgtgga ggcatcaccg gttcgtggca  16200
gtctctggaa ggtcactgag ctctgtgccc agaatcgagt cgggggagtc tgtgcagagg  16260
tggccctgtg tgtggggaca gtgtgtgaca cagacactgc tttggatgga cacctctccc  16320
gtgacctcct agcatccaat cccaaaggaa caactgttgc agagatggac cgctggacac  16380
aaacccacgt gcgtttctct ggagacactg gccaaggaaa acaaaaacatg ctcgaaggcc  16440
aacagctgca tgccccaccg cgatgtgacc gcagacaccc ggggtgtaga agggtctctg  16500
cctggtgggg ggacacgtgc aggccgagga gaggcaggaa ggaggctgcc tccgactccc  16560
cactggactg catggcgacg gcgtgtggtg gggcagtcag ctaagccatt tgcctaaggg  16620
gctgtcgggc atctgcgtgc tggggaccga cagtgtgggt gtgttaggag gatctgtatg  16680
gagcacattg ctgcctctgg ctaggacagg gtggaaaggg tggcgtggct acagcctgac  16740
ccatgggcac cgtcctaccc tttgttctgt gcttccgagt gtcagtcatg tgctggggtc  16800
tgtgggccca tgactcagac ggtgagctct gaccttcctg agccagggct ttgctgtagt  16860
tgtgcctggc tcaggagctc taggacaagg ggaccgctcc aggtctgcat ctacggtgtg  16920
gcagggcccc tcggcactct tgtgcactag tgtcatcttt cccattgaaa tgactgtgag  16980
gaccagaatg tgcacatgca gatgggcagc tacttgtctg ccttggccct ttattacaca  17040
acttgctggg ggtggagatg ccaccccccg gcagtcagag cccctttatg atgtcatggg  17100
gctggttaca tgactgccaa ggggtgctgc tggccacact gcactagcaa gtttgccaga  17160
tggaggacaa gcgatcattg agtatggctc gctgtgaaga aagaaattcg agaggacagg  17220
atcatggctt ggaaagggtg cctttccctc cccagttgca gtcagagacc taccttcacc  17280
cagcagatcc ttcccctgcc tgggacgacc cggggtccac tgggagccct aacttgaggc  17340
tgctgacaga agaaatcgct ttccaacctc tggccgagga agcttcgttc agaaggccgc  17400
accctgacgg tgacgtcccg ccccagggag aagataatct cctctccctc ccctttccac  17460
agaaactgtg gagactggtc agcagcaacc agttttcgtc catctggtgg gatgacagtg  17520
gggcttgtag agtgatcaat caaaaactct ttgaaaagga gattctcaaa agggacgtcg  17580
cacacaaagt gtttgccaca acttcgataa agagcttctt ccgccagcta aacttgtatg  17640
gcttccgaaa acggcgtcaa tgcactttca ggaccttcac ccgcattttc tccgcaaaaa  17700
ggctggtctc catcttgaat aaggtaatga acgacaagcc tctggagggg ttaagtcggt  17760
gggctctggg gcctggtcgg gtggaagtcc caggactgcc tcctgggaag tgggcgacct  17820
caggcagggt gtggggccat cgctgtgggc ctgtgtcccc ctctgggtgg aggtgacatg  17880
aactaagagt gaatgtgggg agagggctga ggatggtgcg ggcccctctc gagtgtgtaa  17940
aatatcacag gtgccaagta gccgtatctg cgtgtcgtcc tccccggggc cagccatgtc  18000
```

```
atctggtggt tgctgtgtcc ccctgactcc acagcacatt accctgtgag gtgagcaggc  18060

caggggagtc tggtatttgt accactgtca ccctagctgg tgtctggaga ggtgctcaag  18120

tggaagcact gaagggcgcc tggcgcagga ggtgcagatg ctcctgctgc ccttggtagg  18180

tgggcccctg gtgtggaaga gccagtaccc agggcctcca acccagccgg ggtgcattct  18240

gttgccagct gacactgcat gggggaggcc cagaatcttc ttccctcctg gtctgcaact  18300

tcaaagaccc tttccgccgg ccatggacac cctaatctgc cattttgagg ctttttccaa  18360

gacggaaagg cccgccacaa cttggtaaac cttgacgatg tgaacgcgag tccccagctt  18420

cctttgggga ctgggacctt ttccagaaag gcctcctggg ccagtagagt tctcttgcac  18480

aggggcgtag atggttggta gttgtagtcc atccttgtga cttg                  18524
```

<210> SEQ ID NO 13
<211> LENGTH: 7695
<212> TYPE: DNA
<213> ORGANISM: Homo sapiens

<400> SEQUENCE: 13

```
ggcccaggag gcctttctgg aaaaggtccc agtccccaaa ggaagctggg gactcgcgtt     60

cacatcgtca aggtttacca agttgtggcg ggcctttccg tcttggaaaa agcctcaaaa    120

tggcagatta gggtgtccat ggccggcgga aagggtcttt gaagttgcag accaggaggg    180

aagaagattc tgggcctccc ccatgcagtg tcagctggca acagaatgca ccccggctgg    240

gttggaggcc ctgggtactg gctcttccac accaggggcc cacctaccaa gggcagcagg    300

agcatctgca cctcctgcgc caggcgccct tcagtgcttc cacttgagca cctctccaga    360

caccagctag ggtgacagtg gtacaaatac cagactcccc tggcctgctc acctcacagg    420

gtaatgtgct gtggagtcag ggggacacag caaccaccag atgacatggc tggccccggg    480

gaggacgaca cgcagatacg gctacttggc acctgtgata ttttacacac tcgagagggg    540

cccgcaccat cctcagccct ctccccacat tcactcttag ttcatgtcac ctccacccag    600

agggggacac aggcccacag cgatggcccc acaccctgcc tgaggtcgcc cacttcccag    660

gaggcagtcc tgggacttcc acccgaccag gccccagagc ccaccgactt aacccctcca    720

gaggcttgtc gttcattacc ttattcaaga tggagaccag ccttttgcg gagaaaatgc     780

gggtgaaggt cctgaaagtg cattgacgcc gttttcggaa gccatacaag tttagctggc    840

ggaagaagct ctttatcgaa gttgtggcaa acactttgtg tgcgacgtcc cttttgagaa    900

tctccttttc aaagagtttt tgattgatca ctctacaagc cccactgtca tcccaccaga    960

tggacgaaaa ctggttgctg ctgaccagtc tccacagttt ctgtggaaag gggagggaga   1020

ggagattatc ttctccctgg ggcgggacgt caccgtcagg gtgcggcctt ctgaacgaag   1080

cttcctcggc cagaggttgg aaagcgattt cttctgtcag cagcctcaag ttagggctcc   1140

cagtggaccc cgggtcgtcc caggcagggg aaggatctgc tgggtgaagg taggtctctg   1200

actgcaactg gggagggaaa ggcacccttt ccaagccatg atcctgtcct ctcgaatttc   1260

tttcttcaca gcgagccata ctcaatgatc gcttgtcctc catctggcaa acttgctagt   1320

gcagtgtggc cagcagcacc ccttggcagt catgtaacca gccccatgac atcataaagg   1380

ggctctgact gccgggggt ggcatctcca cccccagcaa gttgtgtaat aaagggccaa    1440

ggcagacaag tagctgccca tctgcatgtg cacattctgg tcctcacagt catttcaatg   1500

ggaaagatga cactagtgca caagagtgcc gaggggccct gccacaccgt agatgcagac   1560

ctggagcggt ccccttgtcc tagagctcct gagccaggca caactacagc aaagccctgg   1620
```

```
ctcaggaagg tcagagctca ccgtctgagt catgggccca cagaccccag cacatgactg   1680

acactcggaa gcacagaaca aagggtagga cggtgcccat gggtcaggct gtagccacgc   1740

caccctttcc accctgtcct agccagaggc agcaatgtgc tccatacaga tcctcctaac   1800

acacccacac tgtcggtccc cagcacgcag atgcccgaca gcccccttagg caaatggctt   1860

agctgactgc cccaccacac gccgtcgcca tgcagtccag tggggagtcg gaggcagcct   1920

ccttcctgcc tctcctcggc ctgcacgtgt ccccccacca ggcagagacc cttctacacc   1980

ccgggtgtct gcggtcacat cgcggtgggg catgcagctg ttggccttcg agcatgtttt   2040

gttttccttg gccagtgtct ccagagaaac gcacgtgggt ttgtgtccag cggtccatct   2100

ctgcaacagt tgttcctttg ggattggatg ctaggaggtc acgggagagg tgtccatcca   2160

aagcagtgtc tgtgtcacac actgtcccca cacacagggc cacctctgca cagactcccc   2220

cgactcgatt ctgggcacag agctcagtga ccttccagag actgccacga accggtgatg   2280

cctccacgct tgagacatcc tgaccgcagg gcccaaggcg cactggctca gggggtgaca   2340

gtgaggggtc tgcaaacaga ctgctgatgc tcaacccggc cgctgccgag ctgtgtgact   2400

tgggcacgtc acttaacctc tctcggcctc tgtctcctcc cggggataag agtagtagca   2460

cctgcttccc ggggctgtga ggatccagtg ggacgtatag gaactagcga ggcaccggca   2520

gttgggtcag agctactgtt gtcacttcac aaggcatttt cttcaacagc aagtcggaaa   2580

tctcatgagc ctaaggcaga atccacctgt ggcctctggt tacaacccac aggactgaaa   2640

atccttccag ccacagcaac tggtgaattt cctggtcaat tgccacaagt catgagctga   2700

accccacttg agtttcagtt caggcagaac tctagagacg actagggcaa gctagacagc   2760

gactgcagag ccttttgttg cagcgtgagc agtcctcagc tgttgacatc actggggagc   2820

aaacgaggac caggagcggt gaaaggacag tgtctgctgc agattgtcgt agcacccaag   2880

gaacactcca gaaagcctcc taagcagtaa caagtgtggc aaggtgtagc ccagccaaca   2940

gtggcatctg cgaggcgtcc cctccttcct cccactaccc cgtataccct gggacctgtg   3000

cactgaagga ctcattctaa aggctgtgcc cctgcagccg ccagcctcac tcactggctg   3060

cctgtgccag ctagagattt ctttcctctg aggctggctg agaggaccac tccagtttcc   3120

tggcccatcc agcaaagaag atacacatca tgcacgtgta aaatgaggaa ccggtttatt   3180

gaacagctta aggagagcaa aaatagtggc tttagctaca ttttttacac actgagcagg   3240

aaagtctaaa ccatcccgtt cccctgtacc ccaaagagaa cagggcttgc tggaggccag   3300

tgccaagggc ggagtcgtgc tcgcagcaga cttgaattaa ccccatgtag gccggcgagc   3360

agttgcccgc gtgaaaacac caccctcttc tcctggctga gaagatcaaa gctctttttt   3420

taccctcttt tcagcaaagg acctatttgt tttcaggcag gaggatgtta aacttgcagc   3480

ctctgacaca cggtggaacc tgcagtgctt ggagaaacgg cacgcacacg tgaaaacatc   3540

atgcctactc caaagccttc ttgttgctgg caggagggaa gcttgagact ttcccacgca   3600

tagtcgtgac ccgcgtggcc gtttctgctc tcagcaacat tctctagtgt tccggcttca   3660

agcagcgctt gtcaggtttg aagctagcca ctattctgag aacgtcagaa aagcatggac   3720

catctcttgc ttggtgttgc cgttgtggca gtagcagcta ctacgtacct gcacgagttc   3780

cagggcagaa gtggcaatgt cccatgaagg cgtggcaccc cacggggggg gggggggagt   3840

gtgccacggg cgtccacttc tgcagcagaa ggcatgtgcc tacagcacaa gcttgtaaaa   3900

aaatacttga acagaatatg ctgtacagaa ctaggggtta acaccgcata tgaagatgct   3960

aaaacatttg tataaatact ctgtatacaa gcatggagtc actcccgtag aaagggctca   4020
```

-continued

```
tccgtgaggc tatgaaaaac tgctgtcagc atgcccaaag agaaactact tccacagtag   4080
gaacagaaaa aaggactgtg ctgtgtctaa acacgtggtg catcagagac atagttacag   4140
ttcctactga ctgccccagc cacgacctgg gagtgctgag gacctgggag tgctcagcga   4200
gctgcaggag gtcagccctg tggagaaata catttctaaa caatactttt gattgggatt   4260
tcagcaccgt atagacagat gttccttctg gggcctggc aagcagccat ctcccagtgg    4320
gtctgacggg gaagaggggt acctggagcc cctcccagac agacggtaat cccacccctg   4380
ttctcacact cttcctggca tccgcatctg ctggcacaca cccccgtcac ctgccacttc   4440
cgcgtcccgt cgtggtgagt ggctgatagg cgctggatgc aaacaaggca tgagatggac   4500
gtacctggag acccagctcc agtactggtt ctggtctgcg ggtgaacga gggggcagag    4560
gaaggcggag agagtgcgtc ccagtccact taagctctgt ccccggaagt ggcatctaat   4620
ctggcatttc gatatttaat ttgggaggtg ggagcacata cttcccaggg ctctgggtaa   4680
tgaccaccct ggccttcttt cgaaacatgg gtgcgatttt agggggctcc ggaactgggg   4740
tctcttcggt ttcttcatta tcttcgtgat ggagatcata ggaaatgttt ccatattctc   4800
gtagaaatgg gaagatttca agcagaaact gacagaaatc tttgcggata ccaaaccacc   4860
ctgaaaaata agaatttttt atttcacaca cgaggctcaa ctgaccttcc tgttaacttt   4920
ctttccgtaa caagaagttt cactcctaca atgtcataac atactttatc cagactcctg   4980
agtcacaaag cctgaacagg gcttgagtac ccaaaatggg gaagaagtgc aaatgctagc   5040
tctgtggtgc ttggagtggg gttcccggac cggcagggac agcgtccacg gggcctagtt   5100
agggatgcca ttctcgggcc ccagcccaga cctccagaaa ctgagtcggg ctagggtggg   5160
ctccagcggt cccctttcc tggccctttt gggattctgc tggatgccca aatttgagaa    5220
ctactgctcc agtgagtctc aaaatatctg tggtgcgcag actacggtgt cttccgctaa   5280
tcttctccag ccaggataaa ctcatggatg acagtgccac ccaagaacaa gatttctgtc   5340
accctctgga atccgtgagg gcggtagtca tgcacgggtt ggccaggagg gggcctgaac   5400
tcatggagcc accttaaagc cactttccca gtcccactac tcctctctgt aggctactgg   5460
agtgtcagct cggtgcaagc cctccctgct cccgggtgcg gggtaggggg cagaggcaca   5520
aacagcaagc acagcccggg ctgctgggct gcagtgaggc cctgccccca aacccactgg   5580
ctttccgaag ggcaatgctc tgggcttccg tgccatggag cccacagcct tgccaggaag   5640
gcaccctctg cagagatcgt tttggaagtg tctgcctcag caagcaggtg gaggggaata   5700
gagtgttagc aaggcaagac aggcaagact cgggtgatgg cagcaaggat atgggggagg   5760
cagagcggcc aacagggacc taggatgaat cccaggtttg ggtgggagat gtggattttc   5820
catcaaaccc tcccgggcct gggaagaatc tgtcttgatc cccattttgc agaggaggga   5880
acgggatctc tgagaggttg cctgccgtgt ctggttctac ctcaaatggc agcgtgcact   5940
gcgagaaaag tcccggtgca ggccagcaga acaccagagt tacggcatgc ccttccctta   6000
gaaggtccca gaatttcctc agccctcact ttcccacaca agcttctaaa ttggggccct   6060
cggggactca tcccttccta gacttctatc cgccaccccc cacccctgg tccccccca     6120
gacacacacc aaggacttct gaaatgctga gtacatacag tggtttcctc ccttctgtcc   6180
aaatgtggtt gccatcagcg tgatcaacga gagccaaagg gggacaaaga tcgggatgca   6240
ggagaaggcg ttgtggccat ccagtttgtg aaccagcaga atctaaagaa agagacatag   6300
tcccggttga tgccagcacc gaaaatgggc agaggcggaa gccagacttc attaggcagt   6360
tcctccccac caccccaccc ccgcgtgagc tcccacaaga gggaacatca gcaccgccag   6420
```

```
aaaaaggcag gaaaccacct atccctgggg aaagctcgaa atgagctttt atgtccctct   6480

tcagagctcg gcaatagcct atccacttga aaagttccca gtgccagcag ttttatggca   6540

aactcctccg ggtgtttgtt ctaaggagtc aacagctccc attctagaat tctccacgtg   6600

actccaatac acaaatctga catcccactc tgctttcccc agagtggaaa ctggagccat   6660

acagaggcac catggctaaa aaggtgcact cttctccctg ccagccccac gtgctgcccc   6720

caagagaaag gaaggatgct ctcctttcac cgaagctccc tctcggagat ggctgtgttc   6780

tctcccctct cctggagtgg gctcactgtg agctcgaggg acagaggctg cctttctagg   6840

ggtgcagaat cctgtcaggg gaagcgcaag cttcaggggc tgaagaggct tcccgtggaa   6900

cgcttacctc aaatgtaaga aggggcacga cgatggtcat ccagctcagg gccatggtta   6960

tgtgtgtcct gcgctgtccg caatcacatc catagagcgc aagaacaaga cggaccacac   7020

aatgtagtag aggaccacca ggcacagaaa ggacatgaga atccacagcg ggacacacac   7080

aacctggggg tgggtgagag aacagcaaga gaagtctctt tagagcttcc aacctggcct   7140

ctgatggaag gcatctttag caccttgctg tgtctgtcca gttaaggcgg tccttcctgt   7200

gagccgaata aggaccgttc catctcccag gactgctggg agcatcgctc aggacagaaa   7260

aggtatggta tgttcactat ggggcctgct gccaccaggg gacacacacg ctcagtgagt   7320

catcagtccc tcttcctttg ggtgacagac agccctgcac ctggctccgc agcctctact   7380

cttccagagg cccactctcc cacactctct caggctcctc taggttctgc tgccatcaca   7440

gcttcccggg aaatgggaca caactgtcac cctgtgcaca cacacaagat ctcaccccaa   7500

cagactctct tcacaggcaa cattcccaca acctgctggg ggtactttgg caacacaaat   7560

gggaatgggc tccccagaaa gtctggctgc ctgggctcct aaggatccct aacctcaccc   7620

ctaccaagtt agtgaacttg gcgggttgat gctggataca ggttgatgct ggatacgtag   7680

cgctgccggg tgacc                                                    7695
```

<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 14

```
gggcgaattg ggcccgacgt cgcatgctcc cggccgccat ggcggccgcg ggaattcgat     60

atcactagtg aattcgcggc cggcgattgg gcccgacgtc gcatgctccc ggccgccatg    120

gcggccgcgg gaattcgatt ccttaattaa gtcgactggg acccaaactt tggagtcgtt    180

gacagatgtg acaggtgaag cctgggatga catcgccaaa aatgcaacgt ctcactcatt    240

gtcactactc ccagggctca gtcgtcactg ggaaaaatct ccagaaggta gcgcgggcca    300

aggtgacagg tgtctgccaa gatctgcccg ccagactccc gggcggcgcg ctccctccct    360

gcaggccttc agcccgtcag catccccttc ctcggggccc tgctcactcc cagcctccat    420

ccccctgcca tctcctccgc cggtcgcgtg cggacacaag gatggggacc tcccagcgag    480

gagcgctctg ggcggggctc cggacgcatg cgcggccctc gtacggaagc ccggaaggag    540

gggcaggggg cggtggctca ggtttctccg ggcggcggcg gcggcggcgg cggcgacggc    600

gacggcgacg gcagcgggga cggcagcagt agcgggagca gcagcgtgga cgcggctggc    660

gctggcgcca tgaacccgct gtaaggcgca ggctgtgcag cacggggtgc gggggaggag    720

gaggaggacg ccgcggtgaa gttctccgcc atgaacctga ggggcctctt ccaggacttc    780
```

```
aacccgaggt gaggcggcgt cgttggcgcc cccgggagtc cgcgctgcgg gctcgggcgc    840
gggctggtgt tcggctccgg ggaggcacgg cgggcgagat gctgcagccc gaggacccgg    900
gcgcctgccc gagcctccct gcgggtgcaa gcggtcccca ggcaaaacag tcggcctcgg    960
cgcccgcccg cttcctcctc ccgtgcccgg tgctttcagc cctgcccggg ccacggccgg   1020
aagggcccgg ccgcgagccc cgtcctgccc caagggaacc ccattctttt ctgcttgctg   1080
tccctcattg gtgtcccaac ttcttcgtct cggttccatc ctcttctgcg ccgctgcggg   1140
ccctccattc tccgcgtcag ggccgtctca ctcgacccaa cacccctacc cccaccccag   1200
ctgtttcctc cagttcctcg cagtccttgg ggtttttcctt gggtttatgc ccatccctct   1260
cttgtttgct tctttgttga acggatacct gaaacactgt tgaatccttg gagtcagtgt   1320
cggggtatgg caatacctta tataatgcat ttctgggtga gcctgatcat tttccatact   1380
cattttctca tcagtcttca ctacaagttt atttgcagga agtagatatt gctgtccttc   1440
ttttccagat ggggaacacc cagtggacag tgtggagaaa acactggcta agcactcaag   1500
cgcctgtcct tgcacttgcc cgactgtttt gtaactgttc tttaccccag gctgtgagct   1560
ccctgaagct gagaccatct cctgctcatc tcagtgtccc cagcgcctcc cacccaccgt   1620
atctggcaca tagtaggcac atataaaatg tttgtggaac taaactgagc ccaaagactt   1680
ggattggaga cgaggccata tgtaactggg tgattctctg cccttctttg gcccttctgt   1740
aaaatgagga gttggcctaa ctgatctctt aaatgcacta ctctccgaaa ggagtatccg   1800
tttcccttat ttgccagttg ggaagacgtg ctcagtaaat atttgtgtgc tgtaacctat   1860
gttaggtgct ttagatgctg gcggtctcag catggggtga agaagggctt gtacacttaa   1920
gatgccttac agtactgtgc agtgctgtac tgcgggggcc aactctgggg acctatgcct   1980
tggctgcttg ttgaggatga aaggaagttt taggggagta tttgtatgtt gagggtgcag   2040
tctccctagg gatggtgaca ttttaacttg tgagtcattg tgactttgta tgtgccctta   2100
ttccactttg agttcatgtt ctggttagga gtgccagtgt ctctaacacg gtgcagacat   2160
tatcattgtt ggcttcgaag gcatagagga ggtaacagaa ctaactgcag tcccttcctc   2220
tgctgcatca gggggttaag attggtctgc agggtagtag ggttggtgct gtggctggac   2280
aagccctgta tgtcttctat ttggagatgg tgataagaaa gttaagtaaa aactgaattg   2340
ttttgtgccc ttgggcaact cacttatcta ttgttttatc tgtagaatga gtataatctc   2400
tcagtggggt agggaggcca attaaggatt gattacaaag tgccttacaa atagaaagct   2460
acagtgactt gtttgcaagg tgacagagaa ttcagaagcc tcaagaaact gccttaagtg   2520
atcaaacagg ctaacggagt tgccaaagca aaatagtgct gcactgatac tacctttaac   2580
cgtttttttcc tttagccctt ttccccccaa aaaaattagt atatgaaatt acagtgaaat   2640
acctggtatc taagcagatt tatagtaatt ctcaacatat tcatcaatct cttaattcta   2700
cctgcattaa aatgtatttc tacctgaaaa gtttaaaggt cttttatact gtgccatttt   2760
cctgattcat tgttgccaga ggtagtgagt tccttaattt tacagatatt tcaagaggac   2820
attggccagg tattattggt aaatcagatt tgttttttta gctggtagtg tttcacctct   2880
cctgagcact cctagttttt gacagtgtgc tttagtctcc ttccatgctg aggaaggcct   2940
tctctatagg agaaagaaaa ctgaggggtg tacacaggaa gttaccttat gctggggact   3000
caaaccttga tgctactgct ttgctccctg cctctatttt tgaaccaatt caacatctcc   3060
ctcctacccc aggaccttgt cacacactgt tctctttacc aggaatgttt ccctctcttt   3120
tcctctcctc cagacctagt gaactcctat ttatcctcac ttggcacttg ctaagggaag   3180
```

```
cattcctgac ttccctgacc agatttactg ctccctgttt ctacagttcc tgtagtattt   3240
actactcctc catcatagtg catatttgta cccttgtgtc tgtctggatg cttatttgat   3300
taatacctgc ctcccccact aaactttaag ctccatgggg tcaaggccgt gactgtgtca   3360
gtatcgtagc ctgcatactt ggaatagtac ctggctcaat aaatatttgt ggagtaaata   3420
actgaataac tctccagagc ctataagata aatctagagc tgctgctttc aatcactgct   3480
ttcctggtgg tctgtggcct ggttctcttt cttctcacac tcttcccacc ttcagagtgc   3540
agccattgct ttggagagat gggagagaac atggcactaa ggcagaatat ggctatattt   3600
actttgaaga gcatgtcttt gtcatagaaa tagtcactgt catggtttgg tgggtcccaa   3660
ggcatgggtc atggctccag atccccttc cagccttttg gatcttggta agtctgaacc   3720
cactgctgcg ttggcaaggc tctggaaact atagtgacag agaatgattc acaagtgtca   3780
acactcagat gtacagggct gccagctgac ccactctacc tatttccatc tggcactgaa   3840
ctggttgatc atgaacttct tttcataatt gctttttagt tatgcaggtt aagacatgcc   3900
gaaacagatg taccggaccc acaaacaagt ccttccttga atgcctgagg cttcctaaca   3960
gtgaaagagc cctgttctta gagtaggcaa actgattctg aggcattgta ggtggtaggg   4020
atctggtagt aggtagcatt aggtgggctc ccggcactca ccatggagcc ttgaaatttt   4080
ctgctacttt gggggagttg ctggttcaga gaaggccctt ccaccctggt agccatgtgg   4140
cactggaagg ctgtgaaaac tctgctgggc cttcttagtc atctgttgtg agctcctgat   4200
gggagtgtgg tgtatccctc aggtgtgcta gactggaaca aaggctgaga agtgttgctc   4260
tgggggttcc aacttgtggg catggggtac tgatgagatc agtagtgttt ggagacttct   4320
gtatgctcca tcttcagaag acattctgga gtccatataa gttatcttgt ctcttgtttg   4380
aagcaggaaa aaggaatgcg attgctggta atatagttca ctaaagtcag ctacctggcc   4440
tctaacagtt atttgcaaag tatattataa cattgattcc tcaaacatct agattcctat   4500
ctcgtgccaa gtgatgtact aggtgctcta agtacaaaaa taaaggaata tagtcctcct   4560
ctcaatgcgt aagcctagtg gaagaagcag aaatgaaagg gaaataagaa ttcaatagag   4620
tatgaggcat tacagtgaaa gaaaccaaat gtcttagaag tacaaatggc agagctacta   4680
attctgtctc gagcaggcag ggaagagtct atagtggaaa tgacttttga gctagatttt   4740
gaattgagct agtcttttga gccagacttt tgagctagaa ttgtagggtt gtcatcagac   4800
cagagagtag gaagggtacc ttgtgaggaa gagagagaga gatcagattg ttactgtgtc   4860
tatgtagaaa aggaagacat aagaaactcc attttgatct gtactaagaa aaattgtttc   4920
tgctttgaga tgctgttaac ctgtaacttt agtcccaacc ctgtgctcac agaaacctgt   4980
gctgtaatga atcaaggttt aatggattta gggctgtgca ggatgtacct tgttaacaat   5040
atgtttgcag gcagtatgct tggtaaaagt catcgccatt ctccattctc gattaaccag   5100
ggacacagtg cactgcggaa ggccgcaggg acatctgccc aagaaagcct gggtattgtc   5160
caaggtttcc ccccactgag acagcctgag atatggcctt gtgggaaagg aaagacctta   5220
ccacccccca gcccgacacc cgtaaagtgt ctgtgctgag gaggagtagt gaaagagcgg   5280
ggcctctttg cagttgagat aagaggaagg cttctgtctc ctgctcatcc ctgggaatgg   5340
aatgtctctg tgtaaagctg accattccca ttcgttctat tctgagatag gagaaaacca   5400
ccctgtggct ggaggcgaag tatgctggca gcaatactgc tctgttactc tttgctacac   5460
tgagttgttt gggtaaagag aaacataaat ctagcctgcg tgcacatcca ggcacagtac   5520
ctttccttga acttattcat gatacagatt cctttgctca cgtttccctg ctgaccttct   5580
```

```
ccccacctgt tgccctgcta cactcccctc gctaagatag taaaaataat gatcagtaaa   5640
tactgaggta actcagaggc tagcgctggt gcgggtcctc cgtatgctga gtgccggtcc   5700
cctgggccca ctgttctttc tctatacttt gtttctgtgt cttatttctt ttctcagtct   5760
cgtcccacct gacgagaaat acccacaggt gtggaggggc tggccccttt cagtatctca   5820
gaagggacaa agtacacaaa ggcatggggt catgatagtg cctggtatgt tcaggtagtg   5880
aagaggtcca tgtggtatga gcactgcaga tgatatgtgt cgtatgaatt aaaaatacat   5940
agttactgca aatagttttt acaggttatt gtttttaaga aagcagtatc taatgcacga   6000
gtgtactgtc agtactgtca atgaactact taccactcaa gtgactgctt acgcgtcgaa   6060
tcactagtga attcgcggcc gcctgcaggt cgaccatatg ggagagctcc caacgcgttg   6120
gatgcatagc ttgagtattc tatagtgtca cctaaatagc ttggcgtaat catggtcata   6180
gctgtttcct gtgtgaaatt gttatccgct cacaattcca cacaacatac gagccggaag   6240
cataaagtgt aaagcctggg gtgcctaatg agtgagctaa ctcacattaa ttgcgttgcg   6300
ctcactgccc gctttccagt cgggaaacct gtcgtgccag ctgcattaat gaatcggcca   6360
acgcgcgggg agaggcggtt tgcgtattgg gcgctcttcc gcttcctcgc tcactgactc   6420
gctgcgctcg gtcgttcggc tgcggcgagc ggtatcagct cactcaaagg cggtaatacg   6480
gttatccaca gaatcagggg ataacgcagg aaagaacatg tgagcaaaag gccagcaaaa   6540
ggccaggaac cgtaaaaagg ccgcgttgct ggcgtttttc cataggctcc gcccccctga   6600
cgagcatcac aaaaatcgac gctcaagtca gaggtggcga aacccgacag gactataaag   6660
ataccaggcg tttccccctg gaagctccct cgtgcgctct cctgttccga ccctgccgct   6720
taccggatac ctgtccgcct ttctcccttc gggaagcgtg gcgctttctc atagctcacg   6780
ctgtaggtat ctcagttcgg tgtaggtcgt tcgctccaag ctgggctgtg tgcacgaacc   6840
ccccgttcag cccgaccgct gcgccttatc cggtaactat cgtcttgagt ccaacccggt   6900
aagacacgac ttatcgccac tggcagcagc cactggtaac aggattagca gagcgaggta   6960
tgtaggcggt gctacagagt tcttgaagtg gtggcctaac tacggctaca ctagaagaac   7020
agtatttggt atctgcgctc tgctgaagcc agttaccttc ggaaaaagag ttggtagctc   7080
ttgatccggc aaacaaacca ccgctggtag cggtggtttt tttgtttgca agcagcagat   7140
tacgcgcaga aaaaaaggat ctcaagaaga tcctttgatc ttttctacgg ggtctgacgc   7200
tcagtggaac gaaaactcac gttaagggat tttggtcatg agattatcaa aaaggatctt   7260
cacctagatc cttttaaatt aaaaatgaag ttttaaatca atctaaagta tatatgagta   7320
aacttggtct gacagttacc aatgcttaat cagtgaggca cctatctcag cgatctgtct   7380
atttcgttca tccatagttg cctgactccc cgtcgtgtag ataactacga tacgggaggg   7440
cttaccatct ggccccagtg ctgcaatgat accgcgagac ccacgctcac cggctccaga   7500
tttatcagca ataaaccagc cagccggaag ggccgagcgc agaagtggtc ctgcaacttt   7560
atccgcctcc atccagtcta ttaattgttg ccgggaagct agagtaagta gttcgccagt   7620
taatagtttg cgcaacgttg ttgccattgc tacaggcatc gtggtgtcac gctcgtcgtt   7680
tggtatggct tcattcagct ccggttccca acgatcaagg cgagttacat gatcccccat   7740
gttgtgcaaa aaagcggtta gctccttcgg tcctccgatc gttgtcagaa gtaagttggc   7800
cgcagtgtta tcactcatgg ttatggcagc actgcataat tctcttactg tcatgccatc   7860
cgtaagatgc ttttctgtga ctggtgagta ctcaaccaag tcattctgag aatagtgtat   7920
gcggcgaccg agttgctctt gcccggcgtc aatacgggat aataccgcgc cacatagcag   7980
```

```
aactttaaaa gtgctcatca ttggaaaacg ttcttcgggg cgaaaactct caaggatctt   8040
accgctgttg agatccagtt cgatgtaacc cactcgtgca cccaactgat cttcagcatc   8100
ttttactttc accagcgttt ctgggtgagc aaaaacagga aggcaaaatg ccgcaaaaaa   8160
gggaataagg gcgacacgga aatgttgaat actcatactc ttcctttttc aatattattg   8220
aagcatttat cagggttatt gtctcatgag cggatacata tttgaatgta tttagaaaaa   8280
taaacaaata ggggttccgc gcacatttcc ccgaaaagtg ccacctgatg cggtgtgaaa   8340
taccgcacag atgcgtaagg agaaaatacc gcatcaggaa attgtaagcg ttaatatttt   8400
gttaaaattc gcgttaaatt tttgttaaat cagctcattt tttaaccaat aggccgaaat   8460
cggcaaaatc ccttataaat caaaagaata gaccgagata gggttgagtg ttgttccagt   8520
ttggaacaag agtccactat taaagaacgt ggactccaac gtcaaagggc gaaaaaccgt   8580
ctatcagggc gatggcccac tacgtgaacc atcaccctaa tcaagttttt tggggtcgag   8640
gtgccgtaaa gcactaaatc ggaaccctaa agggagcccc cgatttagag cttgacgggg   8700
aaagccggcg aacgtggcga gaaaggaagg gaagaaagcg aaaggagcgg gcgctagggc   8760
gctggcaagt gtagcggtca cgctgcgcgt aaccaccaca cccgccgcgc ttaatgcgcc   8820
gctacagggc gcgtccattc gccattcagg ctgcgcaact gttgggaagg gcgatcggtg   8880
cgggcctctt cgctattacg ccagctggcg aaagggggat gtgctgcaag gcgattaagt   8940
tgggtaacgc cagggttttc ccagtcacga cgttgtaaaa cgacggccag tgaattgtaa   9000
tacgactcac tata                                                     9014
```

<210> SEQ ID NO 15
<211> LENGTH: 5954
<212> TYPE: DNA
<213> ORGANISM: Homo sapiens

<400> SEQUENCE: 15

```
ggccgcggga attcgattcc ttaattaagt cgactgggac ccaaactttg gagtcgttga     60
cagatgtgac aggtgaagcc tgggatgaca tcgccaaaaa tgcaacgtct cactcattgt    120
cactactccc agggctcagt cgtcactggg gaaaatctcc agaaggtagc gcgggccaag    180
gtgacaggtg tctgccaaga tctgcccgcc agactcccgg gcggcgcgct ccctccctgc    240
aggccttcag cccgtcagca tccccttcct cggggccctg ctcactccca gcctccatcc    300
ccctgccatc tcctccgccg gtcgcgtgcg gacacaagga tggggacctc ccagcgagga    360
gcgctctggg cggggctccg gacgcatgcg cggccctcgt acggaagccc ggaaggaggg    420
gcagggggcg gtggctcagg tttctccggg cggcggcggc ggcggcggcg gcgacggcga    480
cggcgacggc agcggggacg gcagcagtag cgggagcagc agcgtggacg cggctggcgc    540
tggcgccatg aacccgctgt aaggcgcagg ctgtgcagca cggggtgcgg gggaggagga    600
ggaggacgcc gcggtgaagt tctccgccat gaacctgagg ggcctcttcc aggacttcaa    660
cccgaggtga ggcggcgtcg ttggcgcccc cgggagtccg cgctgcgggc tcgggcgcgg    720
gctggtgttc ggctccgggg aggcacggcg ggcgagatgc tgcagcccga ggacccgggc    780
gcctgcccga gcctccctgc gggtgcaagc ggtccccagg caaaacagtc ggcctcggcg    840
cccgcccgct tcctcctccc gtgcccggtg ctttcagccc ctgcccggcc acggccggaa    900
gggcccggcc gcgagccccg tcctgcccca agggaacccc attcttttct gcttgctgtc    960
cctcattggt gtcccaactt cttcgtctcg gttccatcct cttctgcgcc gctgcgggcc   1020
ctccattctc cgcgtcaggg ccgtctcact cgacccaaca cccctacccc caccccagct   1080
```

```
gtttcctcca gttcctcgca gtccttgggg ttttccttgg gtttatgccc atccctctct   1140
tgtttgcttc tttgttgaac ggatacctga aacactgttg aatccttgga gtcagtgtcg   1200
gggtatggca ataccttata taatgcattt ctgggtgagc ctgatcattt tccatactca   1260
ttttctcatc agtcttcact acaagtttat ttgcaggaag tagatattgc tgtccttctt   1320
ttccagatgg ggaacaccca gtggacagtg tggagaaaac actggctaag cactcaagcg   1380
cctgtccttg cacttgcccg actgttttgt aactgttctt taccccaggc tgtgagctcc   1440
ctgaagctga gaccatctcc tgctcatctc agtgtcccca gcgcctccca cccaccgtat   1500
ctggcacata gtaggcacat ataaaatgtt tgtggaacta aactgagccc aaagacttgg   1560
attggagacg aggccatatg taactgggtg attctctgcc cttctttggc ccttctgtaa   1620
aatgaggagt tggcctaact gatctcttaa atgcactact ctccgaaagg agtatccgtt   1680
tcccttattt gccagttggg aagacgtgct cagtaaatat ttgtgtgctg taacctatgt   1740
taggtgcttt agatgctggc ggtctcagca tggggtgaag aagggcttgt acacttaaga   1800
tgccttacag tactgtgcag tgctgtactg cgggggccaa ctctggggac ctatgccttg   1860
gctgcttgtt gaggatgaaa ggaagtttta ggggagtatt tgtatgttga gggtgcagtc   1920
tccctaggga tggtgacatt ttaacttgtg agtcattgtg actttgtatg tgcccttatt   1980
ccactttgag ttcatgttct ggttaggagt gccagtgtct ctaacacggt gcagacatta   2040
tcattgttgg cttcgaaggc atagaggagg taacagaact aactgcagtc ccttcctctg   2100
ctgcatcagg gggttaagat tggtctgcag ggtagtaggg ttggtgctgt ggctggacaa   2160
gccctgtatg tcttctattt ggagatggtg ataagaaagt taagtaaaaa ctgaattgtt   2220
ttgtgccctt gggcaactca cttatctatt gttttatctg tagaatgagt ataatctctc   2280
agtggggtag ggaggccaat taaggattga ttacaaagtg ccttacaaat agaaagctac   2340
agtgacttgt ttgcaaggtg acagagaatt cagaagcctc aagaaactgc cttaagtgat   2400
caaacaggct aacggagttg ccaaagcaaa atagtgctgc actgatacta cctttaaccg   2460
tttttccctt tagccctttt ccccccaaaa aaattagtat atgaaattac agtgaaatac   2520
ctggtatcta agcagattta tagtaattct caacatattc atcaatctct taattctacc   2580
tgcattaaaa tgtatttcta cctgaaaagt ttaaaggtct tttatactgt gccattttcc   2640
tgattcattg ttgccagagg tagtgagttc cttaatttta cagatatttc aagaggacat   2700
tggccaggta ttattggtaa atcagatttg ttttttttagc tggtagtgtt tcacctctcc   2760
tgagcactcc tagtttttga cagtgtgctt tagtctcctt ccatgctgag gaaggccttc   2820
tctataggag aaagaaaact gaggggtgta cacaggaagt taccttatgc tggggactca   2880
aaccttgatg ctactgcttt gctccctgcc tctatttttg aaccaattca acatctccct   2940
cctaccccag gaccttgtca cacactgttc tctttaccag gaatgtttcc ctctcttttc   3000
ctctcctcca gacctagtga actcctattt atcctcactt ggcacttgct aagggaagca   3060
ttcctgactt ccctgaccag atttactgct ccctgtttct acagttcctg tagtatttac   3120
tactcctcca tcatagtgca tatttgtacc cttgtgtctg tctggatgct tatttgatta   3180
atacctgcct cccccactaa actttaagct ccatggggtc aaggccgtga ctgtgtcagt   3240
atcgtagcct gcatacttgg aatagtacct ggctcaataa atatttgtgg agtaaataac   3300
tgaataactc tccagagcct ataagataaa tctagagctg ctgctttcaa tcactgcttt   3360
cctggtggtc tgtggcctgg ttctctttct tctcacactc ttcccacctt cagagtgcag   3420
ccattgcttt ggagagatgg gagagaacat ggcactaagg cagaatatgg ctatatttac   3480
```

-continued

```
tttgaagagc atgtctttgt catagaaata gtcactgtca tggtttggtg ggtcccaagg   3540
catgggtcat ggctccagat cccctttcca gccttttgga tcttggtaag tctgaaccca   3600
ctgctgcgtt ggcaaggctc tggaaactat agtgacagag aatgattcac aagtgtcaac   3660
actcagatgt acagggctgc cagctgaccc actctaccta tttccatctg gcactgaact   3720
ggttgatcat gaacttcttt tcataattgc tttttagtta tgcaggttaa gacatgccga   3780
aacagatgta ccggacccac aaacaagtcc ttccttgaat gcctgaggct tcctaacagt   3840
gaaagagccc tgttcttaga gtaggcaaac tgattctgag gcattgtagg tggtagggat   3900
ctggtagtag gtagcattag gtgggctccc ggcactcacc atggagcctt gaaattttct   3960
gctactttgg gggagttgct ggttcagaga aggcccttcc accctggtag ccatgtggca   4020
ctggaaggct gtgaaaactc tgctgggcct tcttagtcat ctgttgtgag ctcctgatgg   4080
gagtgtggtg tatccctcag gtgtgctaga ctggaacaaa ggctgagaag tgttgctctg   4140
ggggttccaa cttgtgggca tggggtactg atgagatcag tagtgtttgg agacttctgt   4200
atgctccatc ttcagaagac attctggagt ccatataagt tatcttgtct cttgtttgaa   4260
gcaggaaaaa ggaatgcgat tgctggtaat atagttcact aaagtcagct acctggcctc   4320
taacagttat ttgcaaagta tattataaca ttgattcctc aaacatctag attcctatct   4380
cgtgccaagt gatgtactag gtgctctaag tacaaaaata aaggaatata gtcctcctct   4440
caatgcgtaa gcctagtgga agaagcagaa atgaaaggga aataagaatt caatagagta   4500
tgaggcatta cagtgaaaga aaccaaatgt cttagaagta caaatggcag agctactaat   4560
tctgtctcga gcaggcaggg aagagtctat agtggaaatg acttttgagc tagattttga   4620
attgagctag tcttttgagc cagacttttg agctagaatt gtagggttgt catcagacca   4680
gagagtagga agggtacctt gtgaggaaga gagagagaga tcagattgtt actgtgtcta   4740
tgtagaaaag gaagacataa gaaactccat tttgatctgt actaagaaaa attgtttctg   4800
ctttgagatg ctgttaacct gtaactttag tcccaaccct gtgctcacag aaacctgtgc   4860
tgtaatgaat caaggtttaa tggatttagg gctgtgcagg atgtaccttg ttaacaatat   4920
gtttgcaggc agtatgcttg gtaaaagtca tcgccattct ccattctcga ttaaccaggg   4980
acacagtgca ctgcggaagg ccgcagggac atctgcccaa gaaagcctgg gtattgtcca   5040
aggtttcccc ccactgagac agcctgagat atggccttgt gggaaaggaa agaccttacc   5100
accccccagc ccgacacccg taaagtgtct gtgctgagga ggagtagtga aagagcgggg   5160
cctctttgca gttgagataa gaggaaggct tctgtctcct gctcatccct gggaatggaa   5220
tgtctctgtg taaagctgac cattcccatt cgttctattc tgagatagga gaaaaccacc   5280
ctgtggctgg aggcgaagta tgctggcagc aatactgctc tgttactctt tgctacactg   5340
agttgtttgg gtaaagagaa acataaatct agcctgcgtg cacatccagg cacagtacct   5400
ttccttgaac ttattcatga tacagattcc tttgctcacg tttccctgct gaccttctcc   5460
ccacctgttg ccctgctaca ctcccctcgc taagatagta aaaataatga tcagtaaata   5520
ctgaggtaac tcagaggcta gcgctggtgc gggtcctccg tatgctgagt gccggtcccc   5580
tgggcccact gttctttctc tatactttgt ttctgtgtct tatttctttt ctcagtctcg   5640
tcccacctga cgagaaatac ccacaggtgt ggaggggctg gcccctttca gtatctcaga   5700
agggacaaag tacacaaagg catggggtca tgatagtgcc tggtatgttc aggtagtgaa   5760
gaggtccatg tggtatgagc actgcagatg atatgtgtcg tatgaattaa aaatacatag   5820
ttactgcaaa tagtttttac aggttattgt ttttaagaaa gcagtatcta atgcacgagt   5880
```

gtactgtcag tactgtcaat gaactactta ccactcaagt gactgcttac gcgtcgaatc 5940
actagtgaat tcgc 5954

<210> SEQ ID NO 16
<211> LENGTH: 30756
<212> TYPE: DNA
<213> ORGANISM: Homo sapiens
<220> FEATURE:
<221> NAME/KEY: misc_feature
<222> LOCATION: (1)..(30756)
<223> OTHER INFORMATION: n= a, c, g, t, unknown or other

<400> SEQUENCE: 16
gtacggaagc ccggaaggag gggcaggggg cggtggctca ggtttctccg ggcggcggcg 60
gcggcggcgg cggcgacggc gacggcgacg gcagcgggga cggcagcagt agcgggagca 120
gcagcgtgga cgcggctggc gctggcgcca tgaacccgct gtaaggcgca ggctgtgcag 180
cacggggtgc gggggaggag gaggaggacg ccgcggtgaa gttctccgcc atgaacctga 240
ggggcctctt ccaggacttc aacccgaggt gaggcggcgt cgttggcgcc cccgggagtc 300
cgcgctgcgg gctcgggcgc gggctggtgt tcggctccgg ggaggcacgg cgggcgagat 360
gctgcagccc gaggacccgg gcgcctgccc gagcctccct gcgggtgcaa gcggtcccca 420
ggcaaaacag tcggcctcgg cgcccgcccg cttcctcctc ccgtgcccgg tgctttcagc 480
ccctgcccgg ccacggccgg aagggcccgg ccgcgagccc cgtcctgccc caagggaacc 540
ccattctttt ctgcttgctg tccctcattg gtgtcccaac ttcttcgtct cggttccatc 600
ctcttctgcg ccgctgcggg ccctccattc tccgcgtcag ggccgtctca ctcgacccaa 660
cacccctacc cccaccccag ctgtttcctc cagttcctcg cagtccttgg ggttttcctt 720
gggtttatgc ccatccctct cttgtttgct tctttgttga acggatacct gaaacactgt 780
tgaatccttg gagtcagtgt cggggtatgg caatacctta tataatgcat ttctgggtga 840
gcctgatcat tttccatact cattttctca tcagtcttca ctacaagttt atttgcagga 900
agtagatatt gctgtccttc ttttccagat ggggaacacc cagtggacag tgtggagaaa 960
acactggcta agcactcaag cgcctgtcct tgcacttgcc cgactgtttt gtaactgttc 1020
tttaccccag gctgtgagct ccctgaagct gagaccatct cctgctcatc tcagtgtccc 1080
cagcgcctcc cacccaccgt atctggcaca tagtaggcac atataaaatg tttgtggaac 1140
taaactgagc ccaaagactt ggattggaga cgaggccata tgtaactggg tgattctctg 1200
cccttctttg gcccttctgt aaaatgagga gttggcctaa ctgatctctt aaatgcacta 1260
ctctccgaaa ggagtatccg tttcccttat ttgccagttg ggaagacgtg ctcagtaaat 1320
atttgtgtgc tgtaacctat gttaggtgct ttagatgctg gcggtctcag catggggtga 1380
agaagggctt gtacacttaa gatgccttac agtactgtgc agtgctgtac tgcgggggcc 1440
aactctgggg acctatgcct tggctgcttg ttgaggatga aaggaagttt taggggagta 1500
tttgtatgtt gagggtgcag tctccctagg gatggtgaca ttttaacttg tgagtcattg 1560
tgactttgta tgtgccctta ttccactttg agttcatgtt ctggttagga gtgccagtgt 1620
ctctaacacg gtgcagacat tatcattgtt ggcttcgaag gcatagagga ggtaacagaa 1680
ctaactgcag tcccttcctc tgctgcatca gggggttaag attggtctgc agggtagtag 1740
ggttggtgct gtggctggac aagccctgta tgtcttctat ttggagatgg tgataagaaa 1800
gttaagtaaa aactgaattg ttttgtgccc ttgggcaact cacttatcta ttgttttatc 1860
tgtagaatga gtataatctc tcagtggggt agggaggcca attaaggatt gattacaaag 1920

```
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgtttttcc tttagccctt ttccccccaa aaaaattagt    2100
atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
cttttatact gtgccatttt cctgattcat tgttgccaga ggtagtgagt tccttaattt   2280
tacagatatt tcaagaggac attggccagg tattattggt aaatcagatt tgttttttta   2340
gctggtagtg tttcacctct cctgagcact cctagttttt gacagtgtgc tttagtctcc   2400
ttccatgctg aggaaggcct tctctatagg agaaagaaaa ctgaggggtg tacacaggaa   2460
gttaccttat gctggggact caaaccttga tgctactgct ttgctccctg cctctatttt   2520
tgaaccaatt caacatctcc ctcctacccc aggaccttgt cacacactgt tctctttacc   2580
aggaatgttt ccctctcttt tcctctcctc cagacctagt gaactcctat ttatcctcac   2640
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctcccccact aaactttaag ctccatgggg   2820
tcaaggccgt gactgtgtca gtatcgtagc ctgcatactt ggaatagtac ctggctcaat   2880
aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atcccctttc cagccttttg   3180
gatcttggta agtctgaacc cactgctgcg ttggcaaggc tctggaaact atagtgacag   3240
agaatgattc acaagtgtca acactcagat gtacagggct gccagctgac ccactctacc   3300
tatttccatc tggcactgaa ctggttgatc atgaacttct tttcataatt gctttttagt   3360
tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt gggggagttg ctggttcaga gaaggccctt   3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tgggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt atttgcaaag tatattataa cattgattcc   3960
tcaaacatct agattcctat ctcgtgccaa gtgatgtact aggtgctcta agtacaaaaa   4020
taaaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200
tgacttttga gctagatttt gaattgagct agtcttttga gccagacttt tgagctagaa   4260
ttgtagggtt gtcatcagac cagagagtag gaagggtacc ttgtgaggaa gagagagaga   4320
```

```
gatcagattg ttactgtgtc tatgtagaaa aggaagacat aagaaactcc attttgatct   4380
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagacctta ccacccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
tgcacatcca ggcacagtac ctttccttga acttattcat gatacagatt cctttgctca   5040
cgtttccctg ctgaccttct ccccacctgt tgccctgcta cactcccctc gctaagatag   5100
taaaaataat gatcagtaaa tactgaggta actcagaggc tagcgctggt gcgggtcctc   5160
cgtatgctga gtgccggtcc cctgggccca ctgttctttc tctatacttt gtttctgtgt   5220
cttatttctt ttctcagtct cgtcccacct gacgagaaat acccacaggt gtggaggggc   5280
tggccccttt cagtatctca gaagggacaa agtacacaaa ggcatggggt catgatagtg   5340
cctggtatgt tcaggtagtg aagaggtcca tgtggtatga gcactgcaga tgatatgtgt   5400
cgtatgaatt aaaaatacat agttactgca aatagttttt acaggttatt gtttttaaga   5460
aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca aacgggccct ctagacgcgt tgacattgat tattgactag ttattaatag   5640
taatcaatta cggggtcatt agttcatagc ccatgatatc atatggagtt ccgcgttaca   5700
taacttacgg taaatggccc gcctggctga ccgcccaacg acccccgccc attgacgtca   5760
ataatgacgt atgttcccat agtaacgcca atagggactt tccattgacg tcaatgggtg   5820
gagtatttac ggtaaactgc ccacttggca gtacatcaag tgtatcatat gccaagtacg   5880
ccccctatt gacgtcaatg acggtaaatg gcccgcctgg cattatgccc agtncatgac   5940
cttatgggac tttcctactt ggcagacatc tacgtattag tcatcgctat taccatggtg   6000
atgcggtttt ggcagtacat caatgggcgt ggatagcggt ttgactcacg gggatttcc   6060
aagtctccac cccattgacg tcaatgggag tttgttttgg caccaaaatc aacgggactt   6120
tccaaaatgt cgtaacaact ccgccccatt gacgcaaatg ggcggtaggc gtgtacggtg   6180
ggaggtctat ataagcagag ctctctggct aactagagaa cccctgctta ctggcttatc   6240
gagatatctg cagaattcat ctgtcgactg ctaccggcag cgcgcagcgg caagaagtgt   6300
ctgggctggg acggacagga gaggctgtcg ccatcggcgt cctgtgcccc tctgctccgg   6360
cacggccctg tcgcagtgcc cgcgctttcc ccggcgcctg cacgcggcgc gcctgggtaa   6420
catgcttggg gtcctggtcc ttggcgcgct ggccctggcc ggcctggggt tccccgcacc   6480
cgcagagccg cagccgggtg gcagccagtg cgtcgagcac gactgcttcg cgctctaccc   6540
gggccccgcg accttcctca atgccagtca gatctgcgac ggactgcggg gccacctaat   6600
gacagtgcgc tcctcggtgg ctgccgatgt catttccttg ctactgaacg gcgacggcgg   6660
cgttggccgc cggcgcctct ggatcggcct gcagctgcca cccggctgcg gcgaccccaa   6720
```

```
gcgcctcggg cccctgcgcg gcttccagtg ggttacggga gacaacaaca ccagctatag   6780
caggtgggca cggctcgacc tcaatggggc tcccctctgc ggcccgttgt gcgtcgctgt   6840
ctccgctgct gaggccactg tgcccagcga gccgatctgg gaggagcagc agtgcgaagt   6900
gaaggccgat ggcttcctct gcgagttcca cttcccagcc acctgcaggc cactggctgt   6960
ggagcccggc gccgcggctg ccgccgtctc gatcacctac ggcaccccgt tcgcggcccg   7020
cggagcggac ttccaggcgc tgccggtggg cagctccgcc gcggtggctc ccctcggctt   7080
acagctaatg tgcaccgcgc cgcccggagc ggtccagggg cactgggcca gggaggcgcc   7140
gggcgcttgg gactgcagcg tggagaacgg cggctgcgag cacgcgtgca atgcgatccc   7200
tggggctccc cgctgccagt gcccagccgg cgccgccctg caggcagacg ggcgctcctg   7260
caccgcatcc gcgacgcagt cctgcaacga cctctgcgag cacttctgcg ttcccaaccc   7320
cgaccagccg ggctcctact cgtgcatgtg cgagaccggc taccggctgg cggccgacca   7380
acaccggtgc gaggacgtgg atgactgcat actggagccc agtccgtgtc cgcagcgctg   7440
tgtcaacaca cagggtggct tcgagtgcca ctgctaccct aactacgacc tggtggacgg   7500
cgagtgtgtg gagcccgtgg acccgtgctt cagagccaac tgcgagtacc agtgccagcc   7560
cctgaaccaa actagctacc tctgcgtctg cgccgagggc ttcgcgccca ttccccacga   7620
gccgcacagg tgccagatgt tttgcaacca gactgcctgt ccagccgact gcgaccccaa   7680
cacccaggct agctgtgagt gccctgaagg ctacatcctg gacgacggtt tcatctgcac   7740
ggacatcgac gagtgcgaaa acggcggctt ctgctccggg gtgtgccaca acctccccgg   7800
taccttcgag tgcatctgcg ggcccgactc ggcccttgcc cgccacattg gcaccgactg   7860
tgactccggc aaggtggacg gtggcgacag cggctctggc gagcccccgc ccagcccgac   7920
gcccggctcc accttgactc ctccggccgt ggggctcgtg cattcgggct tgctcatagg   7980
catctccatc gcgagcctgt gcctggtggt ggcgcttttg gcgctcctct gccacctgcg   8040
caagaagcag ggcgccgcca gggccaagat ggagtacaag tgcgcggccc cttccaagga   8100
ggtagtgctg cagcacgtgc ggaccgagcg gacgccgcag agactctgag cggcctccgt   8160
ccaggagcct ggctccgtcc aggagcctgt gcctcctcac ccccagcttt gctaccaaag   8220
caccttagct ggcattacag ctggagaaga ccctccccgc accccccaag ctgttttctt   8280
ctattccatg gctaactggc gagggggtga ttagagggag gagaatgagc ctcggcctct   8340
tccgtgacgt cactggacca ctgggcaatg atggcaattt tgtaacgaag acacagactg   8400
cgatttgtcc caggtcctca ctaccgggcg caggagggtg agcgttattg gtcggcagcc   8460
ttctgggcag accttgacct cgtgggctag ggatgactaa aatatttatt ttttttaagt   8520
atttaggttt ttgtttgttt cctttgttct tacctgtatg tctccagtat ccactttgca   8580
cagctctccg gtctctctct ctctacaaac tcccacttgt catgtgacag gtaaactatc   8640
ttggtgaatt ttttttttcct agccctctca catttatgaa gcaagcccca cttattcccc   8700
attcttccta gttttctcct cccaggaact gggccaactc acctgagtca ccctacctgt   8760
gcctgaccct acttcttttg ctcttagctg tctgctcaga cagaacccct acatgaaaca   8820
gaaacaaaaa cactaaaaat aaaaatggcc atttgctttt tcaccagatt tgctaattta   8880
tcctgaaatt tcagattccc agagcaaaat aattttaaac aaaggttgag atgtaaaagg   8940
tattaaattg atgttgctgg actgtcatag aaattacacc caaagaggta tttatcttta   9000
cttttaaaca gtgagcctga attttgttgc tgttttgatt tgtactgaaa aatggtaatt   9060
gttgctaatc ttcttatgca atttcctttt ttgttattat tacttatttt tgacagtgtt   9120
```

```
gaaaatgttc agaaggttgc tctagattga gagaagagac aaacacctcc caggagacag   9180
ttcaagaaag cttcaaactg catgattcat gccaattagc aattgactgt cactgttcct   9240
tgtcactggt agaccaaaat aaaaccagct ctactggtct tgtggaattg ggagcttggg   9300
aatggatcct ggaggatgcc caattagggc ctagccttaa tcaggtcctc agagaatttc   9360
taccatttca gagaggcctt ttggaatgtg gcccctgaac aagaattgga agctgccctg   9420
cccatgggag ctggttagaa atgcagaatc ctaggctcca ccccatccag ttcatgagaa   9480
tctatattta acaagatctg cagggggtgt gtctgctcag taatttgagg acaaccattc   9540
cagactgctt ccaattttct ggaatacatg aaatatagat cagttataag tagcaggcca   9600
agtcaggccc ttattttcaa gaaactgagg aatttttcttt gtgtagcttt gctctttggt   9660
agaaaaggct aggtacacag ctctagacac tgccacacag ggtctgcaag gtctttggtt   9720
cagctaagct aggaatgaaa tcctgcttca gtgtatggaa ataaatgtat catagaaatg   9780
taacttttgt aagacaaagg ttttcctctt ctattttgta aactcaaaat atttgtacat   9840
agttatttat ttattggaga taatctagaa cacaggcaaa atccttgctt atgacatcac   9900
ttgtacaaaa taaacaaata acaatgtgaa aaaaaaaaaa aaaaaaaaaa aaaaaaaaaa   9960
aaaaaaaagg tagcagtcga cagatgaatt ccaccacact ggactagtgg atccgagctc  10020
ggtaccaagc ttaagtttgg gctgcaggaa ttctgatggc tctcaaaatt cctgcctcct  10080
ttagggataa aagactttaa gactttttaa caaaaaagaa aaagaaaaaa aaaattcctg  10140
cctcctggtg tacacacaca gaagggttcc ctccccttga atgtgaccag gatctgtgaa  10200
aataacggga tagccgctcc tgtgattagg ttatgtggta gactagagca agattctcct  10260
gctggttttg aagaagtcag ctgccatgtt gtgagactgt catgggctag ggcatgagcc  10320
tttaaatatc tgggagcaac ccctggccag cagccagtga gaaaacgggc cctcagtcct  10380
acaatcacaa ggaactaaat tctgccaaca acctgaagga actttgaaga ggatcatgag  10440
tcccttgatt cagcttgatg agcccctgag cagaggatac agctaacttg tactagggaa  10500
gtataaaaaa catgcatggg aatgatatat atcaacttta aggataattg tcatacttct  10560
gggaatgaag ggaaagaaat ggggctttag ttgtattatg atctttaatt tctcaaaaaa  10620
aataagatca gaagcaaata tggcaaaatg ttaatacttt tgtgggtacg taggtattca  10680
gcataccctt ttttctgagt tcaaaatatt ttataattaa aatgaaatgc aggccaggca  10740
cagtggctca tgcctataat accagcactt tgcgaggccg aggtgggagg atggcttgag  10800
gccagaccag cctggccaac atggcaaaac cccatctcta cttaaaaaaa aaaaaactat  10860
atatatatat atgtgtgtgt gtgtgtatat atatatatgt atatatattt atatatgtgt  10920
gtatatatat atatgtatat atatttatat atgtgtgtgt atatatatat atacacacac  10980
acacatatat acatacatac atacacacac acacacacac aattagccag gcatggtggc  11040
gcacacctgt agtcccagct acttgggagg ctgagacatg agaattgctt gaacctggga  11100
ggcagagtag ttagtgagct gagatcatac cactgcactc cagcctggtg acagagtgag  11160
actctgtctt aaaaaaaata aaaattaaaa ttaaatgcaa aaggtccaag tgaattgaag  11220
aggaaagggg tatcaaggaa ggttttgtgg aggtgacgtt tgagctgggt cttaaatgac  11280
ttaaacatgg gataagaagg gagggaataa ggacatttca ggtacgagaa ataaggagca  11340
aacagtggaa acaacctaac gtctgtcaac cagtgaatgg ataacaaaaa tgtaattcag  11400
atggtatcca acttacgatg gttcaacatg agatttttct gactttagga tagatttatc  11460
aaagtagtaa atccattttc aacttatgat attttcaact tcagatgggt ttatcaggac  11520
```

```
acagttgagg aacacctgtc tatccataca atttggcaat aaaaaggaaa tgagtgcaga  11580
tatactccac aacatgaatg aaccttgaaa acattaagtg agagaagcca gatacaaaag  11640
gccacatatt gtatgattct atttatacaa aatgtccaga ataggcaaat cttatagaca  11700
gcaagtaggt agatgatcag tttgctaggt gctgggggaa ggggaaatgg ggagtgatgg  11760
ctaaggggat tgggtttctt tgtggggcaa tgaaaatgtt ttaaaattga gcgtgataat  11820
gattgcacaa tgctgcatat atatataatc tatagattat atatatataa agagaggctg  11880
ttagacagtg ataagtgata tatatatata tatacataga gagagagaga gagagagaga  11940
gaggctgtta gtgataagtg atcaggaaaa taaaagtatt gaggaggaat acgaagttga  12000
cggtgtgaaa acatgagatt ttatatagga tggccaggga aggccttaat gagaaagtga  12060
cttatgagta aaaacaaggg atcctaaacc ttagcatgca tcagaatcac tcggaaactt  12120
gttaaagcat agcttgctgg gcctcatcac agatattttg attcggtagg ttcttgtctg  12180
atattaatac ttttggtcta gggaaccaca ttttgagaac cactgagcta aaggaagtaa  12240
aggtttccct tagtttacta gctggtaaca ctggcccagg aggcctttct ggaaaaggtc  12300
ccagtcccca aaggaagctg gggactcgcg ttcacatcgt caaggtttac caagttgtgg  12360
cgggcctttc cgtcttggaa aaagcctcaa aatggcagat tagggtgtcc atggccggcg  12420
gaaagggtct ttgaagttgc agaccaggag ggaagaagat tctgggcctc ccccatgcag  12480
tgtcagctgg caacagaatg caccccggct gggttggagg ccctgggtac tggctcttcc  12540
acaccagggg cccacctacc aagggcagca ggagcatctg cacctcctgc gccaggcgcc  12600
cttcagtgct tccacttgag cacctctcca gacaccagct agggtgacag tggtacaaat  12660
accagactcc cctggcctgc tcacctcaca gggtaatgtg ctgtggagtc agggggacac  12720
agcaaccacc agatgacatg gctggccccg gggaggacga cacgcagata cggctacttg  12780
gcacctgtga tattttacac actcgagagg ggcccgcacc atcctcagcc ctctccccac  12840
attcactctt agttcatgtc acctccaccc agagggggac acaggcccac agcgatggcc  12900
ccacaccctg cctgaggtcg cccacttccc aggaggcagt cctgggactt ccacccgacc  12960
aggccccaga gcccaccgac ttaacccctc cagaggcttg tcgttcatta ccttattcaa  13020
gatggagacc agccttttg cggagaaaat gcgggtgaag gtcctgaaag tgcattgacg  13080
ccgttttcgg aagccataca agtttagctg gcggaagaag ctctttatcg aagttgtggc  13140
aaacactttg tgtgcgacgt ccctttgag aatctccttt tcaaagagtt tttgattgat  13200
cactctacaa gccccactgt catcccacca gatggacgaa aactggttgc tgctgaccag  13260
tctccacagt ttctgtggaa aggggaggga gaggagatta tcttctccct ggggcgggac  13320
gtcaccgtca gggtgcggcc ttctgaacga agcttcctcg gccagaggtt ggaaagcgat  13380
ttcttctgtc agcagcctca agttagggct cccagtggac cccgggtcgt cccaggcagg  13440
ggaaggatct gctgggtgaa ggtaggtctc tgactgcaac tggggaggga aaggcaccct  13500
ttccaagcca tgatcctgtc ctctcgaatt tctttcttca cagcgagcca tactcaatga  13560
tcgcttgtcc tccatctggc aaacttgcta gtgcagtgtg gccagcagca ccccttggca  13620
gtcatgtaac cagccccatg acatcataaa ggggctctga ctgccggggg gtggcatctc  13680
cacccccagc aagttgtgta ataaagggcc aaggcagaca agtagctgcc catctgcatg  13740
tgcacattct ggtcctcaca gtcatttcaa tgggaaagat gacactagtg cacaagagtg  13800
ccgaggggcc ctgccacacc gtagatgcag acctggagcg gtccccttgt cctagagctc  13860
ctgagccagg cacaactaca gcaaagccct ggctcaggaa ggtcagagct caccgtctga  13920
```

```
gtcatgggcc cacagacccc agcacatgac tgacactcgg aagcacagaa caaagggtag  13980
gacggtgccc atgggtcagg ctgtagccac gccacccttt ccaccctgtc ctagccagag  14040
gcagcaatgt gctccataca gatcctccta acacacccac actgtcggtc cccagcacgc  14100
agatgcccga cagcccctta ggcaaatggc ttagctgact gccccaccac acgccgtcgc  14160
catgcagtcc agtggggagt cggaggcagc ctccttcctg cctctcctcg gcctgcacgt  14220
gtccccccac caggcagaga cccttctaca ccccgggtgt ctgcggtcac atcgcggtgg  14280
ggcatgcagc tgttggcctt cgagcatgtt ttgttttcct tggccagtgt ctccagagaa  14340
acgcacgtgg gtttgtgtcc agcggtccat ctctgcaaca gttgttcctt tgggattgga  14400
tgctaggagg tcacgggaga ggtgtccatc caaagcagtg tctgtgtcac acactgtccc  14460
cacacacagg gccacctctg cacagactcc cccgactcga ttctgggcac agagctcagt  14520
gaccttccag agactgccac gaaccggtga tgcctccacg cttgagacat cctgaccgca  14580
gggcccaagg cgcactggct caggggtga cagtgagggg tctgcaaaca gactgctgat  14640
gctcaacccg gccgctgccg agctgtgtga cttgggcacg tcacttaacc tctctcggcc  14700
tctgtctcct cccggggata agagtagtag cacctgcttc ccggggctgt gaggatccag  14760
tgggacgtat aggaactagc gaggcaccgg cagttgggtc agagctactg ttgtcacttc  14820
acaaggcatt ttcttcaaca gcaagtcgga aatctcatga gcctaaggca gaatccacct  14880
gtggcctctg gttacaaccc acaggactga aaatccttcc agccacagca actggtgaat  14940
ttcctggtca attgccacaa gtcatgagct gaaccccact tgagtttcag ttcaggcaga  15000
actctagaga cgactagggc aagctagaca gcgactgcag agccttttgt tgcagcgtga  15060
gcagtcctca gctgttgaca tcactgggga gcaaacgagg accaggagcg gtgaaaggac  15120
agtgtctgct gcagattgtc gtagcaccca aggaacactc cagaaagcct cctaagcagt  15180
aacaagtgtg gcaaggtgta gcccagccaa cagtggcatc tgcgaggcgt cccctccttc  15240
ctcccactac cccgtatacc ctgggacctg tgcactgaag gactcattct aaaggctgtg  15300
cccctgcagc cgccagcctc actcactggc tgcctgtgcc agctagagat ttctttcctc  15360
tgaggctggc tgagaggacc actccagttt cctggcccat ccagcaaaga agatacacat  15420
catgcacgtg taaaatgagg aaccggttta ttgaacagct taaggagagc aaaaatagtg  15480
gctttagcta catttttac acactgagca ggaaagtcta aaccatcccg ttcccctgta  15540
ccccaaagag aacagggctt gctggaggcc agtgccaagg gcggagtcgt gctcgcagca  15600
gacttgaatt aaccccatgt aggccggcga gcagttgccc gcgtgaaaac accaccctct  15660
tctcctggct gagaagatca aagctctttt tttaccctct tttcagcaaa ggacctattt  15720
gttttcaggc aggaggatgt taaacttgca gcctctgaca cacggtggaa cctgcagtgc  15780
ttggagaaac ggcacgcaca cgtgaaaaca tcatgcctac tccaaagcct tcttgttgct  15840
ggcaggaggg aagcttgaga ctttcccacg catagtcgtg acccgcgtgg ccgtttctgc  15900
tctcagcaac attctctagt gttccggctt caagcagcgc ttgtcaggtt tgaagctagc  15960
cactattctg agaacgtcag aaaagcatgg accatctctt gcttggtgtt gccgttgtgg  16020
cagtagcagc tactacgtac ctgcacgagt tccagggcag aagtggcaat gtcccatgaa  16080
ggcgtggcac cccacggggg gggggggga gtgtgccacg ggcgtccact tctgcagcag  16140
aaggcatgtg cctacagcac aagcttgtaa aaaaatactt gaacagaata tgctgtacag  16200
aactaggggt taacaccgca tatgaagatg ctaaaacatt tgtataaata ctctgtatac  16260
aagcatggag tcactcccgt agaaagggct catccgtgag gctatgaaaa actgctgtca  16320
```

gcatgcccaa agagaaacta cttccacagt aggaacagaa aaaaggactg tgctgtgtct 16380
aaacacgtgg tgcatcagag acatagttac agttcctact gactgcccca gccacgacct 16440
gggagtgctg aggacctggg agtgctcagc gagctgcagg aggtcagccc tgtggagaaa 16500
tacatttcta aacaatactt ttgattggga tttcagcacc gtatagacag atgttccttc 16560
tgggggcctg gcaagcagcc atctcccagt gggtctgacg gggaagaggg gtacctggag 16620
cccctcccag acagacggta atcccacccc tgttctcaca ctcttcctgg catccgcatc 16680
tgctggcaca cacccccgtc acctgccact tccgcgtccc gtcgtggtga gtggctgata 16740
ggcgctggat gcaaacaagg catgagatgg acgtacctgg agacccagct ccagtactgg 16800
ttctggtctg cggggtgaac gagggggcag aggaaggcgg agagagtgcg tcccagtcca 16860
cttaagctct gtccccggaa gtggcatcta atctggcatt tcgatattta atttgggagg 16920
tgggagcaca tacttcccag ggctctgggt aatgaccacc ctggccttct ttcgaaacat 16980
gggtgcgatt ttagggggct ccggaactgg ggtctcttcg gtttcttcat tatcttcgtg 17040
atggagatca taggaaatgt ttccatattc tcgtagaaat gggaagattt caagcagaaa 17100
ctgacagaaa tctttgcgga taccaaacca ccctgaaaaa taagaatttt ttatttcaca 17160
cacgaggctc aactgacctt cctgttaact ttctttccgt aacaagaagt ttcactccta 17220
caatgtcata acatacttta tccagactcc tgagtcacaa agcctgaaca gggcttgagt 17280
acccaaaatg gggaagaagt gcaaatgcta gctctgtggt gcttggagtg gggttcccgg 17340
accggcaggg acagcgtcca cggggcctag ttagggatgc cattctcggg ccccagccca 17400
gacctccaga aactgagtcg ggctagggtg ggctccagcg gtcccctttt cctggccctt 17460
ttgggattct gctggatgcc caaatttgag aactactgct ccagtgagtc tcaaaatatc 17520
tgtggtgcgc agactacggt gtcttccgct aatcttctcc agccaggata aactcatgga 17580
tgacagtgcc acccaagaac aagatttctg tcaccctctg gaatccgtga gggcggtagt 17640
catgcacggg ttggccagga gggggcctga actcatggag ccaccttaaa gccactttcc 17700
cagtcccact actcctctct gtaggctact ggagtgtcag ctcggtgcaa gccctccctg 17760
ctcccgggtg cggggtaggg ggcagaggca caaacagcaa gcacagcccg ggctgctggg 17820
ctgcagtgag gccctgcccc caaacccact ggctttccga agggcaatgc tctgggcttc 17880
cgtgccatgg agcccacagc cttgccagga aggcaccctc tgcagagatc gttttggaag 17940
tgtctgcctc agcaagcagg tggaggggaa tagagtgtta gcaaggcaag acaggcaaga 18000
ctcgggtgat ggcagcaagg atatggggga ggcagagcgg ccaacaggga cctaggatga 18060
atcccaggtt tgggtgggag atgtggattt tccatcaaac cctcccgggc ctgggaagaa 18120
tctgtcttga tccccatttt gcagaggagg gaacgggatc tctgagaggt tgcctgccgt 18180
gtctggttct acctcaaatg gcagcgtgca ctgcgagaaa agtcccggtg caggccagca 18240
gaacaccaga gttacggcat gcccttccct tagaaggtcc cagaatttcc tcagccctca 18300
ctttcccaca caagcttcta aattggggcc ctcggggact catcccttcc tagacttcta 18360
tccgccaccc cccacccccct ggtccccccc cagacacaca ccaaggactt ctgaaatgct 18420
gagtacatac agtggtttcc tcccttctgt ccaaatgtgg ttgccatcag cgtgatcaac 18480
gagagccaaa gggggacaaa gatcgggatg caggagaagg cgttgtggcc atccagtttg 18540
tgaaccagca gaatctaaag aaagagacat agtcccggtt gatgccagca ccgaaaatgg 18600
gcagaggcgg aagccagact tcattaggca gttcctcccc accaccccac ccccgcgtga 18660
gctcccacaa gagggaacat cagcaccgcc agaaaaaggc aggaaaccac ctatccctgg 18720

```
ggaaagctcg aaatgagctt ttatgtccct cttcagagct cggcaatagc ctatccactt  18780
gaaaagttcc cagtgccagc agttttatgg caaactcctc cgggtgtttg ttctaaggag  18840
tcaacagctc ccattctaga attctccacg tgactccaat acacaaatct gacatcccac  18900
tctgctttcc ccagagtgga aactggagcc atacagaggc accatggcta aaaaggtgca  18960
ctcttctccc tgccagcccc acgtgctgcc cccaagagaa aggaaggatg ctctcctttc  19020
accgaagctc cctctcggag atggctgtgt tctctcccct ctcctggagt gggctcactg  19080
tgagctcgag ggacagaggc tgcctttcta ggggtgcaga atcctgtcag gggaagcgca  19140
agcttcaggg gctgaagagg cttcccgtgg aacgcttacc tcaaatgtaa gaaggggcac  19200
gacgatggtc atccagctca gggccatggt tatgtgtgtc ctgcgctgtc cgcaatcaca  19260
tccatagagc gcaagaacaa gacggaccac acaatgtagt agaggaccac caggcacaga  19320
aaggacatga gaatccacag cgggacacac acaacctggg ggtgggtgag agaacagcaa  19380
gagaagtctc tttagagctt ccaacctggc ctctgatgga aggcatcttt agcaccttgc  19440
tgtgtctgtc cagttaaggc ggtccttcct gtgagccgaa taaggaccgt tccatctccc  19500
aggactgctg ggagcatcgc tcaggacaga aaaggtatgg tatgttcact atggggcctg  19560
ctgccaccag gggacacaca cgctcagtga gtcatcagtc cctcttcctt tgggtgacag  19620
acagccctgc acctggctcc gcagcctcta ctcttccaga ggcccactct cccacactct  19680
ctcaggctcc tctaggttct gctgccatca cagcttcccg ggaaatggga cacaactgtc  19740
accctgtgca cacacacaag atctcacccc aacagactct cttcacaggc aacattccca  19800
caacctgctg ggggtacttt ggcaacacaa atgggaatgg gctccccaga aagtctggct  19860
gcctgggctc ctaaggatcc ctaacctcac ccctaccaag ttagtgaact tggcgggttg  19920
atgctggata caggttgatg ctggatacgt agcgctgccg ggtcgtgacc cctaaggaat  19980
tatccaaact cttgttttta gatgctttat tatatcaaac tctcctttaa acaagtggcc  20040
catctgctgg gatttggaag cctgtaatac tgaaattttc atcataatgg aaattttaaa  20100
aacagaattt gacccacctg tttttaaaac actttcatta cttaacaaga ggtctaatct  20160
tgggcaagtc ttgaaatttc tctggcctta gtttcccatg tgttaaatga aacttgaagc  20220
agttggtctc ttatagtctc ctgactctaa cattctaaga attatatttg tacaataact  20280
caaaaatcac ataatttaat ttaccatatg gactccaaaa tatattttct cattaggcta  20340
aacttgatct gcattttctg gatgtgtcca tattcttgga ctacactaaa acatgatacc  20400
aatgcttcct ctcaccataa accctcactt cgctttctac atttaagaat tttatagctg  20460
gaagagtcct taacagaaaa taccatctaa taattacccc tcaaaatcga gaaagtccta  20520
tctgttctta tgctagttat aagaatgagg cagcatttca cataatggtt ataaacactg  20580
ccacaagaag attcatgatg tgttgtttat ctgtagctct catcatactc tgtcatataa  20640
ctatagcatt aagattttaa tgttctatat attcttctaa gacagtgttt accagagtaa  20700
ggcacaaaag atccactggt ttgcaagaaa gattagaact tttaaatttt ttacctcacc  20760
ttgtttaatc tatattttttg tatgtatttt gtaacatata tattattatt accataaatc  20820
atatataatt taaaatgcat atattagggg taaatgctca ggaaactttt tataaattgg  20880
gcatgcaaat acaagtttga agactcactg ttctaggtat taaaagtaaa gttataacca  20940
agtaaagctt ccacctttc atgtctcaaa gcagtttatt gttggaggta agatctctta  21000
gaagcctaaa caggtccaag tacagaatga agtaaggcta gcccataact tgtggcaagc  21060
aattcatact atttctctca tgctgagctc tcctcagtga agcagctact atagacaact  21120
```

```
gcagcctatt ggtagcctat tttacaggca ggaaaaaaat tactttttat tcaaagtgga  21180
actcaggaca tggggagaaa atgaatacaa aaaatagggt caatccaaag gcacacagca  21240
aatgagtaac acagttatgt ttttttccca tttgtatgag gtcccagtaa attctaagta  21300
aactgcaaat ttaataatac actaaaaaag ccatgcaatt gttcaaatga atcccagcat  21360
ggtacaagga gtacagacac tagagtctaa aaaacaaaag aatgccatta ttgagttttt  21420
gaattatatc aagtagttac atctctactt aataaatgag aaaaacgagg ataagaggcc  21480
atttgataaa atgaaaatag ccaagaagtg gtattagaga cttgaataca ggtattcggg  21540
tccaaagttc atctgctcaa atactaactg gggaaaagag ggaaaaatat ttatatacat  21600
atatatctgc acacaaaaat acccccaaaa gacaaaatga ggccaggcag ggtggctcac  21660
acccgtaatc ccggtacttt gggaggctga ggcaggtgga tacctgagat caggagttgg  21720
agatcagcct ggtcaacatg gtgaaaccct gtctctacta aagataaaaa aattagccag  21780
gcatggtggc gtgcgcctgt aatcccagct acttgggagt ctgaggcagg agaatcactt  21840
gaactgggaa ggggaggttg cagtgagcca agatcgtact actgcactcc agcctgggca  21900
gcagagtgag actccatcac aaaaataaat aaataaataa aatacaatga aacagaaagt  21960
tcaaataatc ccataatctt accaccaaga aataactttc actcgttata cttattgatt  22020
tttccataat aaatgtactt tactgtgact atcatgaaaa gaaagttatt ttagaaacag  22080
agaactgttt cagatcaaat ctatgtagta gaacagagcc attaggtggg aaagacgaga  22140
tcaaactaaa tctcagaagg cctaaaaggc taggtccatt ccagcactaa aaactgacca  22200
gacaagtaat ggcttcaaca gcttctaaat atggacaaag catgctgaaa gggaaggaca  22260
ggtctaacag tggtatatga aatgaacagg aggggcaaag ctcatttctc ctctgaagtt  22320
ttccaaagat gctgaggagg acattagttt gacatgaccc tgatatggga caagataatt  22380
tcacagaagt tttacatgtt aaagttttct tatagatact cattcaagta agcaatgaac  22440
actaaaatct aaagaaagaa aagagcttta gagtcaggtc tgtattcaaa ttcaagctct  22500
accacttact ggttctgtga ctttgggcaa gtcttttaac cttattaagt cttaatttcc  22560
tgatttgtaa aatggggata tcgtctccct cacaggattg ttgtgaaact tttatgagat  22620
taatgccttt atatttggca tagtgtaagt aaacaataac tggcagcttc aaaaaaaaaa  22680
agcagtagca ttccatcatt tattattggt tactctcaaa aagtttttca atgtactaga  22740
agataaatat tcaaatacct taatatctcc attattttca ggtaaacagc atgctcctga  22800
acaaccaatg ggtcaacaaa taaattaaaa gggaaatcta aaaacatctt gatattaaac  22860
tacatggaag cacaatatac caaaaccaat ggttcacact aggagaattt taaggtacaa  22920
gaaaactctt tgagatttct taaaataata gtatgtctga atttattgag tgatttacca  22980
gaaactgttg taagagctct acttgcatta tagcacttaa tcctcttaac tctatggctg  23040
ctattatcaa cctcacccta atcacatatg ggacacagag aggttaagta acttgcccaa  23100
ggtcagagtt aggaagtact aagccatgct ttgaatcagt tgtcaggctc cggaactcac  23160
actttcagcc actacataat actgctttgc tatcttttag gaaactatgt gagtctacct  23220
cacatagact cacataggtt tgtttttttt tttttttaa aggctatctt ttcccccatc  23280
aatgtttttt gaaggatccc aaattagagt cccacagagg cagacagcag tacttgacaa  23340
tatggacatt taaggttaat gttggattct actgtctttt tactacatga cctagggaac  23400
gataattaac ctagactgct tccaagggtt aaataaccca tttagttata ctatgtaaat  23460
tatctcttag tgattgattg aaagcacact gttactaatt gactcggtat gaagtgcttt  23520
```

```
tttttcttcc ctttcaagat acataccttt ccagttaaag ttgagagatc atctccacca  23580
attactttta tgtcccctgt tgactggtca ttctagttaa aaaaaaaaaa aactatatat  23640
atatatatct acacacacat atgtatatgt atatccttat gtacacacac aaacttcaaa  23700
ttaaatgaga actagaagat ttgagaagtt agctagctaa tatccatagc attatgatat  23760
tctaaatgat atgaattata agaattaggt ttcctgaaat gaatgactag aaaactttca  23820
agtagagatt agtaaaaatt aaaaagtcct aatcggccat tactgatttg atgtttttaa  23880
gagtcctaaa aaatgggtta catccatttt taagtgggta gtattataac agccacccat  23940
cttcaatcac agtgatttct gaattgtgag ggaagttatt agcatgacag gtgtctggtt  24000
ctggccctgt acgattccca tgagtcaagc aaattgtaag ggctggtcta tatcacaccc  24060
aaccccaagg atatgtccct caaaagtcta gcccaggccc cgtcatcttc agcatcatct  24120
gggaaaccag gtctgattag tagtccttta aggaatacct cttaggctcc cattttactg  24180
ctatcacaga atccaataaa acccttacag gagattcaat gggaaatgct caacacccac  24240
tgtagttggt ggtgacaatg accataattt ggctgtgctg gattcaggac agaaaatttg  24300
ggtgaaagag caggtgaaca aaagagcttc gacttgccct agcagagagc aagccatacc  24360
ataccacaaa gccacagcaa ttacaacggt gcagtaccag cacagtaaat gaacaaagta  24420
gagcccagaa acagacccag aactatatga ggatttagta tacaataaag atggtatttc  24480
gagtcagtag ggaaaagatg aattattcaa taaatgatgt ttggccaact agtaacccat  24540
ttgggaaaaa ataaaagtat ggtccctacc tcacagcata cacaaaaata aattccagac  24600
ggattaaaat ctaaatgtaa aaaataaagc cataagtgga ctggaagaaa atagagaatt  24660
ttttttaaca tccgtagaaa gggtaaaaac ccaggcatga catgaaccaa aactgaagag  24720
gttctgtaac aaataccccc ttttatatat tgggctccaa caataagaac ccataggaaa  24780
atggagaatg aacacaaata gacaatttat agaagagaag gttataaggt gtaaaattat  24840
atctatctga gaaacaaaca ctaaaacaat gtgattctac tgttctccca cccatactgg  24900
caaaacttaa gcctgataat atgctgaggg gaaataagca ctcttgttgg tgagagtatt  24960
aattggcata gcttcttttg aaaatgacat agcaatacct gttaaaattg caaacatgca  25020
tgtcacttaa tccagtaatc ccacttctgg gaatcaatgc tacaaaaaca ctgacaagta  25080
tacaaagata cattcaagag tgttcactgg gccgggtgcg gtggcttcat gcctgtaatc  25140
ccagggaggc agaggcaaga cgatcgcttg accccaggag ttcaaggcca gcccgagaaa  25200
cacagcaaga ccctgtctct cttttttttta tttaaaaaat aaatgttcac tgtatcagtt  25260
gttcacaaaa acaaaccaac atgtccatta acagggaacc atttaaatta atcaagttca  25320
tctacacaat gtaataccat gcaactatta aaaagcacct gataatccaa agcacactga  25380
gacagaataa tgctattaaa aacaccaagt agtggaacac tgtgttgcct atgacaccat  25440
ttttattcaa catttaaaca aatttgtaac agcaattaca tgagtagtga caatggcgtt  25500
tatgagactt ttcactttta tgtgcttcta tttttgttat gcttctatat atacatccat  25560
ttattatgga gtgttacttt caaaaatcac aaatgggcca gtattatttg gtgttgcaag  25620
gtgagcatat gacttctgat atcaaccttt gcatattact tctcaattta gggaaattac  25680
agacatccct tattctaact aacttaaaac ccagcatttc aaacatacag aattgatggg  25740
gaaaaaaaag aaagaagaaa gaaagaaaag gcaacaagct tcagatgaca gtgactcaca  25800
tcaaattatt tataaaatct gttaaatagt gccatcttct ggagatacct ggtattacag  25860
tccaactcca gttgatgtct ttacagagac aagaggaata aaggaaaaaa tattcaagaa  25920
```

```
ctgaaaagta tggagtcatg gaaaaattgc tgtgatccaa aggctacggt gataggacaa  25980
gaaacaagag aactccaagc agtaagacac tgctgttcta ttagcatcca aacctccata  26040
ctcctgtttg ccccaaggct tttttaaaaa atagagacag gatctcacta ttttgctcag  26100
gctggtcttg aactcctgga ctcaagctat cctcctgcct cggcctccta aagtgccgag  26160
attacaggct tgagtcacca tacctggcta tttatttttt cttaactctc ttgcctggcc  26220
tatagccacc atggaagcta ataaagaata ttaatttaag agtaatggta tagttcacta  26280
cattggaata caggtataag tgcctacatt gtacatgaat ggcatacatg gatcaattac  26340
cccacctggg tggccaaagg aactgcgcga acctccctcc ttggctgtct ggaacaagct  26400
tcccactaga tccctttact gagtgcctcc ctcatcttta attatggtta agtctaggat  26460
aacaggactg gcaaaggtga ggggaaagct tcctccagag ttgctctacc ctctcctcta  26520
ccgtcctatc tcctcactcc tctcagccaa ggagtccaat ctgtcctgaa ctcagagcgt  26580
cactgtcaac tacataaaat tgccagagaa gctctttggg actacaaaca cataccctta  26640
atgtctttat ttctattttg tctacctctt cagtctaggt gaaaaaatag gaaggataat  26700
agggaagaac tttgtttatg cctacttatc cgcccctagg aattttgaaa acctctaggt  26760
agcaataaga actgcagcat ggtatagaaa aagaggagga aagctgtata gaaatgcata  26820
ataaatgggc aggaaaagaa ctgcttggaa caaacaggga ggttgaacta taaggagaga  26880
aagcagagag gctaatcaac aaggctgggt tcccaagagg gcatgatgag actattacta  26940
aggtaggaat tactaagggc tccatgtccc cttagtggct tagtactatg tagcttgctt  27000
tctgcagtga acttcagacc cttcttttag gatcctagaa tggacttttt tttttatcg  27060
gaaaacagtc attctctcaa cattcaagca ggccccaagt ctaccacact caatcacatt  27120
ttctcttcat atcataatct ctcaaccatt ctctgtcctt ttaactgttt ttctataccc  27180
tgatcaaatg ccaacaaaag tgagaatgtt agaatcatgt atttttagag gtagactgta  27240
tctcagataa aaaaaaaggg cagatattcc attttccaaa atatgtatgc agaaaaaata  27300
agtatgaaag gacatatgct caggtaacaa gttaatttgt ttacttgtat tttatgaatt  27360
ccctaaaacc tacgtcaccc gccccgttcc cacgccccgc gccacgtcac aaactccacc  27420
ccctcattat catattggct tcaatccaaa ataaggtata ttattgatga tgttaattaa  27480
catgcatgga tccatatgcg gtgtgaaata ccgcacagat gcgtaaggag aaaataccgc  27540
atcaggcgct cttccgcttc ctcgctcact gactcgctgc gctcggtcgt tcggctgcgg  27600
cgagcggtat cagctcactc aaaggcggta atacggttat ccacagaatc aggggataac  27660
gcaggaaaga acatgtgagc aaaaggccag caaaaggcca ggaaccgtaa aaaggccgcg  27720
ttgctggcgt ttttccatag gctccgcccc cctgacgagc atcacaaaaa tcgacgctca  27780
agtcagaggt ggcgaaaccc gacaggacta taaagatacc aggcgtttcc ccctggaagc  27840
tccctcgtgc gctctcctgt tccgaccctg ccgcttaccg gatacctgtc cgcctttctc  27900
ccttcgggaa gcgtggcgct ttctcatagc tcacgctgta ggtatctcag ttcggtgtag  27960
gtcgttcgct ccaagctggg ctgtgtgcac gaaccccccg ttcagcccga ccgctgcgcc  28020
ttatccggta actatcgtct tgagtccaac ccggtaagac acgacttatc gccactggca  28080
gcagccactg gtaacaggat tagcagagcg aggtatgtag gcggtgctac agagttcttg  28140
aagtggtggc ctaactacgg ctacactaga aggacagtat ttggtatctg cgctctgctg  28200
aagccagtta ccttcggaaa aagagttggt agctcttgat ccggcaaaca aaccaccgct  28260
ggtagcggtg gtttttttgt ttgcaagcag cagattacgc gcagaaaaaa aggatctcaa  28320
```

```
gaagatcctt tgatcttttc tacggggtct gacgctcagt ggaacgaaaa ctcacgttaa  28380
gggattttgg tcatgagatt atcaaaaagg atcttcacct agatcctttt aaattaaaaa  28440
tgaagtttta aatcaatcta aagtatatat gagtaaactt ggtctgacag ttaccaatgc  28500
ttaatcagtg aggcacctat ctcagcgatc tgtctatttc gttcatccat agttgcctga  28560
ctccccgtcg tgtagataac tacgatacgg gagggcttac catctggccc cagtgctgca  28620
atgataccgc gagacccacg ctcaccggct ccagatttat cagcaataaa ccagccagcc  28680
ggaagggccg agcgcagaag tggtcctgca actttatccg cctccatcca gtctattaat  28740
tgttgccggg aagctagagt aagtagttcg ccagttaata gtttgcgcaa cgttgttgcc  28800
attgctgcag ccatgagatt atcaaaaagg atcttcacct agatcctttt cacgtagaaa  28860
gccagtccgc agaaacggtg ctgaccccgg atgaatgtca gctactgggc tatctggaca  28920
agggaaaacg caagcgcaaa gagaaagcag gtagcttgca gtgggcttac atggcgatag  28980
ctagactggg cggttttatg gacagcaagc gaaccggaat tgccagctgg ggcgccctct  29040
ggtaaggttg ggaagccctg caaagtaaac tggatggctt tcttgccgcc aaggatctga  29100
tggcgcaggg gatcaagctc tgatcaagag acaggatgag gatcgtttcg catgattgaa  29160
caagatggat tgcacgcagg ttctccggcc gcttgggtgg agaggctatt cggctatgac  29220
tgggcacaac agacaatcgg ctgctctgat gccgccgtgt tccggctgtc agcgcagggg  29280
cgcccggttc tttttgtcaa gaccgacctg tccggtgccc tgaatgaact gcaagacgag  29340
gcagcgcggc tatcgtggct ggccacgacg ggcgttcctt gcgcagctgt gctcgacgtt  29400
gtcactgaag cgggaaggga ctggctgcta ttgggcgaag tgccggggca ggatctcctg  29460
tcatctcacc ttgctcctgc cgagaaagta tccatcatgg ctgatgcaat gcggcggctg  29520
catacgcttg atccggctac ctgcccattc gaccaccaag cgaaacatcg catcgagcga  29580
gcacgtactc ggatggaagc cggtcttgtc gatcaggatg atctggacga agagcatcag  29640
gggctcgcgc cagccgaact gttcgccagg ctcaaggcga gcatgcccga cggcgaggat  29700
ctcgtcgtga cccatggcga tgcctgcttg ccgaatatca tggtggaaaa tggccgcttt  29760
tctggattca tcgactgtgg ccggctgggt gtggcggacc gctatcagga catagcgttg  29820
gctacccgtg atattgctga agagcttggc ggcgaatggg ctgaccgctt cctcgtgctt  29880
tacggtatcg ccgctcccga ttcgcagcgc atcgccttct atcgccttct tgacgagttc  29940
ttctgaattt tgttaaaatt tttgttaaat cagctcattt tttaaccaat aggccgaaat  30000
cggcaaaatc ccttataaat caaaagaata gaccgagata gggttgagtg ttgttccagt  30060
ttggaacaag agtccactat taaagaacgt ggactccaac gtcaaagggc gaaaaaccgt  30120
ctatcagggc gatggcccac tacgtgaacc atcaccctaa tcaagttttt tggggtcgag  30180
gtgccgtaaa gcactaaatc ggaaccctaa agggagcccc cgatttagag cttgacgggg  30240
aaagccggcg aacgtggcga gaaaggaagg gaagaaagcg aaaggagcgg gcgctagggc  30300
gctggcaagt gtagcggtca cgctgcgcgt aaccaccaca cccgccgcgc ttaatgcgcc  30360
gctacagggc gcgtccattc gccattcagg atcgaattaa ttcttaatta acatcatcaa  30420
taatatacct tattttggat tgaagccaat atgataatga gggggtggag tttgtgacgt  30480
ggcgcggggc gtgggaacgg ggcgggtgac gtagtagtgt ggcggaagtg tgatgttgca  30540
agtgtggcgg aacacatgta agcgacggat gtggcaaaag tgacgttttt ggtgtgcgcc  30600
ggtgtacaca ggaagtgaca attttcgcgc ggttttaggc ggatgttgta gtaaatttgg  30660
gcgtaaccga gtaagatttg gccattttcg cgggaaaact gaataagagg aagtgaaatc  30720
```

tgaataattt tgtgttactc atagcgcgta atactg 30756

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic Foward PCR primer (containing a Fse I restriction site)

<400> SEQUENCE: 17
tatttattgg ccggccgcgt taagatacat tgatgag 37

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic Reverse PCR primer (containing a Sbf I restriction site)

<400> SEQUENCE: 18
tatttattcc tgcaggtcgt aggtcaaggt agtaga 36

<210> SEQ ID NO 19
<211> LENGTH: 1224
<212> TYPE: DNA
<213> ORGANISM: Rattus norvegicus

<400> SEQUENCE: 19
atgcctcaca gtcaaatatc tcctgcagaa ggctctagaa ggatccttga agaataccac 60
atagatgaag atgtgggctt tgctctacca catccactgg aggagctgcc tgatacgtac 120
agaccttgga tccttgtggc tagaaatctg cctaagctga ttgagaatgg gaagctccga 180
gaagaagtcg agaagctgcc cacactgcgc accgaagaac tgaggggaca caggttacag 240
cgcctggcac atttggccct ggggtacatc accatggcgt atgtgtggaa ccgaggggat 300
gatgatattc gaaaggtgct gccccgcaat cttgccgttc cctactgcga gctctcggag 360
aagctggggc tgcctcccat tctgtcttac gcagactgcg tcctggcaaa ctggaagaaa 420
aaggacccca atgggcccat gacatacgag aacatggaca ttctgttctc gtttcctggt 480
ggggactgcg ataaaggctt cttcctggtc tctctaatgg tggaaatcgc agcttctcct 540
gcaatcaaag caattcctac tgtatccagt gcagtagagc atcaagaccc gaaagcactg 600
gagaaggcac tgtgtagtat agctgccagt ctggagaaag ccaaggaaat ttttaagagg 660
atgcgtgact tcgtggatcc agacaccttt ttccacgttc ttcgcatata tttgtctggt 720
tggaagggca accctaagct gccggagggt ctgctgtacg agggcgtctg ggacaccccc 780
aaaaaatttt caggggggcag tgcaggccag agcagcatct ttcagagtct tgatgtcctt 840
ctgggaataa agcatgacgt tggtgaagga tctgctgcag aattcctcca ggaaatgaga 900
gagtacatgc ctccagccca ccggaacttc ctctcctcct tagagtcagc tcccccagtc 960
cgtgagtttg tcattttaag acgcaatgaa gacttgaagg aggcttataa tgagtgtgtg 1020
aatggcctgg tctccctcag aatgttccac ctctcgatag tagatactta cattgtgaag 1080
ccttcgaagc agaagcccat gggtggccac aagtcagaag agccctcaaa cacggaaaac 1140
agagggactg ggggtactga cgtcatgaat ttcctgagga gtgtgaaaga tacaaccaag 1200
aaagcccttc tgagttggcc ttag 1224

```
<210> SEQ ID NO 20
<211> LENGTH: 1212
<212> TYPE: DNA
<213> ORGANISM: Homo sapiens

<400> SEQUENCE: 20

atggcacacg ctatggaaaa ctcctggaca atcagtaaag agtaccatat tgatgaagaa      60

gtgggctttg ctctgccaaa tccacaggaa aatctacctg atttttataa tgactggatg     120

ttcattgcta aacatctgcc tgatctcata gagtctggcc agcttcgaga aagagttgag     180

aagttaaaca tgctcagcat tgatcatctc acagaccaca agtcacagcg ccttgcacgt     240

ctagttctgg gatgcatcac catggcatat gtgtggggca aaggtcatgg agatgtccgt     300

aaggtcttgc caagaaatat tgctgttcct tactgccaac tctccaagaa actggaactg     360

cctcctattt tggtttatgc agactgtgtc ttggcaaact ggaagaaaaa ggatcctaat     420

aagcccctga cttatgagaa catggacgtt ttgttctcat ttcgtgatgg agactgcagt     480

aaaggattct tcctggtctc tctattggtg gaaatagcag ctgcttctgc aatcaaagta     540

attcctactg tattcaaggc aatgcaaatg caagaacggg acactttgct aaaggcgctg     600

ttggaaatag cttcttgctt ggagaaagcc cttcaagtgt ttcaccaaat ccacgatcat     660

gtgaacccaa aagcattttt cagtgttctt cgcatatatt tgtctggctg gaaaggcaac     720

cccagctat cagacggtct ggtgtatgaa gggttctggg aagacccaaa ggagtttgca     780

gggggcagtg caggccaaag cagcgtcttt cagtgctttg acgtcctgct gggcatccag     840

cagactgctg gtggaggaca tgctgctcag ttcctccagg acatgagaag atatatgcca     900

ccagctcaca ggaacttcct gtgctcatta gagtcaaatc cctcagtccg tgagtttgtc     960

ctttcaaaag gtgatgctgg cctgcgggaa gcttatgacg cctgtgtgaa agctctggtc    1020

tccctgagga gctaccatct gcaaatcgtg actaagtaca tcctgattcc tgcaagccag    1080

cagccaaagg agaataagac ctctgaagac ccttcaaaac tggaagccaa aggaactgga    1140

ggcactgatt taatgaattt cctgaagact gtaagaagta caactgagaa atccctttttg    1200

aaggaaggtt aa                                                         1212


<210> SEQ ID NO 21
<211> LENGTH: 2440
<212> TYPE: DNA
<213> ORGANISM: Artificial Sequence
<220> FEATURE:
<223> OTHER INFORMATION: Description of Artificial Sequence: Rat IDO
      expression cassette
<220> FEATURE:
<221> NAME/KEY: misc_feature
<222> LOCATION: (1)..(2440)
<223> OTHER INFORMATION: n= a, c, g, t, unknown or other

<400> SEQUENCE: 21

tatttattcc tgcaggtcgt aggtcaaggt agtagagttt gcgggcagga cggggcgacc      60

atcaatgctg gagcccatca cattctgacg caccccggcc catgggggca tgcgcgttgt     120

caaatatgag ctcacaatgc ttccatcaaa cgagttggtg ctcatggcgg cggcggctgc     180

tgcaaaacag atacaaaact acataagacc cccaccttat atattctttc ccacccttan     240

nntaatagta atcaattacg gggtcattag ttcatagccc atatatggag ttccgcgttg     300

gtaaatggcc cgcctggctg accgcccaac gacccccgcc cattgacgtc aataatgacg     360

tatgttccca tagtaacgcc aatagggact ttccattgac gtcaatgggt ggagtattta     420

cggtaaactg cccacttggc agtacatcaa gtgtatcata tgccaagtac gccccctatt     480
```

```
gacgtcaatg acggtaaatg gcccgcctgg cattatgccc agtacatgac cttatgggac    540
tttcctactt ggcagtacat ctacgtatta gtcatcgcta ttaccatggt gatgcggttt    600
tggcagtaca tcaatgggcg tggatagcgg tttgactcac ggggatttcc aagtctccac    660
cccattgacg tcaatgggag tttgttttgg caccaaaatc aacgggactt tccaaaatgt    720
cgtaacaact ccgccccatt gacgcaaatg ggcggtaggc gtgtacggtg ggaggtctat    780
ataagcagag ctggtttagt gaaccgtcag atccgctaga gatctggtac cgtcgacgcg    840
gccgcgggaa ttcgattatg cctcacagtc aaatatctcc tgcagaaggc tctagaagga    900
tccttgaaga ataccacata gatgaagatg tgggctttgc tctaccacat ccactggagg    960
agctgcctga tacgtacaga ccttggatcc ttgtggctag aaatctgcct aagctgattg   1020
agaatgggaa gctccgagaa gaagtcgaga agctgcccac actgcgcacc gaagaactga   1080
ggggacacag gttacagcgc ctggcacatt tggccctggg gtacatcacc atggcgtatg   1140
tgtggaaccg aggggatgat gatattcgaa aggtgctgcc ccgcaatctt gccgttccct   1200
actgcgagct ctcggagaag ctggggctgc ctcccattct gtcttacgca gactgcgtcc   1260
tggcaaactg gaagaaaaag gaccccaatg ggcccatgac atacgagaac atggacattc   1320
tgttctcgtt tcctggtggg gactgcgata aaggcttctt cctggtctct ctaatggtgg   1380
aaatcgcagc ttctcctgca atcaaagcaa ttcctactgt atccagtgca gtagagcatc   1440
aagacccgaa agcactggag aaggcactgt gtagtatagc tgccagtctg gagaaagcca   1500
aggaaatttt taagaggatg cgtgacttcg tggatccaga cacctttttc cacgttcttc   1560
gcatatattt gtctggttgg aagggcaacc ctaagctgcc ggagggtctg ctgtacgagg   1620
gcgtctggga cacccccaaa aaattttcag gggcagtgc aggccagagc agcatctttc    1680
agagtcttga tgtccttctg ggaataaagc atgacgttgg tgaaggatct gctgcagaat   1740
tcctccagga aatgagagag tacatgcctc cagcccaccg gaacttcctc tcctccttag   1800
agtcagctcc cccagtccgt gagtttgtca ttttaagacg caatgaagac ttgaaggagg   1860
cttataatga gtgtgtgaat ggcctggtct ccctcagaat gttccacctc tcgatagtag   1920
atacttacat tgtgaagcct tcgaagcaga agcccatggg tggccacaag tcagaagagc   1980
cctcaaacac ggaaaacaga gggactgggg gtactgacgt catgaatttc ctgaggagtg   2040
tgaaagatac aaccaagaaa gcccttctga gttggcctta gaatcactag ataagatatc   2100
cgatcnntgg agttcgtgac cgccgccggg atcactctcg gcatggacga gctgtacaag   2160
tccggactca gatccaccgg atctagntaa ctgatcataa tcagccatac cacatttgta   2220
gaggttttac ttgctttaaa aaacctccca cacctccccc tgaacctgaa acataaaatg   2280
aatgcaattg ttgttgttaa cttgtttatt gcagcttata atggttacaa ataaagcaat   2340
agcatcacaa atttcacaaa taaagcattt ttttcactgc attctagttg tggtttgtcc   2400
aaactcatca atgtatctta acgcggccgg ccaataaata                         2440
```

<210> SEQ ID NO 22
<211> LENGTH: 2387
<212> TYPE: DNA
<213> ORGANISM: Artificial Sequence
<220> FEATURE:
<223> OTHER INFORMATION: Description of Artificial Sequence: Human IDO expression cassette
<220> FEATURE:
<221> NAME/KEY: misc_feature
<222> LOCATION: (1)..(2387)
<223> OTHER INFORMATION: n= a, c, g, t, unknown or other

<400> SEQUENCE: 22

```
tatttattcc tgcaggtcgt aggtcaaggt agtagagttt gcgggcagga cggggcgacc     60
atcaatgctg gagcccatca cattctgacg caccccggcc catgggggca tgcgcgttgt    120
caaatatgag ctcacaatgc ttccatcaaa cgagttggtg ctcatggcgg cggcggctgc    180
tgcaaaacag atacaaaact acataagacc cccaccttat atattctttc ccacccttan    240
nntaatagta atcaattacg gggtcattag ttcatagccc atatatggag ttccgcgtta    300
cataacttac ggtaaatggc ccgcctggct gaccgcccaa cgacccccgc ccattgacgt    360
caataatgac gtatgttccc atagtaacgc caatagggac tttccattga cgtcaatggg    420
tggagtattt acggtaaact gcccacttgg cagtacatca agtgtatcat atgccaagta    480
cgccccctat tgacgtcaat gacggtaaat ggcccgcctg gcattatgcc cagtacatga    540
ccttatggga ctttcctact tggcagtaca tctacgtatt agtcatcgct attaccatgg    600
tgatgcggtt ttggcagtac atcaatgggc gtggatagcg gtttgactca cggggatttc    660
caagtctcca ccccattgac gtcaatggga gtttgttttg gcaccaaaat caacgggact    720
ttccaaaatg tcgtaacaac tccgccccat tgacgcaaat gggcggtagg cgtgtacggt    780
gggaggtcta tataagcaga gctggtttag tgaaccgtca gatccgctag agatctccag    840
aggagcagac tacaagaatg gcacacgcta tggaaaactc ctggacaatc agtaaagagt    900
accatattga tgaagaagtg ggctttgctc tgccaaatcc acaggaaaat ctacctgatt    960
tttataatga ctggatgttc attgctaaac atctgcctga tctcatagag tctggccagc   1020
ttcgagaaag agttgagaag ttaaacatgc tcagcattga tcatctcaca gaccacaagt   1080
cacagcgcct tgcacgtcta gttctgggat gcatcaccat ggcatatgtg tggggcaaag   1140
gtcatggaga tgtccgtaag gtcttgccaa gaaatattgc tgttccttac tgccaactct   1200
ccaagaaact ggaactgcct cctattttgg tttatgcaga ctgtgtcttg gcaaactgga   1260
agaaaaagga tcctaataag cccctgactt atgagaacat ggacgttttg ttctcatttc   1320
gtgatggaga ctgcagtaaa ggattcttcc tggtctctct attggtggaa atagcagctg   1380
cttctgcaat caaagtaatt cctactgtat tcaaggcaat gcaaatgcaa gaacgggaca   1440
ctttgctaaa ggcgctgttg gaaatagctt cttgcttgga gaaagccctt caagtgtttc   1500
accaaatcca cgatcatgtg aacccaaaag catttttcag tgttcttcgc atatatttgt   1560
ctggctggaa aggcaacccc cagctatcag acggtctggt gtatgaaggg ttctgggaag   1620
acccaaagga gtttgcaggg ggcagtgcag gccaaagcag cgtctttcag tgctttgacg   1680
tcctgctggg catccagcag actgctggtg gaggacatgc tgctcagttc ctccaggaca   1740
tgagaagata tatgccacca gctcacagga acttcctgtg ctcattagag tcaaatccct   1800
cagtccgtga gtttgtcctt tcaaaaggtg atgctggcct gcgggaagct tatgacgcct   1860
gtgtgaaagc tctggtctcc ctgaggagct accatctgca aatcgtgact aagtacatcc   1920
tgattcctgc aagccagcag ccaaaggaga ataagacctc tgaagaccct tcaaaactgg   1980
aagccaaagg aactggaggc actgatttaa tgaatttcct gaagactgta agaagtacaa   2040
ctgagaaatc ccttttgaag gaaggttaat gtaacccaac aagagcactc gagcctaagc   2100
ttctagataa gatatccgat ccaccggatc tagataactg atcataatca gccataccac   2160
atttgtagag gttttacttg ctttaaaaaa cctcccacac ctccccctga acctgaaaca   2220
taaaatgaat gcaattgttg ttgttaactt gtttattgca gcttataatg gttacaaata   2280
aagcaatagc atcacaaatt tcacaaataa agcatttttt tcactgcatt ctagttgtgg   2340
tttgtccaaa ctcatcaatg tatcttaacg cggccggcca ataaata                  2387
```

<210> SEQ ID NO 23
<211> LENGTH: 30756
<212> TYPE: DNA
<213> ORGANISM: Artificial Sequence
<220> FEATURE:
<223> OTHER INFORMATION: Description of Artificial Sequence: Synthetic gutless backbone
<220> FEATURE:
<221> NAME/KEY: misc_feature
<222> LOCATION: (1)..(30756)
<223> OTHER INFORMATION: n=a, c, g, t, unknown or other

<400> SEQUENCE: 23
gtacggaagc ccggaaggag gggcaggggg cggtggctca ggtttctccg ggcggcggcg 60
gcggcggcgg cggcgacggc gacggcgacg gcagcgggga cggcagcagt agcgggagca 120
gcagcgtgga cgcggctggc gctggcgcca tgaacccgct gtaaggcgca ggctgtgcag 180
cacggggtgc gggggaggag gaggaggacg ccgcggtgaa gttctccgcc atgaacctga 240
ggggcctctt ccaggacttc aacccgaggt gaggcggcgt cgttggcgcc cccgggagtc 300
cgcgctgcgg gctcgggcgc gggctggtgt tcggctccgg ggaggcacgg cgggcgagat 360
gctgcagccc gaggacccgg gcgcctgccc gagcctccct gcgggtgcaa gcggtcccca 420
ggcaaaacag tcggcctcgg cgcccgcccg cttcctcctc ccgtgcccgg tgctttcagc 480
ccctgcccgg ccacggccgg aagggcccgg ccgcgagccc cgtcctgccc caagggaacc 540
ccattctttt ctgcttgctg tccctcattg gtgtcccaac ttcttcgtct cggttccatc 600
ctcttctgcg ccgctgcggg ccctccattc tccgcgtcag ggccgtctca ctcgacccaa 660
cacccctacc cccaccccag ctgtttcctc cagttcctcg cagtccttgg ggtttttcctt 720 gggtttatgc ccatccctct cttgtttgct tctttgttga acggatacct gaaacactgt 780
tgaatccttg gagtcagtgt cggggtatgg caatacctta tataatgcat ttctgggtga 840
gcctgatcat tttccatact cattttctca tcagtcttca ctacaagttt atttgcagga 900
agtagatatt gctgtccttc ttttccagat ggggaacacc cagtggacag tgtggagaaa 960
acactggcta agcactcaag cgcctgtcct tgcacttgcc cgactgtttt gtaactgttc 1020
tttaccccag gctgtgagct ccctgaagct gagaccatct cctgctcatc tcagtgtccc 1080
cagcgcctcc cacccaccgt atctggcaca tagtaggcac atataaaatg tttgtggaac 1140
taaactgagc ccaaagactt ggattggaga cgaggccata tgtaactggg tgattctctg 1200
cccttctttg gcccttctgt aaaatgagga gttggcctaa ctgatctctt aaatgcacta 1260
ctctccgaaa ggagtatccg tttcccttat ttgccagttg ggaagacgtg ctcagtaaat 1320
atttgtgtgc tgtaacctat gttaggtgct ttagatgctg gcggtctcag catggggtga 1380
agaagggctt gtacacttaa gatgccttac agtactgtgc agtgctgtac tgcgggggcc 1440
aactctgggg acctatgcct tggctgcttg ttgaggatga aaggaagttt taggggagta 1500
tttgtatgtt gagggtgcag tctccctagg gatggtgaca ttttaacttg tgagtcattg 1560
tgactttgta tgtgccctta ttccactttg agttcatgtt ctggttagga gtgccagtgt 1620
ctctaacacg gtgcagacat tatcattgtt ggcttcgaag gcatagagga ggtaacagaa 1680
ctaactgcag tcccttcctc tgctgcatca gggggttaag attggtctgc agggtagtag 1740
ggttggtgct gtggctggac aagccctgta tgtcttctat ttggagatgg tgataagaaa 1800
gttaagtaaa aactgaattg ttttgtgccc ttgggcaact cacttatcta ttgttttatc 1860
tgtagaatga gtataatctc tcagtggggt agggaggcca attaaggatt gattacaaag 1920

-continued

```
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgtttttttcc tttagccctt ttccccccaa aaaaattagt   2100
atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
cttttatact gtgccatttt cctgattcat tgttgccaga ggtagtgagt tccttaattt   2280
tacagatatt tcaagaggac attggccagg tattattggt aaatcagatt tgttttttta   2340
gctggtagtg tttcacctct cctgagcact cctagttttt gacagtgtgc tttagtctcc   2400
ttccatgctg aggaaggcct tctctatagg agaaagaaaa ctgaggggtg tacacaggaa   2460
gttaccttat gctggggact caaaccttga tgctactgct ttgctccctg cctctatttt   2520
tgaaccaatt caacatctcc ctcctacccc aggaccttgt cacacactgt tctctttacc   2580
aggaatgttt ccctctcttt tcctctcctc cagacctagt gaactcctat ttatcctcac   2640
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctccccccact aaactttaag ctccatgggg   2820
tcaaggccgt gactgtgtca gtatcgtagc ctgcatactt ggaatagtac ctggctcaat   2880
aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atcccctttc cagcctttttg   3180
gatcttggta agtctgaacc cactgctgcg ttggcaaggc tctggaaact atagtgacag   3240
agaatgattc acaagtgtca acactcagat gtacagggct gccagctgac ccactctacc   3300
tatttccatc tggcactgaa ctggttgatc atgaacttct tttcataatt gctttttagt   3360
tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt gggggagttg ctggttcaga gaaggccctt   3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tgggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt atttgcaaag tatattataa cattgattcc   3960
tcaaacatct agattcctat ctcgtgccaa gtgatgtact aggtgctcta agtacaaaaa   4020
taaaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200
tgacttttga gctagatttt gaattgagct agtcttttga gccagacttt tgagctagaa   4260
ttgtagggtt gtcatcagac cagagagtag gaagggtacc ttgtgaggaa gagagagaga   4320
```

-continued

```
gatcagattg ttactgtgtc tatgtagaaa aggaagacat aagaaactcc attttgatct   4380
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagacctta ccacccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
tgcacatcca ggcacagtac ctttccttga acttattcat gatacagatt cctttgctca   5040
cgtttccctg ctgaccttct ccccacctgt tgccctgcta cactcccctc gctaagatag   5100
taaaaataat gatcagtaaa tactgaggta actcagaggc tagcgctggt gcgggtcctc   5160
cgtatgctga gtgccggtcc cctgggccca ctgttctttc tctatacttt gtttctgtgt   5220
cttatttctt ttctcagtct cgtcccacct gacgagaaat acccacaggt gtggaggggc   5280
tggccccttt cagtatctca gaagggacaa agtacacaaa ggcatggggt catgatagtg   5340
cctggtatgt tcaggtagtg aagaggtcca tgtggtatga gcactgcaga tgatatgtgt   5400
cgtatgaatt aaaaatacat agttactgca aatagttttt acaggttatt gtttttaaga   5460
aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca aacgggccct ctagacgcgt tgacattgat tattgactag ttattaatag   5640
taatcaatta cggggtcatt agttcatagc ccatgatatc atatggagtt ccgcgttaca   5700
taacttacgg taaatggccc gcctggctga ccgcccaacg acccccgccc attgacgtca   5760
ataatgacgt atgttcccat agtaacgcca atagggactt tccattgacg tcaatgggtg   5820
gagtatttac ggtaaactgc ccacttggca gtacatcaag tgtatcatat gccaagtacg   5880
ccccctatt gacgtcaatg acggtaaatg gcccgcctgg cattatgccc agtncatgac   5940
cttatgggac tttcctactt ggcagacatc tacgtattag tcatcgctat taccatggtg   6000
atgcggtttt ggcagtacat caatgggcgt ggatagcggt ttgactcacg gggatttcc   6060
aagtctccac cccattgacg tcaatgggag tttgttttgg caccaaaatc aacgggactt   6120
tccaaaatgt cgtaacaact ccgccccatt gacgcaaatg ggcggtaggc gtgtacggtg   6180
ggaggtctat ataagcagag ctctctggct aactagagaa cccctgctta ctggcttatc   6240
gagatatctg cagaattcat ctgtcgactg ctaccggcag cgcgcagcgg caagaagtgt   6300
ctgggctggg acggacagga gaggctgtcg ccatcggcgt cctgtgcccc tctgctccgg   6360
cacggccctg tcgcagtgcc cgcgctttcc ccggcgcctg cacgcggcgc gcctgggtaa   6420
catgcttggg gtcctggtcc ttggcgcgct ggccctggcc ggcctggggt tccccgcacc   6480
cgcagagccg cagccgggtg gcagccagtg cgtcgagcac gactgcttcg cgctctaccc   6540
gggccccgcg accttcctca atgccagtca gatctgcgac ggactgcggg gccacctaat   6600
gacagtgcgc tcctcggtgg ctgccgatgt catttccttg ctactgaacg gcgacggcgg   6660
cgttggccgc cggcgcctct ggatcggcct gcagctgcca cccggctgcg gcgaccccaa   6720
```

```
gcgcctcggg cccctgcgcg gcttccagtg ggttacggga gacaacaaca ccagctatag   6780
caggtgggca cggctcgacc tcaatggggc tcccctctgc ggcccgttgt gcgtcgctgt   6840
ctccgctgct gaggccactg tgcccagcga gccgatctgg gaggagcagc agtgcgaagt   6900
gaaggccgat ggcttcctct gcgagttcca cttcccagcc acctgcaggc cactggctgt   6960
ggagcccggc gccgcggctg ccgccgtctc gatcacctac ggcacccgt tcgcggcccg    7020
cggagcggac ttccaggcgc tgccggtggg cagctccgcc gcggtggctc ccctcggctt   7080
acagctaatg tgcaccgcgc cgcccggagc ggtccagggg cactgggcca gggaggcgcc   7140
gggcgcttgg gactgcagcg tggagaacgg cggctgcgag cacgcgtgca atgcgatccc   7200
tggggctccc cgctgccagt gcccagccgg cgccgccctg caggcagacg ggcgctcctg   7260
caccgcatcc gcgacgcagt cctgcaacga cctctgcgag cacttctgcg ttcccaaccc   7320
cgaccagccg ggctcctact cgtgcatgtg cgagaccggc taccggctgg cggccgacca   7380
acaccggtgc gaggacgtgg atgactgcat actggagccc agtccgtgtc cgcagcgctg   7440
tgtcaacaca cagggtggct tcgagtgcca ctgctaccct aactacgacc tggtggacgg   7500
cgagtgtgtg gagcccgtgg acccgtgctt cagagccaac tgcgagtacc agtgccagcc   7560
cctgaaccaa actagctacc tctgcgtctg cgccgagggc ttcgcgccca ttccccacga   7620
gccgcacagg tgccagatgt tttgcaacca gactgcctgt ccagccgact gcgaccccaa   7680
cacccaggct agctgtgagt gccctgaagg ctacatcctg gacgacggtt tcatctgcac   7740
ggacatcgac gagtgcgaaa acggcggctt ctgctccggg gtgtgccaca acctccccgg   7800
taccttcgag tgcatctgcg ggcccgactc ggcccttgcc cgccacattg gcaccgactg   7860
tgactccggc aaggtggacg gtggcgacag cggctctggc gagcccccgc ccagcccgac   7920
gcccggctcc accttgactc ctccggccgt ggggctcgtg cattcgggct tgctcatagg   7980
catctccatc gcgagcctgt gcctggtggt ggcgcttttg gcgctcctct gccacctgcg   8040
caagaagcag ggcgccgcca gggccaagat ggagtacaag tgcgcggccc cttccaagga   8100
ggtagtgctg cagcacgtgc ggaccgagcg gacgccgcag agactctgag cggcctccgt   8160
ccaggagcct ggctccgtcc aggagcctgt gcctcctcac ccccagcttt gctaccaaag   8220
caccttagct ggcattacag ctggagaaga ccctccccgc accccccaag ctgttttctt   8280
ctattccatg gctaactggc gagggggtga ttagagggag gagaatgagc ctcggcctct   8340
tccgtgacgt cactggacca ctgggcaatg atggcaattt tgtaacgaag acacagactg   8400
cgatttgtcc caggtcctca ctaccgggcg caggagggtg agcgttattg gtcggcagcc   8460
ttctgggcag accttgacct cgtgggctag ggatgactaa aatatttatt ttttttaagt   8520
atttaggttt ttgtttgttt cctttgttct tacctgtatg tctccagtat ccactttgca   8580
cagctctccg gtctctctct ctctacaaac tcccacttgt catgtgacag gtaaactatc   8640
ttggtgaatt ttttttcct agccctctca catttatgaa gcaagcccca cttattcccc    8700
attcttccta gttttctcct cccaggaact gggccaactc acctgagtca ccctacctgt   8760
gcctgaccct acttcttttg ctcttagctg tctgctcaga cagaacccct acatgaaaca   8820
gaaacaaaaa cactaaaaat aaaaatggcc atttgctttt tcaccagatt tgctaattta   8880
tcctgaaatt tcagattccc agagcaaaat aattttaaac aaaggttgag atgtaaaagg   8940
tattaaattg atgttgctgg actgtcatag aaattacacc caaagaggta tttatcttta   9000
cttttaaaca gtgagcctga attttgttgc tgttttgatt tgtactgaaa aatggtaatt   9060
gttgctaatc ttcttatgca atttcctttt ttgttattat tacttatttt tgacagtgtt   9120
```

```
gaaaatgttc agaaggttgc tctagattga gagaagagac aaacacctcc caggagacag   9180
ttcaagaaag cttcaaactg catgattcat gccaattagc aattgactgt cactgttcct   9240
tgtcactggt agaccaaaat aaaaccagct ctactggtct tgtggaattg ggagcttggg   9300
aatggatcct ggaggatgcc caattagggc ctagccttaa tcaggtcctc agagaatttc   9360
taccatttca gagaggcctt ttggaatgtg gcccctgaac aagaattgga agctgccctg   9420
cccatgggag ctggttagaa atgcagaatc ctaggctcca ccccatccag ttcatgagaa   9480
tctatattta acaagatctg cagggggtgt gtctgctcag taatttgagg acaaccattc   9540
cagactgctt ccaattttct ggaatacatg aaatatagat cagttataag tagcaggcca   9600
agtcaggccc ttattttcaa gaaactgagg aatttctttt gtgtagcttt gctctttggt   9660
agaaaaggct aggtacacag ctctagacac tgccacacag ggtctgcaag gtctttggtt   9720
cagctaagct aggaatgaaa tcctgcttca gtgtatggaa ataaatgtat catagaaatg   9780
taacttttgt aagacaaagg ttttcctctt ctattttgta aactcaaaat atttgtacat   9840
agttatttat ttattggaga taatctagaa cacaggcaaa atccttgctt atgacatcac   9900
ttgtacaaaa taaacaaata acaatgtgaa aaaaaaaaaa aaaaaaaaaa aaaaaaaaaa   9960
aaaaaaaagg tagcagtcga cagatgaatt ccaccacact ggactagtgg atccgagctc  10020
ggtaccaagc ttaagtttgg gctgcaggaa ttctgatggc tctcaaaatt cctgcctcct  10080
ttagggataa aagactttaa gactttttaa caaaaaagaa aaagaaaaaa aaaattcctg  10140
cctcctggtg tacacacaca gaagggttcc ctccccttga atgtgaccag gatctgtgaa  10200
aataacggga tagccgctcc tgtgattagg ttatgtggta gactagagca agattctcct  10260
gctggttttg aagaagtcag ctgccatgtt gtgagactgt catgggctag ggcatgagcc  10320
tttaaatatc tgggagcaac ccctggccag cagccagtga gaaaacgggc cctcagtcct  10380
acaatcacaa ggaactaaat tctgccaaca acctgaagga actttgaaga ggatcatgag  10440
tcccttgatt cagcttgatg agcccctgag cagaggatac agctaacttg tactagggaa  10500
gtataaaaaa catgcatggg aatgatatat atcaacttta aggataattg tcatacttct  10560
gggaatgaag ggaaagaaat ggggctttag ttgtattatg atctttaatt tctcaaaaaa  10620
aataagatca gaagcaaata tggcaaaatg ttaatacttt tgtgggtacg taggtattca  10680
gcataccctt ttttctgagt tcaaaatatt ttataattaa aatgaaatgc aggccaggca  10740
cagtggctca tgcctataat accagcactt tgcgaggccg aggtgggagg atggcttgag  10800
gccagaccag cctggccaac atggcaaaac cccatctcta cttaaaaaaa aaaaaactat  10860
atatatatat atgtgtgtgt gtgtgtatat atatatatgt atatatattt atatatgtgt  10920
gtatatatat atatgtatat atatttatat atgtgtgtgt atatatatat atacacacac  10980
acacatatat acatacatac atacacacac acacacacac aattagccag gcatggtggc  11040
gcacacctgt agtcccagct acttgggagg ctgagacatg agaattgctt gaacctggga  11100
ggcagagtag ttagtgagct gagatcatac cactgcactc cagcctggtg acagagtgag  11160
actctgtctt aaaaaaaata aaaattaaaa ttaaatgcaa aaggtccaag tgaattgaag  11220
aggaaagggg tatcaaggaa ggttttgtgg aggtgacgtt tgagctgggt cttaaatgac  11280
ttaaacatgg gataagaagg gagggaataa ggacatttca ggtacgagaa ataaggagca  11340
aacagtggaa acaacctaac gtctgtcaac cagtgaatgg ataacaaaaa tgtaattcag  11400
atggtatcca acttacgatg gttcaacatg agatttttct gactttagga tagatttatc  11460
aaagtagtaa atccattttc aacttatgat attttcaact tcagatgggt ttatcaggac  11520
```

```
acagttgagg aacacctgtc tatccataca atttggcaat aaaaaggaaa tgagtgcaga  11580
tatactccac aacatgaatg aaccttgaaa acattaagtg agagaagcca gatacaaaag  11640
gccacatatt gtatgattct atttatacaa aatgtccaga ataggcaaat cttatagaca  11700
gcaagtaggt agatgatcag tttgctaggt gctgggggaa ggggaaatgg ggagtgatgg  11760
ctaaggggat tgggtttctt tgtggggcaa tgaaaatgtt ttaaaattga gcgtgataat  11820
gattgcacaa tgctgcatat atatataatc tatagattat atatatataa agagaggctg  11880
ttagacagtg ataagtgata tatatatata tatacataga gagagagaga gagagagaga  11940
gaggctgtta gtgataagtg atcaggaaaa taaaagtatt gaggaggaat acgaagttga  12000
cggtgtgaaa acatgagatt ttatatagga tggccaggga aggccttaat gagaaagtga  12060
cttatgagta aaaacaaggg atcctaaacc ttagcatgca tcagaatcac tcggaaactt  12120
gttaaagcat agcttgctgg gcctcatcac agatattttg attcggtagg ttcttgtctg  12180
atattaatac ttttggtcta gggaaccaca ttttgagaac cactgagcta aaggaagtaa  12240
aggtttccct tagtttacta gctggtaaca ctggcccagg aggcctttct ggaaaaggtc  12300
ccagtcccca aaggaagctg gggactcgcg ttcacatcgt caaggtttac caagttgtgg  12360
cgggcctttc cgtcttggaa aaagcctcaa aatggcagat tagggtgtcc atggccggcg  12420
gaaagggtct ttgaagttgc agaccaggag ggaagaagat tctgggcctc ccccatgcag  12480
tgtcagctgg caacagaatg caccccggct gggttggagg ccctgggtac tggctcttcc  12540
acaccagggg cccacctacc aagggcagca ggagcatctg cacctcctgc gccaggcgcc  12600
cttcagtgct tccacttgag cacctctcca gacaccagct agggtgacag tggtacaaat  12660
accagactcc cctggcctgc tcacctcaca gggtaatgtg ctgtggagtc aggggggacac  12720
agcaaccacc agatgacatg gctggccccg gggaggacga cacgcagata cggctacttg  12780
gcacctgtga tattttacac actcgagagg ggcccgcacc atcctcagcc ctctccccac  12840
attcactctt agttcatgtc acctccaccc agagggggac acaggcccac agcgatggcc  12900
ccacaccctg cctgaggtcg cccacttccc aggaggcagt cctgggactt ccacccgacc  12960
aggccccaga gcccaccgac ttaacccctc cagaggcttg tcgttcatta ccttattcaa  13020
gatggagacc agccttttg cggagaaaat gcgggtgaag gtcctgaaag tgcattgacg  13080
ccgttttcgg aagccataca agtttagctg gcggaagaag ctctttatcg aagttgtggc  13140
aaacactttg tgtgcgacgt cccttttgag aatctccttt tcaaagagtt tttgattgat  13200
cactctacaa gccccactgt catcccacca gatggacgaa aactggttgc tgctgaccag  13260
tctccacagt ttctgtggaa aggggaggga gaggagatta tcttctccct ggggcgggac  13320
gtcaccgtca gggtgcggcc ttctgaacga agcttcctcg gccagaggtt ggaaagcgat  13380
ttcttctgtc agcagcctca agttagggct cccagtggac cccgggtcgt cccaggcagg  13440
ggaaggatct gctgggtgaa ggtaggtctc tgactgcaac tggggaggga aaggcaccct  13500
ttccaagcca tgatcctgtc ctctcgaatt tctttcttca cagcgagcca tactcaatga  13560
tcgcttgtcc tccatctggc aaacttgcta gtgcagtgtg gccagcagca cccccttggca  13620
gtcatgtaac cagccccatg acatcataaa ggggctctga ctgccggggg gtggcatctc  13680
cacccccagc aagttgtgta ataaagggcc aaggcagaca agtagctgcc catctgcatg  13740
tgcacattct ggtcctcaca gtcatttcaa tgggaaagat gacactagtg cacaagagtg  13800
ccgaggggcc ctgccacacc gtagatgcag acctggagcg gtccccttgt cctagagctc  13860
ctgagccagg cacaactaca gcaaagccct ggctcaggaa ggtcagagct caccgtctga  13920
```

```
gtcatgggcc cacagacccc agcacatgac tgacactcgg aagcacagaa caaagggtag  13980
gacggtgccc atgggtcagg ctgtagccac gccacccttt ccaccctgtc ctagccagag  14040
gcagcaatgt gctccataca gatcctccta acacacccac actgtcggtc cccagcacgc  14100
agatgcccga cagcccctta ggcaaatggc ttagctgact gccccaccac acgccgtcgc  14160
catgcagtcc agtggggagt cggaggcagc ctccttcctg cctctcctcg gcctgcacgt  14220
gtccccccac caggcagaga cccttctaca ccccgggtgt ctgcggtcac atcgcggtgg  14280
ggcatgcagc tgttggcctt cgagcatgtt ttgttttcct tggccagtgt ctccagagaa  14340
acgcacgtgg gtttgtgtcc agcggtccat ctctgcaaca gttgttcctt tgggattgga  14400
tgctaggagg tcacgggaga ggtgtccatc caaagcagtg tctgtgtcac acactgtccc  14460
cacacacagg gccacctctg cacagactcc cccgactcga ttctgggcac agagctcagt  14520
gaccttccag agactgccac gaaccggtga tgcctccacg cttgagacat cctgaccgca  14580
gggcccaagg cgcactggct caggggggtga cagtgagggg tctgcaaaca gactgctgat  14640
gctcaacccg gccgctgccg agctgtgtga cttgggcacg tcacttaacc tctctcggcc  14700
tctgtctcct cccggggata agagtagtag cacctgcttc ccggggctgt gaggatccag  14760
tgggacgtat aggaactagc gaggcaccgg cagttgggtc agagctactg ttgtcacttc  14820
acaaggcatt ttcttcaaca gcaagtcgga aatctcatga gcctaaggca gaatccacct  14880
gtggcctctg gttacaaccc acaggactga aaatccttcc agccacagca actggtgaat  14940
ttcctggtca attgccacaa gtcatgagct gaaccccact tgagtttcag ttcaggcaga  15000
actctagaga cgactagggc aagctagaca gcgactgcag agccttttgt tgcagcgtga  15060
gcagtcctca gctgttgaca tcactgggga gcaaacgagg accaggagcg gtgaaaggac  15120
agtgtctgct gcagattgtc gtagcaccca aggaacactc cagaaagcct cctaagcagt  15180
aacaagtgtg gcaaggtgta gcccagccaa cagtggcatc tgcgaggcgt cccctccttc  15240
ctcccactac cccgtatacc ctgggacctg tgcactgaag gactcattct aaaggctgtg  15300
cccctgcagc cgccagcctc actcactggc tgcctgtgcc agctagagat ttctttcctc  15360
tgaggctggc tgagaggacc actccagttt cctggcccat ccagcaaaga agatacacat  15420
catgcacgtg taaaatgagg aaccggttta ttgaacagct taaggagagc aaaaatagtg  15480
gctttagcta catttttac acactgagca ggaaagtcta aaccatcccg ttcccctgta  15540
ccccaaagag aacagggctt gctggaggcc agtgccaagg gcggagtcgt gctcgcagca  15600
gacttgaatt aaccccatgt aggccggcga gcagttgccc gcgtgaaaac accaccctct  15660
tctcctggct gagaagatca aagctctttt tttaccctct tttcagcaaa ggacctattt  15720
gttttcaggc aggaggatgt taaacttgca gcctctgaca cacggtggaa cctgcagtgc  15780
ttggagaaac ggcacgcaca cgtgaaaaca tcatgcctac tccaaagcct tcttgttgct  15840
ggcaggaggg aagcttgaga ctttcccacg catagtcgtg acccgcgtgg ccgtttctgc  15900
tctcagcaac attctctagt gttccggctt caagcagcgc ttgtcaggtt tgaagctagc  15960
cactattctg agaacgtcag aaaagcatgg accatctctt gcttggtgtt gccgttgtgg  16020
cagtagcagc tactacgtac ctgcacgagt tccagggcag aagtggcaat gtcccatgaa  16080
ggcgtggcac cccacggggg gggggggga gtgtgccacg ggcgtccact tctgcagcag  16140
aaggcatgtg cctacagcac aagcttgtaa aaaaatactt gaacagaata tgctgtacag  16200
aactaggggt taacaccgca tatgaagatg ctaaaacatt tgtataaata ctctgtatac  16260
aagcatggag tcactcccgt agaaagggct catccgtgag gctatgaaaa actgctgtca  16320
```

```
gcatgcccaa agagaaacta cttccacagt aggaacagaa aaaaggactg tgctgtgtct  16380
aaacacgtgg tgcatcagag acatagttac agttcctact gactgcccca gccacgacct  16440
gggagtgctg aggacctggg agtgctcagc gagctgcagg aggtcagccc tgtggagaaa  16500
tacatttcta aacaatactt ttgattggga tttcagcacc gtatagacag atgttccttc  16560
tgggggcctg gcaagcagcc atctcccagt gggtctgacg gggaagaggg gtacctggag  16620
cccctcccag acagacggta atcccacccc tgttctcaca ctcttcctgg catccgcatc  16680
tgctggcaca caccccgtc acctgccact tccgcgtccc gtcgtggtga gtggctgata  16740
ggcgctggat gcaaacaagg catgagatgg acgtacctgg agacccagct ccagtactgg  16800
ttctggtctg cggggtgaac gagggggcag aggaaggcgg agagagtgcg tcccagtcca  16860
cttaagctct gtccccggaa gtggcatcta atctggcatt tcgatattta atttgggagg  16920
tgggagcaca tacttcccag ggctctgggt aatgaccacc ctggccttct ttcgaaacat  16980
gggtgcgatt ttagggggct ccggaactgg ggtctcttcg gtttcttcat tatcttcgtg  17040
atggagatca taggaaatgt ttccatattc tcgtagaaat gggaagattt caagcagaaa  17100
ctgacagaaa tctttgcgga taccaaacca ccctgaaaaa taagaatttt ttatttcaca  17160
cacgaggctc aactgacctt cctgttaact ttctttccgt aacaagaagt ttcactccta  17220
caatgtcata acatacttta tccagactcc tgagtcacaa agcctgaaca gggcttgagt  17280
acccaaaatg gggaagaagt gcaaatgcta gctctgtggt gcttggagtg gggttcccgg  17340
accggcaggg acagcgtcca cggggcctag ttagggatgc cattctcggg ccccagccca  17400
gacctccaga aactgagtcg ggctagggtg ggctccagcg gtccccttt cctggccctt  17460
ttgggattct gctggatgcc caaatttgag aactactgct ccagtgagtc tcaaaatatc  17520
tgtggtgcgc agactacggt gtcttccgct aatcttctcc agccaggata aactcatgga  17580
tgacagtgcc acccaagaac aagatttctg tcaccctctg gaatccgtga gggcggtagt  17640
catgcacggg ttggccagga gggggcctga actcatggag ccaccttaaa gccactttcc  17700
cagtcccact actcctctct gtaggctact ggagtgtcag ctcggtgcaa gccctccctg  17760
ctcccgggtg cggggtaggg ggcagaggca caaacagcaa gcacagcccg ggctgctggg  17820
ctgcagtgag gccctgcccc caaacccact ggctttccga agggcaatgc tctgggcttc  17880
cgtgccatgg agcccacagc cttgccagga aggcaccctc tgcagagatc gttttggaag  17940
tgtctgcctc agcaagcagg tggaggggaa tagagtgtta gcaaggcaag acaggcaaga  18000
ctcgggtgat ggcagcaagg atatggggga ggcagagcgg ccaacaggga cctaggatga  18060
atcccaggtt tgggtgggag atgtggattt tccatcaaac cctcccgggc ctgggaagaa  18120
tctgtcttga tccccatttt gcagaggagg gaacgggatc tctgagaggt tgcctgccgt  18180
gtctggttct acctcaaatg gcagcgtgca ctgcgagaaa agtcccggtg caggccagca  18240
gaacaccaga gttacggcat gcccttccct tagaaggtcc cagaatttcc tcagccctca  18300
ctttcccaca caagcttcta aattggggcc ctcggggact catcccttcc tagacttcta  18360
tccgccaccc cccaccccct ggtccccccc cagacacaca ccaaggactt ctgaaatgct  18420
gagtacatac agtggtttcc tcccttctgt ccaaatgtgg ttgccatcag cgtgatcaac  18480
gagagccaaa gggggacaaa gatcgggatg caggagaagg cgttgtggcc atccagtttg  18540
tgaaccagca gaatctaaag aaagagacat agtcccggtt gatgccagca ccgaaaatgg  18600
gcagaggcgg aagccagact tcattaggca gttcctcccc accaccccac ccccgcgtga  18660
gctcccacaa gagggaacat cagcaccgcc agaaaaaggc aggaaaccac ctatccctgg  18720
```

```
ggaaagctcg aaatgagctt ttatgtccct cttcagagct cggcaatagc ctatccactt  18780
gaaaagttcc cagtgccagc agttttatgg caaactcctc cgggtgtttg ttctaaggag  18840
tcaacagctc ccattctaga attctccacg tgactccaat acacaaatct gacatcccac  18900
tctgctttcc ccagagtgga aactggagcc atacagaggc accatggcta aaaaggtgca  18960
ctcttctccc tgccagcccc acgtgctgcc cccaagagaa aggaaggatg ctctcctttc  19020
accgaagctc cctctcggag atggctgtgt tctctcccct ctcctggagt gggctcactg  19080
tgagctcgag ggacagaggc tgcctttcta ggggtgcaga atcctgtcag gggaagcgca  19140
agcttcaggg gctgaagagg cttcccgtgg aacgcttacc tcaaatgtaa gaaggggcac  19200
gacgatggtc atccagctca gggccatggt tatgtgtgtc ctgcgctgtc cgcaatcaca  19260
tccatagagc gcaagaacaa gacggaccac acaatgtagt agaggaccac caggcacaga  19320
aaggacatga gaatccacag cgggacacac acaacctggg ggtgggtgag agaacagcaa  19380
gagaagtctc tttagagctt ccaacctggc ctctgatgga aggcatcttt agcaccttgc  19440
tgtgtctgtc cagttaaggc ggtccttcct gtgagccgaa taaggaccgt tccatctccc  19500
aggactgctg ggagcatcgc tcaggacaga aaaggtatgg tatgttcact atggggcctg  19560
ctgccaccag ggacacacac cgctcagtga gtcatcagtc cctcttcctt tgggtgacag  19620
acagccctgc acctggctcc gcagcctcta ctcttccaga ggcccactct cccacactct  19680
ctcaggctcc tctaggttct gctgccatca cagcttcccg ggaaatggga cacaactgtc  19740
accctgtgca cacacacaag atctcacccc aacagactct cttcacaggc aacattccca  19800
caacctgctg gggtactttt ggcaacacaa atgggaatgg gctccccaga aagtctggct  19860
gcctgggctc ctaaggatcc ctaacctcac ccctaccaag ttagtgaact tggcgggttg  19920
atgctggata caggttgatg ctggatacgt agcgctgccg ggtcgtgacc cctaaggaat  19980
tatccaaact cttgttttta gatgctttat tatatcaaac tctcctttaa acaagtggcc  20040
catctgctgg gatttggaag cctgtaatac tgaaattttc atcataatgg aaattttaaa  20100
aacagaattt gacccacctg tttttaaaac actttcatta cttaacaaga ggtctaatct  20160
tgggcaagtc ttgaaatttc tctggcctta gtttcccatg tgttaaatga aacttgaagc  20220
agttggtctc ttatagtctc ctgactctaa cattctaaga attatatttg tacaataact  20280
caaaaatcac ataatttaat ttaccatatg gactccaaaa tatattttct cattaggcta  20340
aacttgatct gcattttctg gatgtgtcca tattcttgga ctacactaaa acatgatacc  20400
aatgcttcct ctcaccataa accctcactt cgctttctac atttaagaat tttatagctg  20460
gaagagtcct taacagaaaa taccatctaa taattacccc tcaaaatcga gaaagtccta  20520
tctgttctta tgctagttat aagaatgagg cagcatttca cataatggtt ataaacactg  20580
ccacaagaag attcatgatg tgttgtttat ctgtagctct catcatactc tgtcatataa  20640
ctatagcatt aagattttaa tgttctatat attcttctaa gacagtgttt accagagtaa  20700
ggcacaaaag atccactggt ttgcaagaaa gattagaact tttaaatttt ttacctcacc  20760
ttgtttaatc tatattttg tatgtatttt gtaacatata tattattatt accataaatc  20820
atatataatt taaaatgcat atattagggg taaatgctca ggaaactttt tataaattgg  20880
gcatgcaaat acaagtttga agactcactg ttctaggtat taaaagtaaa gttataacca  20940
agtaaagctt ccacctttc atgtctcaaa gcagtttatt gttggaggta agatctctta  21000
gaagcctaaa caggtccaag tacagaatga agtaaggcta gcccataact tgtggcaagc  21060
aattcatact atttctctca tgctgagctc tcctcagtga agcagctact atagacaact  21120
```

```
gcagcctatt ggtagcctat tttacaggca ggaaaaaaat tacttttat tcaaagtgga  21180
actcaggaca tggggagaaa atgaatacaa aaaatagggt caatccaaag gcacacagca  21240
aatgagtaac acagttatgt ttttttccca tttgtatgag gtcccagtaa attctaagta  21300
aactgcaaat ttaataatac actaaaaaag ccatgcaatt gttcaaatga atcccagcat  21360
ggtacaagga gtacagacac tagagtctaa aaaacaaaag aatgccatta ttgagttttt  21420
gaattatatc aagtagttac atctctactt aataaatgag aaaaacgagg ataagaggcc  21480
atttgataaa atgaaaatag ccaagaagtg gtattagaga cttgaataca ggtattcggg  21540
tccaaagttc atctgctcaa atactaactg gggaaaagag ggaaaaatat ttatatacat  21600
atatatctgc acacaaaaat acccccaaaa gacaaaatga ggccaggcag ggtggctcac  21660
acccgtaatc ccggtacttt gggaggctga ggcaggtgga tacctgagat caggagttgg  21720
agatcagcct ggtcaacatg gtgaaaccct gtctctacta aagataaaaa aattagccag  21780
gcatggtggc gtgcgcctgt aatcccagct acttgggagt ctgaggcagg agaatcactt  21840
gaactgggaa ggggaggttg cagtgagcca agatcgtact actgcactcc agcctgggca  21900
gcagagtgag actccatcac aaaaataaat aaataaataa aatacaatga aacagaaagt  21960
tcaaataatc ccataatctt accaccaaga aataactttc actcgttata cttattgatt  22020
tttccataat aaatgtactt tactgtgact atcatgaaaa gaaagttatt ttagaaacag  22080
agaactgttt cagatcaaat ctatgtagta gaacagagcc attaggtggg aaagacgaga  22140
tcaaactaaa tctcagaagg cctaaaaggc taggtccatt ccagcactaa aaactgacca  22200
gacaagtaat ggcttcaaca gcttctaaat atggacaaag catgctgaaa gggaaggaca  22260
ggtctaacag tggtatatga aatgaacagg aggggcaaag ctcatttctc ctctgaagtt  22320
ttccaaagat gctgaggagg acattagttt gacatgaccc tgatatggga caagataatt  22380
tcacagaagt tttacatgtt aaagttttct tatagatact cattcaagta agcaatgaac  22440
actaaaatct aaagaaagaa aagagcttta gagtcaggtc tgtattcaaa ttcaagctct  22500
accacttact ggttctgtga ctttgggcaa gtcttttaac cttattaagt cttaatttcc  22560
tgatttgtaa aatggggata tcgtctccct cacaggattg ttgtgaaact tttatgagat  22620
taatgccttt atatttggca tagtgtaagt aaacaataac tggcagcttc aaaaaaaaaa  22680
agcagtagca ttccatcatt tattattggt tactctcaaa aagtttttca atgtactaga  22740
agataaatat tcaaatacct taatatctcc attattttca ggtaaacagc atgctcctga  22800
acaaccaatg ggtcaacaaa taaattaaaa gggaaatcta aaaacatctt gatattaaac  22860
tacatggaag cacaatatac caaaaccaat ggttcacact aggagaattt taaggtacaa  22920
gaaaactctt tgagatttct taaaataata gtatgtctga atttattgag tgatttacca  22980
gaaactgttg taagagctct acttgcatta tagcacttaa tcctcttaac tctatggctg  23040
ctattatcaa cctcacccta atcacatatg ggacacagag aggttaagta acttgcccaa  23100
ggtcagagtt aggaagtact aagccatgct ttgaatcagt tgtcaggctc cggaactcac  23160
actttcagcc actacataat actgctttgc tatcttttag gaaactatgt gagtctacct  23220
cacatagact cacataggtt tgtttttttt tttttttaa aggctatctt ttcccccatc  23280
aatgtttttt gaaggatccc aaattagagt cccacagagg cagacagcag tacttgacaa  23340
tatggacatt taaggttaat gttggattct actgtctttt tactacatga cctagggaac  23400
gataattaac ctagactgct tccaagggtt aaataaccca tttagttata ctatgtaaat  23460
tatctcttag tgattgattg aaagcacact gttactaatt gactcggtat gaagtgcttt  23520
```

```
tttttcttcc ctttcaagat acataccttt ccagttaaag ttgagagatc atctccacca  23580
attactttta tgtcccctgt tgactggtca ttctagttaa aaaaaaaaaa aactatatat  23640
atatatatct acacacacat atgtatatgt atatccttat gtacacacac aaacttcaaa  23700
ttaaatgaga actagaagat ttgagaagtt agctagctaa tatccatagc attatgatat  23760
tctaaatgat atgaattata agaattaggt ttcctgaaat gaatgactag aaaactttca  23820
agtagagatt agtaaaaatt aaaaagtcct aatcggccat tactgatttg atgtttttaa  23880
gagtcctaaa aaatgggtta catccatttt taagtgggta gtattataac agccacccat  23940
cttcaatcac agtgatttct gaattgtgag ggaagttatt agcatgacag gtgtctggtt  24000
ctggccctgt acgattccca tgagtcaagc aaattgtaag ggctggtcta tatcacaccc  24060
aaccccaagg atatgtccct caaaagtcta gcccaggccc cgtcatcttc agcatcatct  24120
gggaaaccag gtctgattag tagtccttta aggaatacct cttaggctcc cattttactg  24180
ctatcacaga atccaataaa acccttacag gagattcaat gggaaatgct caacacccac  24240
tgtagttggt ggtgacaatg accataattt ggctgtgctg gattcaggac agaaaatttg  24300
ggtgaaagag caggtgaaca aaagagcttc gacttgccct agcagagagc aagccatacc  24360
ataccacaaa gccacagcaa ttacaacggt gcagtaccag cacagtaaat gaacaaagta  24420
gagcccagaa acagacccag aactatatga ggatttagta tacaataaag atggtatttc  24480
gagtcagtag ggaaaagatg aattattcaa taaatgatgt ttggccaact agtaacccat  24540
ttgggaaaaa ataaaagtat ggtccctacc tcacagcata cacaaaaata aattccagac  24600
ggattaaaat ctaaatgtaa aaaataaagc cataagtgga ctggaagaaa atagagaatt  24660
ttttttaaca tccgtagaaa gggtaaaaac ccaggcatga catgaaccaa aactgaagag  24720
gttctgtaac aaataccccc ttttatatat tgggctccaa caataagaac ccataggaaa  24780
atggagaatg aacacaaata gacaatttat agaagagaag gttataaggt gtaaaattat  24840
atctatctga gaaacaaaca ctaaaacaat gtgattctac tgttctccca cccatactgg  24900
caaaacttaa gcctgataat atgctgaggg gaaataagca ctcttgttgg tgagagtatt  24960
aattggcata gcttcttttg aaaatgacat agcaatacct gttaaaattg caaacatgca  25020
tgtcacttaa tccagtaatc ccacttctgg gaatcaatgc tacaaaaaca ctgacaagta  25080
tacaaagata cattcaagag tgttcactgg gccgggtgcg gtggcttcat gcctgtaatc  25140
ccagggaggc agaggcaaga cgatcgcttg accccaggag ttcaaggcca gcccgagaaa  25200
cacagcaaga ccctgtctct cttttttttta tttaaaaaat aaatgttcac tgtatcagtt  25260
gttcacaaaa acaaaccaac atgtccatta acagggaacc atttaaatta atcaagttca  25320
tctacacaat gtaataccat gcaactatta aaaagcacct gataatccaa agcacactga  25380
gacagaataa tgctattaaa aacaccaagt agtggaacac tgtgttgcct atgacaccat  25440
ttttattcaa catttaaaca aatttgtaac agcaattaca tgagtagtga caatggcgtt  25500
tatgagactt ttcactttta tgtgcttcta tttttgttat gcttctatat atacatccat  25560
ttattatgga gtgttacttt caaaaatcac aaatgggcca gtattatttg gtgttgcaag  25620
gtgagcatat gacttctgat atcaaccttt gcatattact tctcaattta gggaaattac  25680
agacatccct tattctaact aacttaaaac ccagcatttc aaacatacag aattgatggg  25740
gaaaaaaaag aaagaagaaa gaaagaaaag gcaacaagct tcagatgaca gtgactcaca  25800
tcaaattatt tataaaatct gttaaatagt gccatcttct ggagatacct ggtattacag  25860
tccaactcca gttgatgtct ttacagagac aagaggaata aaggaaaaaa tattcaagaa  25920
```

-continued

```
ctgaaaagta tggagtcatg gaaaaattgc tgtgatccaa aggctacggt gataggacaa  25980
gaaacaagag aactccaagc agtaagacac tgctgttcta ttagcatcca aacctccata  26040
ctcctgtttg ccccaaggct tttttaaaaa atagagacag gatctcacta ttttgctcag  26100
gctggtcttg aactcctgga ctcaagctat cctcctgcct cggcctccta aagtgccgag  26160
attacaggct tgagtcacca tacctggcta tttatttttt cttaactctc ttgcctggcc  26220
tatagccacc atggaagcta ataaagaata ttaatttaag agtaatggta tagttcacta  26280
cattggaata caggtataag tgcctacatt gtacatgaat ggcatacatg gatcaattac  26340
cccacctggg tggccaaagg aactgcgcga acctccctcc ttggctgtct ggaacaagct  26400
tcccactaga tccctttact gagtgcctcc ctcatcttta attatggtta agtctaggat  26460
aacaggactg gcaaaggtga ggggaaagct tcctccagag ttgctctacc ctctcctcta  26520
ccgtcctatc tcctcactcc tctcagccaa ggagtccaat ctgtcctgaa ctcagagcgt  26580
cactgtcaac tacataaaat tgccagagaa gctctttggg actacaaaca catacccta  26640
atgtctttat ttctattttg tctacctctt cagtctaggt gaaaaaatag gaaggataat  26700
agggaagaac tttgtttatg cctacttatc cgcccctagg aattttgaaa acctctaggt  26760
agcaataaga actgcagcat ggtatagaaa aagaggagga aagctgtata gaaatgcata  26820
ataaatgggc aggaaaagaa ctgcttggaa caaacaggga ggttgaacta taaggagaga  26880
aagcagagag gctaatcaac aaggctgggt tcccaagagg gcatgatgag actattacta  26940
aggtaggaat tactaagggc tccatgtccc cttagtggct tagtactatg tagcttgctt  27000
tctgcagtga acttcagacc cttcttttag gatcctagaa tggacttttt ttttttatcg  27060
gaaaacagtc attctctcaa cattcaagca ggccccaagt ctaccacact caatcacatt  27120
ttctcttcat atcataatct ctcaaccatt ctctgtcctt ttaactgttt ttctataccc  27180
tgatcaaatg ccaacaaaag tgagaatgtt agaatcatgt atttttagag gtagactgta  27240
tctcagataa aaaaaaaggg cagatattcc attttccaaa atatgtatgc agaaaaaata  27300
agtatgaaag gacatatgct caggtaacaa gttaatttgt ttacttgtat tttatgaatt  27360
ccctaaaacc tacgtcaccc gccccgttcc cacgccccgc gccacgtcac aaactccacc  27420
ccctcattat catattggct tcaatccaaa ataaggtata ttattgatga tgttaattaa  27480
catgcatgga tccatatgcg gtgtgaaata ccgcacagat gcgtaaggag aaaataccgc  27540
atcaggcgct cttccgcttc ctcgctcact gactcgctgc gctcggtcgt tcggctgcgg  27600
cgagcggtat cagctcactc aaaggcggta atacggttat ccacagaatc aggggataac  27660
gcaggaaaga acatgtgagc aaaaggccag caaaaggcca ggaaccgtaa aaaggccgcg  27720
ttgctggcgt ttttccatag gctccgcccc cctgacgagc atcacaaaaa tcgacgctca  27780
agtcagaggt ggcgaaaccc gacaggacta taaagatacc aggcgtttcc ccctggaagc  27840
tccctcgtgc gctctcctgt tccgaccctg ccgcttaccg gatacctgtc cgcctttctc  27900
ccttcgggaa gcgtggcgct ttctcatagc tcacgctgta ggtatctcag ttcggtgtag  27960
gtcgttcgct ccaagctggg ctgtgtgcac gaaccccccg ttcagcccga ccgctgcgcc  28020
ttatccggta actatcgtct tgagtccaac ccggtaagac acgacttatc gccactggca  28080
gcagccactg gtaacaggat tagcagagcg aggtatgtag gcggtgctac agagttcttg  28140
aagtggtggc ctaactacgg ctacactaga aggacagtat ttggtatctg cgctctgctg  28200
aagccagtta ccttcggaaa aagagttggt agctcttgat ccggcaaaca aaccaccgct  28260
ggtagcggtg gtttttttgt ttgcaagcag cagattacgc gcagaaaaaa aggatctcaa  28320
```

```
gaagatcctt tgatcttttc tacggggtct gacgctcagt ggaacgaaaa ctcacgttaa  28380
gggattttgg tcatgagatt atcaaaaagg atcttcacct agatcctttt aaattaaaaa  28440
tgaagtttta aatcaatcta aagtatatat gagtaaactt ggtctgacag ttaccaatgc  28500
ttaatcagtg aggcacctat ctcagcgatc tgtctatttc gttcatccat agttgcctga  28560
ctccccgtcg tgtagataac tacgatacgg gagggcttac catctggccc cagtgctgca  28620
atgataccgc gagacccacg ctcaccggct ccagatttat cagcaataaa ccagccagcc  28680
ggaagggccg agcgcagaag tggtcctgca actttatccg cctccatcca gtctattaat  28740
tgttgccggg aagctagagt aagtagttcg ccagttaata gtttgcgcaa cgttgttgcc  28800
attgctgcag ccatgagatt atcaaaaagg atcttcacct agatcctttt cacgtagaaa  28860
gccagtccgc agaaacggtg ctgaccccgg atgaatgtca gctactgggc tatctggaca  28920
agggaaaacg caagcgcaaa gagaaagcag gtagcttgca gtgggcttac atggcgatag  28980
ctagactggg cggttttatg gacagcaagc gaaccggaat tgccagctgg ggcgccctct  29040
ggtaaggttg ggaagccctg caaagtaaac tggatggctt tcttgccgcc aaggatctga  29100
tggcgcaggg gatcaagctc tgatcaagag acaggatgag gatcgtttcg catgattgaa  29160
caagatggat tgcacgcagg ttctccggcc gcttgggtgg agaggctatt cggctatgac  29220
tgggcacaac agacaatcgg ctgctctgat gccgccgtgt tccggctgtc agcgcagggg  29280
cgcccggttc tttttgtcaa gaccgacctg tccggtgccc tgaatgaact gcaagacgag  29340
gcagcgcggc tatcgtggct ggccacgacg ggcgttcctt gcgcagctgt gctcgacgtt  29400
gtcactgaag cgggaaggga ctggctgcta ttgggcgaag tgccggggca ggatctcctg  29460
tcatctcacc ttgctcctgc cgagaaagta tccatcatgg ctgatgcaat gcggcggctg  29520
catacgcttg atccggctac ctgcccattc gaccaccaag cgaaacatcg catcgagcga  29580
gcacgtactc ggatggaagc cggtcttgtc gatcaggatg atctggacga agagcatcag  29640
gggctcgcgc cagccgaact gttcgccagg ctcaaggcga gcatgcccga cggcgaggat  29700
ctcgtcgtga cccatggcga tgcctgcttg ccgaatatca tggtggaaaa tggccgcttt  29760
tctggattca tcgactgtgg ccggctgggt gtggcggacc gctatcagga catagcgttg  29820
gctacccgtg atattgctga agagcttggc ggcgaatggg ctgaccgctt cctcgtgctt  29880
tacggtatcg ccgctcccga ttcgcagcgc atcgccttct atcgccttct tgacgagttc  29940
ttctgaattt tgttaaaatt tttgttaaat cagctcattt tttaaccaat aggccgaaat  30000
cggcaaaatc ccttataaat caaaagaata gaccgagata gggttgagtg ttgttccagt  30060
ttggaacaag agtccactat taaagaacgt ggactccaac gtcaaagggc gaaaaaccgt  30120
ctatcagggc gatggcccac tacgtgaacc atcaccctaa tcaagttttt tggggtcgag  30180
gtgccgtaaa gcactaaatc ggaaccctaa agggagcccc cgatttagag cttgacgggg  30240
aaagccggcg aacgtggcga gaaaggaagg gaagaaagcg aaaggagcgg gcgctagggc  30300
gctggcaagt gtagcggtca cgctgcgcgt aaccaccaca cccgccgcgc ttaatgcgcc  30360
gctacagggc gcgtccattc gccattcagg atcgaattaa ttcttaatta acatcatcaa  30420
taatatacct tattttggat tgaagccaat atgataatga gggggtggag tttgtgacgt  30480
ggcgcggggc gtgggaacgg ggcgggtgac gtagtagtgt ggcggaagtg tgatgttgca  30540
agtgtggcgg aacacatgta agcgacggat gtggcaaaag tgacgttttt ggtgtgcgcc  30600
ggtgtacaca ggaagtgaca attttcgcgc ggttttaggc ggatgttgta gtaaatttgg  30660
gcgtaaccga gtaagatttg gccattttcg cgggaaaact gaataagagg aagtgaaatc  30720
```

tgaataattt tgtgttactc atagcgcgta atactg 30756

<210> SEQ ID NO 24
<211> LENGTH: 32392
<212> TYPE: DNA
<213> ORGANISM: Artificial Sequence
<220> FEATURE:
<223> OTHER INFORMATION: Description of Artificial Sequence: Synthetic PrIDO-final
<220> FEATURE:
<221> NAME/KEY: misc_feature
<222> LOCATION: (1)..(32392)
<223> OTHER INFORMATION: n= a, c, g, t , unknown or other

<400> SEQUENCE: 24
gtacggaagc ccggaaggag gggcaggggg cggtggctca ggtttctccg ggcggcggcg 60
gcggcggcgg cggcgacggc gacggcgacg gcagcgggga cggcagcagt agcgggagca 120
gcagcgtgga cgcggctggc gctggcgcca tgaacccgct gtaaggcgca ggctgtgcag 180
cacggggtgc gggggaggag gaggaggacg ccgcggtgaa gttctccgcc atgaacctga 240
ggggcctctt ccaggacttc aacccgaggt gaggcggcgt cgttggcgcc cccgggagtc 300
cgcgctgcgg gctcgggcgc gggctggtgt tcggctccgg ggaggcacgg cgggcgagat 360
gctgcagccc gaggacccgg gcgcctgccc gagcctccct gcgggtgcaa gcggtcccca 420
ggcaaaacag tcggcctcgg cgcccgcccg cttcctcctc ccgtgcccgg tgctttcagc 480
ccctgcccgg ccacggccgg aagggcccgg ccgcgagccc cgtcctgccc caagggaacc 540
ccattctttt ctgcttgctg tccctcattg gtgtcccaac ttcttcgtct cggttccatc 600
ctcttctgcg ccgctgcggg ccctccattc tccgcgtcag ggccgtctca ctcgacccaa 660
cacccctacc cccaccccag ctgtttcctc cagttcctcg cagtccttgg ggttttcctt 720
gggtttatgc ccatccctct cttgtttgct tctttgttga acggatacct gaaacactgt 780
tgaatccttg gagtcagtgt cggggtatgg caatacctta tataatgcat ttctgggtga 840
gcctgatcat tttccatact cattttctca tcagtcttca ctacaagttt atttgcagga 900
agtagatatt gctgtccttc ttttccagat ggggaacacc cagtggacag tgtggagaaa 960
acactggcta agcactcaag cgcctgtcct tgcacttgcc cgactgtttt gtaactgttc 1020
tttaccccag gctgtgagct ccctgaagct gagaccatct cctgctcatc tcagtgtccc 1080
cagcgcctcc cacccaccgt atctggcaca tagtaggcac atataaaatg tttgtggaac 1140
taaactgagc ccaaagactt ggattggaga cgaggccata tgtaactggg tgattctctg 1200
cccttctttg gcccttctgt aaaatgagga gttggcctaa ctgatctctt aaatgcacta 1260
ctctccgaaa ggagtatccg tttcccttat ttgccagttg ggaagacgtg ctcagtaaat 1320
atttgtgtgc tgtaacctat gttaggtgct ttagatgctg gcggtctcag catggggtga 1380
agaagggctt gtacacttaa gatgccttac agtactgtgc agtgctgtac tgcgggggcc 1440
aactctgggg acctatgcct tggctgcttg ttgaggatga aaggaagttt taggggagta 1500
tttgtatgtt gagggtgcag tctccctagg gatggtgaca ttttaacttg tgagtcattg 1560
tgactttgta tgtgccctta ttccactttg agttcatgtt ctggttagga gtgccagtgt 1620
ctctaacacg gtgcagacat tatcattgtt ggcttcgaag gcatagagga ggtaacagaa 1680
ctaactgcag tcccttcctc tgctgcatca gggggttaag attggtctgc agggtagtag 1740
ggttggtgct gtggctggac aagccctgta tgtcttctat ttggagatgg tgataagaaa 1800
gttaagtaaa aactgaattg ttttgtgccc ttgggcaact cacttatcta ttgttttatc 1860
tgtagaatga gtataatctc tcagtggggt agggaggcca attaaggatt gattacaaag 1920

```
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgttttttcc tttagccctt ttccccccaa aaaaattagt   2100
atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
cttttatact gtgccatttt cctgattcat tgttgccaga ggtagtgagt tccttaattt   2280
tacagatatt tcaagaggac attggccagg tattattggt aaatcagatt tgttttttta   2340
gctggtagtg tttcacctct cctgagcact cctagttttt gacagtgtgc tttagtctcc   2400
ttccatgctg aggaaggcct tctctatagg agaaagaaaa ctgaggggtg tacacaggaa   2460
gttaccttat gctggggact caaaccttga tgctactgct ttgctccctg cctctatttt   2520
tgaaccaatt caacatctcc ctcctacccc aggaccttgt cacacactgt tctctttacc   2580
aggaatgttt ccctctcttt tcctctcctc cagacctagt gaactcctat ttatcctcac   2640
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctcccccact aaactttaag ctccatgggg   2820
tcaaggccgt gactgtgtca gtatcgtagc ctgcatactt ggaatagtac ctggctcaat   2880
aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atcccctttc cagccttttg   3180
gatcttggta agtctgaacc cactgctgcg ttggcaaggc tctggaaact atagtgacag   3240
agaatgattc acaagtgtca acactcagat gtacagggct gccagctgac ccactctacc   3300
tatttccatc tggcactgaa ctggttgatc atgaacttct tttcataatt gctttttagt   3360
tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt gggggagttg ctggttcaga gaaggcccctt  3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tgggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt atttgcaaag tatattataa cattgattcc   3960
tcaaacatct agattcctat ctcgtgccaa gtgatgtact aggtgctcta agtacaaaaa   4020
taaaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200
tgacttttga gctagatttt gaattgagct agtcttttga gccagacttt tgagctagaa   4260
ttgtagggtt gtcatcagac cagagagtag gaagggtacc ttgtgaggaa gagagagaga   4320
```

```
gatcagattg ttactgtgtc tatgtagaaa aggaagacat aagaaactcc attttgatct   4380
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagacctta ccacccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
tgcacatcca ggcacagtac ctttccttga acttattcat gatacagatt cctttgctca   5040
cgtttccctg ctgaccttct ccccacctgt tgccctgcta cactcccctc gctaagatag   5100
taaaaataat gatcagtaaa tactgaggta actcagaggc tagcgctggt gcgggtcctc   5160
cgtatgctga gtgccggtcc cctgggccca ctgttctttc tctatacttt gtttctgtgt   5220
cttatttctt ttctcagtct cgtcccacct gacgagaaat acccacaggt gtggaggggc   5280
tggccccttt cagtatctca gaagggacaa agtacacaaa ggcatggggt catgatagtg   5340
cctggtatgt tcaggtagtg aagaggtcca tgtggtatga gcactgcaga tgatatgtgt   5400
cgtatgaatt aaaaatacat agttactgca aatagttttt acaggttatt gtttttaaga   5460
aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca aacgggccct ctagacgcgt tgacattgat tattgactag ttattaatag   5640
taatcaatta cggggtcatt agttcatagc ccatgatatc atatggagtt ccgcgttaca   5700
taacttacgg taaatggccc gcctggctga ccgcccaacg acccccgccc attgacgtca   5760
ataatgacgt atgttcccat agtaacgcca atagggactt tccattgacg tcaatgggtg   5820
gagtatttac ggtaaactgc ccacttggca gtacatcaag tgtatcatat gccaagtacg   5880
ccccctatt gacgtcaatg acggtaaatg gcccgcctgg cattatgccc agtncatgac   5940
cttatgggac tttcctactt ggcagacatc tacgtattag tcatcgctat taccatggtg   6000
atgcggtttt ggcagtacat caatgggcgt ggatagcggt ttgactcacg gggatttcc    6060
aagtctccac cccattgacg tcaatgggag tttgttttgg caccaaaatc aacgggactt   6120
tccaaaatgt cgtaacaact ccgccccatt gacgcaaatg ggcggtaggc gtgtacggtg   6180
ggaggtctat ataagcagag ctctctggct aactagagaa cccctgctta ctggcttatc   6240
gagatatctg cagaattcat ctgtcgactg ctaccggcag cgcgcagcgg caagaagtgt   6300
ctgggctggg acggacagga gaggctgtcg ccatcggcgt cctgtgcccc tctgctccgg   6360
cacggccctg tcgcagtgcc cgcgctttcc ccggcgcctg cacgcggcgc gcctgggtaa   6420
catgcttggg gtcctggtcc ttggcgcgct ggccctggcc ggccgcgtta agatacattg   6480
atgagtttgg acaaaccaca actagaatgc agtgaaaaaa atgctttatt tgtgaaattt   6540
gtgatgctat tgctttattt gtaaccatta taagctgcaa taaacaagtt aacaacaaca   6600
attgcattca ttttatgttt caggttcagg gggaggtgtg ggaggttttt taaagcaagt   6660
aaaacctcta caaatgtggt atggctgatt atgatcagtt anctagatcc ggtggatctg   6720
```

```
agtccggact tgtacagctc gtccatgccg agagtgatcc cggcggcggt cacgaactcc   6780
anngatcgga tatcttatct agtgattcta aggccaactc agaagggctt tcttggttgt   6840
atctttcaca ctcctcagga aattcatgac gtcagtaccc ccagtccctc tgttttccgt   6900
gtttgagggc tcttctgact tgtggccacc catgggcttc tgcttcgaag gcttcacaat   6960
gtaagtatct actatcgaga ggtggaacat tctgagggag accaggccat tcacacactc   7020
attataagcc tccttcaagt cttcattgcg tcttaaaatg acaaactcac ggactggggg   7080
agctgactct aaggaggaga ggaagttccg gtgggctgga ggcatgtact ctctcatttc   7140
ctggaggaat tctgcagcag atccttcacc aacgtcatgc tttattccca gaaggacatc   7200
aagactctga aagatgctgc tctggcctgc actgcccccct gaaaattttt tgggggtgtc   7260
ccagacgccc tcgtacagca gaccctccgg cagcttaggg ttgcccttcc aaccagacaa   7320
atatatgcga agaacgtgga aaaaggtgtc tggatccacg aagtcacgca tcctcttaaa   7380
aatttccttg gctttctcca gactggcagc tatactacac agtgccttct ccagtgcttt   7440
cgggtcttga tgctctactg cactggatac agtaggaatt gctttgattg caggagaagc   7500
tgcgatttcc accattagag agaccaggaa gaagccttta tcgcagtccc caccaggaaa   7560
cgagaacaga atgtccatgt tctcgtatgt catgggccca ttggggtcct ttttcttcca   7620
gtttgccagg acgcagtctg cgtaagacag aatgggaggc agccccagct tctccgagag   7680
ctcgcagtag ggaacggcaa gattgcgggg cagcaccttt cgaatatcat catcccctcg   7740
gttccacaca tacgccatgg tgatgtaccc cagggccaaa tgtgccaggc gctgtaacct   7800
gtgtcccctc agttcttcgg tgcgcagtgt gggcagcttc tcgacttctt ctcggagctt   7860
cccattctca atcagcttag gcagatttct agccacaagg atccaaggtc tgtacgtatc   7920
aggcagctcc tccagtggat gtggtagagc aaagcccaca tcttcatcta tgtggtattc   7980
ttcaaggatc cttctagagc cttctgcagg agatatttga ctgtgaggca taatcgaatt   8040
cccgcggccg cgtcgacggt accagatctc tagcggatct gacggttcac taaaccagct   8100
ctgcttatat agacctccca ccgtacacgc ctaccgccca tttgcgtcaa tggggcggag   8160
ttgttacgac attttggaaa gtcccgttga ttttggtgcc aaaacaaact cccattgacg   8220
tcaatggggt ggagacttgg aaatccccgt gagtcaaacc gctatccacg cccattgatg   8280
tactgccaaa accgcatcac catggtaata gcgatgacta atacgtagat gtactgccaa   8340
gtaggaaagt cccataaggt catgtactgg gcataatgcc aggcgggcca tttaccgtca   8400
ttgacgtcaa tagggggcgt acttggcata tgatacactt gatgtactgc caagtgggca   8460
gtttaccgta aatactccac ccattgacgt caatggaaag tccctattgg cgttactatg   8520
ggaacatacg tcattattga cgtcaatggg cgggggtcgt tgggcggtca gccaggcggg   8580
ccatttacca acgcggaact ccatatatgg gctatgaact aatgaccccg taattgatta   8640
ctattannnt aagggtggga aagaatatat aaggtggggg tcttatgtag ttttgtatct   8700
gttttgcagc agccgccgcc gccatgagca ccaactcgtt tgatggaagc attgtgagct   8760
catatttgac aacgcgcatg cccccatggg ccggggtgcg tcagaatgtg atgggctcca   8820
gcattgatgg tcgccccgtc ctgcccgcaa actctactac cttgacctac gacctgcagg   8880
cagacgggcg ctcctgcacc gcatccgcga cgcagtcctg caacgacctc tgcgagcact   8940
tctgcgttcc caaccccgac cagccgggct cctactcgtg catgtgcgag accggctacc   9000
ggctggcggc cgaccaacac cggtgcgagg acgtggatga ctgcatactg gagcccagtc   9060
cgtgtccgca gcgctgtgtc aacacacagg gtggcttcga gtgccactgc taccctaact   9120
```

```
acgacctggt ggacggcgag tgtgtggagc ccgtggaccc gtgcttcaga gccaactgcg   9180
agtaccagtg ccagcccctg aaccaaacta gctacctctg cgtctgcgcc gagggcttcg   9240
cgcccattcc ccacgagccg cacaggtgcc agatgttttg caaccagact gcctgtccag   9300
ccgactgcga ccccaacacc caggctagct gtgagtgccc tgaaggctac atcctggacg   9360
acggtttcat ctgcacggac atcgacgagt gcgaaaacgg cggcttctgc tccggggtgt   9420
gccacaacct ccccggtacc ttcgagtgca tctgcgggcc cgactcggcc cttgcccgcc   9480
acattggcac cgactgtgac tccggcaagg tggacggtgg cgacagcggc tctggcgagc   9540
ccccgcccag cccgacgccc ggctccacct tgactcctcc ggccgtgggg ctcgtgcatt   9600
cgggcttgct cataggcatc tccatcgcga gcctgtgcct ggtggtggcg cttttggcgc   9660
tcctctgcca cctgcgcaag aagcagggcg ccgccagggc caagatggag tacaagtgcg   9720
cggccccttc caaggaggta gtgctgcagc acgtgcggac cgagcggacg ccgcagagac   9780
tctgagcggc ctccgtccag gagcctggct ccgtccagga gcctgtgcct cctcaccccc   9840
agctttgcta ccaaagcacc ttagctggca ttacagctgg agaagaccct ccccgcaccc   9900
cccaagctgt tttcttctat tccatggcta actggcgagg gggtgattag agggaggaga   9960
atgagcctcg gcctcttccg tgacgtcact ggaccactgg gcaatgatgg caattttgta  10020
acgaagacac agactgcgat ttgtcccagg tcctcactac cgggcgcagg agggtgagcg  10080
ttattggtcg gcagccttct gggcagacct tgacctcgtg ggctagggat gactaaaata  10140
tttatttttt ttaagtattt aggtttttgt ttgtttcctt tgttcttacc tgtatgtctc  10200
cagtatccac tttgcacagc tctccggtct ctctctctct acaaactccc acttgtcatg  10260
tgacaggtaa actatcttgg tgaatttttt tttcctagcc ctctcacatt tatgaagcaa  10320
gccccactta ttccccattc ttcctagttt tctcctccca ggaactgggc caactcacct  10380
gagtcaccct acctgtgcct gaccctactt cttttgctct tagctgtctg ctcagacaga  10440
acccctacat gaaacagaaa caaaaacact aaaaataaaa atggccattt gctttttcac  10500
cagatttgct aatttatcct gaaatttcag attcccagag caaaataatt ttaaacaaag  10560
gttgagatgt aaaaggtatt aaattgatgt tgctggactg tcatagaaat tacacccaaa  10620
gaggtattta tctttacttt taaacagtga gcctgaattt tgttgctgtt ttgatttgta  10680
ctgaaaaatg gtaattgttg ctaatcttct tatgcaattt ccttttttgt tattattact  10740
tatttttgac agtgttgaaa atgttcagaa ggttgctcta gattgagaga agagacaaac  10800
acctcccagg agacagttca agaaagcttc aaactgcatg attcatgcca attagcaatt  10860
gactgtcact gttccttgtc actggtagac caaaataaaa ccagctctac tggtcttgtg  10920
gaattgggag cttgggaatg gatcctggag gatgcccaat tagggcctag ccttaatcag  10980
gtcctcagag aatttctacc atttcagaga ggccttttgg aatgtggccc ctgaacaaga  11040
attggaagct gccctgccca tgggagctgg ttagaaatgc agaatcctag gctccacccc  11100
atccagttca tgagaatcta tatttaacaa gatctgcagg gggtgtgtct gctcagtaat  11160
ttgaggacaa ccattccaga ctgcttccaa ttttctggaa tacatgaaat atagatcagt  11220
tataagtagc aggccaagtc aggcccttat tttcaagaaa ctgaggaatt ttctttgtgt  11280
agctttgctc tttggtagaa aaggctaggt acacagctct agacactgcc acacagggtc  11340
tgcaaggtct ttggttcagc taagctagga atgaaatcct gcttcagtgt atggaaataa  11400
atgtatcata gaaatgtaac ttttgtaaga caaaggtttt cctcttctat tttgtaaact  11460
caaaatattt gtacatagtt atttatttat tggagataat ctagaacaca ggcaaaatcc  11520
```

```
ttgcttatga catcacttgt acaaaataaa caaataacaa tgtgaaaaaa aaaaaaaaaa  11580
aaaaaaaaaa aaaaaaaaaa aaaaggtagc agtcgacaga tgaattccac cacactggac  11640
tagtggatcc gagctcggta ccaagcttaa gtttgggctg caggaattct gatggctctc  11700
aaaattcctg cctcctttag ggataaaaga ctttaagact ttttaacaaa aaagaaaaag  11760
aaaaaaaaaa ttcctgcctc ctggtgtaca cacacagaag ggttccctcc ccttgaatgt  11820
gaccaggatc tgtgaaaata acgggatagc cgctcctgtg attaggttat gtggtagact  11880
agagcaagat tctcctgctg gttttgaaga agtcagctgc catgttgtga gactgtcatg  11940
ggctagggca tgagccttta aatatctggg agcaacccct ggccagcagc cagtgagaaa  12000
acgggccctc agtcctacaa tcacaaggaa ctaaattctg ccaacaacct gaaggaactt  12060
tgaagaggat catgagtccc ttgattcagc ttgatgagcc cctgagcaga ggatacagct  12120
aacttgtact agggaagtat aaaaaacatg catgggaatg atatatatca actttaagga  12180
taattgtcat acttctggga atgaagggaa agaaatgggg ctttagttgt attatgatct  12240
ttaatttctc aaaaaaaata agatcagaag caaatatggc aaaatgttaa tacttttgtg  12300
ggtacgtagg tattcagcat accctttttt ctgagttcaa aatattttat aattaaaatg  12360
aaatgcaggc caggcacagt ggctcatgcc tataatacca gcactttgcg aggccgaggt  12420
gggaggatgg cttgaggcca gaccagcctg gccaacatgg caaaacccca tctctactta  12480
aaaaaaaaaa aactatatat atatatatgt gtgtgtgtgt gtatatatat atatgtatat  12540
atatttatat atgtgtgtat atatatatat gtatatatat ttatatatgt gtgtgtatat  12600
atatatatac acacacacac atatatacat acatacatac acacacacac acacacaatt  12660
agccaggcat ggtggcgcac acctgtagtc ccagctactt gggaggctga gacatgagaa  12720
ttgcttgaac ctgggaggca gagtagttag tgagctgaga tcataccact gcactccagc  12780
ctggtgacag agtgagactc tgtcttaaaa aaaataaaaa ttaaaattaa atgcaaaagg  12840
tccaagtgaa ttgaagagga aaggggtatc aaggaaggtt ttgtggaggt gacgtttgag  12900
ctgggtctta aatgacttaa acatgggata agaagggagg gaataaggac atttcaggta  12960
cgagaaataa ggagcaaaca gtggaaacaa cctaacgtct gtcaaccagt gaatggataa  13020
caaaaatgta attcagatgg tatccaactt acgatggttc aacatgagat ttttctgact  13080
ttaggataga tttatcaaag tagtaaatcc attttcaact tatgatattt tcaacttcag  13140
atgggtttat caggacacag ttgaggaaca cctgtctatc catacaattt ggcaataaaa  13200
aggaaatgag tgcagatata ctccacaaca tgaatgaacc ttgaaaacat taagtgagag  13260
aagccagata caaaaggcca catattgtat gattctattt atacaaaatg tccagaatag  13320
gcaaatctta tagacagcaa gtaggtagat gatcagtttg ctaggtgctg ggggaagggg  13380
aaatggggag tgatggctaa ggggattggg tttctttgtg gggcaatgaa aatgttttaa  13440
aattgagcgt gataatgatt gcacaatgct gcatatatat ataatctata gattatatat  13500
atataaagag aggctgttag acagtgataa gtgatatata tatatatata catagagaga  13560
gagagagaga gagagagagg ctgttagtga taagtgatca ggaaaataaa agtattgagg  13620
aggaatacga agttgacggt gtgaaaacat gagattttat ataggatggc cagggaaggc  13680
cttaatgaga aagtgactta tgagtaaaaa caagggatcc taaaccttag catgcatcag  13740
aatcactcgg aaacttgtta aagcatagct tgctgggcct catcacagat attttgattc  13800
ggtaggttct tgtctgatat taatactttt ggtctaggga accacatttt gagaaccact  13860
gagctaaagg aagtaaaggt ttcccttagt ttactagctg gtaacactgg cccaggaggc  13920
```

```
ctttctggaa aaggtcccag tccccaaagg aagctgggga ctcgcgttca catcgtcaag  13980
gtttaccaag ttgtggcggg cctttccgtc ttggaaaaag cctcaaaatg gcagattagg  14040
gtgtccatgg ccggcggaaa gggtctttga agttgcagac caggagggaa gaagattctg  14100
ggcctccccc atgcagtgtc agctggcaac agaatgcacc ccggctgggt tggaggccct  14160
gggtactggc tcttccacac caggggccca cctaccaagg gcagcaggag catctgcacc  14220
tcctgcgcca ggcgcccttc agtgcttcca cttgagcacc tctccagaca ccagctaggg  14280
tgacagtggt acaaatacca gactcccctg gcctgctcac ctcacagggt aatgtgctgt  14340
ggagtcaggg ggacacagca accaccagat gacatggctg gccccgggga ggacgacacg  14400
cagatacggc tacttggcac ctgtgatatt ttacacactc gagaggggcc cgcaccatcc  14460
tcagccctct ccccacattc actcttagtt catgtcacct ccacccagag ggggacacag  14520
gcccacagcg atggccccac accctgcctg aggtcgccca cttcccagga ggcagtcctg  14580
ggacttccac ccgaccaggc cccagagccc accgacttaa cccctccaga ggcttgtcgt  14640
tcattacctt attcaagatg gagaccagcc tttttgcgga gaaaatgcgg gtgaaggtcc  14700
tgaaagtgca ttgacgccgt tttcggaagc catacaagtt tagctggcgg aagaagctct  14760
ttatcgaagt tgtggcaaac actttgtgtg cgacgtccct tttgagaatc tccttttcaa  14820
agagtttttg attgatcact ctacaagccc cactgtcatc ccaccagatg gacgaaaact  14880
ggttgctgct gaccagtctc cacagtttct gtggaaaggg gagggagagg agattatctt  14940
ctccctgggg cgggacgtca ccgtcagggt gcggccttct gaacgaagct tcctcggcca  15000
gaggttggaa agcgatttct tctgtcagca gcctcaagtt agggctccca gtggaccccg  15060
ggtcgtccca ggcaggggaa ggatctgctg ggtgaaggta ggtctctgac tgcaactggg  15120
gagggaaagg cacccctttcc aagccatgat cctgtcctct cgaatttctt tcttcacagc  15180
gagccatact caatgatcgc ttgtcctcca tctggcaaac ttgctagtgc agtgtggcca  15240
gcagcacccc ttggcagtca tgtaaccagc cccatgacat cataaagggg ctctgactgc  15300
cggggggtgg catctccacc cccagcaagt tgtgtaataa agggccaagg cagacaagta  15360
gctgcccatc tgcatgtgca cattctggtc ctcacagtca tttcaatggg aaagatgaca  15420
ctagtgcaca agagtgccga ggggccctgc cacaccgtag atgcagacct ggagcggtcc  15480
ccttgtccta gagctcctga gccaggcaca actacagcaa agccctggct caggaaggtc  15540
agagctcacc gtctgagtca tgggcccaca gaccccagca catgactgac actcggaagc  15600
acagaacaaa gggtaggacg gtgcccatgg gtcaggctgt agccacgcca ccctttccac  15660
cctgtcctag ccagaggcag caatgtgctc catacagatc ctcctaacac acccacactg  15720
tcggtcccca gcacgcagat gcccgacagc cccttaggca aatggcttag ctgactgccc  15780
caccacacgc cgtcgccatg cagtccagtg gggagtcgga ggcagcctcc ttcctgcctc  15840
tcctcggcct gcacgtgtcc ccccaccagg cagagaccct tctacacccc gggtgtctgc  15900
ggtcacatcg cggtggggca tgcagctgtt ggccttcgag catgttttgt tttccttggc  15960
cagtgtctcc agagaaacgc acgtgggttt gtgtccagcg gtccatctct gcaacagttg  16020
ttcctttggg attggatgct aggaggtcac gggagaggtg tccatccaaa gcagtgtctg  16080
tgtcacacac tgtccccaca cacagggcca cctctgcaca gactcccccg actcgattct  16140
gggcacagag ctcagtgacc ttccagagac tgccacgaac cggtgatgcc tccacgcttg  16200
agacatcctg accgcagggc ccaaggcgca ctggctcagg gggtgacagt gaggggtctg  16260
caaacagact gctgatgctc aacccggccg ctgccgagct gtgtgacttg ggcacgtcac  16320
```

```
ttaacctctc tcggcctctg tctcctcccg gggataagag tagtagcacc tgcttcccgg  16380
ggctgtgagg atccagtggg acgtatagga actagcgagg caccggcagt tgggtcagag  16440
ctactgttgt cacttcacaa ggcattttct tcaacagcaa gtcggaaatc tcatgagcct  16500
aaggcagaat ccacctgtgg cctctggtta caacccacag gactgaaaat ccttccagcc  16560
acagcaactg gtgaatttcc tggtcaattg ccacaagtca tgagctgaac cccacttgag  16620
tttcagttca ggcagaactc tagagacgac tagggcaagc tagacagcga ctgcagagcc  16680
ttttgttgca gcgtgagcag tcctcagctg ttgacatcac tggggagcaa acgaggacca  16740
ggagcggtga aaggacagtg tctgctgcag attgtcgtag cacccaagga acactccaga  16800
aagcctccta agcagtaaca agtgtggcaa ggtgtagccc agccaacagt ggcatctgcg  16860
aggcgtcccc tccttcctcc cactaccccg tataccctgg gacctgtgca ctgaaggact  16920
cattctaaag gctgtgcccc tgcagccgcc agcctcactc actggctgcc tgtgccagct  16980
agagatttct ttcctctgag gctggctgag aggaccactc cagtttcctg gcccatccag  17040
caaagaagat acacatcatg cacgtgtaaa atgaggaacc ggtttattga acagcttaag  17100
gagagcaaaa atagtggctt tagctacatt ttttacacac tgagcaggaa agtctaaacc  17160
atcccgttcc cctgtacccc aaagagaaca gggcttgctg gaggccagtg ccaagggcgg  17220
agtcgtgctc gcagcagact tgaattaacc ccatgtaggc cggcgagcag ttgcccgcgt  17280
gaaaacacca ccctcttctc ctggctgaga agatcaaagc tcttttttta ccctcttttc  17340
agcaaaggac ctatttgttt tcaggcagga ggatgttaaa cttgcagcct ctgacacacg  17400
gtggaacctg cagtgcttgg agaaacggca cgcacacgtg aaaacatcat gcctactcca  17460
aagccttctt gttgctggca ggagggaagc ttgagacttt cccacgcata gtcgtgaccc  17520
gcgtggccgt ttctgctctc agcaacattc tctagtgttc cggcttcaag cagcgcttgt  17580
caggtttgaa gctagccact attctgagaa cgtcagaaaa gcatggacca tctcttgctt  17640
ggtgttgccg ttgtggcagt agcagctact acgtacctgc acgagttcca gggcagaagt  17700
ggcaatgtcc catgaaggcg tggcacccca cggggggggg gggggagtgt gccacgggcg  17760
tccacttctg cagcagaagg catgtgccta cagcacaagc ttgtaaaaaa atacttgaac  17820
agaatatgct gtacagaact aggggttaac accgcatatg aagatgctaa aacatttgta  17880
taaatactct gtatacaagc atggagtcac tcccgtagaa agggctcatc cgtgaggcta  17940
tgaaaaactg ctgtcagcat gcccaaagag aaactacttc cacagtagga acagaaaaaa  18000
ggactgtgct gtgtctaaac acgtggtgca tcagagacat agttacagtt cctactgact  18060
gccccagcca cgacctggga gtgctgagga cctgggagtg ctcagcgagc tgcaggaggt  18120
cagccctgtg gagaaataca tttctaaaca atacttttga ttgggatttc agcaccgtat  18180
agacagatgt tccttctggg ggcctggcaa gcagccatct cccagtgggt ctgacgggga  18240
agaggggtac ctggagcccc tcccagacag acggtaatcc cacccctgtt ctcacactct  18300
tcctggcatc cgcatctgct ggcacacacc cccgtcacct gccacttccg cgtcccgtcg  18360
tggtgagtgg ctgataggcg ctggatgcaa acaaggcatg agatggacgt acctggagac  18420
ccagctccag tactggttct ggtctgcggg gtgaacgagg gggcagagga aggcggagag  18480
agtgcgtccc agtccactta agctctgtcc ccggaagtgg catctaatct ggcatttcga  18540
tatttaattt gggaggtggg agcacatact tcccagggct ctgggtaatg accaccctgg  18600
ccttctttcg aaacatgggt gcgattttag gggctccgg aactggggtc tcttcggttt  18660
cttcattatc ttcgtgatgg agatcatagg aaatgtttcc atattctcgt agaaatggga  18720
```

```
agatttcaag cagaaactga cagaaatctt tgcggatacc aaaccaccct gaaaaataag  18780
aattttttat ttcacacacg aggctcaact gaccttcctg ttaactttct ttccgtaaca  18840
agaagtttca ctcctacaat gtcataacat actttatcca gactcctgag tcacaaagcc  18900
tgaacagggc ttgagtaccc aaaatgggga agaagtgcaa atgctagctc tgtggtgctt  18960
ggagtggggt tcccggaccg gcagggacag cgtccacggg gcctagttag ggatgccatt  19020
ctcgggcccc agcccagacc tccagaaact gagtcgggct agggtgggct ccagcggtcc  19080
ccttttcctg gccctttgg gattctgctg gatgcccaaa tttgagaact actgctccag  19140
tgagtctcaa aatatctgtg gtgcgcagac tacggtgtct tccgctaatc ttctccagcc  19200
aggataaact catggatgac agtgccaccc aagaacaaga tttctgtcac cctctggaat  19260
ccgtgagggc ggtagtcatg cacgggttgg ccaggagggg gcctgaactc atggagccac  19320
cttaaagcca ctttcccagt cccactactc ctctctgtag gctactggag tgtcagctcg  19380
gtgcaagccc tccctgctcc cgggtgcggg gtagggggca gaggcacaaa cagcaagcac  19440
agcccgggct gctgggctgc agtgaggccc tgcccccaaa cccactggct ttccgaaggg  19500
caatgctctg ggcttccgtg ccatggagcc cacagccttg ccaggaaggc accctctgca  19560
gagatcgttt tggaagtgtc tgcctcagca agcaggtgga ggggaataga gtgttagcaa  19620
ggcaagacag gcaagactcg ggtgatggca gcaaggatat gggggaggca gagcggccaa  19680
cagggaccta ggatgaatcc caggtttggg tgggagatgt ggattttcca tcaaaccctc  19740
ccgggcctgg gaagaatctg tcttgatccc cattttgcag aggagggaac gggatctctg  19800
agaggttgcc tgccgtgtct ggttctacct caaatggcag cgtgcactgc gagaaaagtc  19860
ccggtgcagg ccagcagaac accagagtta cggcatgccc ttcccttaga aggtcccaga  19920
atttcctcag ccctcacttt cccacacaag cttctaaatt ggggccctcg ggactcatc  19980
ccttcctaga cttctatccg ccacccccca ccccctggtc cccccccaga cacacaccaa  20040
ggacttctga aatgctgagt acatacagtg gtttcctccc ttctgtccaa atgtggttgc  20100
catcagcgtg atcaacgaga gccaaagggg gacaaagatc gggatgcagg agaaggcgtt  20160
gtggccatcc agtttgtgaa ccagcagaat ctaaagaaag agacatagtc ccggttgatg  20220
ccagcaccga aaatgggcag aggcggaagc cagacttcat taggcagttc ctccccacca  20280
ccccaccccc gcgtgagctc ccacaagagg gaacatcagc accgccagaa aaaggcagga  20340
aaccacctat ccctggggaa agctcgaaat gagcttttat gtccctcttc agagctcggc  20400
aatagcctat ccacttgaaa agttcccagt gccagcagtt ttatggcaaa ctcctccggg  20460
tgtttgttct aaggagtcaa cagctcccat tctagaattc tccacgtgac tccaatacac  20520
aaatctgaca tcccactctg ctttccccag agtggaaact ggagccatac agaggcacca  20580
tggctaaaaa ggtgcactct tctccctgcc agccccacgt gctgccccca agagaaagga  20640
aggatgctct cctttcaccg aagctccctc tcggagatgg ctgtgttctc tcccctctcc  20700
tggagtgggc tcactgtgag ctcgagggac agaggctgcc tttctagggg tgcagaatcc  20760
tgtcagggga agcgcaagct tcaggggctg aagaggcttc ccgtggaacg cttacctcaa  20820
atgtaagaag gggcacgacg atggtcatcc agctcagggc catggttatg tgtgtcctgc  20880
gctgtccgca atcacatcca tagagcgcaa gaacaagacg gaccacacaa tgtagtagag  20940
gaccaccagg cacagaaagg acatgagaat ccacagcggg acacacacaa cctgggggtg  21000
ggtgagagaa cagcaagaga agtctcttta gagcttccaa cctggcctct gatggaaggc  21060
atctttagca ccttgctgtg tctgtccagt taaggcggtc cttcctgtga gccgaataag  21120
```

```
gaccgttcca tctcccagga ctgctgggag catcgctcag gacagaaaag gtatggtatg  21180
ttcactatgg ggcctgctgc caccagggga cacacacgct cagtgagtca tcagtccctc  21240
ttcctttggg tgacagacag ccctgcacct ggctccgcag cctctactct tccagaggcc  21300
cactctccca cactctctca ggctcctcta ggttctgctg ccatcacagc ttcccgggaa  21360
atgggacaca actgtcaccc tgtgcacaca cacaagatct caccccaaca gactctcttc  21420
acaggcaaca ttcccacaac ctgctggggg tactttggca acacaaatgg gaatgggctc  21480
cccagaaagt ctggctgcct gggctcctaa ggatccctaa cctcacccct accaagttag  21540
tgaacttggc gggttgatgc tggatacagg ttgatgctgg atacgtagcg ctgccgggtc  21600
gtgaccccta aggaattatc caaactcttg tttttagatg ctttattata tcaaactctc  21660
ctttaaacaa gtggcccatc tgctgggatt tggaagcctg taatactgaa attttcatca  21720
taatggaaat tttaaaaaca gaatttgacc cacctgtttt taaaacactt tcattactta  21780
acaagaggtc taatcttggg caagtcttga aatttctctg gccttagttt cccatgtgtt  21840
aaatgaaact tgaagcagtt ggtctcttat agtctcctga ctctaacatt ctaagaatta  21900
tatttgtaca ataactcaaa aatcacataa tttaatttac catatggact ccaaaatata  21960
ttttctcatt aggctaaact tgatctgcat tttctggatg tgtccatatt cttggactac  22020
actaaaacat gataccaatg cttcctctca ccataaaccc tcacttcgct ttctacattt  22080
aagaatttta tagctggaag agtccttaac agaaaatacc atctaataat tacccctcaa  22140
aatcgagaaa gtcctatctg ttcttatgct agttataaga atgaggcagc atttcacata  22200
atggttataa acactgccac aagaagattc atgatgtgtt gtttatctgt agctctcatc  22260
atactctgtc atataactat agcattaaga ttttaatgtt ctatatattc ttctaagaca  22320
gtgtttacca gagtaaggca caaaagatcc actggtttgc aagaaagatt agaactttta  22380
aatttttttac ctcaccttgt ttaatctata tttttgtatg tattttgtaa catatatatt  22440
attattacca taaatcatat ataatttaaa atgcatatat taggggtaaa tgctcaggaa  22500
actttttata aattgggcat gcaaatacaa gtttgaagac tcactgttct aggtattaaa  22560
agtaaagtta taaccaagta aagcttccac cttttcatgt ctcaaagcag tttattgttg  22620
gaggtaagat ctcttagaag cctaaacagg tccaagtaca gaatgaagta aggctagccc  22680
ataacttgtg gcaagcaatt catactattt ctctcatgct gagctctcct cagtgaagca  22740
gctactatag acaactgcag cctattggta gcctatttta caggcaggaa aaaaattact  22800
ttttattcaa agtggaactc aggacatggg gagaaaatga atacaaaaaa tagggtcaat  22860
ccaaaggcac acagcaaatg agtaacacag ttatgttttt ttcccatttg tatgaggtcc  22920
cagtaaattc taagtaaact gcaaatttaa taatacacta aaaaagccat gcaattgttc  22980
aaatgaatcc cagcatggta caaggagtac agacactaga gtctaaaaaa caaaagaatg  23040
ccattattga gtttttgaat tatatcaagt agttacatct ctacttaata aatgagaaaa  23100
acgaggataa gaggccattt gataaaatga aaatagccaa gaagtggtat tagagacttg  23160
aatacaggta ttcgggtcca aagttcatct gctcaaatac taactgggga aaagagggaa  23220
aaatatttat atacatatat atctgcacac aaaaataccc ccaaaagaca aaatgaggcc  23280
aggcagggtg gctcacaccc gtaatcccgg tactttggga ggctgaggca ggtggatacc  23340
tgagatcagg agttggagat cagcctggtc aacatggtga aaccctgtct ctactaaaga  23400
taaaaaaatt agccaggcat ggtggcgtgc gcctgtaatc ccagctactt gggagtctga  23460
ggcaggagaa tcacttgaac tgggaagggg aggttgcagt gagccaagat cgtactactg  23520
```

```
cactccagcc tgggcagcag agtgagactc catcacaaaa ataaataaat aaataaaata  23580
caatgaaaca gaaagttcaa ataatcccat aatcttacca ccaagaaata actttcactc  23640
gttatactta ttgatttttc cataataaat gtactttact gtgactatca tgaaaagaaa  23700
gttattttag aaacagagaa ctgtttcaga tcaaatctat gtagtagaac agagccatta  23760
ggtgggaaag acgagatcaa actaaatctc agaaggccta aaaggctagg tccattccag  23820
cactaaaaac tgaccagaca agtaatggct tcaacagctt ctaaatatgg acaaagcatg  23880
ctgaaaggga aggacaggtc taacagtggt atatgaaatg aacaggaggg gcaaagctca  23940
tttctcctct gaagttttcc aaagatgctg aggaggacat tagtttgaca tgaccctgat  24000
atgggacaag ataatttcac agaagtttta catgttaaag ttttcttata gatactcatt  24060
caagtaagca atgaacacta aaatctaaag aaagaaaaga gctttagagt caggtctgta  24120
ttcaaattca agctctacca cttactggtt ctgtgacttt gggcaagtct tttaacctta  24180
ttaagtctta atttcctgat ttgtaaaatg gggatatcgt ctccctcaca ggattgttgt  24240
gaaactttta tgagattaat gcctttatat ttggcatagt gtaagtaaac aataactggc  24300
agcttcaaaa aaaaaaagca gtagcattcc atcatttatt attggttact ctcaaaaagt  24360
ttttcaatgt actagaagat aaatattcaa ataccttaat atctccatta ttttcaggta  24420
aacagcatgc tcctgaacaa ccaatgggtc aacaaataaa ttaaaaggga aatctaaaaa  24480
catcttgata ttaaactaca tggaagcaca atataccaaa accaatggtt cacactagga  24540
gaattttaag gtacaagaaa actctttgag atttcttaaa ataatagtat gtctgaattt  24600
attgagtgat ttaccagaaa ctgttgtaag agctctactt gcattatagc acttaatcct  24660
cttaactcta tggctgctat tatcaacctc accctaatca catatgggac acagagaggt  24720
taagtaactt gcccaaggtc agagttagga agtactaagc catgctttga atcagttgtc  24780
aggctccgga actcacactt tcagccacta cataatactg ctttgctatc ttttaggaaa  24840
ctatgtgagt ctacctcaca tagactcaca taggtttgtt tttttttttt ttttaaaggc  24900
tatcttttcc cccatcaatg ttttttgaag gatcccaaat tagagtccca cagaggcaga  24960
cagcagtact tgacaatatg gacatttaag gttaatgttg gattctactg tctttttact  25020
acatgaccta gggaacgata attaacctag actgcttcca agggttaaat aacccattta  25080
gttatactat gtaaattatc tcttagtgat tgattgaaag cacactgtta ctaattgact  25140
cggtatgaag tgcttttttt tcttcccttt caagatacat acctttccag ttaaagttga  25200
gagatcatct ccaccaatta cttttatgtc ccctgttgac tggtcattct agttaaaaaa  25260
aaaaaaaact atatatatat atatctacac acacatatgt atatgtatat ccttatgtac  25320
acacacaaac ttcaaattaa atgagaacta gaagatttga gaagttagct agctaatatc  25380
catagcatta tgatattcta aatgatatga attataagaa ttaggtttcc tgaaatgaat  25440
gactagaaaa ctttcaagta gagattagta aaaattaaaa agtcctaatc ggccattact  25500
gatttgatgt ttttaagagt cctaaaaaat gggttacatc catttttaag tgggtagtat  25560
tataacagcc acccatcttc aatcacagtg atttctgaat tgtgagggaa gttattagca  25620
tgacaggtgt ctggttctgg ccctgtacga ttcccatgag tcaagcaaat tgtaagggct  25680
ggtctatatc acacccaacc ccaaggatat gtccctcaaa agtctagccc aggccccgtc  25740
atcttcagca tcatctggga aaccaggtct gattagtagt cctttaagga atacctctta  25800
ggctcccatt ttactgctat cacagaatcc aataaaaccc ttacaggaga ttcaatggga  25860
aatgctcaac acccactgta gttggtggtg acaatgacca taatttggct gtgctggatt  25920
```

caggacagaa aatttgggtg aaagagcagg tgaacaaaag agcttcgact tgccctagca 25980
gagagcaagc cataccatac cacaaagcca cagcaattac aacggtgcag taccagcaca 26040
gtaaatgaac aaagtagagc ccagaaacag acccagaact atatgaggat ttagtataca 26100
ataaagatgg tatttcgagt cagtagggaa aagatgaatt attcaataaa tgatgtttgg 26160
ccaactagta acccatttgg gaaaaaataa aagtatggtc cctacctcac agcatacaca 26220
aaaataaatt ccagacggat taaaatctaa atgtaaaaaa taaagccata agtggactgg 26280
aagaaaatag agaatttttt ttaacatccg tagaaagggt aaaaaaccag gcatgacatg 26340
aaccaaaact gaagaggttc tgtaacaaat acccccttt atatattggg ctccaacaat 26400
aagaacccat aggaaaatgg agaatgaaca caaatagaca atttatagaa gagaaggtta 26460
taaggtgtaa aattatatct atctgagaaa caaacactaa aacaatgtga ttctactgtt 26520
ctcccaccca tactggcaaa acttaagcct gataatatgc tgaggggaaa taagcactct 26580
tgttggtgag agtattaatt ggcatagctt cttttgaaaa tgacatagca atacctgtta 26640
aaattgcaaa catgcatgtc acttaatcca gtaatcccac ttctgggaat caatgctaca 26700
aaaacactga caagtataca aagatacatt caagagtgtt cactgggccg ggtgcggtgg 26760
cttcatgcct gtaatcccag ggaggcagag gcaagacgat cgcttgaccc caggagttca 26820
aggccagccc gagaaacaca gcaagaccct gtctctcttt tttttattta aaaaataaat 26880
gttcactgta tcagttgttc acaaaaacaa accaacatgt ccattaacag ggaaccattt 26940
aaattaatca agttcatcta cacaatgtaa taccatgcaa ctattaaaaa gcacctgata 27000
atccaaagca cactgagaca gaataatgct attaaaaaca ccaagtagtg gaacactgtg 27060
ttgcctatga caccattttt attcaacatt taaacaaatt tgtaacagca attacatgag 27120
tagtgacaat ggcgtttatg agacttttca cttttatgtg cttctatttt tgttatgctt 27180
ctatatatac atccatttat tatggagtgt tactttcaaa aatcacaaat gggccagtat 27240
tatttggtgt tgcaaggtga gcatatgact tctgatatca acctttgcat attacttctc 27300
aatttaggga aattacagac atcccttatt ctaactaact taaaacccag catttcaaac 27360
atacagaatt gatggggaaa aaaaagaaag aagaaagaaa gaaaaggcaa caagcttcag 27420
atgacagtga ctcacatcaa attatttata aaatctgtta aatagtgcca tcttctggag 27480
atacctggta ttacagtcca actccagttg atgtctttac agagacaaga ggaataaagg 27540
aaaaaatatt caagaactga aaagtatgga gtcatggaaa aattgctgtg atccaaaggc 27600
tacggtgata ggacaagaaa caagagaact ccaagcagta agacactgct gttctattag 27660
catccaaacc tccatactcc tgtttgcccc aaggcttttt taaaaaatag agacaggatc 27720
tcactatttt gctcaggctg gtcttgaact cctggactca agctatcctc ctgcctcggc 27780
ctcctaaagt gccgagatta caggcttgag tcaccatacc tggctattta ttttttctta 27840
actctcttgc ctggcctata gccaccatgg aagctaataa agaatattaa tttaagagta 27900
atggtatagt tcactacatt ggaatacagg tataagtgcc tacattgtac atgaatggca 27960
tacatggatc aattacccca cctgggtggc caaaggaact gcgcgaacct ccctccttgg 28020
ctgtctggaa caagcttccc actagatccc tttactgagt gcctccctca tctttaatta 28080
tggttaagtc taggataaca ggactggcaa aggtgagggg aaagcttcct ccagagttgc 28140
tctaccctct cctctaccgt cctatctcct cactcctctc agccaaggag tccaatctgt 28200
cctgaactca gagcgtcact gtcaactaca taaaattgcc agagaagctc tttgggacta 28260
caaacacata cccttaatgt ctttatttct attttgtcta cctcttcagt ctaggtgaaa 28320

```
aaataggaag gataataggg aagaactttg tttatgccta cttatccgcc cctaggaatt  28380
ttgaaaacct ctaggtagca ataagaactg cagcatggta tagaaaaaga ggaggaaagc  28440
tgtatagaaa tgcataataa atgggcagga aaagaactgc ttggaacaaa cagggaggtt  28500
gaactataag gagagaaagc agagaggcta atcaacaagg ctgggttccc aagagggcat  28560
gatgagacta ttactaaggt aggaattact aagggctcca tgtcccctta gtggcttagt  28620
actatgtagc ttgctttctg cagtgaactt cagacccttc ttttaggatc ctagaatgga  28680
cttttttttt ttatcggaaa acagtcattc tctcaacatt caagcaggcc ccaagtctac  28740
cacactcaat cacattttct cttcatatca taatctctca accattctct gtccttttaa  28800
ctgtttttct ataccctgat caaatgccaa caaaagtgag aatgttagaa tcatgtattt  28860
ttagaggtag actgtatctc agataaaaaa aaagggcaga tattccattt tccaaaatat  28920
gtatgcagaa aaaataagta tgaaaggaca tatgctcagg taacaagtta atttgtttac  28980
ttgtatttta tgaattccct aaaacctacg tcacccgccc cgttcccacg ccccgcgcca  29040
cgtcacaaac tccacccccct cattatcata ttggcttcaa tccaaaataa ggtatattat  29100
tgatgatgtt aattaacatg catggatcca tatgcggtgt gaaataccgc acagatgcgt  29160
aaggagaaaa taccgcatca ggcgctcttc cgcttcctcg ctcactgact cgctgcgctc  29220
ggtcgttcgg ctgcggcgag cggtatcagc tcactcaaag gcggtaatac ggttatccac  29280
agaatcaggg gataacgcag gaaagaacat gtgagcaaaa ggccagcaaa aggccaggaa  29340
ccgtaaaaag gccgcgttgc tggcgttttt ccataggctc cgcccccctg acgagcatca  29400
caaaaatcga cgctcaagtc agaggtggcg aaacccgaca ggactataaa gataccaggc  29460
gtttccccct ggaagctccc tcgtgcgctc tcctgttccg accctgccgc ttaccggata  29520
cctgtccgcc tttctccctt cgggaagcgt ggcgctttct catagctcac gctgtaggta  29580
tctcagttcg gtgtaggtcg ttcgctccaa gctgggctgt gtgcacgaac cccccgttca  29640
gcccgaccgc tgcgccttat ccggtaacta tcgtcttgag tccaacccgg taagacacga  29700
cttatcgcca ctggcagcag ccactggtaa caggattagc agagcgaggt atgtaggcgg  29760
tgctacagag ttcttgaagt ggtggcctaa ctacggctac actagaagga cagtatttgg  29820
tatctgcgct ctgctgaagc cagttacctt cggaaaaaga gttggtagct cttgatccgg  29880
caaacaaacc accgctggta gcggtggttt ttttgtttgc aagcagcaga ttacgcgcag  29940
aaaaaaagga tctcaagaag atcctttgat cttttctacg gggtctgacg ctcagtggaa  30000
cgaaaactca cgttaaggga ttttggtcat gagattatca aaaaggatct tcacctagat  30060
ccttttaaat taaaaatgaa gttttaaatc aatctaaagt atatatgagt aaacttggtc  30120
tgacagttac caatgcttaa tcagtgaggc acctatctca gcgatctgtc tatttcgttc  30180
atccatagtt gcctgactcc ccgtcgtgta gataactacg atacgggagg gcttaccatc  30240
tggccccagt gctgcaatga taccgcgaga cccacgctca ccggctccag atttatcagc  30300
aataaaccag ccagccggaa gggccgagcg cagaagtggt cctgcaactt tatccgcctc  30360
catccagtct attaattgtt gccgggaagc tagagtaagt agttcgccag ttaatagttt  30420
gcgcaacgtt gttgccattg ctgcagccat gagattatca aaaaggatct tcacctagat  30480
ccttttcacg tagaaagcca gtccgcagaa acggtgctga ccccggatga atgtcagcta  30540
ctgggctatc tggacaaggg aaaacgcaag cgcaaagaga aagcaggtag cttgcagtgg  30600
gcttacatgg cgatagctag actgggcggt tttatggaca gcaagcgaac cggaattgcc  30660
agctggggcg ccctctggta aggttgggaa gccctgcaaa gtaaactgga tggctttctt  30720
```

gccgccaagg atctgatggc gcaggggatc aagctctgat caagagacag gatgaggatc 30780
gtttcgcatg attgaacaag atggattgca cgcaggttct ccggccgctt gggtggagag 30840
gctattcggc tatgactggg cacaacagac aatcggctgc tctgatgccg ccgtgttccg 30900
gctgtcagcg caggggcgcc cggttctttt tgtcaagacc gacctgtccg gtgccctgaa 30960
tgaactgcaa gacgaggcag cgcggctatc gtggctggcc acgacgggcg ttccttgcgc 31020
agctgtgctc gacgttgtca ctgaagcggg aagggactgg ctgctattgg gcgaagtgcc 31080
ggggcaggat ctcctgtcat ctcaccttgc tcctgccgag aaagtatcca tcatggctga 31140
tgcaatgcgg cggctgcata cgcttgatcc ggctacctgc ccattcgacc accaagcgaa 31200
acatcgcatc gagcgagcac gtactcggat ggaagccggt cttgtcgatc aggatgatct 31260
ggacgaagag catcaggggc tcgcgccagc cgaactgttc gccaggctca aggcgagcat 31320
gcccgacggc gaggatctcg tcgtgaccca tggcgatgcc tgcttgccga atatcatggt 31380
ggaaaatggc cgcttttctg gattcatcga ctgtggccgg ctgggtgtgg cggaccgcta 31440
tcaggacata gcgttggcta cccgtgatat tgctgaagag cttggcggcg aatgggctga 31500
ccgcttcctc gtgctttacg gtatcgccgc tcccgattcg cagcgcatcg ccttctatcg 31560
ccttcttgac gagttcttct gaattttgtt aaaatttttg ttaaatcagc tcatttttta 31620
accaataggc cgaaatcggc aaaatccctt ataaatcaaa agaatagacc gagatagggt 31680
tgagtgttgt tccagtttgg aacaagagtc cactattaaa gaacgtggac tccaacgtca 31740
aagggcgaaa aaccgtctat cagggcgatg gcccactacg tgaaccatca ccctaatcaa 31800 gtttttttggg gtcgaggtgc cgtaaagcac taaatcggaa ccctaaaggg agcccccgat 31860
ttagagcttg acggggaaag ccggcgaacg tggcgagaaa ggaagggaag aaagcgaaag 31920
gagcgggcgc tagggcgctg gcaagtgtag cggtcacgct gcgcgtaacc accacacccg 31980
ccgcgcttaa tgcgccgcta cagggcgcgt ccattcgcca ttcaggatcg aattaattct 32040
taattaacat catcaataat ataccttatt ttggattgaa gccaatatga taatgagggg 32100
gtggagtttg tgacgtggcg cggggcgtgg gaacggggcg ggtgacgtag tagtgtggcg 32160
gaagtgtgat gttgcaagtg tggcggaaca catgtaagcg acggatgtgg caaaagtgac 32220
gtttttggtg tgcgccggtg tacacaggaa gtgacaattt tcgcgcggtt ttaggcggat 32280
gttgtagtaa atttgggcgt aaccgagtaa gatttggcca ttttcgcggg aaaactgaat 32340
aagaggaagt gaaatctgaa taattttgtg ttactcatag cgcgtaatac tg 32392

<210> SEQ ID NO 25
<211> LENGTH: 32339
<212> TYPE: DNA
<213> ORGANISM: Artificial Sequence
<220> FEATURE:
<223> OTHER INFORMATION: Description of Artificial Sequence: Synthetic
PhIDO-final
<220> FEATURE:
<221> NAME/KEY: misc_feature
<222> LOCATION: (1)..(32339)
<223> OTHER INFORMATION: n= a, c, g, t, unknown or other

<400> SEQUENCE: 25
gtacggaagc ccggaaggag gggcaggggg cggtggctca ggtttctccg ggcggcggcg 60
gcggcggcgg cggcgacggc gacggcgacg gcagcgggga cggcagcagt agcgggagca 120
gcagcgtgga cgcggctggc gctggcgcca tgaacccgct gtaaggcgca ggctgtgcag 180
cacggggtgc gggggaggag gaggaggacg ccgcggtgaa gttctccgcc atgaacctga 240

```
ggggcctctt ccaggacttc aacccgaggt gaggcggcgt cgttggcgcc cccgggagtc    300
cgcgctgcgg gctcgggcgc gggctggtgt tcggctccgg ggaggcacgg cgggcgagat    360
gctgcagccc gaggacccgg gcgcctgccc gagcctccct gcgggtgcaa gcggtcccca    420
ggcaaaacag tcggcctcgg cgcccgcccg cttcctcctc ccgtgcccgg tgctttcagc    480
ccctgcccgg ccacggccgg aagggcccgg ccgcgagccc cgtcctgccc caagggaacc    540
ccattctttt ctgcttgctg tccctcattg gtgtcccaac ttcttcgtct cggttccatc    600
ctcttctgcg ccgctgcggg ccctccattc tccgcgtcag ggccgtctca ctcgacccaa    660
cacccctacc cccaccccag ctgtttcctc cagttcctcg cagtccttgg ggtttccttt    720
gggtttatgc ccatccctct cttgtttgct tctttgttga acggatacct gaaacactgt    780
tgaatccttg gagtcagtgt cggggtatgg caataccta tataatgcat ttctgggtga    840
gcctgatcat tttccatact cattttctca tcagtcttca ctacaagttt atttgcagga    900
agtagatatt gctgtccttc ttttccagat ggggaacacc cagtggacag tgtggagaaa    960
acactggcta agcactcaag cgcctgtcct tgcacttgcc cgactgtttt gtaactgttc   1020
tttaccccag gctgtgagct ccctgaagct gagaccatct cctgctcatc tcagtgtccc   1080
cagcgcctcc cacccaccgt atctggcaca tagtaggcac atataaaatg tttgtggaac   1140
taaactgagc ccaaagactt ggattggaga cgaggccata tgtaactggg tgattctctg   1200
cccttctttg gcccttctgt aaaatgagga gttggcctaa ctgatctctt aaatgcacta   1260
ctctccgaaa ggagtatccg tttcccttat ttgccagttg ggaagacgtg ctcagtaaat   1320
atttgtgtgc tgtaacctat gttaggtgct ttagatgctg gcggtctcag catggggtga   1380
agaagggctt gtacacttaa gatgccttac agtactgtgc agtgctgtac tgcgggggcc   1440
aactctgggg acctatgcct tggctgcttg ttgaggatga aaggaagttt taggggagta   1500
tttgtatgtt gagggtgcag tctccctagg gatggtgaca ttttaacttg tgagtcattg   1560
tgactttgta tgtgccctta ttccactttg agttcatgtt ctggttagga gtgccagtgt   1620
ctctaacacg gtgcagacat tatcattgtt ggcttcgaag gcatagagga ggtaacagaa   1680
ctaactgcag tcccttcctc tgctgcatca gggggttaag attggtctgc agggtagtag   1740
ggttggtgct gtggctggac aagccctgta tgtcttctat ttggagatgg tgataagaaa   1800
gttaagtaaa aactgaattg ttttgtgccc ttgggcaact cacttatcta ttgttttatc   1860
tgtagaatga gtataatctc tcagtggggt agggaggcca attaaggatt gattacaaag   1920
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgttttttcc tttagccctt ttccccccaa aaaaattagt   2100
atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
cttttatact gtgccatttt cctgattcat tgttgccaga ggtagtgagt tccttaattt   2280
tacagatatt tcaagaggac attggccagg tattattggt aaatcagatt tgttttttta   2340
gctggtagtg tttcacctct cctgagcact cctagttttt gacagtgtgc tttagtctcc   2400
ttccatgctg aggaaggcct tctctatagg agaaagaaaa ctgaggggtg tacacaggaa   2460
gttaccttat gctggggact caaaccttga tgctactgct ttgctccctg cctctatttt   2520
tgaaccaatt caacatctcc ctcctacccc aggaccttgt cacacactgt tctctttacc   2580
aggaatgttt ccctctcttt tcctctcctc cagacctagt gaactcctat ttatcctcac   2640
```

```
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctccccccact aaactttaag ctccatgggg   2820
tcaaggccgt gactgtgtca gtatcgtagc ctgcatactt ggaatagtac ctggctcaat   2880
aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atcccctttc cagccttttg   3180
gatcttggta agtctgaacc cactgctgcg ttggcaaggc tctggaaact atagtgacag   3240
agaatgattc acaagtgtca acactcagat gtacagggct gccagctgac ccactctacc   3300
tatttccatc tggcactgaa ctggttgatc atgaacttct tttcataatt gctttttagt   3360
tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt gggggagttg ctggttcaga gaaggccctt   3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tggggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt atttgcaaag tatattataa cattgattcc   3960
tcaaacatct agattcctat ctcgtgccaa gtgatgtact aggtgctcta agtacaaaaa   4020
taaaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200
tgacttttga gctagatttt gaattgagct agtcttttga gccagacttt tgagctagaa   4260
ttgtagggtt gtcatcagac cagagagtag gaagggtacc ttgtgaggaa gagagagaga   4320
gatcagattg ttactgtgtc tatgtagaaa aggaagacat aagaaactcc attttgatct   4380
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagacctta ccaccccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
tgcacatcca ggcacagtac ctttccttga acttattcat gatacagatt cctttgctca   5040
```

-continued

```
cgtttccctg ctgaccttct ccccacctgt tgccctgcta cactcccctc gctaagatag   5100

taaaaataat gatcagtaaa tactgaggta actcagaggc tagcgctggt gcgggtcctc   5160

cgtatgctga gtgccggtcc cctgggccca ctgttctttc tctatacttt gtttctgtgt   5220

cttatttctt ttctcagtct cgtcccacct gacgagaaat acccacaggt gtggaggggc   5280

tggccccttt cagtatctca gaagggacaa agtacacaaa ggcatggggt catgatagtg   5340

cctggtatgt tcaggtagtg aagaggtcca tgtggtatga gcactgcaga tgatatgtgt   5400

cgtatgaatt aaaaatacat agttactgca aatagttttt acaggttatt gtttttaaga   5460

aagcagtatc taatgcacga gtgtactgtc agtactgtca atgaactact taccactcaa   5520

gtgactgctt acgcgtcgaa tcactagtga attcgcggcc gcctcgagtc tagaactagt   5580

ggatccccca aacgggccct ctagacgcgt tgacattgat tattgactag ttattaatag   5640

taatcaatta cggggtcatt agttcatagc ccatgatatc atatggagtt ccgcgttaca   5700

taacttacgg taaatggccc gcctggctga ccgcccaacg acccccgccc attgacgtca   5760

ataatgacgt atgttcccat agtaacgcca atagggactt tccattgacg tcaatgggtg   5820

gagtatttac ggtaaactgc ccacttggca gtacatcaag tgtatcatat gccaagtacg   5880

ccccctatt gacgtcaatg acggtaaatg gcccgcctgg cattatgccc agtncatgac   5940

cttatgggac tttcctactt ggcagacatc tacgtattag tcatcgctat taccatggtg   6000

atgcggtttt ggcagtacat caatgggcgt ggatagcggt ttgactcacg gggatttcc   6060

aagtctccac cccattgacg tcaatgggag tttgttttgg caccaaaatc aacgggactt   6120

tccaaaatgt cgtaacaact ccgccccatt gacgcaaatg ggcggtaggc gtgtacggtg   6180

ggaggtctat ataagcagag ctctctggct aactagagaa cccctgctta ctggcttatc   6240

gagatatctg cagaattcat ctgtcgactg ctaccggcag cgcgcagcgg caagaagtgt   6300

ctgggctggg acggacagga gaggctgtcg ccatcggcgt cctgtgcccc tctgctccgg   6360

cacggccctg tcgcagtgcc cgcgctttcc ccggcgcctg cacgcggcgc gcctgggtaa   6420

catgcttggg gtcctggtcc ttggcgcgct ggccctggcc ggccgcgtta agatacattg   6480

atgagtttgg acaaaccaca actagaatgc agtgaaaaaa atgctttatt tgtgaaattt   6540

gtgatgctat tgctttattt gtaaccatta taagctgcaa taaacaagtt aacaacaaca   6600

attgcattca ttttatgttt caggttcagg gggaggtgtg ggaggttttt taaagcaagt   6660

aaaacctcta caaatgtggt atggctgatt atgatcagtt atctagatcc ggtggatcgg   6720

atatcttatc tagaagctta ggctcgagtg ctcttgttgg gttacattaa ccttccttca   6780

aaagggattt ctcagttgta cttcttacag tcttcaggaa attcattaaa tcagtgcctc   6840

cagttccttt ggcttccagt tttgaagggt cttcagaggt cttattctcc tttggctgct   6900

ggcttgcagg aatcaggatg tacttagtca cgatttgcag atggtagctc ctcagggaga   6960

ccagagcttt cacacaggcg tcataagctt cccgcaggcc agcatcacct tttgaaagga   7020

caaactcacg gactgaggga tttgactcta atgagcacag gaagttcctg tgagctggtg   7080

gcatatatct tctcatgtcc tggaggaact gagcagcatg tcctccacca gcagtctgct   7140

ggatgcccag caggacgtca aagcactgaa agacgctgct ttggcctgca ctgccccctg   7200

caaactcctt tgggtcttcc cagaaccctt catacaccag accgtctgat agctgggggt   7260

tgcctttcca gccagacaaa tatatgcgaa gaacactgaa aaatgctttt gggttcacat   7320

gatcgtggat ttggtgaaac acttgaaggg ctttctccaa gcaagaagct atttccaaca   7380

gcgcctttag caaagtgtcc cgttcttgca tttgcattgc cttgaataca gtaggaatta   7440
```

```
ctttgattgc agaagcagct gctatttcca ccaatagaga gaccaggaag aatcctttac   7500
tgcagtctcc atcacgaaat gagaacaaaa cgtccatgtt ctcataagtc aggggcttat   7560
taggatcctt tttcttccag tttgccaaga cacagtctgc ataaaccaaa ataggaggca   7620
gttccagttt cttggagagt tggcagtaag gaacagcaat atttcttggc aagaccttac   7680
ggacatctcc atgacctttg ccccacacat atgccatggt gatgcatccc agaactagac   7740
gtgcaaggcg ctgtgacttg tggtctgtga gatgatcaat gctgagcatg tttaacttct   7800
caactctttc tcgaagctgg ccagactcta tgagatcagg cagatgttta gcaatgaaca   7860
tccagtcatt ataaaaatca ggtagatttt cctgtggatt tggcagagca aagcccactt   7920
cttcatcaat atggtactct ttactgattg tccaggagtt ttccatagcg tgtgccattc   7980
ttgtagtctg ctcctctgga gatctctagc ggatctgacg gttcactaaa ccagctctgc   8040
ttatatagac ctcccaccgt acacgcctac cgcccatttg cgtcaatggg gcggagttgt   8100
tacgacattt tggaaagtcc cgttgatttt ggtgccaaaa caaactccca ttgacgtcaa   8160
tggggtggag acttggaaat ccccgtgagt caaaccgcta tccacgccca ttgatgtact   8220
gccaaaaccg catcaccatg gtaatagcga tgactaatac gtagatgtac tgccaagtag   8280
gaaagtccca taaggtcatg tactgggcat aatgccaggc gggccattta ccgtcattga   8340
cgtcaatagg gggcgtactt ggcatatgat acacttgatg tactgccaag tgggcagttt   8400
accgtaaata ctccacccat tgacgtcaat ggaaagtccc tattggcgtt actatgggaa   8460
catacgtcat tattgacgtc aatgggcggg ggtcgttggg cggtcagcca ggcgggccat   8520
ttaccgtaag ttatgtaacg cggaactcca tatatgggct atgaactaat gaccccgtaa   8580
ttgattacta ttannntaag ggtgggaaag aatatataag gtgggggtct tatgtagttt   8640
tgtatctgtt ttgcagcagc cgccgccgcc atgagcacca actcgtttga tggaagcatt   8700
gtgagctcat atttgacaac gcgcatgccc ccatgggccg gggtgcgtca gaatgtgatg   8760
ggctccagca ttgatggtcg ccccgtcctg cccgcaaact ctactacctt gacctacgac   8820
ctgcaggcag acgggcgctc ctgcaccgca tccgcgacgc agtcctgcaa cgacctctgc   8880
gagcacttct gcgttcccaa ccccgaccag ccgggctcct actcgtgcat gtgcgagacc   8940
ggctaccggc tggcggccga ccaacaccgg tgcgaggacg tggatgactg catactggag   9000
cccagtccgt gtccgcagcg ctgtgtcaac acacagggtg gcttcgagtg ccactgctac   9060
cctaactacg acctggtgga cggcgagtgt gtggagcccg tggacccgtg cttcagagcc   9120
aactgcgagt accagtgcca gcccctgaac caaactagct acctctgcgt ctgcgccgag   9180
ggcttcgcgc ccattcccca cgagccgcac aggtgccaga tgttttgcaa ccagactgcc   9240
tgtccagccg actgcgaccc caacacccag gctagctgtg agtgccctga aggctacatc   9300
ctggacgacg gtttcatctg cacggacatc gacgagtgcg aaaacggcgg cttctgctcc   9360
ggggtgtgcc acaacctccc cggtaccttc gagtgcatct gcgggcccga ctcggccctt   9420
gcccgccaca ttggcaccga ctgtgactcc ggcaaggtgg acggtggcga cagcggctct   9480
ggcgagcccc cgcccagccc gacgcccggc tccaccttga ctcctccggc cgtggggctc   9540
gtgcattcgg gcttgctcat aggcatctcc atcgcgagcc tgtgcctggt ggtggcgctt   9600
ttggcgctcc tctgccacct gcgcaagaag cagggcgccg ccagggccaa gatggagtac   9660
aagtgcgcgg ccccttccaa ggaggtagtg ctgcagcacg tgcggaccga gcggacgccg   9720
cagagactct gagcggcctc cgtccaggag cctggctccg tccaggagcc tgtgcctcct   9780
cacccccagc tttgctacca aagcacctta gctggcatta cagctggaga agaccctccc   9840
```

-continued

```
cgcacccccc aagctgtttt cttctattcc atggctaact ggcgaggggg tgattagagg   9900
gaggagaatg agcctcggcc tcttccgtga cgtcactgga ccactgggca atgatggcaa   9960
ttttgtaacg aagacacaga ctgcgatttg tcccaggtcc tcactaccgg gcgcaggagg  10020
gtgagcgtta ttggtcggca gccttctggg cagaccttga cctcgtgggc tagggatgac  10080
taaaatattt atttttttta agtatttagg tttttgtttg tttcctttgt tcttacctgt  10140
atgtctccag tatccacttt gcacagctct ccggtctctc tctctctaca aactcccact  10200
tgtcatgtga caggtaaact atcttggtga attttttttt cctagccctc tcacatttat  10260
gaagcaagcc ccacttattc cccattcttc ctagttttct cctcccagga actgggccaa  10320
ctcacctgag tcaccctacc tgtgcctgac cctacttctt ttgctcttag ctgtctgctc  10380
agacagaacc cctacatgaa acagaaacaa aaacactaaa aataaaaatg gccatttgct  10440
ttttcaccag atttgctaat ttatcctgaa atttcagatt cccagagcaa aataatttta  10500
aacaaaggtt gagatgtaaa aggtattaaa ttgatgttgc tggactgtca tagaaattac  10560
acccaaagag gtatttatct ttacttttaa acagtgagcc tgaattttgt tgctgttttg  10620
atttgtactg aaaaatggta attgttgcta atcttcttat gcaatttcct tttttgttat  10680
tattacttat ttttgacagt gttgaaaatg ttcagaaggt tgctctagat tgagagaaga  10740
gacaaacacc tcccaggaga cagttcaaga aagcttcaaa ctgcatgatt catgccaatt  10800
agcaattgac tgtcactgtt ccttgtcact ggtagaccaa aataaaacca gctctactgg  10860
tcttgtggaa ttgggagctt gggaatggat cctggaggat gcccaattag ggcctagcct  10920
taatcaggtc ctcagagaat ttctaccatt tcagagaggc cttttggaat gtggcccctg  10980
aacaagaatt ggaagctgcc ctgcccatgg gagctggtta gaaatgcaga atcctaggct  11040
ccaccccatc cagttcatga gaatctatat ttaacaagat ctgcaggggg tgtgtctgct  11100
cagtaatttg aggacaacca ttccagactg cttccaattt tctggaatac atgaaatata  11160
gatcagttat aagtagcagg ccaagtcagg ccccttattt caagaaactg aggaattttc  11220
tttgtgtagc tttgctcttt ggtagaaaag gctaggtaca cagctctaga cactgccaca  11280
cagggtctgc aaggtctttg gttcagctaa gctaggaatg aaatcctgct tcagtgtatg  11340
gaaataaatg tatcatagaa atgtaacttt tgtaagacaa aggttttcct cttctatttt  11400
gtaaactcaa aatatttgta catagttatt tatttattgg agataatcta gaacacaggc  11460
aaaatccttg cttatgacat cacttgtaca aaataaacaa ataacaatgt gaaaaaaaaa  11520
aaaaaaaaaa aaaaaaaaaa aaaaaaaaaa aggtagcagt cgacagatga attccaccac  11580
actggactag tggatccgag ctcggtacca agcttaagtt tgggctgcag gaattctgat  11640
ggctctcaaa attcctgcct cctttaggga taaaagactt taagactttt taacaaaaaa  11700
gaaaaagaaa aaaaaaattc ctgcctcctg gtgtacacac acagaagggt tccctcccct  11760
tgaatgtgac caggatctgt gaaaataacg ggatagccgc tcctgtgatt aggttatgtg  11820
gtagactaga gcaagattct cctgctggtt ttgaagaagt cagctgccat gttgtgagac  11880
tgtcatgggc tagggcatga gcctttaaat atctgggagc aacccctggc cagcagccag  11940
tgagaaaacg ggccctcagt cctacaatca caaggaacta aattctgcca acaacctgaa  12000
ggaactttga agaggatcat gagtcccttg attcagcttg atgagcccct gagcagagga  12060
tacagctaac ttgtactagg gaagtataaa aaacatgcat gggaatgata tatatcaact  12120
ttaaggataa ttgtcatact tctgggaatg aagggaaaga aatggggctt tagttgtatt  12180
atgatcttta atttctcaaa aaaaataaga tcagaagcaa atatggcaaa atgttaatac  12240
```

-continued

```
ttttgtgggt acgtaggtat tcagcatacc cttttttctg agttcaaaat attttataat  12300
taaaatgaaa tgcaggccag gcacagtggc tcatgcctat aataccagca ctttgcgagg  12360
ccgaggtggg aggatggctt gaggccagac cagcctggcc aacatggcaa aaccccatct  12420
ctacttaaaa aaaaaaaaac tatatatata tatatgtgtg tgtgtgtgta tatatatata  12480
tgtatatata tttatatatg tgtgtatata tatatatgta tatatattta tatatgtgtg  12540
tgtatatata tatatacaca cacacacata tatacataca tacatacaca cacacacaca  12600
cacaattagc caggcatggt ggcgcacacc tgtagtccca gctacttggg aggctgagac  12660
atgagaattg cttgaacctg ggaggcagag tagttagtga gctgagatca taccactgca  12720
ctccagcctg gtgacagagt gagactctgt cttaaaaaaa ataaaaatta aaattaaatg  12780
caaaaggtcc aagtgaattg aagaggaaag gggtatcaag gaaggttttg tggaggtgac  12840
gtttgagctg ggtcttaaat gacttaaaca tgggataaga agggagggaa taaggacatt  12900
tcaggtacga gaaataagga gcaaacagtg gaaacaacct aacgtctgtc aaccagtgaa  12960
tggataacaa aaatgtaatt cagatggtat ccaacttacg atggttcaac atgagatttt  13020
tctgacttta ggatagattt atcaaagtag taaatccatt ttcaacttat gatattttca  13080
acttcagatg ggtttatcag gacacagttg aggaacacct gtctatccat acaatttggc  13140
aataaaaagg aaatgagtgc agatatactc cacaacatga atgaaccttg aaaacattaa  13200
gtgagagaag ccagatacaa aaggccacat attgtatgat tctatttata caaaatgtcc  13260
agaataggca aatcttatag acagcaagta ggtagatgat cagtttgcta ggtgctgggg  13320
gaaggggaaa tggggagtga tggctaaggg gattgggttt ctttgtgggg caatgaaaat  13380
gttttaaaat tgagcgtgat aatgattgca caatgctgca tatatatata atctatagat  13440
tatatatata taaagagagg ctgttagaca gtgataagtg atatatatat atatatacat  13500
agagagagag agagagagag agagaggctg ttagtgataa gtgatcagga aaataaaagt  13560
attgaggagg aatacgaagt tgacggtgtg aaaacatgag attttatata ggatggccag  13620
ggaaggcctt aatgagaaag tgacttatga gtaaaaacaa gggatcctaa accttagcat  13680
gcatcagaat cactcggaaa cttgttaaag catagcttgc tgggcctcat cacagatatt  13740
ttgattcggt aggttcttgt ctgatattaa tacttttggt ctagggaacc acattttgag  13800
aaccactgag ctaaaggaag taaaggtttc ccttagttta ctagctggta acactggccc  13860
aggaggcctt tctggaaaag gtcccagtcc ccaaaggaag ctggggactc gcgttcacat  13920
cgtcaaggtt taccaagttg tggcgggcct ttccgtcttg gaaaaagcct caaaatggca  13980
gattagggtg tccatggccg gcggaaaggg tctttgaagt tgcagaccag gagggaagaa  14040
gattctgggc ctcccccatg cagtgtcagc tggcaacaga atgcaccccg gctgggttgg  14100
aggccctggg tactggctct tccacaccag gggcccacct accaagggca gcaggagcat  14160
ctgcacctcc tgcgccaggc gcccttcagt gcttccactt gagcacctct ccagacacca  14220
gctagggtga cagtggtaca aataccagac tcccctggcc tgctcacctc acagggtaat  14280
gtgctgtgga gtcaggggga cacagcaacc accagatgac atggctggcc ccggggagga  14340
cgacacgcag atacggctac ttggcacctg tgatatttta cacactcgag aggggcccgc  14400
accatcctca gccctctccc cacattcact cttagttcat gtcacctcca cccagagggg  14460
gacacaggcc cacagcgatg gccccacacc ctgcctgagg tcgcccactt cccaggaggc  14520
agtcctggga cttccacccg accaggcccc agagcccacc gacttaaccc ctccagaggc  14580
ttgtcgttca ttaccttatt caagatggag accagccttt ttgcggagaa aatgcgggtg  14640
```

```
aaggtcctga aagtgcattg acgccgtttt cggaagccat acaagtttag ctggcggaag  14700
aagctcttta tcgaagttgt ggcaaacact ttgtgtgcga cgtccctttt gagaatctcc  14760
ttttcaaaga gtttttgatt gatcactcta caagccccac tgtcatccca ccagatggac  14820
gaaaactggt tgctgctgac cagtctccac agtttctgtg gaaaggggag ggagaggaga  14880
ttatcttctc cctggggcgg gacgtcaccg tcagggtgcg gccttctgaa cgaagcttcc  14940
tcggccagag gttggaaagc gatttcttct gtcagcagcc tcaagttagg gctcccagtg  15000
gaccccgggt cgtcccaggc aggggaagga tctgctgggt gaaggtaggt ctctgactgc  15060
aactggggag ggaaaggcac cctttccaag ccatgatcct gtcctctcga atttctttct  15120
tcacagcgag ccatactcaa tgatcgcttg tcctccatct ggcaaacttg ctagtgcagt  15180
gtggccagca gcaccccttg gcagtcatgt aaccagcccc atgacatcat aaaggggctc  15240
tgactgccgg ggggtggcat ctccaccccc agcaagttgt gtaataaagg gccaaggcag  15300
acaagtagct gcccatctgc atgtgcacat tctggtcctc acagtcattt caatgggaaa  15360
gatgacacta gtgcacaaga gtgccgaggg gccctgccac accgtagatg cagacctgga  15420
gcggtcccct tgtcctagag ctcctgagcc aggcacaact acagcaaagc cctggctcag  15480
gaaggtcaga gctcaccgtc tgagtcatgg gcccacagac cccagcacat gactgacact  15540
cggaagcaca gaacaaaggg taggacggtg cccatgggtc aggctgtagc cacgccaccc  15600
tttccaccct gtcctagcca gaggcagcaa tgtgctccat acagatcctc ctaacacacc  15660
cacactgtcg gtccccagca cgcagatgcc cgacagcccc ttaggcaaat ggcttagctg  15720
actgccccac cacacgccgt cgccatgcag tccagtgggg agtcggaggc agcctccttc  15780
ctgcctctcc tcggcctgca cgtgtccccc caccaggcag agacccttct acaccccggg  15840
tgtctgcggt cacatcgcgg tggggcatgc agctgttggc cttcgagcat gttttgtttt  15900
ccttggccag tgtctccaga gaaacgcacg tgggtttgtg tccagcggtc catctctgca  15960
acagttgttc ctttgggatt ggatgctagg aggtcacggg agaggtgtcc atccaaagca  16020
gtgtctgtgt cacacactgt ccccacacac agggccacct ctgcacagac tcccccgact  16080
cgattctggg cacagagctc agtgaccttc cagagactgc cacgaaccgg tgatgcctcc  16140
acgcttgaga catcctgacc gcagggccca aggcgcactg gctcaggggg tgacagtgag  16200
gggtctgcaa acagactgct gatgctcaac ccggccgctg ccgagctgtg tgacttgggc  16260
acgtcactta acctctctcg gcctctgtct cctcccgggg ataagagtag tagcacctgc  16320
ttcccggggc tgtgaggatc cagtgggacg tataggaact agcgaggcac cggcagttgg  16380
gtcagagcta ctgttgtcac ttcacaaggc attttcttca acagcaagtc ggaaatctca  16440
tgagcctaag gcagaatcca cctgtggcct ctggttacaa cccacaggac tgaaaatcct  16500
tccagccaca gcaactggtg aatttcctgg tcaattgcca caagtcatga gctgaacccc  16560
acttgagttt cagttcaggc agaactctag agacgactag ggcaagctag acagcgactg  16620
cagagccttt tgttgcagcg tgagcagtcc tcagctgttg acatcactgg ggagcaaacg  16680
aggaccagga gcggtgaaag gacagtgtct gctgcagatt gtcgtagcac ccaaggaaca  16740
ctccagaaag cctcctaagc agtaacaagt gtggcaaggt gtagcccagc caacagtggc  16800
atctgcgagg cgtcccctcc ttcctcccac taccccgtat accctgggac ctgtgcactg  16860
aaggactcat tctaaaggct gtgcccctgc agccgccagc ctcactcact ggctgcctgt  16920
gccagctaga gatttctttc ctctgaggct ggctgagagg accactccag tttcctggcc  16980
catccagcaa agaagataca catcatgcac gtgtaaaatg aggaaccggt ttattgaaca  17040
```

-continued

```
gcttaaggag agcaaaaata gtggctttag ctacattttt tacacactga gcaggaaagt  17100
ctaaaccatc ccgttcccct gtaccccaaa gagaacaggg cttgctggag gccagtgcca  17160
agggcggagt cgtgctcgca gcagacttga attaacccca tgtaggccgg cgagcagttg  17220
cccgcgtgaa aacaccaccc tcttctcctg gctgagaaga tcaaagctct ttttttaccc  17280
tcttttcagc aaaggaccta tttgttttca ggcaggagga tgttaaactt gcagcctctg  17340
acacacggtg gaacctgcag tgcttggaga aacggcacgc acacgtgaaa acatcatgcc  17400
tactccaaag ccttcttgtt gctggcagga gggaagcttg agactttccc acgcatagtc  17460
gtgacccgcg tggccgtttc tgctctcagc aacattctct agtgttccgg cttcaagcag  17520
cgcttgtcag gtttgaagct agccactatt ctgagaacgt cagaaaagca tggaccatct  17580
cttgcttggt gttgccgttg tggcagtagc agctactacg tacctgcacg agttccaggg  17640
cagaagtggc aatgtcccat gaaggcgtgg caccccacgg gggggggggg ggagtgtgcc  17700
acgggcgtcc acttctgcag cagaaggcat gtgcctacag cacaagcttg taaaaaaata  17760
cttgaacaga atatgctgta cagaactagg ggttaacacc gcatatgaag atgctaaaac  17820
atttgtataa atactctgta tacaagcatg gagtcactcc cgtagaaagg gctcatccgt  17880
gaggctatga aaaactgctg tcagcatgcc caaagagaaa ctacttccac agtaggaaca  17940
gaaaaaagga ctgtgctgtg tctaaacacg tggtgcatca gagacatagt tacagttcct  18000
actgactgcc ccagccacga cctgggagtg ctgaggacct gggagtgctc agcgagctgc  18060
aggaggtcag ccctgtggag aaatacattt ctaaacaata cttttgattg ggatttcagc  18120
accgtataga cagatgttcc ttctggggc ctggcaagca gccatctccc agtgggtctg  18180
acggggaaga ggggtacctg gagcccctcc cagacagacg gtaatcccac ccctgttctc  18240
acactcttcc tggcatccgc atctgctggc acacaccccc gtcacctgcc acttccgcgt  18300
cccgtcgtgg tgagtggctg ataggcgctg gatgcaaaca aggcatgaga tggacgtacc  18360
tggagaccca gctccagtac tggttctggt ctgcggggtg aacgaggggg cagaggaagg  18420
cggagagagt gcgtcccagt ccacttaagc tctgtccccg gaagtggcat ctaatctggc  18480
atttcgatat ttaatttggg aggtgggagc acatacttcc cagggctctg ggtaatgacc  18540
accctggcct tctttcgaaa catgggtgcg attttagggg gctccggaac tggggtctct  18600
tcggtttctt cattatcttc gtgatggaga tcataggaaa tgtttccata ttctcgtaga  18660
aatgggaaga tttcaagcag aaactgacag aaatctttgc ggataccaaa ccaccctgaa  18720
aaataagaat tttttatttc acacacgagg ctcaactgac cttcctgtta actttctttc  18780
cgtaacaaga agtttcactc ctacaatgtc ataacatact ttatccagac tcctgagtca  18840
caaagcctga acagggcttg agtacccaaa atggggaaga agtgcaaatg ctagctctgt  18900
ggtgcttgga gtggggttcc cggaccggca gggacagcgt ccacggggcc tagttaggga  18960
tgccattctc gggccccagc ccagacctcc agaaactgag tcgggctagg gtgggctcca  19020
gcggtcccct tttcctggcc cttttgggat tctgctggat gcccaaattt gagaactact  19080
gctccagtga gtctcaaaat atctgtggtg cgcagactac ggtgtcttcc gctaatcttc  19140
tccagccagg ataaactcat ggatgacagt gccacccaag aacaagattt ctgtcaccct  19200
ctggaatccg tgagggcggt agtcatgcac gggttggcca ggagggggcc tgaactcatg  19260
gagccacctt aaagccactt tcccagtccc actactcctc tctgtaggct actggagtgt  19320
cagctcggtg caagccctcc ctgctcccgg gtgcggggta gggggcagag gcacaaacag  19380
caagcacagc ccgggctgct gggctgcagt gaggccctgc ccccaaaccc actggctttc  19440
```

```
cgaagggcaa tgctctgggc ttccgtgcca tggagcccac agccttgcca ggaaggcacc  19500
ctctgcagag atcgttttgg aagtgtctgc ctcagcaagc aggtggaggg gaatagagtg  19560
ttagcaaggc aagacaggca agactcgggt gatggcagca aggatatggg ggaggcagag  19620
cggccaacag ggacctagga tgaatcccag gtttgggtgg gagatgtgga ttttccatca  19680
aaccctcccg ggcctgggaa gaatctgtct tgatccccat tttgcagagg agggaacggg  19740
atctctgaga ggttgcctgc cgtgtctggt tctacctcaa atggcagcgt gcactgcgag  19800
aaaagtcccg gtgcaggcca gcagaacacc agagttacgg catgcccttc ccttagaagg  19860
tcccagaatt tcctcagccc tcactttccc acacaagctt ctaaattggg gccctcgggg  19920
actcatccct tcctagactt ctatccgcca ccccccaccc cctggtcccc ccccagacac  19980
acaccaagga cttctgaaat gctgagtaca tacagtggtt tcctcccttc tgtccaaatg  20040
tggttgccat cagcgtgatc aacgagagcc aaagggggac aaagatcggg atgcaggaga  20100
aggcgttgtg gccatccagt ttgtgaacca gcagaatcta aagaaagaga catagtcccg  20160
gttgatgcca gcaccgaaaa tgggcagagg cggaagccag acttcattag gcagttcctc  20220
cccaccaccc cacccccgcg tgagctccca caagagggaa catcagcacc gccagaaaaa  20280
ggcaggaaac cacctatccc tggggaaagc tcgaaatgag cttttatgtc cctcttcaga  20340
gctcggcaat agcctatcca cttgaaaagt tcccagtgcc agcagtttta tggcaaactc  20400
ctccgggtgt ttgttctaag gagtcaacag ctcccattct agaattctcc acgtgactcc  20460
aatacacaaa tctgacatcc cactctgctt tccccagagt ggaaactgga gccatacaga  20520
ggcaccatgg ctaaaaaggt gcactcttct ccctgccagc cccacgtgct gcccccaaga  20580
gaaaggaagg atgctctcct ttcaccgaag ctccctctcg gagatggctg tgttctctcc  20640
cctctcctgg agtgggctca ctgtgagctc gagggacaga ggctgccttt ctaggggtgc  20700
agaatcctgt caggggaagc gcaagcttca ggggctgaag aggcttcccg tggaacgctt  20760
acctcaaatg taagaagggg cacgacgatg gtcatccagc tcagggccat ggttatgtgt  20820
gtcctgcgct gtccgcaatc acatccatag agcgcaagaa caagacggac cacacaatgt  20880
agtagaggac caccaggcac agaaaggaca tgagaatcca cagcgggaca cacacaacct  20940
gggggtgggt gagagaacag caagagaagt ctctttagag cttccaacct ggcctctgat  21000
ggaaggcatc tttagcacct tgctgtgtct gtccagttaa ggcggtcctt cctgtgagcc  21060
gaataaggac cgttccatct cccaggactg ctgggagcat cgctcaggac agaaaaggta  21120
tggtatgttc actatggggc ctgctgccac caggggacac acacgctcag tgagtcatca  21180
gtccctcttc ctttgggtga cagacagccc tgcacctggc tccgcagcct ctactcttcc  21240
agaggcccac tctcccacac tctctcaggc tcctctaggt tctgctgcca tcacagcttc  21300
ccgggaaatg ggacacaact gtcaccctgt gcacacacac aagatctcac cccaacagac  21360
tctcttcaca ggcaacattc ccacaacctg ctgggggtac tttggcaaca caaatgggaa  21420
tgggctcccc agaaagtctg gctgcctggg ctcctaagga tccctaacct cacccctacc  21480
aagttagtga acttggcggg ttgatgctgg atacaggttg atgctggata cgtagcgctg  21540
ccgggtcgtg accctaagg aattatccaa actcttgttt ttagatgctt tattatatca  21600
aactctcctt taaacaagtg gcccatctgc tgggatttgg aagcctgtaa tactgaaatt  21660
ttcatcataa tggaaatttt aaaaacagaa tttgacccac ctgtttttaa aacactttca  21720
ttacttaaca agaggtctaa tcttgggcaa gtcttgaaat ttctctggcc ttagtttccc  21780
atgtgttaaa tgaaacttga agcagttggt ctcttatagt ctcctgactc taacattcta  21840
```

-continued

```
agaattatat ttgtacaata actcaaaaat cacataattt aatttaccat atggactcca  21900
aaatatattt tctcattagg ctaaacttga tctgcatttt ctggatgtgt ccatattctt  21960
ggactacact aaaacatgat accaatgctt cctctcacca taaaccctca cttcgctttc  22020
tacatttaag aattttatag ctggaagagt ccttaacaga aaataccatc taataattac  22080
ccctcaaaat cgagaaagtc ctatctgttc ttatgctagt tataagaatg aggcagcatt  22140
tcacataatg gttataaaca ctgccacaag aagattcatg atgtgttgtt tatctgtagc  22200
tctcatcata ctctgtcata taactatagc attaagattt taatgttcta tatattcttc  22260
taagacagtg tttaccagag taaggcacaa aagatccact ggtttgcaag aaagattaga  22320
acttttaaat tttttacctc accttgttta atctatattt ttgtatgtat tttgtaacat  22380
atatattatt attaccataa atcatatata atttaaaatg catatattag gggtaaatgc  22440
tcaggaaact ttttataaat tgggcatgca aatacaagtt tgaagactca ctgttctagg  22500
tattaaaagt aaagttataa ccaagtaaag cttccacctt ttcatgtctc aaagcagttt  22560
attgttggag gtaagatctc ttagaagcct aaacaggtcc aagtacagaa tgaagtaagg  22620
ctagcccata acttgtggca agcaattcat actatttctc tcatgctgag ctctcctcag  22680
tgaagcagct actatagaca actgcagcct attggtagcc tattttacag gcaggaaaaa  22740
aattactttt tattcaaagt ggaactcagg acatggggag aaaatgaata caaaaaatag  22800
ggtcaatcca aaggcacaca gcaaatgagt aacacagtta tgtttttttc ccatttgtat  22860
gaggtcccag taaattctaa gtaaactgca aatttaataa tacactaaaa aagccatgca  22920
attgttcaaa tgaatcccag catggtacaa ggagtacaga cactagagtc taaaaaacaa  22980
aagaatgcca ttattgagtt tttgaattat atcaagtagt tacatctcta cttaataaat  23040
gagaaaaacg aggataagag gccatttgat aaaatgaaaa tagccaagaa gtggtattag  23100
agacttgaat acaggtattc gggtccaaag ttcatctgct caaatactaa ctggggaaaa  23160
gagggaaaaa tatttatata catatatatc tgcacacaaa aatacccccca aaagacaaaa  23220
tgaggccagg cagggtggct cacacccgta atcccggtac tttgggaggc tgaggcaggt  23280
ggatacctga gatcaggagt tggagatcag cctggtcaac atggtgaaac cctgtctcta  23340
ctaaagataa aaaaattagc caggcatggt ggcgtgcgcc tgtaatccca gctacttggg  23400
agtctgaggc aggagaatca cttgaactgg gaaggggagg ttgcagtgag ccaagatcgt  23460
actactgcac tccagcctgg gcagcagagt gagactccat cacaaaaata aataaataaa  23520
taaaatacaa tgaaacagaa agttcaaata atcccataat cttaccacca agaaataact  23580
ttcactcgtt atacttattg atttttccat aataaatgta ctttactgtg actatcatga  23640
aaagaaagtt attttagaaa cagagaactg tttcagatca aatctatgta gtagaacaga  23700
gccattaggt gggaaagacg agatcaaact aaatctcaga aggcctaaaa ggctaggtcc  23760
attccagcac taaaaactga ccagacaagt aatggcttca acagcttcta aatatggaca  23820
aagcatgctg aaagggaagg acaggtctaa cagtggtata tgaaatgaac aggaggggca  23880
aagctcattt ctcctctgaa gttttccaaa gatgctgagg aggacattag tttgacatga  23940
ccctgatatg ggacaagata atttcacaga agttttacat gttaaagttt tcttatagat  24000
actcattcaa gtaagcaatg aacactaaaa tctaaagaaa gaaaagagct ttagagtcag  24060
gtctgtattc aaattcaagc tctaccactt actggttctg tgactttggg caagtctttt  24120
aaccttatta agtcttaatt tcctgatttg taaaatgggg atatcgtctc cctcacagga  24180
ttgttgtgaa acttttatga gattaatgcc tttatatttg gcatagtgta agtaaacaat  24240
```

```
aactggcagc ttcaaaaaaa aaaagcagta gcattccatc atttattatt ggttactctc  24300
aaaaagtttt tcaatgtact agaagataaa tattcaaata ccttaatatc tccattattt  24360
tcaggtaaac agcatgctcc tgaacaacca atgggtcaac aaataaatta aaagggaaat  24420
ctaaaaacat cttgatatta aactacatgg aagcacaata taccaaaacc aatggttcac  24480
actaggagaa ttttaaggta caagaaaact ctttgagatt tcttaaaata atagtatgtc  24540
tgaatttatt gagtgattta ccagaaactg ttgtaagagc tctacttgca ttatagcact  24600
taatcctctt aactctatgg ctgctattat caacctcacc ctaatcacat atgggacaca  24660
gagaggttaa gtaacttgcc caaggtcaga gttaggaagt actaagccat gctttgaatc  24720
agttgtcagg ctccggaact cacactttca gccactacat aatactgctt tgctatcttt  24780
taggaaacta tgtgagtcta cctcacatag actcacatag gtttgttttt tttttttttt  24840
taaaggctat cttttccccc atcaatgttt tttgaaggat cccaaattag agtcccacag  24900
aggcagacag cagtacttga caatatggac atttaaggtt aatgttggat tctactgtct  24960
ttttactaca tgacctaggg aacgataatt aacctagact gcttccaagg gttaaataac  25020
ccatttagtt atactatgta aattatctct tagtgattga ttgaaagcac actgttacta  25080
attgactcgg tatgaagtgc tttttttttct tccctttcaa gatacatacc tttccagtta  25140
aagttgagag atcatctcca ccaattactt ttatgtcccc tgttgactgg tcattctagt  25200
taaaaaaaaa aaaaactata tatatatata tctacacaca catatgtata tgtatatcct  25260
tatgtacaca cacaaacttc aaattaaatg agaactagaa gatttgagaa gttagctagc  25320
taatatccat agcattatga tattctaaat gatatgaatt ataagaatta ggtttcctga  25380
aatgaatgac tagaaaactt tcaagtagag attagtaaaa attaaaaagt cctaatcggc  25440
cattactgat ttgatgtttt taagagtcct aaaaaatggg ttacatccat ttttaagtgg  25500
gtagtattat aacagccacc catcttcaat cacagtgatt tctgaattgt gagggaagtt  25560
attagcatga caggtgtctg gttctggccc tgtacgattc ccatgagtca agcaaattgt  25620
aagggctggt ctatatcaca cccaacccca aggatatgtc cctcaaaagt ctagcccagg  25680
ccccgtcatc ttcagcatca tctgggaaac caggtctgat tagtagtcct ttaaggaata  25740
cctcttaggc tcccatttta ctgctatcac agaatccaat aaaaccctta caggagattc  25800
aatgggaaat gctcaacacc cactgtagtt ggtggtgaca atgaccataa tttggctgtg  25860
ctggattcag gacagaaaat ttgggtgaaa gagcaggtga acaaaagagc ttcgacttgc  25920
cctagcagag agcaagccat accataccac aaagccacag caattacaac ggtgcagtac  25980
cagcacagta aatgaacaaa gtagagccca gaaacagacc cagaactata tgaggattta  26040
gtatacaata aagatggtat ttcgagtcag tagggaaaag atgaattatt caataaatga  26100
tgtttggcca actagtaacc catttgggaa aaaataaaag tatggtccct acctcacagc  26160
atacacaaaa ataaattcca gacggattaa aatctaaatg taaaaaataa agccataagt  26220
ggactggaag aaaatagaga atttttttta acatccgtag aaagggtaaa aacccaggca  26280
tgacatgaac caaaactgaa gaggttctgt aacaaatacc ccttttttata tattgggctc  26340
caacaataag aacccatagg aaaatggaga atgaacacaa atagacaatt tatagaagag  26400
aaggttataa ggtgtaaaat tatatctatc tgagaaacaa acactaaaac aatgtgattc  26460
tactgttctc ccacccatac tggcaaaact taagcctgat aatatgctga ggggaaataa  26520
gcactcttgt tggtgagagt attaattggc atagcttctt ttgaaaatga catagcaata  26580
cctgttaaaa ttgcaaacat gcatgtcact taatccagta atcccacttc tgggaatcaa  26640
```

-continued

```
tgctacaaaa acactgacaa gtatacaaag atacattcaa gagtgttcac tgggccgggt  26700
gcggtggctt catgcctgta atcccaggga ggcagaggca agacgatcgc ttgaccccag  26760
gagttcaagg ccagcccgag aaacacagca agaccctgtc tctctttttt ttatttaaaa  26820
aataaatgtt cactgtatca gttgttcaca aaaacaaacc aacatgtcca ttaacaggga  26880
accatttaaa ttaatcaagt tcatctacac aatgtaatac catgcaacta ttaaaaagca  26940
cctgataatc caaagcacac tgagacagaa taatgctatt aaaaacacca agtagtggaa  27000
cactgtgttg cctatgacac catttttatt caacatttaa acaaatttgt aacagcaatt  27060
acatgagtag tgacaatggc gtttatgaga cttttcactt ttatgtgctt ctatttttgt  27120
tatgcttcta tatatacatc catttattat ggagtgttac tttcaaaaat cacaaatggg  27180
ccagtattat ttggtgttgc aaggtgagca tatgacttct gatatcaacc tttgcatatt  27240
acttctcaat ttagggaaat tacagacatc ccttattcta actaacttaa aacccagcat  27300
ttcaaacata cagaattgat ggggaaaaaa aagaaagaag aaagaaagaa aaggcaacaa  27360
gcttcagatg acagtgactc acatcaaatt atttataaaa tctgttaaat agtgccatct  27420
tctggagata cctggtatta cagtccaact ccagttgatg tctttacaga gacaagagga  27480
ataaaggaaa aaatattcaa gaactgaaaa gtatggagtc atggaaaaat tgctgtgatc  27540
caaaggctac ggtgatagga caagaaacaa gagaactcca agcagtaaga cactgctgtt  27600
ctattagcat ccaaacctcc atactcctgt ttgccccaag gctttttaa aaaatagaga  27660
caggatctca ctattttgct caggctggtc ttgaactcct ggactcaagc tatcctcctg  27720
cctcggcctc ctaaagtgcc gagattacag gcttgagtca ccatacctgg ctatttattt  27780
tttcttaact ctcttgcctg gcctatagcc accatggaag ctaataaaga atattaattt  27840
aagagtaatg gtatagttca ctacattgga atacaggtat aagtgcctac attgtacatg  27900
aatggcatac atggatcaat taccccacct gggtggccaa aggaactgcg cgaacctccc  27960
tccttggctg tctggaacaa gcttcccact agatcccttt actgagtgcc tccctcatct  28020
ttaattatgg ttaagtctag gataacagga ctggcaaagg tgaggggaaa gcttcctcca  28080
gagttgctct accctctcct ctaccgtcct atctcctcac tcctctcagc caaggagtcc  28140
aatctgtcct gaactcagag cgtcactgtc aactacataa aattgccaga gaagctcttt  28200
gggactacaa acacataccc ttaatgtctt tatttctatt ttgtctacct cttcagtcta  28260
ggtgaaaaaa taggaaggat aatagggaag aactttgttt atgcctactt atccgcccct  28320
aggaattttg aaaacctcta ggtagcaata agaactgcag catggtatag aaaaagagga  28380
ggaaagctgt atagaaatgc ataataaatg ggcaggaaaa gaactgcttg gaacaaacag  28440
ggaggttgaa ctataaggag agaaagcaga gaggctaatc aacaaggctg ggttcccaag  28500
agggcatgat gagactatta ctaaggtagg aattactaag ggctccatgt ccccttagtg  28560
gcttagtact atgtagcttg ctttctgcag tgaacttcag acccttcttt taggatccta  28620
gaatggactt ttttttttta tcggaaaaca gtcattctct caacattcaa gcaggcccca  28680
agtctaccac actcaatcac attttctctt catatcataa tctctcaacc attctctgtc  28740
cttttaactg tttttctata ccctgatcaa atgccaacaa aagtgagaat gttagaatca  28800
tgtattttta gaggtagact gtatctcaga taaaaaaaaa gggcagatat tccattttcc  28860
aaaatatgta tgcagaaaaa ataagtatga aaggacatat gctcaggtaa caagttaatt  28920
tgtttacttg tattttatga attccctaaa acctacgtca cccgccccgt tcccacgccc  28980
cgcgccacgt cacaaactcc accccctcat tatcatattg gcttcaatcc aaaataaggt  29040
```

```
atattattga tgatgttaat taacatgcat ggatccatat gcggtgtgaa ataccgcaca  29100
gatgcgtaag gagaaaatac cgcatcaggc gctcttccgc ttcctcgctc actgactcgc  29160
tgcgctcggt cgttcggctg cggcgagcgg tatcagctca ctcaaaggcg gtaatacggt  29220
tatccacaga atcaggggat aacgcaggaa agaacatgtg agcaaaaggc cagcaaaagg  29280
ccaggaaccg taaaaaggcc gcgttgctgg cgtttttcca taggctccgc ccccctgacg  29340
agcatcacaa aaatcgacgc tcaagtcaga ggtggcgaaa cccgacagga ctataaagat  29400
accaggcgtt tccccctgga agctccctcg tgcgctctcc tgttccgacc ctgccgctta  29460
ccggatacct gtccgccttt ctcccttcgg gaagcgtggc gctttctcat agctcacgct  29520
gtaggtatct cagttcggtg taggtcgttc gctccaagct gggctgtgtg cacgaacccc  29580
ccgttcagcc cgaccgctgc gccttatccg gtaactatcg tcttgagtcc aacccggtaa  29640
gacacgactt atcgccactg gcagcagcca ctggtaacag gattagcaga gcgaggtatg  29700
taggcggtgc tacagagttc ttgaagtggt ggcctaacta cggctacact agaaggacag  29760
tatttggtat ctgcgctctg ctgaagccag ttaccttcgg aaaaagagtt ggtagctctt  29820
gatccggcaa acaaaccacc gctggtagcg gtggtttttt tgtttgcaag cagcagatta  29880
cgcgcagaaa aaaaggatct caagaagatc ctttgatctt ttctacgggg tctgacgctc  29940
agtggaacga aaactcacgt taagggattt tggtcatgag attatcaaaa aggatcttca  30000
cctagatcct tttaaattaa aaatgaagtt ttaaatcaat ctaaagtata tatgagtaaa  30060
cttggtctga cagttaccaa tgcttaatca gtgaggcacc tatctcagcg atctgtctat  30120
ttcgttcatc catagttgcc tgactccccg tcgtgtagat aactacgata cgggagggct  30180
taccatctgg ccccagtgct gcaatgatac cgcgagaccc acgctcaccg gctccagatt  30240
tatcagcaat aaaccagcca gccggaaggg ccgagcgcag aagtggtcct gcaactttat  30300
ccgcctccat ccagtctatt aattgttgcc gggaagctag agtaagtagt tcgccagtta  30360
atagtttgcg caacgttgtt gccattgctg cagccatgag attatcaaaa aggatcttca  30420
cctagatcct tttcacgtag aaagccagtc cgcagaaacg gtgctgaccc cggatgaatg  30480
tcagctactg ggctatctgg acaagggaaa acgcaagcgc aaagagaaag caggtagctt  30540
gcagtgggct tacatggcga tagctagact gggcggtttt atggacagca agcgaaccgg  30600
aattgccagc tggggcgccc tctggtaagg ttgggaagcc ctgcaaagta aactggatgg  30660
ctttcttgcc gccaaggatc tgatggcgca ggggatcaag ctctgatcaa gagacaggat  30720
gaggatcgtt tcgcatgatt gaacaagatg gattgcacgc aggttctccg gccgcttggg  30780
tggagaggct attcggctat gactgggcac aacagacaat cggctgctct gatgccgccg  30840
tgttccggct gtcagcgcag gggcgcccgg ttctttttgt caagaccgac ctgtccggtg  30900
ccctgaatga actgcaagac gaggcagcgc ggctatcgtg gctggccacg acgggcgttc  30960
cttgcgcagc tgtgctcgac gttgtcactg aagcgggaag ggactggctg ctattgggcg  31020
aagtgccggg gcaggatctc ctgtcatctc accttgctcc tgccgagaaa gtatccatca  31080
tggctgatgc aatgcggcgg ctgcatacgc ttgatccggc tacctgccca ttcgaccacc  31140
aagcgaaaca tcgcatcgag cgagcacgta ctcggatgga agccggtctt gtcgatcagg  31200
atgatctgga cgaagagcat caggggctcg cgccagccga actgttcgcc aggctcaagg  31260
cgagcatgcc cgacggcgag gatctcgtcg tgacccatgg cgatgcctgc ttgccgaata  31320
tcatggtgga aaatggccgc ttttctggat tcatcgactg tggccggctg ggtgtggcgg  31380
accgctatca ggacatagcg ttggctaccc gtgatattgc tgaagagctt ggcggcgaat  31440
```

-continued

```
gggctgaccg cttcctcgtg ctttacggta tcgccgctcc cgattcgcag cgcatcgcct  31500

tctatcgcct tcttgacgag ttcttctgaa ttttgttaaa atttttgtta aatcagctca  31560

ttttttaacc aataggccga aatcggcaaa atcccttata aatcaaaaga atagaccgag  31620

atagggttga gtgttgttcc agtttggaac aagagtccac tattaaagaa cgtggactcc  31680

aacgtcaaag ggcgaaaaac cgtctatcag ggcgatggcc cactacgtga accatcaccc  31740

taatcaagtt ttttggggtc gaggtgccgt aaagcactaa atcggaaccc taaagggagc  31800

ccccgattta gagcttgacg gggaaagccg gcgaacgtgg cgagaaagga agggaagaaa  31860

gcgaaaggag cgggcgctag ggcgctggca agtgtagcgg tcacgctgcg cgtaaccacc  31920

acacccgccg cgcttaatgc gccgctacag ggcgcgtcca ttcgccattc aggatcgaat  31980

taattcttaa ttaacatcat caataatata ccttattttg gattgaagcc aatatgataa  32040

tgagggggtg gagtttgtga cgtggcgcgg ggcgtgggaa cggggcgggt gacgtagtag  32100

tgtggcggaa gtgtgatgtt gcaagtgtgg cggaacacat gtaagcgacg gatgtggcaa  32160

aagtgacgtt tttggtgtgc gccggtgtac acaggaagtg acaattttcg cgcggtttta  32220

ggcggatgtt gtagtaaatt tgggcgtaac cgagtaagat ttggccattt tcgcgggaaa  32280

actgaataag aggaagtgaa atctgaataa ttttgtgtta ctcatagcgc gtaatactg   32339
```